US011773065B2

(12) United States Patent
Zhou et al.

(10) Patent No.: US 11,773,065 B2
(45) Date of Patent: Oct. 3, 2023

(54) HETEROCYCLIC G-PROTEIN-COUPLED RECEPTOR 52 (GPR52) AGONISTS

(71) Applicant: Board of Regents, The University of Texas System, Austin, TX (US)

(72) Inventors: Jia Zhou, Galveston, TX (US); John A. Allen, Galveston, TX (US); Pingyuan Wang, Galveston, TX (US); Daniel E. Felsing, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/499,299

(22) Filed: Oct. 12, 2021

(65) Prior Publication Data

US 2022/0112164 A1  Apr. 14, 2022

Related U.S. Application Data

(60) Provisional application No. 63/090,519, filed on Oct. 12, 2020.

(51) Int. Cl.
| | | |
|---|---|---|
| *C07D 213/74* | (2006.01) | |
| *C07D 405/12* | (2006.01) | |
| *C07D 403/14* | (2006.01) | |
| *C07D 401/04* | (2006.01) | |
| *C07D 403/04* | (2006.01) | |
| *C07D 401/12* | (2006.01) | |

(52) U.S. Cl.
CPC ......... *C07D 213/74* (2013.01); *C07D 401/04* (2013.01); *C07D 401/12* (2013.01); *C07D 403/04* (2013.01); *C07D 403/14* (2013.01); *C07D 405/12* (2013.01)

(58) Field of Classification Search
CPC .............................. C07D 213/74; A61K 31/44
See application file for complete search history.

(56) References Cited

FOREIGN PATENT DOCUMENTS

CN     111269215 A  *  6/2020

OTHER PUBLICATIONS

Machine translation of CN 111269215 A, 59 pages (2020).*
Allen and Roth, Annu. Rev. Pharmacol. Toxicol. 2011, 51, 117-144.
Wold et al., J. Med. Chem. 2019, 62, 88-127.
Zhou and Wild, Curr. Top. Med. Chem. 2019, 19, 1363-1364.
Overington et al., Nat. Rev. Drug Discov. 2006, 5, 993-996.
Lagerstrom and Schioth, Nat. Rev. Drug Discov. 2008, 7, 339-357.
Hauser et al., Nat. Rev. Drug Discov. 2017, 16, 829-842.
Roth et al., Nat. Chem. Biol. 2017, 13, 1143-1151.
Ye et al., ACS Chem. Neurosci. 2019, 10, 190-200.
Sawzdargo et al., Mol. Brain Res. 1999, 64, 193-198.
Komatsu et al., PLoS One 2014, 9, e90134.
Yang et al., bioRxiv 2018, 311563.
Lin et al., Nature 2020, 579, 152-157.
Martin et al., PLoS One 2015, 10, e0138463.
Setoh et al., J. Med. Chem. 2014, 57, 5226-5237.
Nishiyama et al., J. Pharmacol. Exp. Ther. 2017, 363, 253-264.
Xiong et al., WO2016176571 A1, Nov. 3, 2016.
Tokumaru et al., Bioorg. Med. Chem. 2017, 25, 3098-3115.
Nakahata et al., Bioorg. Med. Chem. 2018, 26, 1598-1608.
Meanwell, J. Med. Chem. 2011, 54, 2529-2591.
Meanwell, Top. Med. Chem. 2015, 9, 283-382.
Pennington and Moustakas, J. Med. Chem. 2017, 60, 3552-3579.
Cesta et al., Asian J. Org. Chem. 2019, 8, 1053-1057.
Sengmany et al., Tetrahedron 2015, 71, 4859-4867.
Loksha, J. Het. Chem. 2009, 46, 1296-1301.
Gray et al., Nat. Commun. 2018, 9, 674.
Besnard et al., Nature 2012, 492, 215-220.
Kalyaanamoorthy and Barakat, Med. Res. Rev. 2018, 38, 525-555.
Jones et al., Br. J. Pharmacol. 2011, 164, 1162-1194.
Dichter et al., J. Neurodev. Disord. 2012, 4, 19.
Komatsu, Int. J. Mol. Sci. 2015, 16, 14109-14121.
Grundmann et al., Nat. Commun. 2018, 9, 341.
Simmler et al., Br. J. Pharmacol. 2017, 174, 2716-2738.
Cortez et al., Behav. Brain Res. 2017, 322, 212-222.
Cunningham et al., ACS Chem. Neurosci. 2013, 4, 110-121.
Kenakin. Mol Pharmacol. Oct. 2017;92(4):414-424.

* cited by examiner

*Primary Examiner* — Deepak R Rao

(57) ABSTRACT

Embodiments are directed to novel GPR52 activators. In particular, a series of novel 1-(pyrimidin-4-yl)indoline-4-carboxamide analogs that have been identified as potent and selective GPR52 agonists. The optimized GPR52 agonist that, for example, can be used as a valuable pharmacological tool or a drug candidate for investigating the physiological and therapeutic potential of GPR52 activation for various human diseases.

4 Claims, 7 Drawing Sheets

Specification includes a Sequence Listing.

SEQUENCE LISTING

```
<160> NUMBER OF SEQ ID NOS: 2

<210> SEQ ID NO 1
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 1
gctaacagct gttccatcta agataccggt ggacgcacc                              39

<210> SEQ ID NO 2
<211> LENGTH: 39
<212> TYPE: DNA
<213> ORGANISM: Artificial Sequence
<220> FEATURE:
```

```
<223> OTHER INFORMATION: synthetic oligonucleotide

<400> SEQUENCE: 2
cgattgtcga caaggtagat tctatggcca cctgcgtgg                                    39
```

HETEROCYCLIC G-PROTEIN-COUPLED RECEPTOR 52 (GPR52) AGONISTS

PRIORITY PARAGRAPH

This Application claims priority to U.S. Provisional Patent Application Ser. No. 63/090,519 filed Oct. 12, 2020 which is incorporated herein by reference in its entirety.

STATEMENT REGARDING FEDERALLY FUNDED RESEARCH

This invention was made with government support under T32 DA 007287 and U18 DA052543 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference. The sequence listing that is contained in the file named "UTMBP0401US" which is 0.718 KB (as measured in Microsoft Windows®) and was created on Oct. 17, 2022.

BACKGROUND

G-protein-coupled receptors (GPCRs) are a superfamily of seven-transmembrane spanning receptor proteins, with over 800 members. GPCRs play critical roles in cellular communication and regulate a wide range of physiological and pathological processes.[1] To date, GPCRs have accounted for approximately 30% of all U.S Food and Drug Administration (FDA) approved drugs for the therapies of numerous human diseases including cancer, central nervous system (CNS) disorders, metabolic disorders, inflammation diseases, infection, immune diseases and others.[2-5] However, only a fraction of GPCRs are successfully targeted in drug development,[6] and roughly one third of the non-sensory GPCRs remain orphan receptors whose endogenous ligands and physiological functions are largely unknown. Despite the limited knowledge of these orphan GPCRs, their crucial roles in physiological signaling pathways and putative druggability make them attractive novel therapeutic targets.[2, 7-9]

GPR52 is an understudied brain orphan receptor selectively expressed in the striatum and cortex with the highest level of expression in the nucleus accumbens (NAc).[10, 11] The selective expression of GPR52 in the NAc and other striatal regions suggests an important function for this receptor in primary striatal neurons and broader corticostriatal circuitry.[12] Moreover, GPR52 is co-localized exclusively with dopamine D2 receptors in medium spiny neurons (MSNs) in the striatum, and has lesser expression in neurons of the medial prefrontal cortex.[11] Notably in transgenic mice, the overexpression of GPR52 significantly decreased methamphetamine-induced locomotion, while GPR52 knockout mice showed an anxiolytic-like phenotype.[11] Studies have indicated GPR52 couples to $G_{as/olf}$-G proteins to activate adenylyl cyclase and modulate 5'-cyclic adenosine monophosphate (cAMP) signaling and displays high levels of constitutive activity.[13, 14] Thus GPR52 signaling via cAMP could oppose activity of D2 signaling in the striatum while stimulating D1/N-methyl-D-aspartate (NMDA) function in the frontal cortex.[15] Therefore, GPR52 may serve as a promising novel target for psychiatric disorders[11] including schizophrenia,[16] and substance-use disorders (SUDs).[17]

To date, the natural ligand of GPR52 has not been elucidated, but several surrogate ligands have been reported.[15, 17-19] Most recently, Lin et al. found that the orthosteric ligand binding pocket of GPR52 (PDB codes: 6LI1 and 6LI2) was occupied by its extracellular loop 2 (ECL2).[13] They suggested that GPR52 was an unprecedented self-activating receptor and GPR52 ligands could function as allosteric agonists to control GPR52 self-activation.[13] Compound 1 (FIG. 1) is the first reported potent GPR52 agonist with half maximal effective concentration ($EC_{50}$) of about 30 nM, on the basis of their high-throughput screening (HTS) hits.[15] Particularly, compound 1 had excellent bioavailability (F=73%) and brain penetration (brain/plasma AUC ratio=0.94).[15] Additionally, compound 1 significantly inhibited rodent methamphetamine-induced hyperactivity at a dose of 3 mg/kg. However, compound 1 has some drawbacks including high lipophilicity/poor aqueous solubility which limit its application for further use.[19] Further modifications of compound 1 resulted in optimized compound 2 (FIG. 1) with slightly improved GPR52 potency ($EC_{50}$=21 nM, $E_{max}$=103%) and water solubility (21 μg/mL at pH 6.8) and similar activity to inhibit stimulant-induced hyperactivity.[19] Interestingly, the co-crystal structure of GPR52 and compound 2 (PDB code: 6LI0) was recently solved.[13] Compound 2 was found located in a small extracellular pocket of GPR52 surrounded by ECL2, transmembrane helix 1 (TM1), TM2 and TM7. The agonist formed multiple interactions with GPR52 including hydrogen bonds with residues Cys40, Glu191, Ile189, Asp188 in ECL2, π-π stacking with residue Phe300 of TM7 and hydrophobic contacts with residues Phe117, Thr303, Trp304 and Ile307. The elucidation of this GPR52 ligand-binding pocket is anticipated to facilitate further drug discovery of potent and selective GPR52 modulators.

Recently, Takeda reported another series of novel GPR52 agonists.[18] Among those GPR52 agonists, compound 3 (FIG. 1) was an effective agonist with good potency and efficacy ($EC_{50}$ of 75 nM and $E_{max}$ of 122%).[18] Animal model studies indicated that compound 3 inhibited MK-801-induced hyperactivity and improved memory recognition.[16] Likewise, Arena Pharmaceuticals patented and disclosed a series of 1-heteroaryl-indoline-4-carboxamines as GPR52 agonists, among which, compound 4 displayed potent GPR52 agonist activity.[17]

There remains a need for additional compounds that bind and target GPR52.

SUMMARY

GPR52 is emerging as a promising neurotherapeutic target of interest for the treatment of schizophrenia and substance abuse disorders (SUDs), and the reported agonists as well as the recently disclosed co-crystal structural analysis serve as new starting points to facilitate further drug discovery of novel GPR52 ligands as pharmacological tools and potential drug candidates for preclinical and clinical development. To provide additional compounds, the inventors used compound 4 as a starting point for medicinal chemistry efforts due to its amenability to chemical synthesis, physical-chemical properties, and lack of previously known structure-activity relationship (SAR).

Described herein is the chemical optimization and pharmacological evaluation of novel GPR52 activators. Systematic SAR studies around three pharmacological moieties of compound 4 have been explored. A series of novel 1-(pyrimidin-4-yl)indoline-4-carboxamide analogs have been identified as potent and selective GPR52 agonists with nanomolar range potency, and varied levels of improved efficacy. This work culminated in discovery of compounds with a new pyrimidine core scaffold that is an orally bioavailable, brain penetrant, potent and selective GPR52 agonist, which dose-dependently suppresses amphetamine-evoked hyperactivity, suggesting a therapeutic potential for neuropsychiatric diseases.

Several more potent and efficacious GPR52 agonists (12c, 23a, 23d, 23e, 23f and 23h) were identified with nanomolar range potency based on a systematic structure-activity relationship exploration. Further studies of the representative compound 12c indicate enhanced efficacy, excellent target selectivity and pharmacokinetic properties including good brain permeability. In vivo proof-of-concept investigations revealed that 12c displayed antipsychotic-like activity by significantly inhibiting amphetamine-induced hyperlocomotor behavior in mice. Collectively, these findings have resulted in an optimized GPR52 agonist that, for example, can be used as a valuable pharmacological tool for investigating the physiological and therapeutic potential of GPR52 activation.

GPCRs and Beta-arrestin Signaling. GPCRs desensitize via a common mechanism involving β-arrestin binding which prevents G protein-coupling (and thus G protein activation). See Louis M. Luttrell et. Al., "The role of β-arrestins in the termination and transduction of G-protein-coupled receptor signals"; J Cell Sci. 2002 Feb. 1; 115(Pt 3):455-65. In addition to their well-established role in GPCR desensitization, β-arrestins may also enable GPCR-mediated "arrestinergic" signaling by functioning as scaffolds for downstream effector molecules such as the extracellular regulated kinases (ERKs). See Reiter E, et. Al, "Molecular mechanism of beta-arrestin-biased agonism at seven-transmembrane receptors", Annual review of pharmacology and toxicology. 2012; 52:179-97; and Allen J A, et al. "Discovery of beta-arrestin-biased dopamine D2 ligands for probing signal transduction pathways essential for antipsychotic efficacy," Proceedings of the National Academy of Sciences of the United States of America. 2011; 108(45): 18488-93. Agonist ligands which activate GPCRs for G protein signaling but have reduced or absent activity for recruitment of β-arrestins, are referred to as biased agonists. Violin J D, et al. "Beta-arrestin-biased ligands at seven-transmembrane receptors," Trends Pharmacol Sci. 2007 August; 28(8):416-22.

Aspects of the present invention relate to methods for treating or preventing a psychotic disorder in an individual, treating or preventing a movement disorder in an individual, treating or preventing a substance-use disorder, including an addictive disorder to stimulants such as amphetamines or cocaine, where administering to the individual a therapeutically effective amount of a compound, a pharmaceutical product or a pharmaceutical composition of the present invention.

Certain embodiments are directed to a compound according to Formula I or a pharmaceutically acceptable salt thereof, wherein:

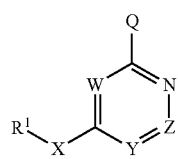

Formula I wherein: $R^1$ is aryl or heteroaryl, wherein each ring is optionally substituted with one or more groups selected independently from H, alkyl, cycloalkyl, alkenyl, aryl, heteroaryl, benzyl, alkoxy, halogen, cyan, nitro, amino, hydroxyl, $CF_3$ or —$OCF_3$, wherein the alkyl is optionally substituted with one or more chosen substituents chosen from hydroxyl, cyan, amino, or halogen; X is independently chosen from O, S, NH or $CT^1T^2$, where $T^1$ is independently chosen from H, OH, alkyl or F, and $T^2$ is independently chosen from H or F; W is $CP^1$ or N, where $P^1$ is independently chosen from H, alkyl, alkoxy, halogen, cyan, amino, hydroxyl, $NO_2$, $CF_3$ or —$OCF_3$; Y is $CP^1$ or N, where $P^1$ is independently chosen from H, alkyl, alkoxy, halogen, cyan, amino, hydroxyl, $NO_2$, $CF_3$ or —$OCF_3$; Z is $CP^1$ or N, where $P^1$ is independently chosen from: H, alkyl, alkoxy, halogen, cyan, amino, hydroxyl, $NO_2$, $CF_3$ or —$OCF_3$; Q is

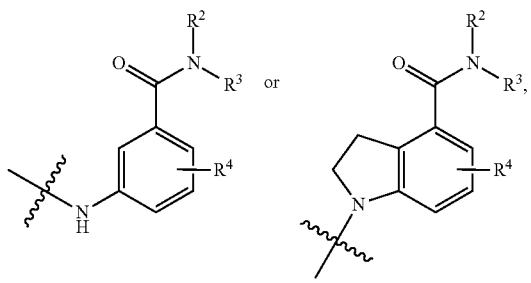

where $R^2$ is H; and $R^3$ is selected from H, alkyl, heteroaryl, heterocyclyl, heterocylclyl-alkyl, and hydroxyl-alkyl; and each group is optionally substituted with one or more groups selected independently from alkyl, cycloalkyl, alkenyl, aryl, heteroaryl, benzyl, alkoxy, halogen, cyan, nitro, amino, hydroxyl, $CF_3$ or —$OCF_3$; or $R^2$ and $R^3$ together form a 4-12 membered cycloalkyl ring, and the -12 membered cycloalkyl is optionally substituted with one or more groups selected independently from alkyl, cycloalkyl, alkenyl, aryl, heteroaryl, benzyl, alkoxy, halogen, cyan, nitro, amino, hydroxyl, $CF_3$ or —$OCF_3$; $R^4$ is independently chosen from H, alkyl, alkoxy, halogen, cyan, amino, hydroxyl, nitro, $CF_3$ or —$OCF_3$. Provided that when Q is

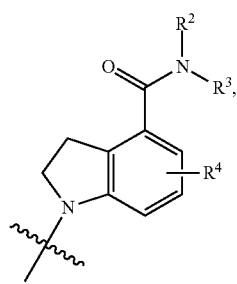

then at least one of W, Y, Z is N. In certain aspects, X is $CH_2$; W, Y, and Z are CH; and Q is

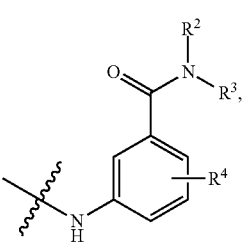

forming
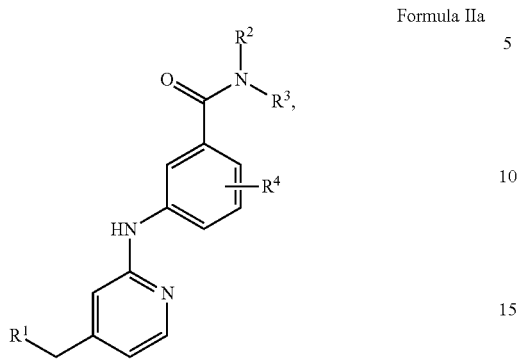
Formula IIa
wherein R1, R2, R3, and R4 are as described above.
In certain aspect, a compound is:
| Compound | Structure |
|---|---|
| PW0671 | 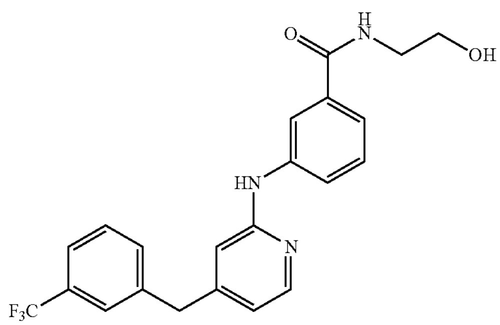 [SMILES: O=C(NCCO)c1cccc(Nc2cc(Cc3cccc(C(F)(F)F)c3)ccn2)c1] |
| PW0715 | 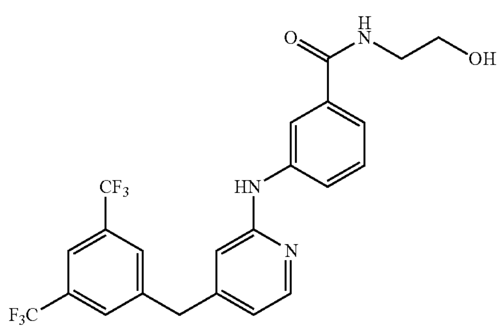 [SMILES: O=C(NCCO)c1cccc(Nc2cc(Cc3cc(C(F)(F)F)cc(C(F)(F)F)c3)ccn2)c1] |
| PW0724 | 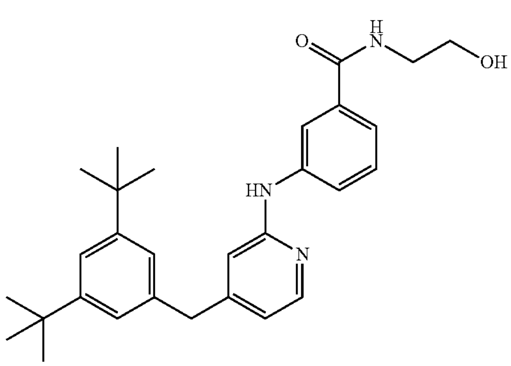 [SMILES: CC(C)(C)c1cc(Cc2ccnc(Nc3cccc(C(=O)NCCO)c3)c2)cc(C(C)(C)C)c1] |

-continued

| Compound | Structure |
|---|---|
| PW0723 | 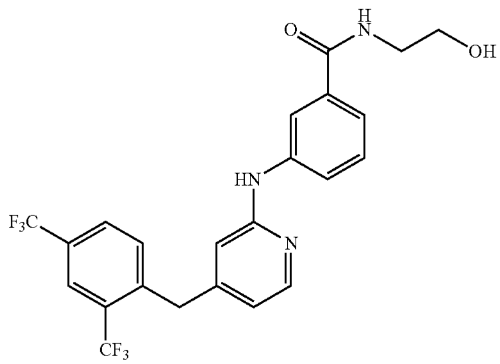 [SMILES: O=C(NCCO)c1cccc(Nc2cc(Cc3ccc(C(F)(F)F)cc3C(F)(F)F)ccn2)c1] |
| PW0673 | 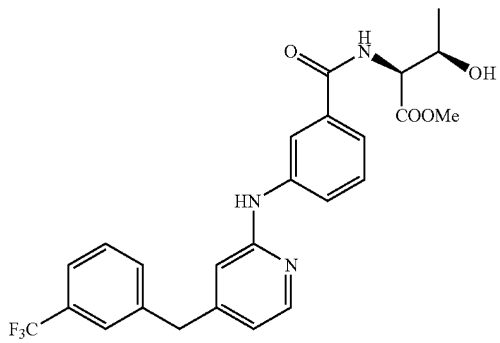 [SMILES: COC(=O)[C@@H](NC(=O)c1cccc(Nc2cc(Cc3cccc(C(F)(F)F)c3)ccn2)c1)[C@@H](C)O] |
| PW0674 | 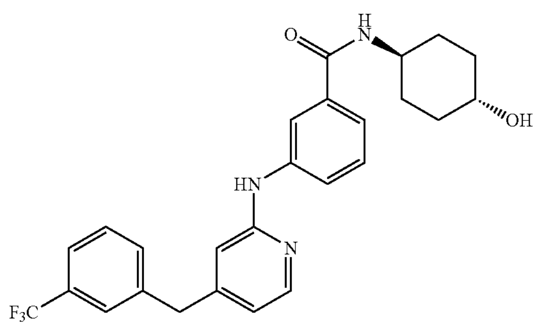 [SMILES: O=C(N[C@H]1CC[C@H](O)CC1)c1cccc(Nc2cc(Cc3cccc(C(F)(F)F)c3)ccn2)c1] |
| PW0675 | 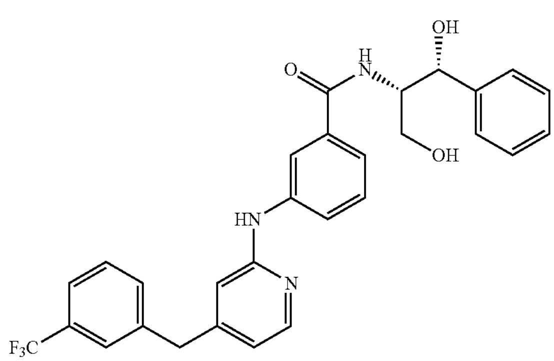 [SMILES: O=C(N[C@@H](CO)[C@H](O)c1ccccc1)c1cccc(Nc2cc(Cc3cccc(C(F)(F)F)c3)ccn2)c1] |

-continued
| Compound | Structure |
|---|---|
| PW0676 | 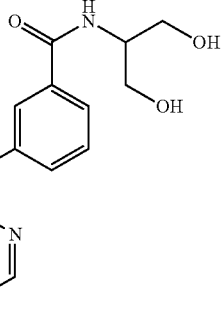 |
| PW0677 | 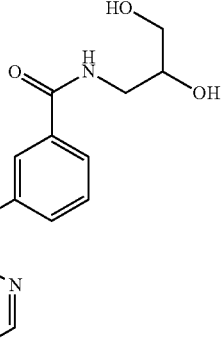 |
| PW0689 | 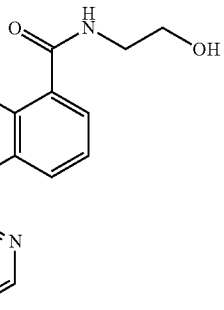 |
| PW0693 | 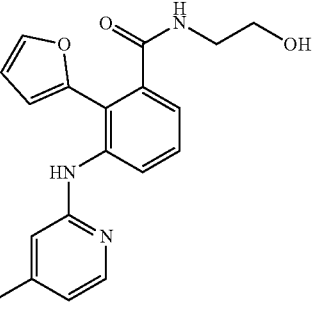 |

-continued
| Compound | Structure |
|---|---|
| PW0698 | 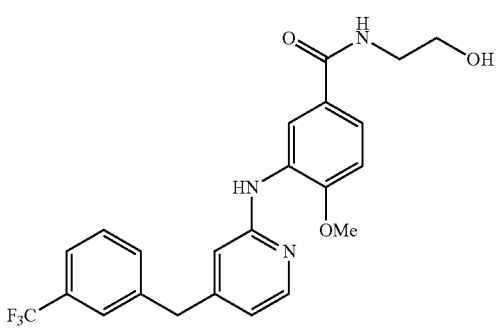 |
| PW0729 | 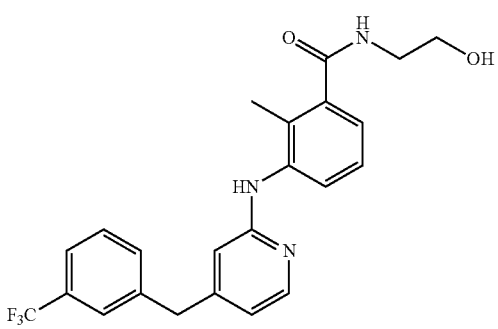 |
| PW0730 | 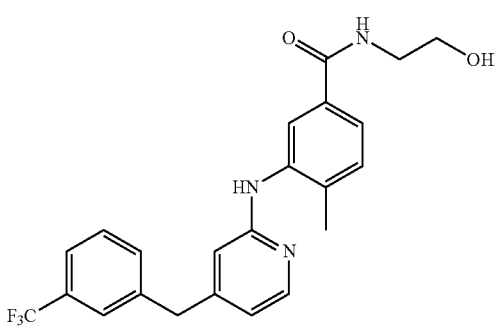 [SMILES: Cc1ccc(C(=O)NCCO)cc1Nc1cc(Cc2cccc(C(F)(F)F)c2)ccn1] |
| PW0823 | 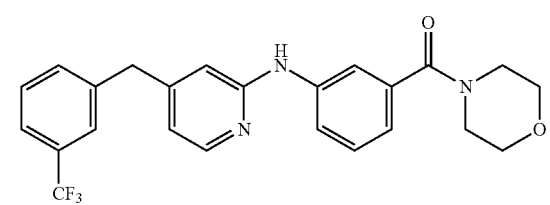 |
| PW0824 | 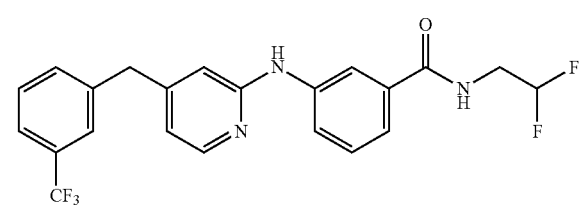 [SMILES: O=C(NCC(F)F)c1cccc(Nc2cc(Cc3cccc(C(F)(F)F)c3)ccn2)c1] |

-continued
| Compound | Structure |
|---|---|
| PW0825 | 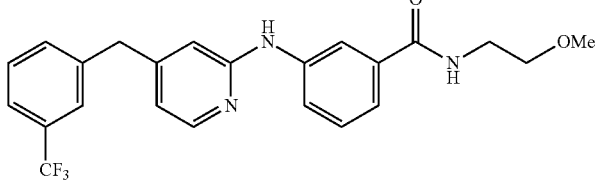<br>Chemical Formula: $C_{23}H_{22}F_3N_3O_2$<br>Molecular Weight: 429.4432 |
| PW0826 | 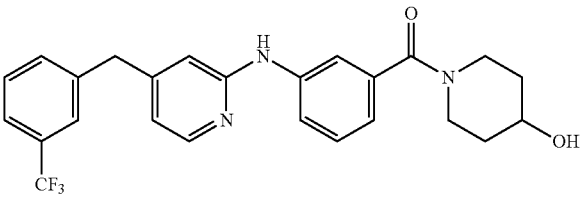 [SMILES: O=C(c1cccc(Nc2cc(Cc3cccc(C(F)(F)F)c3)ccn2)c1)N1CCC(O)CC1] |
| PW0831 | 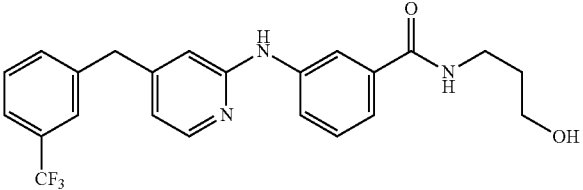 [SMILES: O=C(NCCCO)c1cccc(Nc2cc(Cc3cccc(C(F)(F)F)c3)ccn2)c1] |
| PW0832 | 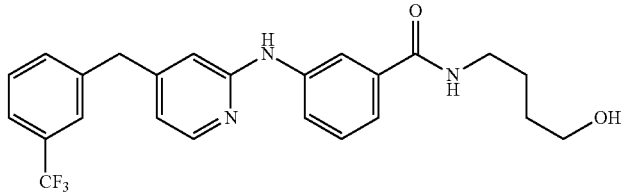 [SMILES: O=C(NCCCCO)c1cccc(Nc2cc(Cc3cccc(C(F)(F)F)c3)ccn2)c1] |
| PW0839 | 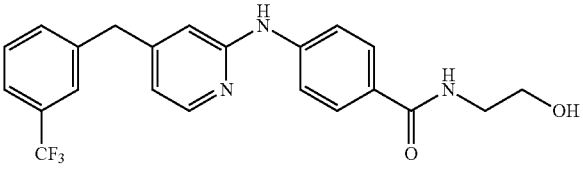 |
| PW0840 | 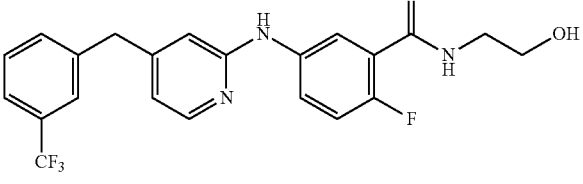 |
| PW0841 | 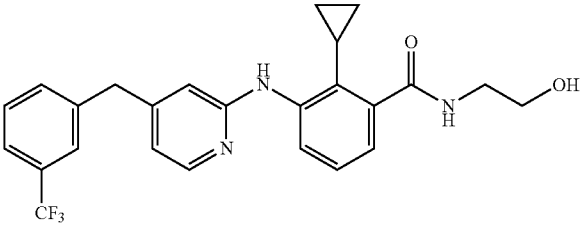 [SMILES: O=C(NCCO)c1cccc(Nc2cc(Cc3cccc(C(F)(F)F)c3)ccn2)c1C1CC1] |

-continued

| Compound | Structure |
| --- | --- |
| PW0842 | 3-[[4-[(3-trifluoromethylphenyl)methyl]pyridin-2-yl]amino]-2-methoxy-N-(2-hydroxyethyl)benzamide |
| PW0861 | 3-[[4-[(3,5-bis(trifluoromethyl)phenyl)methyl]pyridin-2-yl]amino]-2-methyl-N-(2-hydroxyethyl)benzamide |
| PW0862 | 3-[[4-[(2,4-bis(trifluoromethyl)phenyl)methyl]pyridin-2-yl]amino]-2-methyl-N-(2-hydroxyethyl)benzamide |
| PW0863 | 3-[[4-[(4-trifluoromethylphenyl)methyl]pyridin-2-yl]amino]-2-methyl-N-(2-hydroxyethyl)benzamide |
| PW0864 | 3-[[4-[(2-trifluoromethylphenyl)methyl]pyridin-2-yl]amino]-2-methyl-N-(2-hydroxyethyl)benzamide |
| PW0865 | 3-[[4-[(3-chloro-5-fluorophenyl)methyl]pyridin-2-yl]amino]-2-methyl-N-(2-hydroxyethyl)benzamide |
| PW0866 | 3-[[4-[(3-methoxyphenyl)methyl]pyridin-2-yl]amino]-2-methyl-N-(2-hydroxyethyl)benzamide |
| PW0867 | 3-[[4-(phenylmethyl)pyridin-2-yl]amino]-2-methyl-N-(2-hydroxyethyl)benzamide |

-continued
| Compound | Structure |
|---|---|
| PW0868 | 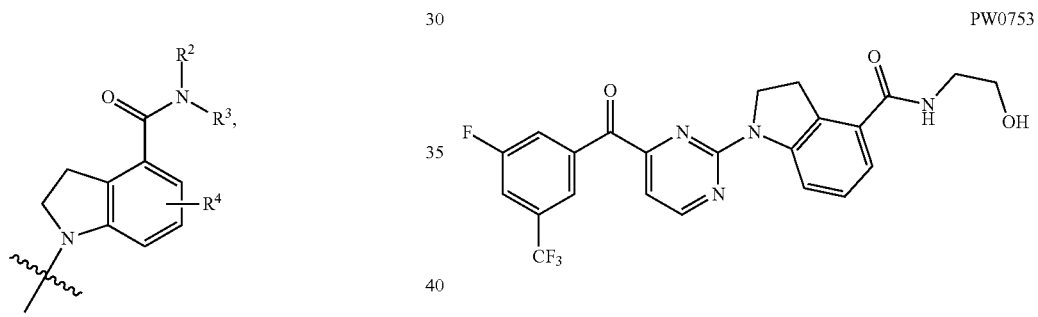 |
| PW0869 | 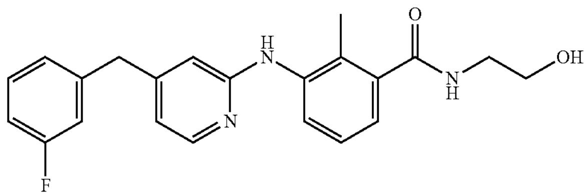 [SMILES: Cc1c(Nc2cc(Cc3cccc(F)c3)ccn2)cccc1C(=O)NCCO] |
| PW0870 | 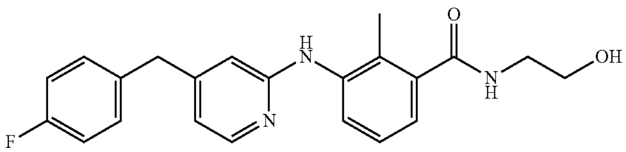 [SMILES: Cc1c(Nc2cc(Cc3ccc(F)cc3)ccn2)cccc1C(=O)NCCO] |
In certain aspects are directed to a compound of Formula 1 where X is CH$_2$; W, and Z are CH; Y is N; and Q is
where R$^4$ is H, forming
Formula IIb, wherein R$^1$, R$^2$, and R$^3$ are as described above.
In certain aspects a compound is:
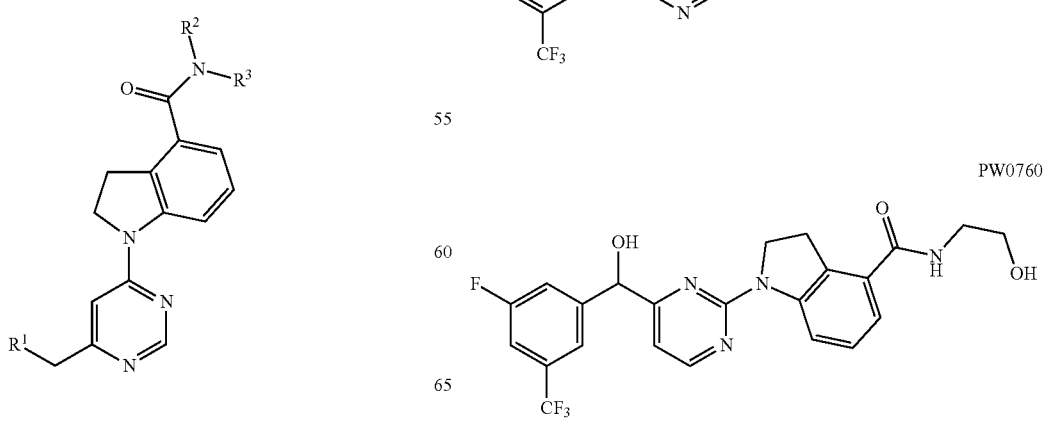

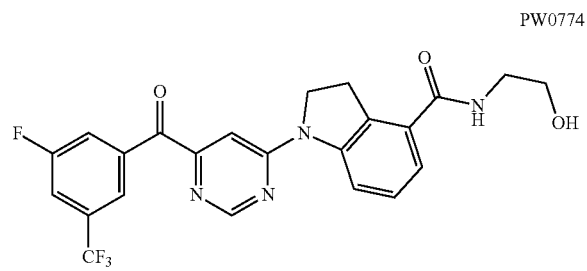
PW0774
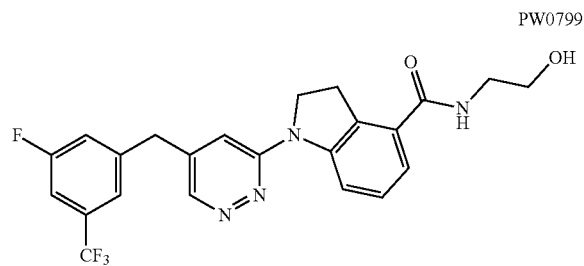
PW0799
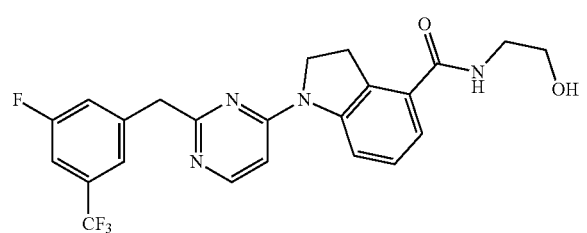
PW0776
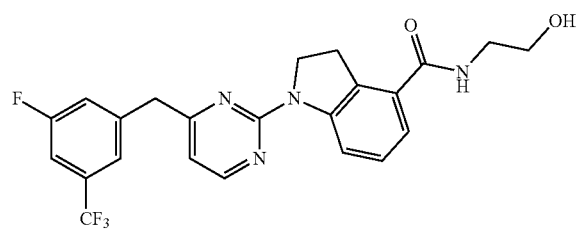
PW0807
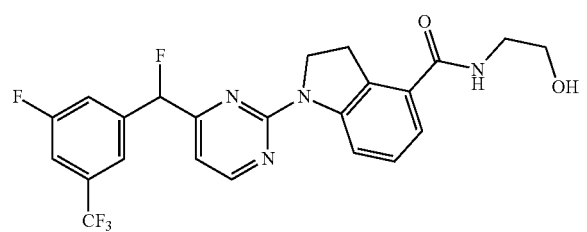
PW0781
Chemical Formula: C$_{23}$H$_{19}$F$_5$N$_4$O$_2$
Exact Mass: 478.1428
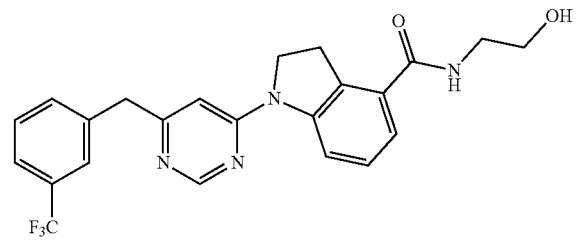
PW0860
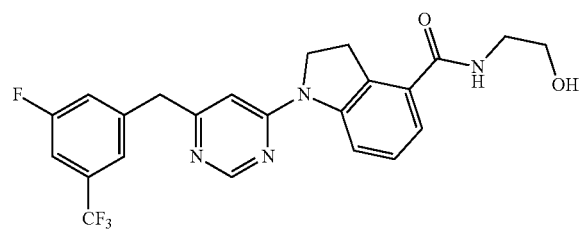
PW0787
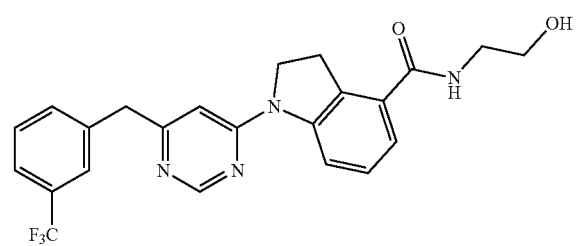
PW0873
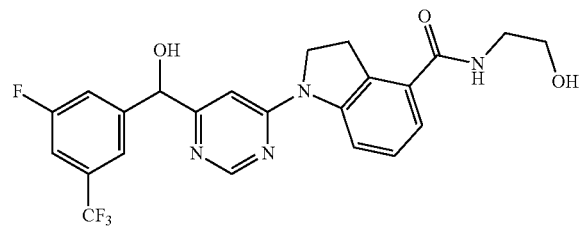
PW0788
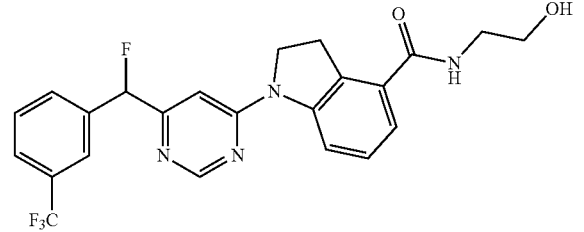
PW0875
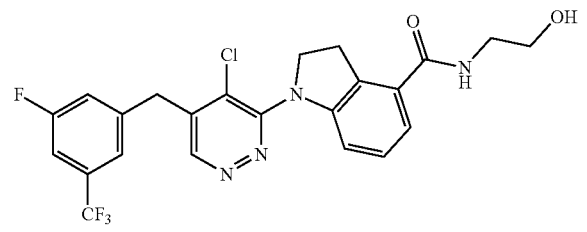
PW0796
PW0878

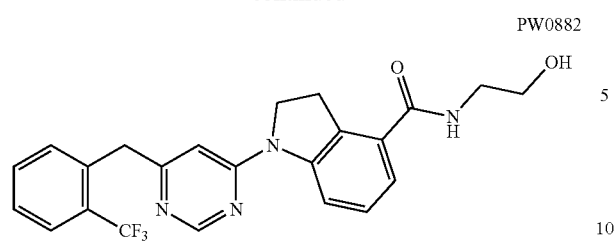
PW0882
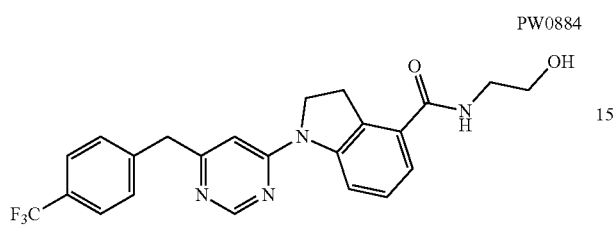
PW0884
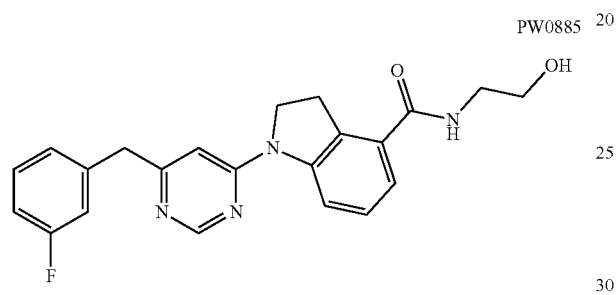
PW0885
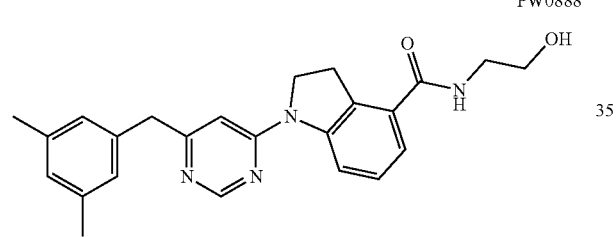
PW0888
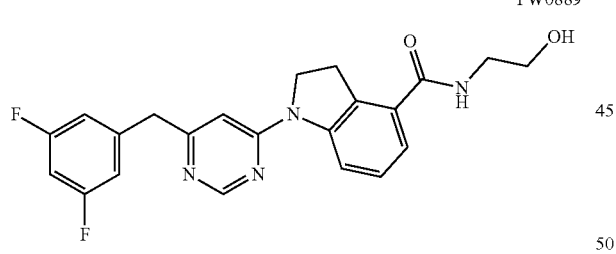
PW0889
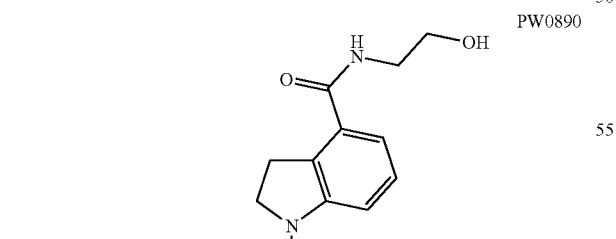
PW0890
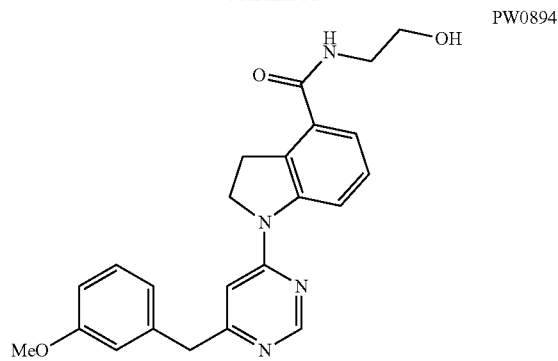
PW0894
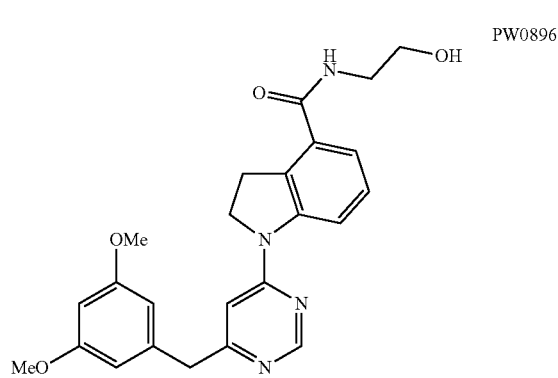
PW0896
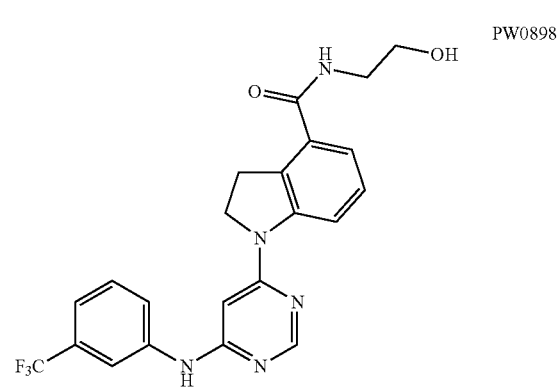
PW0898
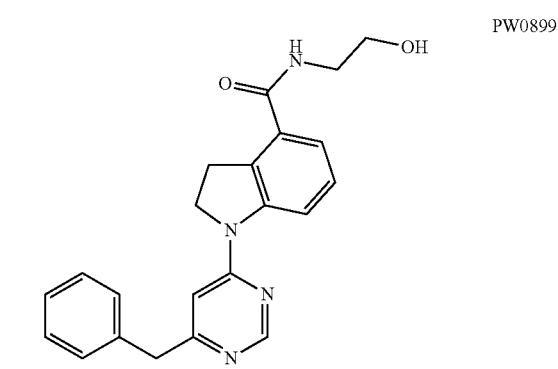
PW0899

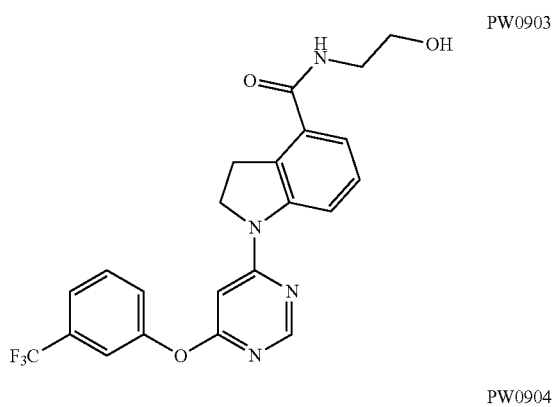
PW0903
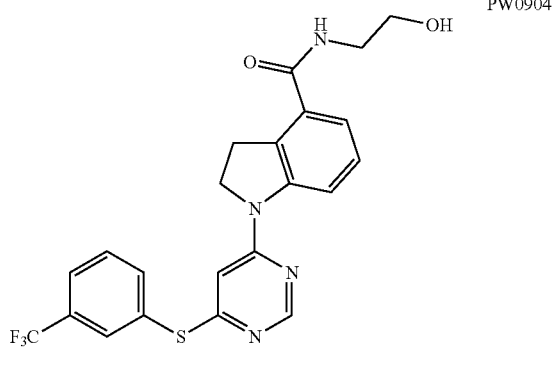
PW0904
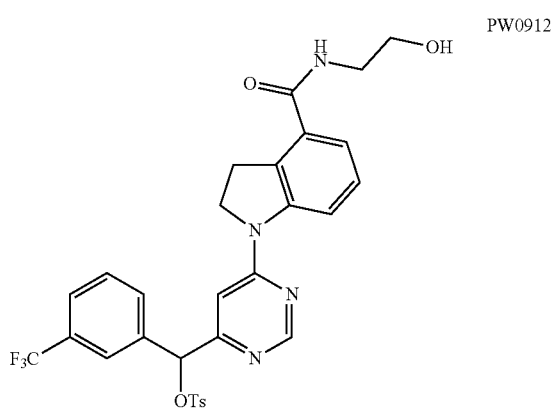
PW0912
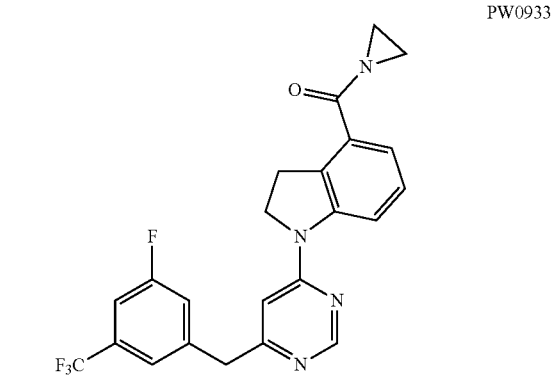
PW0933
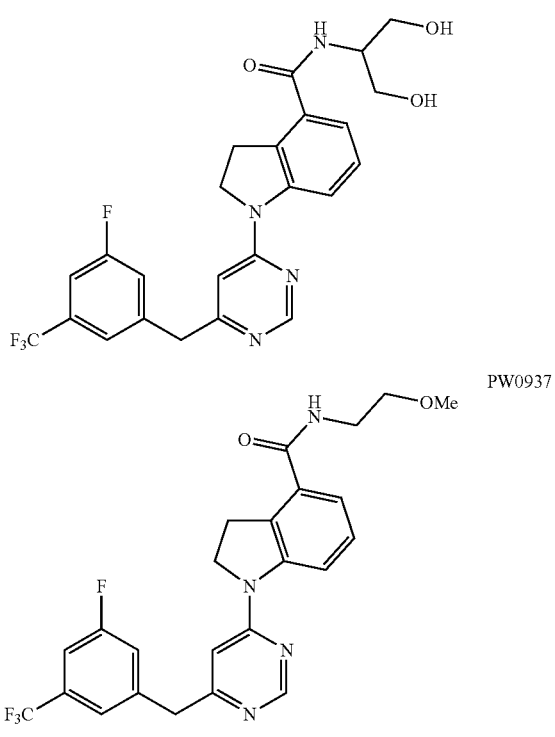
PW0936
PW0937
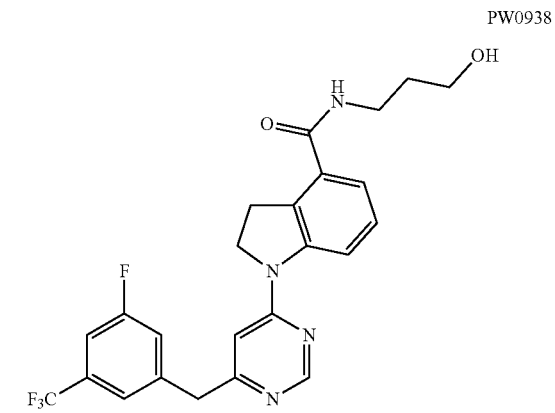
PW0938
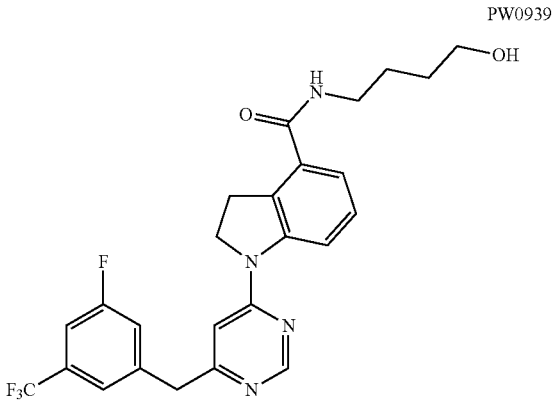
PW0939

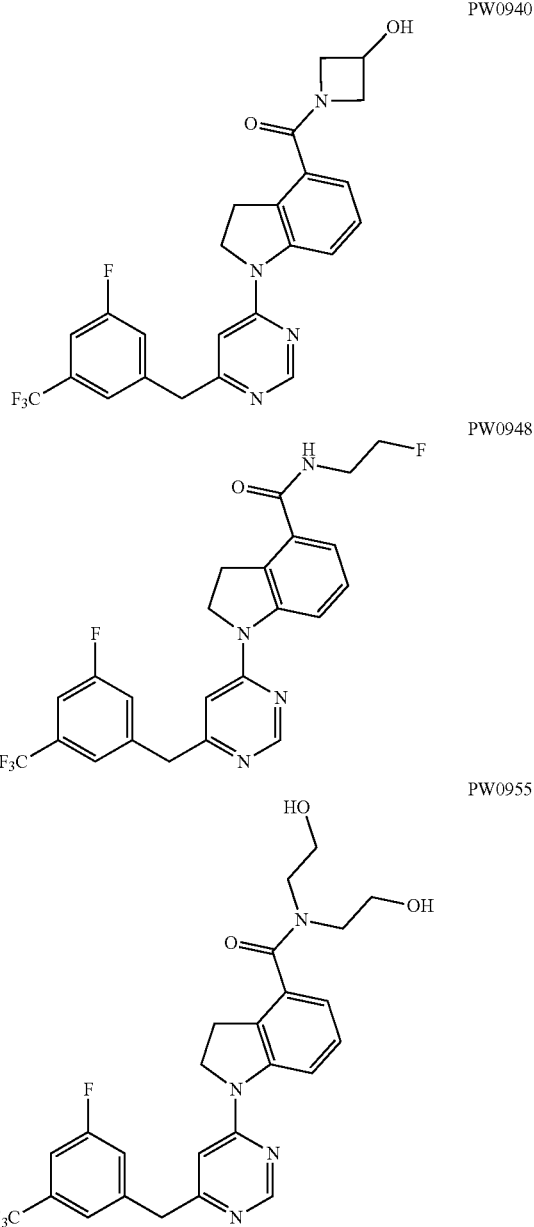

In some embodiments, a compound according to Formula I or a pharmaceutically acceptable salt thereof, that is a GPR52 agonist for G protein cAMP signaling but with reduced (β-arrestin recruitment activity.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

I. Compound Design

Figure 1:
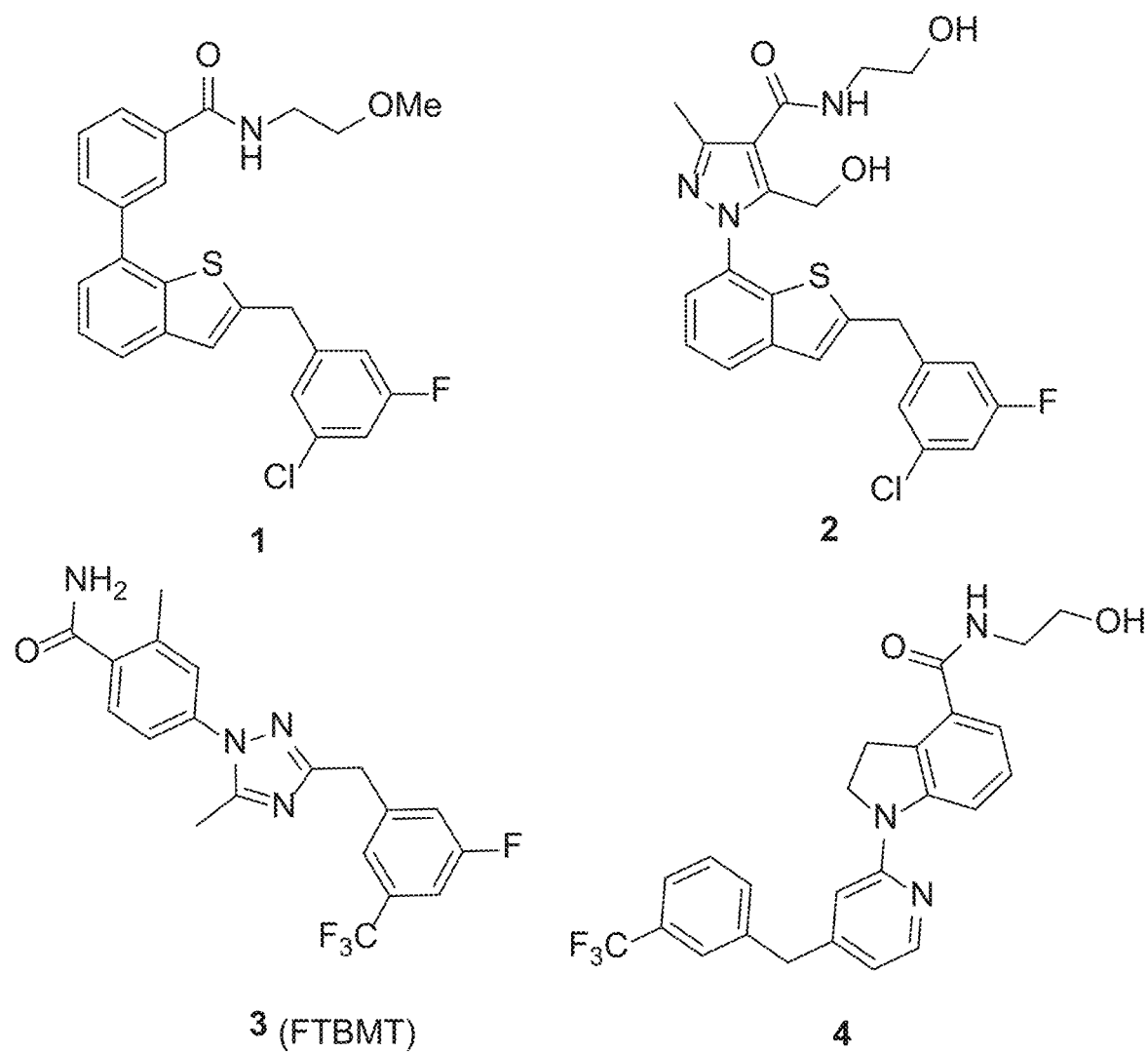
FIG. 1. Structures of representative reported GPR52 agonists.
Figure 2:
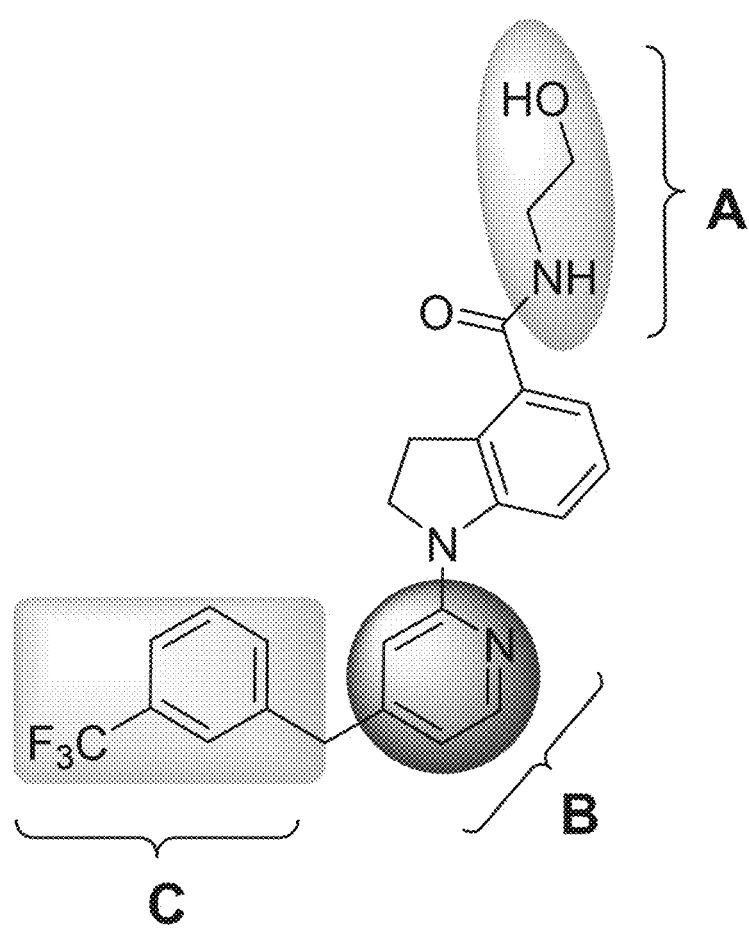
FIG. 2. Proposed structural modifications of three pharmacophores (A, B and C) based on advanced chemical lead 4 for SAR exploration to understand the key interactions of agonist with the receptor GPR52 and to identify newer ligands.

One of the drawbacks of previously reported GPR52 agonists is the poor aqueous solubility, limiting their use as pharmacological tools or potential drug candidates. The replacement of a CH group with an N atom in aromatic and heteroaromatic rings of the pharmacophore could improve its physicochemical properties for better in vivo pharmacokinetic (PK) properties.[20-22] Additionally, compared to the CH group, the N atom has an extra unshared electron pair which could form hydrogen bonds to potentially improve binding affinity. On this basis, the inventors contemplated that an extra N atom in the core heteroaromatic ring B of lead compound 4 could improve its potency as well as physicochemical properties. Therefore, the inventors first altered moiety B (FIG. 2) by insertion of a nitrogen atom in pyridine ring of compound 4 as the starting point to systematically pursue SAR studies. Next, various moieties were substituted onto the aromatic ring of moiety C (FIG. 2). Then the methylene linker between moieties B and C was also investigated. Finally, the inventors interrogated substituents on moiety A (FIG. 2) of compound 4 by replacement of the aminoethanol with various side chains to understand the critical ligand-receptor interactions.

Chemistry. The synthetic procedures of these newly synthesized GPR52 agonists are depicted in Schemes 1-7. As outlined in Scheme 1, the intermediate 6 was prepared by reduction of the starting material 5 with triethylsilane and trifluoroacetic acid.[23] Intermediates 8a-8c were generated by reaction of compound 6 with commercially available compounds 7a-7c in the presence of Et$_3$N in yields of 63%-67%.[24] The intermediates 10a-10c were produced via nucleophilic substitution of compounds 8a-8c with commercially available 2-(3-fluoro-5-(trifluoromethyl)phenyl)acetonitrile (9a).[25] Refluxing of intermediates 10a-10c in the HCl/AcOH/H$_2$O mixed solvent system led to key intermediates 11a-11c in excellent yields.[25] Coupling of the intermediates 11a-11c with the aminoethanol produced compounds 12a-12c resulted in good yields (73%-83%).

Scheme 1.
Synthetic Routes of Compounds 12a-12c[a]

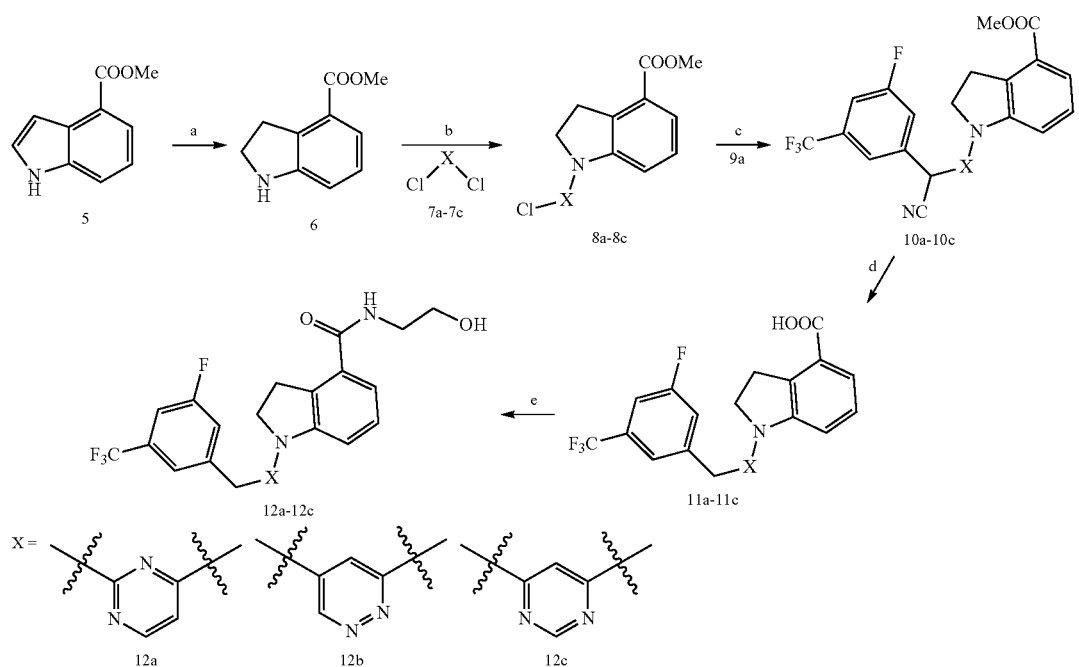

[a]Reagents and conditions: (a) CF$_3$COOH, Et$_3$SiH, CH$_2$Cl$_2$, overnight, 89%. (b) Et$_3$N, EtOH, rt, overnight, 63%-67%. (c) 2-(3-Fluoro-5-(trifluoromethyl)phenyl)acetonitrile (9a), NaH, DMF, 0° C. to rt, 2 h, 53%-66%. (d) con. HCl/AcOH/H$_2$O, reflux, overnight, 91%-93%. (e) NH$_2$CH$_2$CH$_2$OH, EDCI, DMAP, DMF, rt, overnight, 73%-83%.

As outlined in Scheme 2, the intermediate 13 was obtained by reaction of compound 9a with 7a in the presence of NaH. Refluxing of intermediate 13 in the HCl/AcOH/H$_2$O solvent system, followed by chlorination with phosphorus oxychloride produced compound 14. Compound 15 was prepared via palladium catalyzed C—N coupling reaction of 14 with 6 in a yield of 56%. Hydrolysis of intermediate 15 generated the key intermediate acid 16. Further, condensation of compound 16 with aminoethanol afforded compound 12d following the same procedure as that of preparing compound 12a.

Scheme 2.
Synthetic Routes of Compound 12d[a]

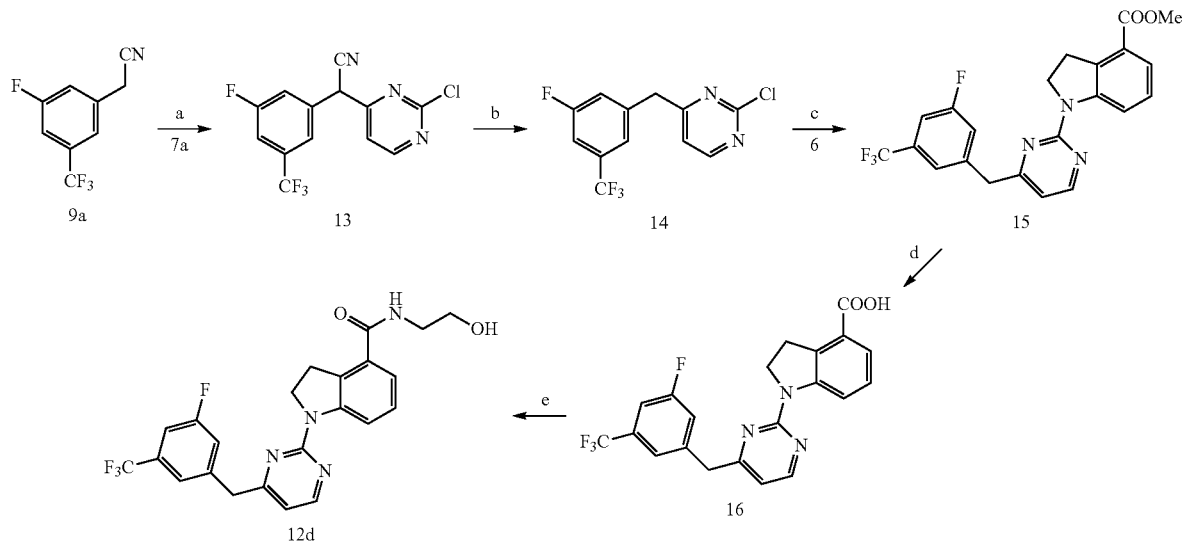

[a]Reagents and conditions: (a) NaH, DMF, 0° C. to rt. 2 h 73%. (b) (1) con. HCl/AcOH/H$_2$O, reflux, overnight; (2) POCl$_3$, reflux, 3 h, 51% for two steps. (c) 6, Pd(OAc)$_2$, XantPhos, Cs$_2$CO$_3$, 1-4-dioxane, 100° C., overnight, 56%. (d) (1) 2 N NaOH, MeOH, reflux, 1 h; (2) 2 N HCl, rt, 95%. (e) NH$_2$CH$_2$CH$_2$OH, EDCI, DMAP, DMF, rt, overnight, 83%.

As outlined in Scheme 3, with starting material 9a and compounds 7d[26] and 7e[26], the intermediates 17a and 17b were obtained following the similar synthetic procedure to that of preparing compound 13, respectively. Removing the cyano and the tetrahydro-2H-pyran protection groups of 17a and 17b at the same time led to compounds 18a and 18b in the HCl/AcOH/H$_2$O solvent system. Compound 18a and 18b were converted into compounds 19a and 19b by a standard chlorination reaction. The key intermediates 20a and 20b were synthesized by C—N coupling reaction of intermediates 19a and 19b with compound 6, respectively, under the palladium-catalyzed conditions. The acids 21a and 21b were prepared by hydrolysis of intermediates 20a and 20b. Compounds 12e and 12f were synthesized following the similar procedure to that of preparing 12a by coupling 21a and 21b with aminoethanol, respectively.

Scheme 3.
Synthetic Routes of Compounds 12e and 12f[a]

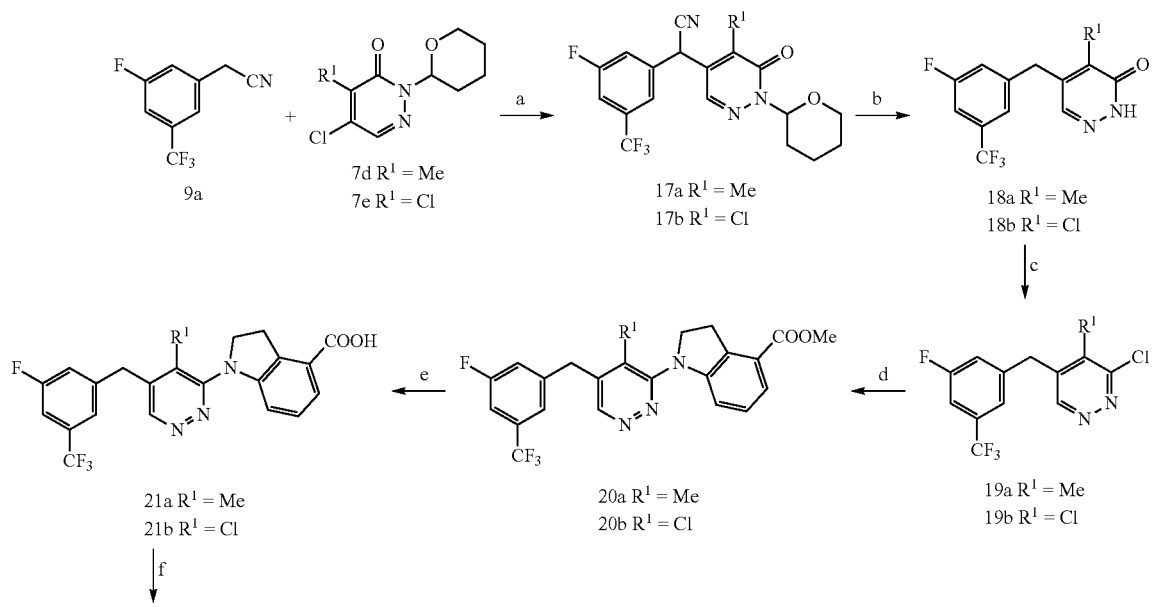

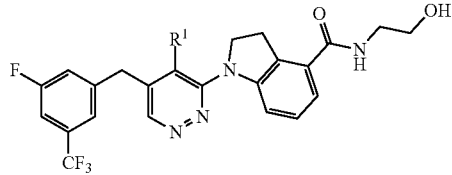

12e R$^1$ = Me
12f R$^1$ = Cl $^a$Reagents and conditions: (a) NaH, DMF, 0° C. to rt. 2 h, 36% for 17a, 63% for 17b. (b) HCl, AcOH, H$_2$O, 120° C., overnight, 78% for 18a, 83% for 18b. (c) POCl$_3$, 120° C., 12 h, 83% for 19a, 80% for 19b. (d) 6, Pd(OAc)$_2$, XantPhos, Cs$_2$CO$_3$, 1-4-dioxnae, 100° C., overnight, 64% for 20a, 60% for 20b. (e) (i) 2 N NaOH, MeOH, reflux, 1 h; (ii) 2 N HCl, rt, 92% for 21a, 90% for 21b. (f) NH$_2$CH$_2$CH$_2$OH, EDCI, DMAP, DMF, rt, overnight, 79% for 12e, 59%.

Compounds 23a-23k were synthesized following the same procedures for preparing 12a from various commercially available substituted 2-phenylacetonitriles (9b-9l) (Scheme 4). As outlined in Scheme 5, the intermediate 24a was obtained by reaction of compound 9a with compound 7a in the presence of NaH, followed by oxidation of the cyano group, and then coupling with compound 6. Compounds 24b and 24c were synthesized via reaction of compound 9a and 9b with compound 8c, respectively, following similar processes to the synthesis of compound 24a. Hydrolysis of esters 24a-24c followed by condensation with aminoethanol provided compounds 25a-25c in yields of 33%-63% over two steps. Treatment of 25a-25c with NaBH$_4$ as the reduction agent afforded compounds 25d-25f, accordingly. The ester intermediates 24a-24c were converted into intermediates 26a-26c by a reduction reaction, and then a hydrolysis reaction. Fluoridation of the acid intermediates 26a-26c by using diethylaminosulfur trifluoride, followed by hydrolysis reactions led to acid compounds 27a-27c. Compounds 25g-25i were produced following the same procedure as that of preparing 12a from compounds 27a-27c.

Scheme 4.
Synthetic Routes of Compounds 23a-23k$^a$

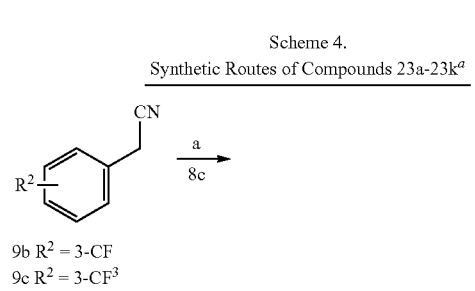

9b R$^2$ = 3-CF
9c R$^2$ = 3-CF$^3$
9d R$^2$ = 4-CF$^3$
9e R$^2$ = 3-Me$^3$
9f R$^2$ = 3-F
9g R$^2$ = 3,5-di-Me
9h R$^2$ = 3,5-di-F
9i R$^2$ = 3-OCF
9j R$^2$ = 3-OMe$^3$
9k R$^2$ = 3,5-di-OMe
9l R$^2$ = H

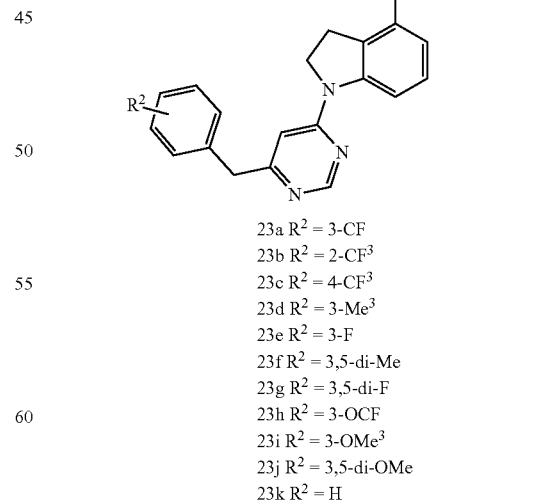

22a R$^2$ = 3-CF
22b R$^2$ = 2-CF$^3$
22c R$^2$ = 4-CF$^3$
22d R$^2$ = 3-Me$^3$
22e R$^2$ = 3-F
22f R$^2$ = 3,5-di-Me
22g R$^2$ = 3,5-di-F
22h R$^2$ = 3-OCF
22i R$^2$ = 3-OMe$^3$
22j R$^2$ = 3,5-di-OMe
22k R$^2$ = H

23a R$^2$ = 3-CF
23b R$^2$ = 2-CF$^3$
23c R$^2$ = 4-CF$^3$
23d R$^2$ = 3-Me$^3$
23e R$^2$ = 3-F
23f R$^2$ = 3,5-di-Me
23g R$^2$ = 3,5-di-F
23h R$^2$ = 3-OCF
23i R$^2$ = 3-OMe$^3$
23j R$^2$ = 3,5-di-OMe
23k R$^2$ = H $^a$Reagents and conditions: (a) (1) NaH, DMF, 0° C. to rt, 2 h; (2) con. HCl/AcOH/H$_2$O, reflux, overnight, 54%-90% for two steps. (b) NH$_2$CH$_2$CH$_2$OH, EDCI, DMAP, DMF, rt, overnight, 29%-83%.

Scheme 5.
Synthetic Routes of Compounds 25a-25i[a]

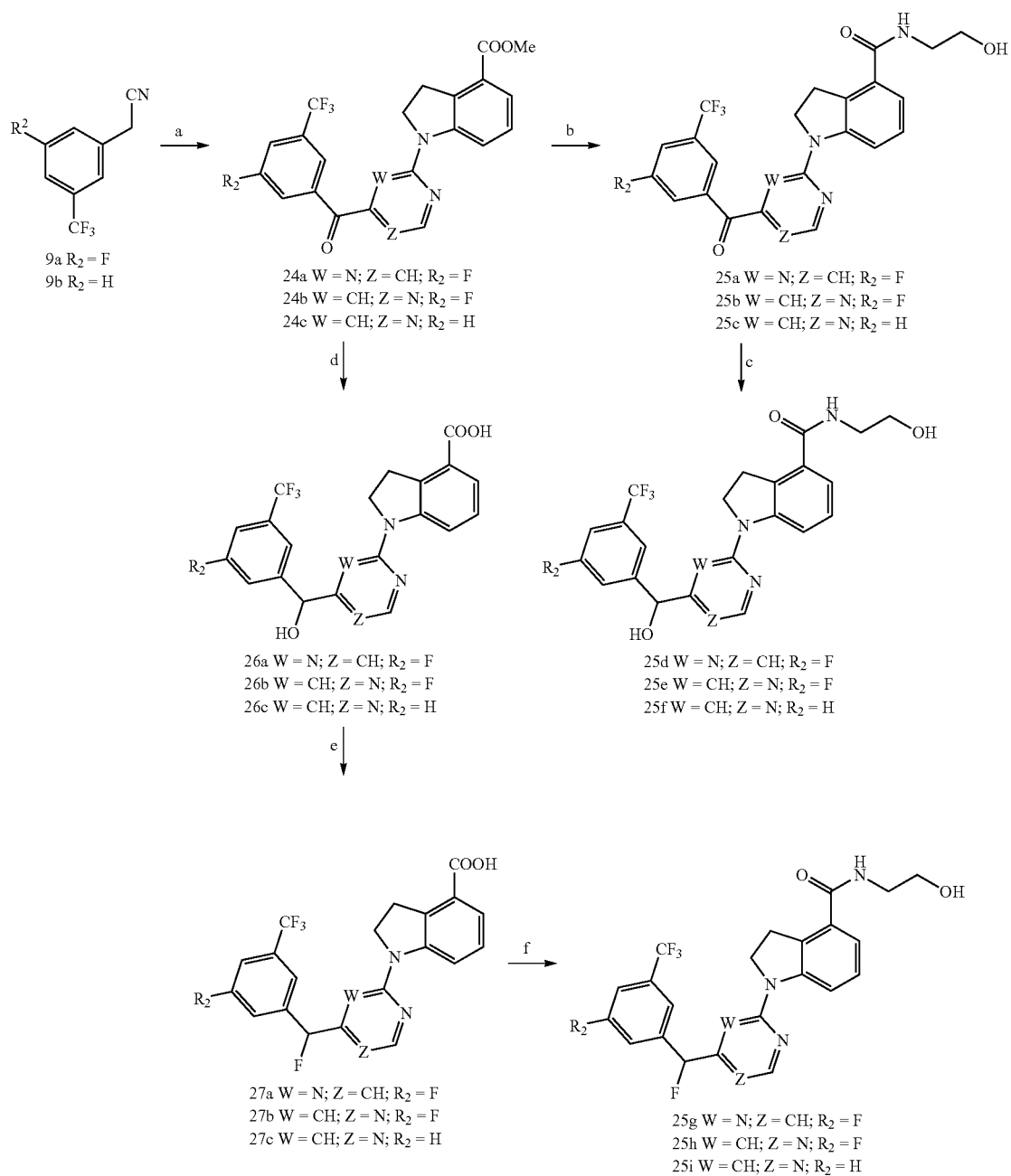

[a]Reagents and conditions: (a) For 24a, (i) 7a, NaH, DMF, 0° C. to rt. 2 h; (ii) mCPBA, 0° C. to rt, 10 min, 47% for two steps; (iii) 6, XantPhos, Cs₂CO₃, Pd(OAc)₂, 1,4-dioxane, 100° C., overnight, 82%; For 24b and 24c, (i) 8c, NaH, DMF, 0° C. to rt. 2 h; (ii) mCPBA, 0° C. to rt, 10 min, 49% over two steps for 24b, 79% over two steps for 24c. (b) (i) con. HCl/AcOH/H₂O, reflux, overnight; (ii) NH₂CH₂CH₂OH, EDCI, DMAP, DMF, rt, overnight, 63%-77% for two steps. (c) NaBH₄, DMF/MeOH, 0° C. to rt. 30 min, 68%-90%. (d) (i) NaBH₄, DMF/MeOH, 0° C. to rt. 30 min; (ii) con. HCl/AcOH/H₂O, reflux, overnight, 78%-90%. (e) (i) DAST, CH₂Cl₂, 0° C. to rt. 10 min; (ii) THF/H₂O, reflux, overnight, 60%-76% for two steps. (f) NH₂CH₂CH₂OH, EDCI, DMAP, DMF, rt, overnight, 68%-86%.

As depicted in Scheme 6, compounds 29a-29c were produced via coupling reaction of 8c with corresponding commercially available compounds 28a-28c in yields of 63-71%. Subsequently, the intermediates 29a-29c were converted to the corresponding final compounds 25j-25l by acidolysis and coupling with aminoethanol, following the similar procedures to that of preparing 25a. Compounds 30a-30g were prepared by coupling 11c with corresponding aminoethanol derivatives following the similar procedure to that of preparing 12a, as outlined in Scheme 7.

Scheme 6.
Synthetic Routes of Compounds 25j-25l[a]

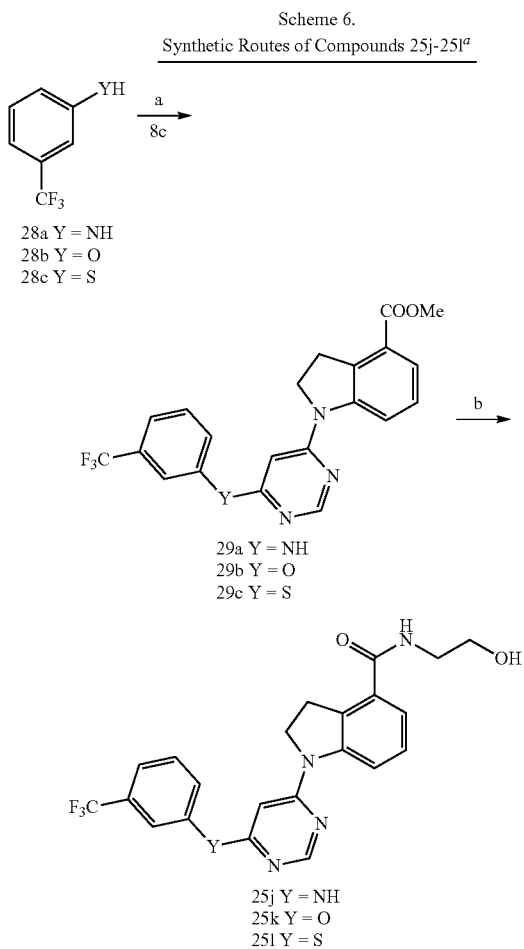

28a Y = NH
28b Y = O
28c Y = S

29a Y = NH
29b Y = O
29c Y = S

25j Y = NH
25k Y = O
25l Y = S

[a]Reagents and conditions: (a) For 29a, Pd(OAc)$_2$, XantPhos, Cs$_2$CO$_3$, 1,4-dioxnae, 100° C., overnight, 69%; For 29b and 29c, Cs$_2$CO$_3$, DMF, 120° C., overnight, 63% for 29b, 71% for 29c. (b) (i) con. HCl/AcOH/H$_2$O, reflux, overnight; (ii) NH$_2$CH$_2$CH$_2$OH, EDCI, DMAP, DMF, rt, overnight, 43%-73% for two steps.

Scheme 7.
Synthetic Routes of Compounds 30a-30g[a]

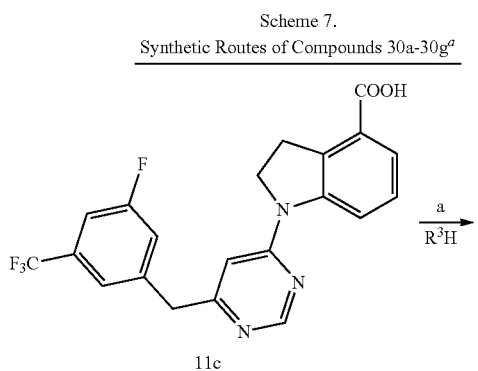

11c

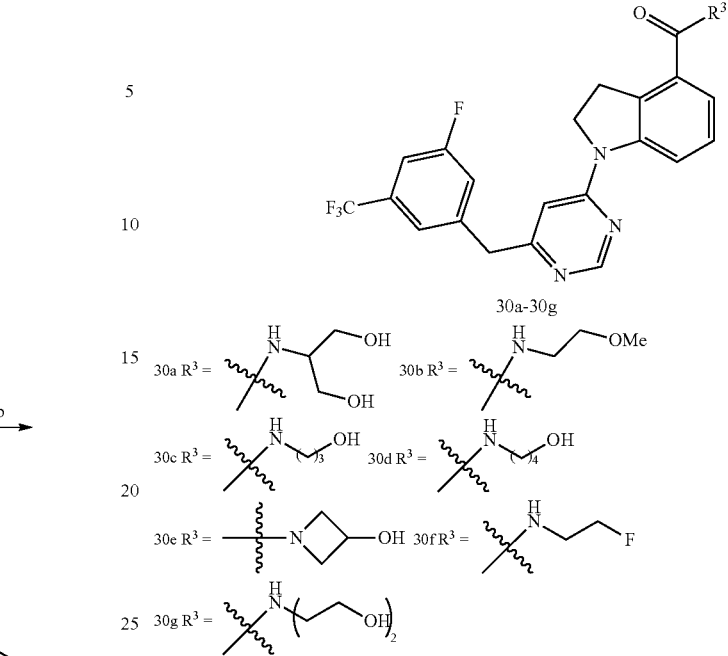

30a-30g

30a R$^3$ = ⸺NH⸺CH(CH$_2$OH)⸺CH$_2$OH
30b R$^3$ = ⸺NH⸺CH$_2$CH$_2$OMe
30c R$^3$ = ⸺NH⸺(CH$_2$)$_3$⸺OH
30d R$^3$ = ⸺NH⸺(CH$_2$)$_4$⸺OH
30e R$^3$ = azetidine-N-CH$_2$CH$_2$OH
30f R$^3$ = ⸺NH⸺CH$_2$CH$_2$F
30g R$^3$ = ⸺NH⸺CH(CH$_2$OH)$_2$

[a]Reagents and conditions: (a) EDCI, DMAP, DMF, rt, overnight, 37%-78%.

Figure 6:
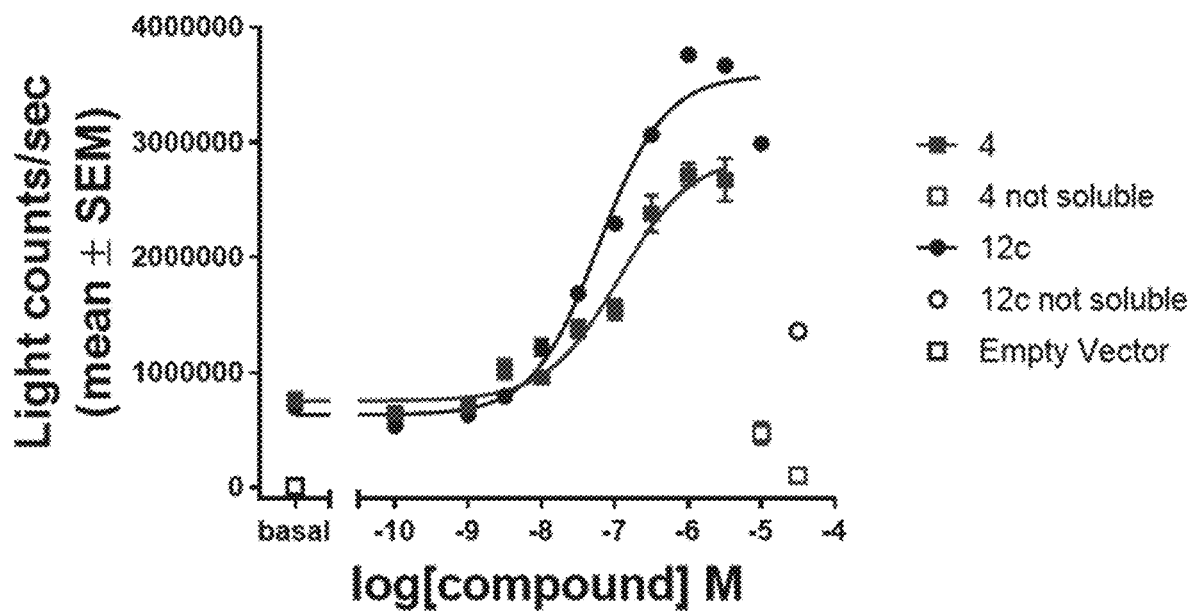
FIG. 6. Representative concentration-responses of compound 4 and 12c on cAMP signaling in HEK293 cells transiently expressing GPR52 and cAMP Glosensor reporter. Transient expression of GPR52 resulted in >100 fold light counts/sec over empty vector, indicating high constitutive receptor activity. Compound 4 (positive control) yields a robust ~3-fold increase in light counts/sec over basal values. Compounds were tested in twelve-point concentration-responses (0.1 nM-30 μM); however, due to poor water solubility of compound 4, 10 and 30 μM points were excluded for the potency and efficacy analysis. Similarly, if a severe drop in light counts was observed at high concentration points (i.e. 30 μM for compound 12c), these points were excluded for curve fitting analyses.

In Vitro Evaluation of GPR52 Activation. Newly synthesized compounds were evaluated in a twelve-point concentration-response for GPR52 agonist activity using the Glosensor™ cAMP assay in HEK293 cells transiently expressing human GPR52. Transient expression of GPR52 resulted in a dramatic increase in basal cAMP levels (>100 fold over empty vector, FIG. 6), indicating that GPR52 displays high constitutive activity for the cAMP pathway. As summarized in Tables 1-4, the EC$_{50}$ (nM) indicates the potency of these novel GPR52 agonists, while the efficacy (E$_{max}$) indicates the maximal activity to increase cAMP. The previously reported GPR52 agonist compound 4 was used as the reference compound to highlight SAR comparisons.[17] E$_{max}$ (%) was evaluated with compound 4 as 100% and 0.5% DMSO (vehicle control) as 0%. Compound 4 exhibited very good potency and robust efficacy in the cAMP assay (EC$_{50}$ of 137 nM, E$_{max}$ of ~3 fold over basal values, FIG. 6). All synthesized ligands were screened in the assay in a full concentration-response (0.1 nM to 30 μM). Some data points, at higher concentrations, were excluded from pharmacological analysis due to limited aqueous solubility (as shown in FIG. 6).

As summarized in Table 1, to begin a systematic SAR study of the scaffold of compound 4[17], the inventors first investigated the core ring B (FIG. 2) by insertion of an additional N atom in the pyridine ring of compound 4. Replacement of the pyridine ring by a pyrimidine ring with two N atoms at positions 2 and 4, leading to compound 12a, resulted in ~3-fold loss of potency with an EC$_{50}$ value of 373 nM relative to compound 4. However, compared to compound 4, the efficacy of compound 12a increased with an E$_{max}$ of 144%. In addition, 12a has a more favorable ClogP relative to that of 4 (3.64 vs 4.11), suggesting that 12a may have a better PK profile. In the further SAR studies, the pyridine ring of compound 4 was replaced with a pyridazine ring to obtain compound 12b (EC$_{50}$=158 nM, E$_{max}$=158%), which exhibited comparable potency to that of 4, with improved efficacy. Next, modification of the pyridine ring of compound 4 to a pyrimidine ring with the two N atoms fixed at positions 4 and 6, led to compound 12c (Table 1 and FIG. 3A). Compound 12c showed equal potency as that of the lead 4 (135 nM vs 137 nM), but excitingly resulted in a superior efficacy ($E_{max}$ of 136%), which was the best compound among this series. However, when the two N atoms were moved to positions 2 and 6 to obtain 12d, the potency decreased slightly ($EC_{50}$=186 nM) compared to 12c. To explore the effect of adding a substituent on potency, the inventors introduced a methyl or a chlorine at the 2-position on compound 12b, leading to compounds 12e and 12f, respectively. However, both compounds showed substantial loss of potency (>4-fold decreased $EC_{50}$), indicating that adding a substituent on core moiety B was not favorable.

Having identified an optimal heterocycle in moiety B that maintains potency while increasing efficacy, the inventors next focused on probing the role of the substituents on the benzene ring of moiety C (FIG. 2), with results summarized in Table 2. To evaluate the importance of the F substituent, the F from compound 12c was removed, leading to compound 23a, resulting in a slight increase in potency ($EC_{50}$ of 101 nM) and minor decrease in efficacy relative to compound 12c (127% vs 134%) (Table 2). Compounds 23b and 23c were then designed and synthesized to explore whether the $CF_3$ position had an influence on agonist potency. The $CF_3$ at the ortho-position (23b) resulted in a dramatic loss of potency (>7-fold loss) compared with the $CF_3$ at the meta-position (23a). Remarkably, when the $CF_3$ moiety was moved to the para-position (23c), a similar potency and efficacy was observed to that of 23a (109 nM vs 101 nM for $EC_{50}$, 136% vs 127% for $E_{max}$ (Table 2 and FIG. 3B). From these results, the inventors conclude that the substituent position on the benzene ring of moiety C has an important role in compound potency and their preferred order is meta>para>ortho position. Further, the electronic properties of substituents on the benzene ring of moiety C were probed. Replacement of the meta-$CF_3$ of 23a with a methyl group led to compound 23d, which displayed the best potency among this series with an $EC_{50}$ of 90 nM, while maintaining excellent efficacy with an $E_{max}$ of 144% (Table 2 and FIG. 3B). Similarly, compound 23e was obtained by substitution of the meta-$CF_3$ of 23a with an F atom, which displayed no change in potency, $EC_{50}$ of 106 nM, and maintained excellent efficacy, $E_{max}$ of 148%, (Table 2). Next, the inventors probed whether a second additional electron-withdrawing moiety in the 5-position would further improve potency and efficacy. Di-substituted variants of 23d and 23e, leading to compounds 23f and 23g, respectively, displayed identical pharmacologic profiles as their mono-substituted counter parts (Table 2 and FIG. 3B). These data suggest that the addition of an extra electron-withdrawing substituent at 5-position of the benzene ring C has limited influence on the potency and efficacy. However, substitution of the meta-$CF_3$ of 23a with electron-donating group such as $OCF_3$ (23h), OMe (23i) and 3,5-di-OMe (23j), dramatically decreased the potency as well as the efficacy (Table 2 and FIG. 3B). Moreover, compound 23k was synthesized without any substituent on the benzene ring C, resulting in ~3-fold loss of potency relative to 23a, suggesting that an electron-withdrawing substituent (e.g., 23a, 23c and 23e) on the benzene ring of moiety C is favorable for the potency. Taken together, these findings suggest that electron-withdrawing or small alkyl substituents at 3-position are favorable for improved potency, with an additional small substituent at 5-position also well-tolerated, while compounds without any substituent on the benzene ring or with electron-donating groups are not tolerated.

TABLE 1

$EC_{50}$ and $E_{max}$ of Compounds 12a-12f

| Compound | X | ClogP[a] | $EC_{50}$ (nM)[b] | $E_{max}$ (%)[b] |
|---|---|---|---|---|
| 4 | | 4.11 | 137 ± 18 | 100 ± 5 |
| 12a | pyrimidine (N at 1,4) | 3.64 | 373 ± 35 | 144 ± 7 |
| 12b | pyridazine (N at 5,6) | 3.64 | 158 ± 48 | 158 ± 12 |
| 12c | pyrimidine (N at 4,6) | 3.64 | 135 ± 16 | 136 ± 6 |
| 12d | pyrimidine (N at 2,6) | 3.64 | 186 ± 44 | 138 ± 8 |
| 12e | 4-methyl pyridazine | 3.95 | 754 ± 62 | 119 ± 6 |
| 12f | 4-chloro pyridazine | 4.30 | 562 ± 80 | 97 ± 7 |

[a]cLogP: URL biosig.unimelb.edu.au/pkcsm/prediction.

[b]The values are the mean ± SEM of at least three independent experiments.

$E_{max}$ (%) is the efficacy maximum of the compounds in the cAMP assay relative to compound 4 as 100% and 0.5% DMSO as 0%.

TABLE 2

EC$_{50}$ and E$_{max}$ of Compounds 23a-23k

| Compound | R$^2$ | ClogP$^a$ | EC$_{50}$ (nM)$^b$ | E$_{max}$ (%)$^b$ |
|---|---|---|---|---|
| 4 | | 4.11 | 137 ± 18 | 100 ± 5 |
| 23a | 3-CF$_3$ | 3.50 | 101 ± 31 | 127 ± 10 |
| 23b | 2-CF$_3$ | 3.50 | 711 ± 160 | 115 ± 6 |
| 23c | 4-CF$_3$ | 3.50 | 109 ± 19 | 136 ± 7 |
| 23d | 3-Me | 2.79 | 90 ± 19 | 144 ± 9 |
| 23e | 3-F | 2.62 | 106 ± 35 | 148 ± 14 |
| 23f | 3,5-di-Me | 3.10 | 97 ± 20 | 140 ± 11 |
| 23g | 3,5-di-F | 2.76 | 115 ± 19 | 142 ± 10 |
| 23h | 3-OCF$_3$ | 3.38 | 131 ± 24 | 113 ± 11 |
| 23i | 3-OMe | 2.49 | 351 ± 6 | 122 ± 8 |
| 23j | 3,5-di-OMe | 2.50 | 850 ± 35 | 113 ± 2 |
| 23k | H | 2.48 | 292 ± 17 | 134 ± 4 |

$^a$cLogP: URL biosig.unimelb.edu.au/pkcsm/prediction.
$^b$The values are the mean ± SEM of at least three independent experiments.
E$_{max}$ (%) is the efficacy maximum of the compounds in the cAMP assay relative to compound 4 as 100% and 0.5% DMSO as 0%.

TABLE 3

EC$_{50}$ and E$_{max}$ of Compounds 25a-25l

| Compound | R$^2$ | Y | W | Z | ClogP$^a$ | EC$_{50}$ (nm)$^b$ | E$_{max}$ (%)$^b$ |
|---|---|---|---|---|---|---|---|
| 4 | | | | | 4.11 | 137 ± 18 | 100 ± 5 |
| 25a | F | CO | N | CH | 3.28 | 1589 ± 166 | 96 ± 7 |
| 25b | F | CO | CH | N | 3.28 | 1693 ± 437 | 22 ± 3 |
| 25c | H | CO | CH | N | 3.14 | 1008 ± 237 | 22 ± 4 |
| 25d | F | CHOH | N | CH | 3.13 | 399 ± 68 | 130 ± 9 |
| 25e | F | CHOH | CH | N | 3.13 | 338 ± 26 | 134 ± 28 |
| 25f | H | CHOH | CH | N | 2.99 | — | — |
| 25g | F | CHF | N | CH | 4.10 | 329 ± 113 | 144 ± 9 |
| 25h | F | CHF | CH | N | 4.10 | — | — |
| 25i | H | CHF | CH | N | 3.97 | 557 ± 273 | 83 ± 5 |
| 25j | H | NH | CH | N | 3.66 | 1105 ± 24 | 81 ± 2 |
| 25k | H | O | CH | N | 3.70 | 2404 ± 292 | 99 ± 4 |
| 25l | H | S | CH | N | 4.06 | 371 ± 47 | 123 ± 6 |

$^a$cLogP: URL biosig.unimelb.edu.au/pkcsm/prediction.
$^b$The values are the mean ± SEM of at least three independent experiments.
E$_{max}$ (%) is the efficacy maximum of the compounds in the cAMP assay relative to compound 4 as 100% and 0.5% DMSO as 0%.
"—" not detected.

To probe the impact of the flexibility and steric availability around the linker between moieties B and C, compounds 25a-25l were designed, synthesized, and evaluated, with the results summarized in Table 3. The inventors first replaced the methylene linker with a carbonyl moiety to yield compounds 25a-25c, which were found to dramatically decrease the potency and efficacy, likely due to limited flexibility. Reduction of the carbonyl moiety of compounds 25a-25c produced compounds 25d-25f, and this restored a certain degree of the potency and efficacy, but still at least 3-fold less potency than compound 23a. Fluorination of compounds 25d-25f yielded compounds 25g-25i which failed to improve the potency or efficacy (Table 3 and FIG. 3C). Replacement of the methylene linker of compound 23a with either an NH, O or S led to corresponding compounds 25j-25l; however, none of these three compounds showed favorable potency and efficacy (Table 3 and FIG. 3C). Taken together, these results suggest that GPR52 ligands of this scaffold need to have a flexible and sterically limited linker to achieve good potency. These SAR results are consistent with the recently disclosed co-crystal structure of compound 2 and GPR52, suggesting that the GPR52 binding region for these molecules is a narrow sterically limited pocket.[13]

Figure 3:
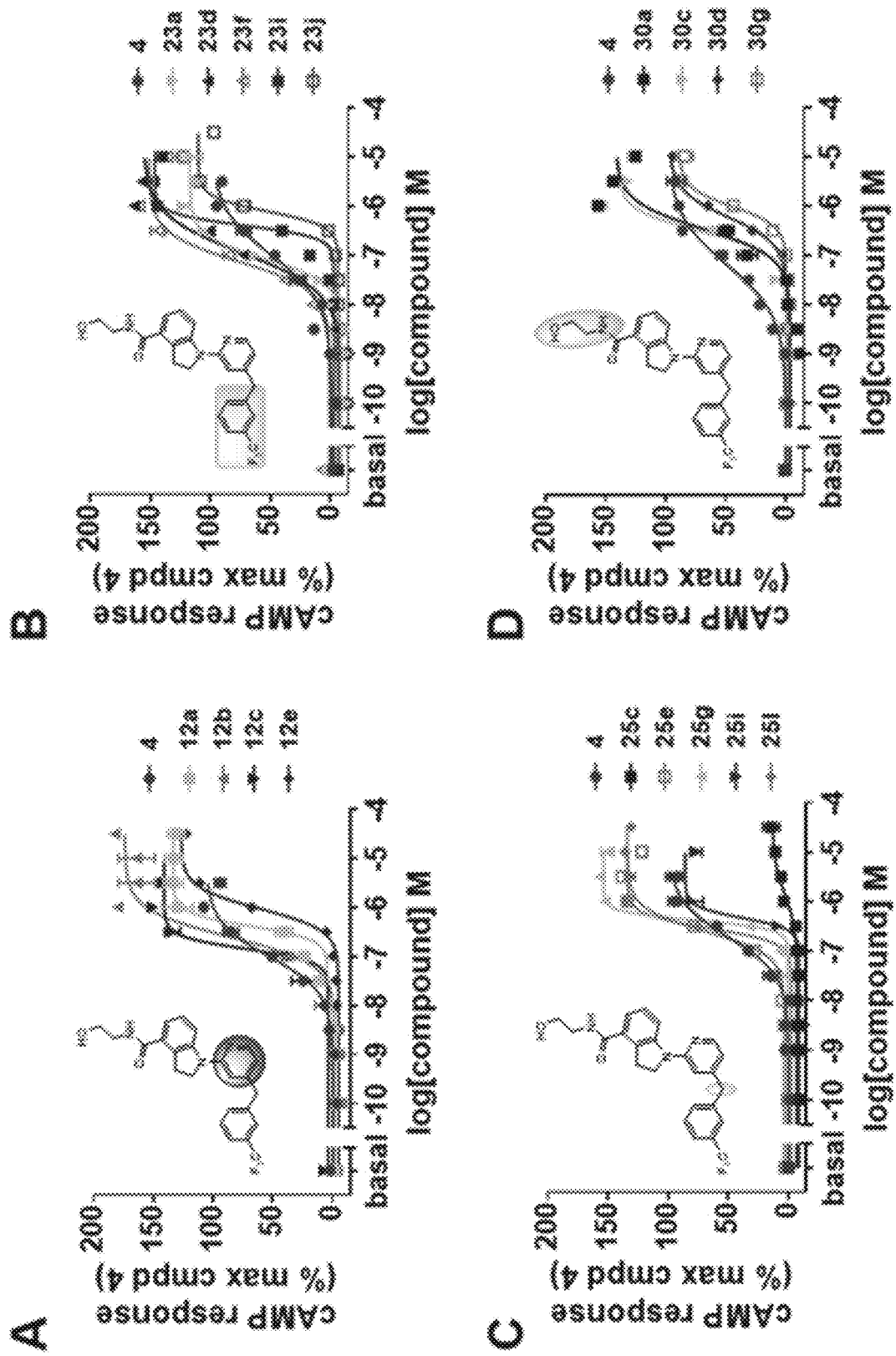
FIG. 3. Concentration-responses of select GPR52 agonists on cAMP signaling in HEK293 cells. HEK293 cells expressing human GPR52 and cAMP Glosensor reporter were subjected to twelve-point concentration-response (0.3 nM-30 μM) testing. (A) Modifications around ring B: comparison with compounds 4, 12a, 12b, 12c, and 12e. (B) Modifications around ring C comparison with compounds 4, 23a, 23d, 23f, 23i, 23j. (C) Modifications around carbon linker comparison with compounds 4, 25c, 25e, 25g, 25i, and 25l. (D) Modifications around head group A comparison with compounds 4, 30a, 30c, 30d, and 30g. All results are presented as the Mean±SEM from triplicate testing in a representative experiment, with similar results observed in 3-17 experiments.

Finally, to detect the impact of amino alcohol side chain in moiety A, compounds with various lengths and flexibilities were designed through different strategies, including introducing extra hydroxyl groups (30a and 30g), modification of the terminal hydroxyl group (30b and 30f), changing the length of alkyl linker between amino and hydroxyl group (30c-30e) (FIG. 3D). Unfortunately, these seven compounds substantially lost GPR52 potency compared to compound 12c (Table 4), indicating that moiety A is critical and unlikely amenable for further optimization.

TABLE 4

EC$_{50}$ and E$_{max}$ of Compounds 30a-30g

| Compound | R³ | ClogP$^a$ | EC$_{50}$ (nM)$^b$ | E$_{max}$ (%)$^b$ |
|---|---|---|---|---|
| 4 | | 4.11 | 137 ± 18 | 100 ± 5 |
| 30a | -NH-CH(CH$_2$OH)-CH$_2$OH | 3.00 | 346 ± 19 | 115 ± 15 |
| 30b | -NH-CH$_2$CH$_2$-OMe | 4.30 | 489 ± 86 | 119 ± 7 |
| 30c | -NH-CH$_2$CH$_2$CH$_2$-OH | 4.03 | 275 ± 13 | 120 ± 15 |
| 30d | -NH-(CH$_2$)$_4$-OH | 4.42 | 399 ± 51 | 120 ± 18 |
| 30e | -N(azetidinyl)-OH | 3.73 | 760 ± 176 | 111 ± 10 |
| 30f | -NH-CH$_2$CH$_2$-F | 4.62 | 431 ± 7 | 129 ± 17 |
| 30g | -N(CH$_2$CH$_2$OH)$_2$ | 3.35 | 673 ± 135 | 119 ± 15 |

$^a$cLogP: URL biosig.unimelb.edu.au/pkcsm/prediction.

$^b$The values are the mean ± SEM of at least three independent experiments.

E$_{max}$ (%) is the efficacy maximum of the compounds in the cAMP assay relative to compound 4 as 100% and 0.5% DMSO as 0%.

Figure 8:
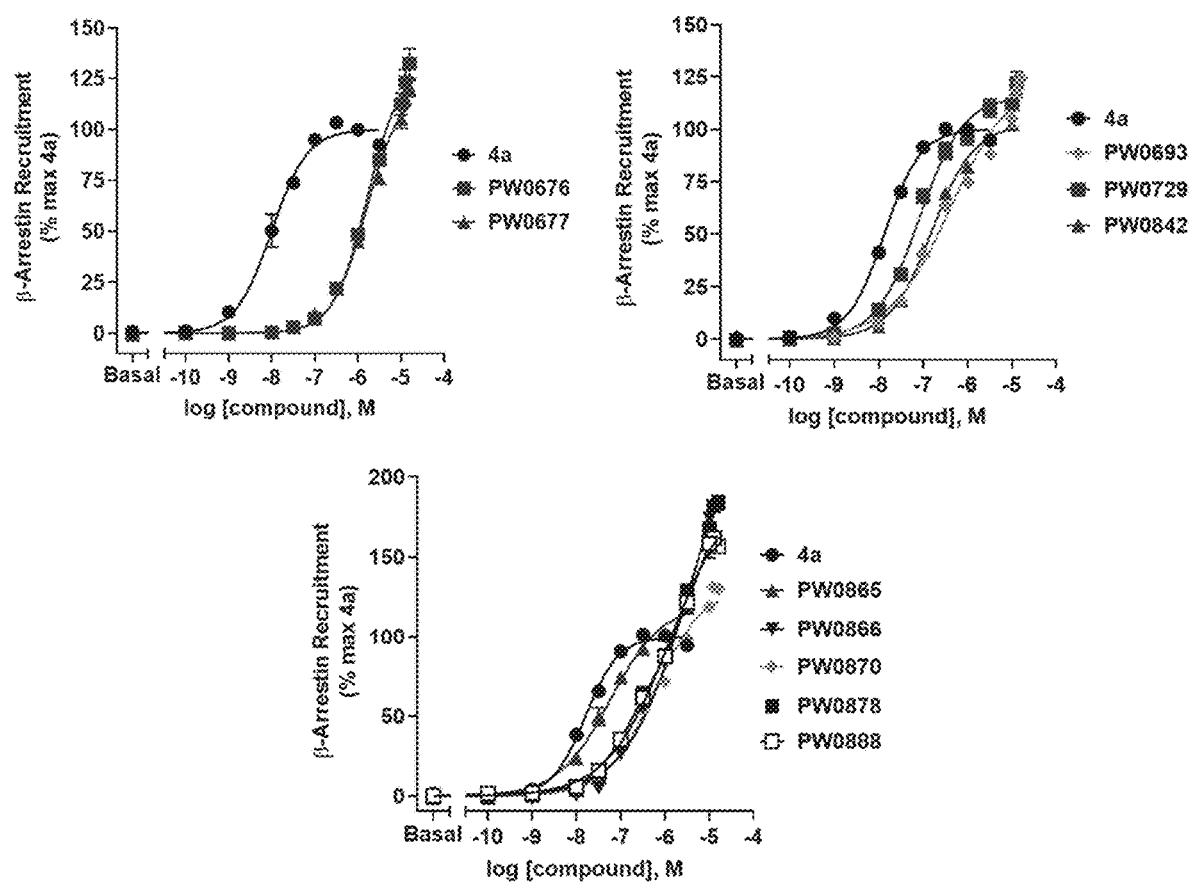
FIG. 8. Concentration responses of select GPR52 agonists for β-arrestin recruitment in HTLA HEK293 cells expressing the human GPR52 TANGO construct. Modifications around the indoline ring system or in the lower aromatic ring C of 4a (diagram in FIG. 2) generally reduced compound potency for GPR52 β-arrestin recruitment. All results are presented as the mean±SEM from triplicate testing in a representative experiment, with similar results observed in 3-6 experiments.

As another assessment of GPR52 agonist activation, select ligands with good potency for GPR52 G protein cAMP signaling were also analyzed for GPR52 β-arrestin recruitment activity using the TANGO assay. Several compounds, including PW0676, PW0677, PW0842, PW0866, PW0870, and PW0878 showed reduced GPR52 potency to recruit β-arrestin compared to compound 4a (see FIG. 8 and Table 5). To quantify the relative activity of the ligands to activate GPR52 G protein (cAMP) versus β-Arrestin recruitment, bias factors were calculated and compared to the activity of 4a. This analysis determined several of the agonists have GPR52 G protein biased agonist activity with reduced β-Arrestin recruitment, with relatively large G protein bias factors>60 determined for PW0676, PW0677 and PW0866 (Table 5).

TABLE 5

β-Arrestin Recruitment $EC_{50}$ and $E_{max}$ and Bias Factors of Select Compounds.

| Compound 4a | $EC_{50}$ $(nM)^a$ | $E_{max}$ $(\%)^a$ | G Protein Bias Factor[b] | β-Arrestin Bias Factor[b] |
|---|---|---|---|---|
| PW0667 | 22 ± 6 | 100 ± 8 | 1.00 | 1.00 |
| PW0671 | 483 ± 46 | 70 ± 6 | 25.8 | 0.039 |
| PW0676 | 1585 ± 250 | 125 ± 12 | 66.3 | 0.015 |
| PW0677 | 1582 ± 149 | 127 ± 7 | 63.2 | 0.016 |
| PW0693 | 335 ± 69 | 118 ± 5 | 26.9 | 0.037 |
| PW0729 | 110 ± 11 | 109 ± 3 | 16.4 | 0.061 |
| PW0842 | 247 ± 62 | 100 ± 7 | 31.2 | 0.032 |
| PW0865 | 89 ± 12 | 120 ± 3 | 11.7 | 0.085 |
| PW0866 | 1036 ± 136 | 172 ± 7 | 81.9 | 0.012 |
| PW0870 | 563 ± 28 | 142 ± 6 | 34.7 | 0.029 |
| PW0878 | 951 ± 88 | 180 ± 9 | 45.7 | 0.022 |
| PW0888 | 774 ± 139 | 204 ± 15 | 29.7 | 0.033 |

[a]The values are the mean ± SEM of at least three independent experiments. $E_{max}$ (%) is the efficacy maximum of the compounds in the β-arrestin recruitment assay relative to compound 4a as 100% and DMSO as 0%.
[b]Formulae for bias factor calculations are listed in the methods.

Figure 4:
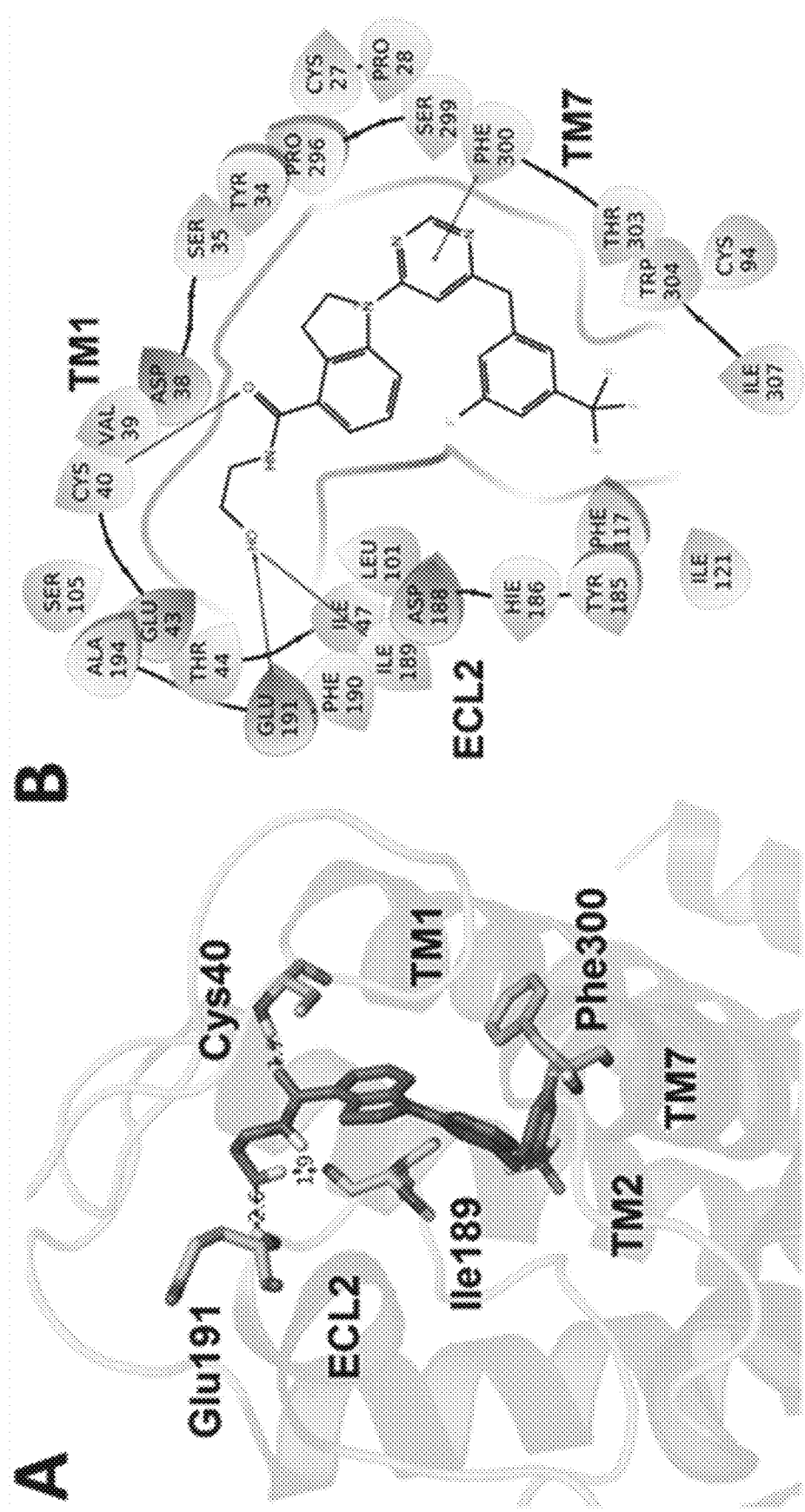
FIG. 4. Putative binding mode and molecular docking of compound 12c with GPR52 (PDB code: 6LI0). (A) Docking of compound 12c into the binding pocket of GPR52. Important residues are drawn as sticks. Hydrogen bonds are shown as dashed lines. (B) Docking of compound 12c into the binding pocket of GPR52 in 2D view. Hydrogen bonds and π-π interaction are shown.

Molecular Docking Study of Compound 12c with GPR52. To understand the potential binding mode and the receptor-ligand interactions that are important for agonist activity at GPR52, molecular docking using the Schrödinger Drug Discovery Suite was employed. Excitingly, the co-crystal structure of GPR52 bound to compound 2 was recently solved (PDB code: 6LI0), affording an unprecedented opportunity to pursue computational docking studies with an orphan GPCR.[13] Compound 12c was selected as the example of an optimized compound to further explore the binding interactions with GPR52. As shown in FIG. 4, the docking results indicated compound 12c has energetically favorable interactions with the narrow pocket surrounded by ECL2, TM1, TM2 and TM7, and forms a similar binding pose to compound 2 with GPR52 in the solved co-crystal structure.[13] Notably, there are three critical hydrogen bonding interactions between compound 12c and the residues of the ECL2 and TM1 of the receptor: the 12c terminal hydroxyl group forms hydrogen bonds with residues Glu191 and Ile189 of ECL2, and the 12c carbonyl group of the amide hydrogen bonds with residue Cys40 from TM1. This binding model may explain the significant activity loss when replacing the amino alcohol sidechain into other sidechains. The pyrimidine ring (core ring B) forms a π-π stacking interaction with the residue Phe300 of TM7. Moreover, the benzene ring (moiety C) of compound 12c pointed into a narrow hydrophobic pocket and formed hydrophobic interactions with residues Phe117, Cys94, Tyr185, Ile47, Ile121, Ile307 and Trp304. This may explain why modifications with only small substitutions on moiety C are tolerated, and why the hydrophobic groups (e.g., F and $CF_3$) are more favorable for the binding to drive potency. This docking also indicates the binding pocket near ECL2 is a hotspot of interaction for both previously identified GPR52 agonists as well as 12c and likely other indoline-carboxamide-based ligands.

Figure 7:
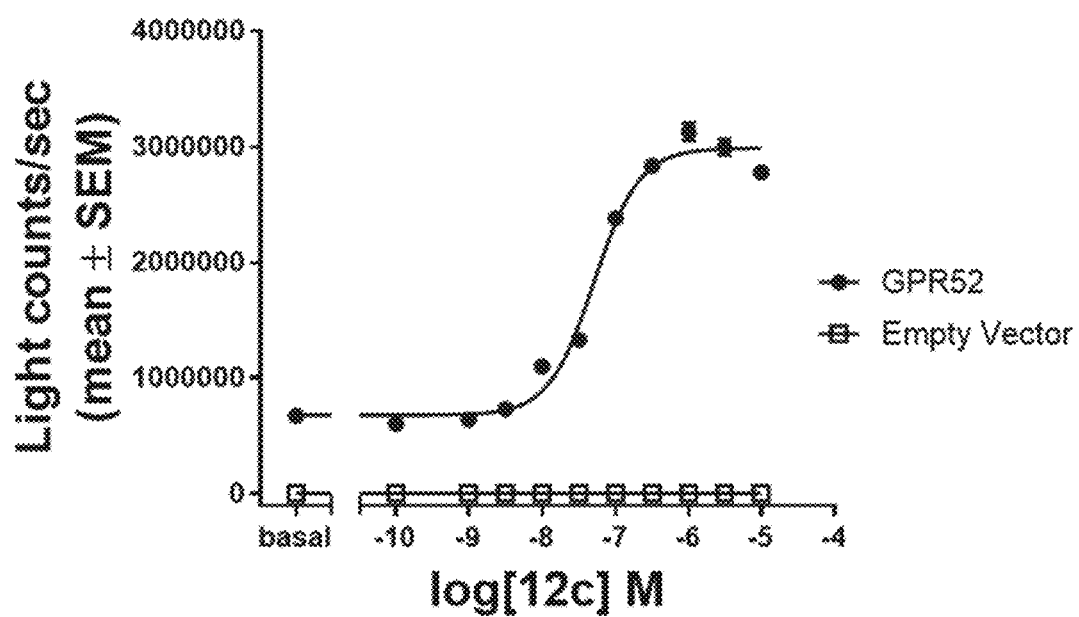
FIG. 7. Representative concentration-responses of compound 12c on cAMP signaling in HEK293 cells transiently expressing GPR52 or an empty vector (control) and cAMP Glosensor reporter. Compound 12c was tested in twelve-point concentration-responses (0.1 nM-10 μM). Compound 12c yields a robust ~3-fold increase in light counts/sec over basal values in cells expressing GPR52 (blue circles). Importantly, no increase in cAMP was observed in cells expressing empty vector (black squares), indicating that compound 12c elevation of cAMP is due to selectively activating GPR52.

In Vitro Assessment of Off-target Effects of Compound 12c. To evaluate if the cAMP signaling activity of optimized compound 12c is indeed due to GPR52 agonist activation, 12c was further tested in control studies using HEK293 cells lacking GPR52. Results determined 12c did not increase cAMP in the cells lacking GPR52 (FIG. 7). Therefore, compound 12c regulates cAMP increases through a direct interaction with GPR52 in this cellular system. To determine the selectivity of 12c against other GPCRs, a broad-panel counter screening was tested by the National Institute of Mental Health Psychoactive Drug Screening Program (NIMH-PDSP)[27]. This testing determined compound 12c at concentration of 10 μM displayed no significant binding affinity ($K_i$) at over 30 brain receptors or channels, including important GPCRs that are current targets of antipsychotic medications (e.g., $5-HT_{2A}$ and $D_2$ receptors), as shown in Table 6. In addition, compound 12c at 10 μM did not show any human ether-a-go-go-related gene (hERG) potassium channel binding activity (Table 6), indicating compound 12c should not have undesirable hERG inhibition known to cause cardiotoxicity.[28]

TABLE 6

Broad-Panel Counter Screening of 12c against Other GPCRs and Transporters[a]

| GPCRs | % inhibition (10 μM)[b] | $K_i$ (μM)[b] | GPCRs, Transporters, Ion Channels | % inhibition (10 μM) | $K_i$ (μM)[b] |
|---|---|---|---|---|---|
| 5-HT1A | 8.68 | ND | D1 | 12.29 | ND |
| 5-HT1B | 6.3 | ND | D2 | 2.51 | ND |
| 5-HT1D | 29.64 | ND | D3 | 10.64 | ND |
| 5-HT1E | 7.71 | ND | D4 | 29.91 | ND |
| 5-HT2A | 10.62 | ND | D5 | -7.17 | ND |
| 5-HT2B | 28.69 | ND | DAT | 24.83 | ND |
| 5-HT2C | 52.62 | >10 | GABAA | 5.98 | ND |
| 5-HT3 | 26.82 | ND | H1 | 6.43 | ND |
| 5-HT5A | 13.95 | ND | H2 | 22.36 | ND |
| 5-HT6 | 7.98 | ND | KOR | 1.48 | ND |
| 5-HT7A | 5.16 | ND | M1 | 2.86 | ND |
| Alpha1A | 13.56 | ND | M2 | -1.87 | ND |
| Alpha1B | -5.42 | ND | M3 | 45.38 | ND |
| Alpha2A | 4.45 | ND | M4 | 29.26 | ND |
| Beta1 | 17.2 | ND | M5 | 0.82 | ND |
| Beta2 | -14.07 | ND | MOR | 16.24 | ND |
|  |  |  | hERG | 11.04 | ND |

[a]The broad-panel counter screening of 12c against a panel of GPCRs and transporters were generously provided by the NIMH Psychoactive Drug Screening Program.
[b]The values are the mean percent inhibition of binding from at least three independent experiments, SEM <20%.
"ND" means a $K_i$ binding affinity was not detected.

In Vivo PK Profile of Compound 12c. Based on its potency and efficacy, compound 12c was selected as the representative compound for further PK evaluations. Compound 12c was evaluated in rats after single dose of 20 mg/kg by oral (PO) or 10 mg/kg by intravenous (IV) administration, and the results are summarized in Table 7. Compound 12c has excellent plasma exposure after PO ($AUC_{0-inf}$=13749 ng·h/mL) and IV dosing ($AUC_{0-inf}$=9030 ng·h/mL), as well as high maximum serum concentration following PO ($C_{max}$=3407 ng/mL) and IV administration ($C_{max}$=6726 ng/mL). Additionally, compound 12c displayed good volume of plasma distribution ($V_{SS}$=1.5 L/kg) and acceptable plasma clearance (CL=1.1 L/h/kg) after 10 mg/kg IV. Excellent oral bioavailability (F) with the value of 76% was observed. Compound 12c was evaluated in rats for brain permeability and concentration after single dose of 10 mg/kg by IV administration, and the concentrations of 12c in brain and plasma were measured at 0.25 and 1 h after administration. As shown in Table 8, compound 12c exhibits a good concentration in brain at 0.25 h with the value of 1807 ng/g, and also exhibits an acceptable brain permeability with a brain/plasma ratio of 0.28. The high brain concentration and brain permeability of 12c persisted for at least 1 h, with a brain concentration over 1000 ng/g and a brain/plasma ratio of 0.39 after 1 h injection. Based upon these collective findings, compound 12c was selected for further in vivo evaluation.

TABLE 7

In Vivo Pharmacokinetic Parameters of Compound 12c in Rats[a]

| Route | $AUC_{0-\infty}$ (ng·h/mL) | $t_{1/2}$ (h) | $C_{max}$ (ng/mL) | CL (L/h/kg) | $V_{ss}$(L/kg) | F (%) |
|---|---|---|---|---|---|---|
| PO | 13749 ± 2710 | 2.5 ± 0.2 | 3407 ± 179 | 1.5 ± 0.3 | 5.5 ± 1.16 | 76 ± 15 |
| IV | 9030 ± 1018 | 1.0 ± 0.1 | 6726 ± 727 | 1.1 ± 0.1 | 1.5 ± 0.2 | |

[a]$AUC_{0-\infty}$, area under the curve (t = 0 to 24 h), $t_{1/2}$, terminal half-life; $C_{max}$, maximum concentration of drug in plasma; CL, plasma clearance; $V_{ss}$, volume of distribution at steady state; F, absolute oral bioavailability. Experiments were studied in biological triplicates, and data values are shown as the mean ± SEM.

TABLE 8

Brain Permeability of Compound 12c in Rats[a]

| Route | Time (h) | Brain Conc. (ng/g) | Plasma Conc. (ng/g) | Brain/Plasma Ratio |
|---|---|---|---|---|
| IV | 0.25 | 1807 ± 198 | 6324 ± 271 | 0.28 ± 0.02 |
| | 1 | 1006 ± 43 | 2589 ± 241 | 0.39 ± 0.02 |

[a]Concentrations of compound 12c in the brain and plasma were determined at 0.25 and 1 h after a single dose of 10 mg/kg by IV. Experiments were studied in biological triplicates, and data values are shown as the mean ± SEM.

Figure 5:
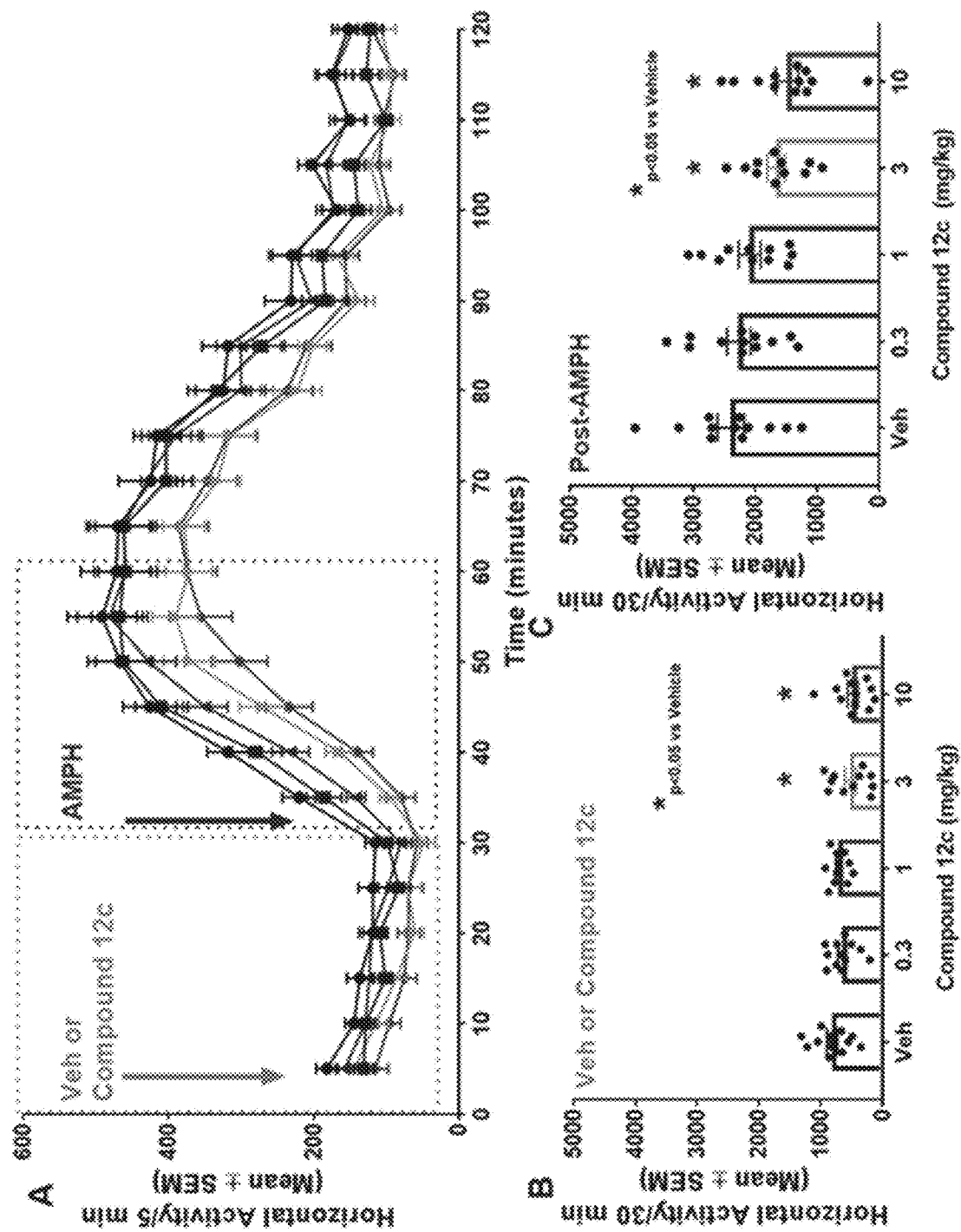
FIG. 5. Compound 12c shows antipsychotic-like activity in mice. (A) The time course of horizontal activity (counts/5 min; mean±SEM) following injection of vehicle or compound 12c (0.3, 1, 3 or 10 mg/kg; IP) is shown during automated activity monitoring for 30 min (left dotted box). Mice were then injected with amphetamine (AMPH; 3 mg/kg, IP) and activity monitored for the next 90 min. Horizontal activity (counts/5 min; mean±SEM) during the first 30 min following AMPH injection is illustrated (right dotted box). (B) The bar graph shows horizontal activity/30 min (mean±SEM) following injection of vehicle (Veh) or Compound 12c. (C) The bar graph shows horizontal activity (mean±SEM) in the first 30-min period after AMPH injection. n=11-12 subjects per drug treatment group; black filled circles indicate horizontal activity for individual animals. *P<0.05 vs. Veh.

Efficacy Evaluation of Compound 12c In Vivo. Compound 12c exhibited potent GPR52 activity in vitro, and a good PK profile to support further in vivo assessment. Amphetamine-induced hyperlocomotion in rodents is a well-characterized task with high translational validity for predicting preclinical antipsychotic-like activity.[29, 30] Given that GPR52 agonists inhibit hyperactivity induced by psychostimulants,[11, 31] the inventors employed this assay to investigate the efficacy of compound 12c in vivo. Mice were injected intraperitoneally (IP) with vehicle or compound 12c (0.3, 1, 3 or 10 mg/kg in vehicle; FIG. 5A); automated activity monitoring began immediately and continued for 30 min. Mice were then injected with amphetamine (AMPH; 3 mg/kg, IP) and activity monitored for the next 90 min (FIG. 5A). A one-way ANOVA indicated that compound 12c suppressed horizontal activity ($F_{4,53}$=3.392, P<0.05); Dunnett's a priori comparisons indicated that 3 mg/kg (P<0.05) and 10 mg/kg (P<0.05) suppressed horizontal activity (FIG. 5B). This profile is consistent with a low risk for impaired motor function seen in prior studies of GPR52 agonists.[15, 16] Compound 12c suppressed AMPH-induced horizontal activity ($F_{4,53}$=4.59, P<0.05; FIG. 5C) at both 3 mg/kg (P<0.05) and 10 mg/kg doses (P<0.05). Taken together, compound 12c is an orally bioavailable and brain penetrant GPR52 agonist which dose-dependently inhibits amphetamine-evoked hyperactivity, suggesting therapeutic potential for neuropsychiatric diseases.

A comprehensive structural optimization campaign has been conducted based on reported advanced chemical lead 4 through a systematic SAR study by introduction of various amino alcohol side chains, and modifications of numerous substituents on the core B ring and C ring. Among them, several compounds 12c (PW0787), 23a (PW0860), 23d (PW0878), 23e (PW0885), 23f (PW0888) and 23h (PW0890) were identified as novel GPR52 agonists that elevated cAMP signaling and were more potent than the reference compound 4. Compound 12c has a favorable ClogP and a good in vivo PK profile. Therefore, compound 12c was selected for further in vivo efficacy determination. Molecular docking studies of compound 12c and GPR52 suggest a binding mode with three critical hydrogen bond pairs, π-π stacking with ring B, and hydrophobic interactions with ring C. This binding model offers theoretical studies for further SAR studies of compound 12c. Compound 12c was also counter screened and displayed no off-target affinities at other important brain GPCRs and ion channels. In addition, compound 12c has excellent oral plasma exposure, maximum serum concentration, bioavailability, and brain concentration. In vivo studies showed that compound 12c significantly inhibited amphetamine-induced hyperactivity in mice. Therefore, the newly discovered GPR52 agonist 12c provides a useful pharmacological tool for studying GPR52 function and for evaluating GPR52 agonist therapeutic potential for the treatment of brain diseases such as neuropsychiatric disorders.

II. Chemical Definitions

Various chemical definitions related to such compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein, the term "water soluble" means that the compound dissolves in water at least to the extent of 0.010 mole/liter or is classified as soluble according to literature precedence.

As used herein, the term "nitro" means —$NO_2$; the term "halo" designates —F, —Cl, —Br or —I; the term "mercapto" means —SH; the term "cyano" means —CN; the term "azido" means —$N_3$; the term "silyl" means —$SiH_3$, and the term "hydroxyl" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —$CH_3$ (Me), —$CH_2CH_3$ (Et), —$CH_2CH_2CH_3$ (n-Pr), —$CH(CH_3)_2$(iso-Pr), —$CH_2CH_2CH_2CH_3$ (n-Bu), —$CH(CH_3)CH_2CH_3$ (sec-butyl), —$CH_2CH(CH_3)_2$(iso-butyl), —$C(CH_3)_3$(tert-butyl), —$CH_2C(CH_3)_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of 0 and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —$CH_2$ F, —$CH_2$ Cl, —$CH_2$ Br, —$CH_2$ OH, —$CH_2$ $OCH_3$, —$CH_2$ $OCH_2$ $CF_3$, —$CH_2OC(O)CH_3$, —$CH_2$ $NH_2$, —$CH_2$ $NHCH_3$, —$CH_2$ $N(CH_3)_2$, —$CH_2CH_2Cl$, —$CH_2CH_2OH$, $CH_2CH_2OC(O)CH_3$, —$CH_2CH_2$ $NHCO_2C$ $(CH_3)_3$, and —$CH_2$ $Si(CH_3)_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkylsulfonyl, arylsulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, $C_{1-4}$alkyl, phenyl, benzyl, —$NH_2$, —$NH(C_{1-4}alkyl)$, —$N(C_{1-4}alkyl)_2$, —$NO_2$, —$S(C_{1-4}alkyl)$, —$SO_2(C_{1-4}alkyl)$, —$CO_2(C_{1-4}alkyl)$, and —$O(C_{1-4}alkyl)$.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —$S(O_2)$—R', where R' is an alkyl group. R' may have a specified number of carbons (e.g. "$C_{1-4}$ alkylsulfonyl")

The term "monosaccharide" refers to a cyclized monomer unit based on a compound having a chemical structure $H(CHOH)_nC(=O)(CHOH)_mH$ wherein n+m is 4 or 5. Thus, monosaccharides include, but are not limited to, aldohexoses, aldopentoses, ketohexoses, and ketopentoses such as arabinose, lyxose, ribose, xylose, ribulose, xylulose, allose, altrose, galactose, glucose, gulose, idose, mannose, talose, fructose, psicose, sorbose, and tagatose.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

General. All commercially available starting materials and solvents were reagent grade and used without further purification. Reactions were performed under a nitrogen atmosphere in dry glassware with magnetic stirring. Preparative column chromatography was performed using silica gel 60, particle size 0.063-0.200 mm (70-230 mesh, flash). Analytical TLC was carried out employing silica gel 60 F254 plates (Merck, Darmstadt). Visualization of the developed chromatograms was performed with detection by UV (254 nm). NMR spectra were recorded on a Bruker-600 ($^1$H, 300 MHz; $^{13}$C, 75 MHz) spectrometer. $^1$H and $^{13}$C NMR spectra were recorded with TMS as an internal reference. Chemical shifts downfield from TMS were expressed in ppm, and J values were given in Hz. High-resolution mass spectra (HRMS) were obtained from Thermo Fisher LTQ Orbitrap Elite mass spectrometer. Parameters include the following: nano ESI spray voltage was 1.8 kV, capillary temperature was 275° C., and the resolution was 60000; ionization was achieved by positive mode. Purity of final compounds was determined by analytical HPLC, which was carried out on a Shimadzu HPLC system (model: CBM-20A LC-20AD SPD-20A UV/vis). HPLC analysis conditions: Waters µBondapak C18 (300 mm×3.9 mm), flow rate 0.5 mL/min, UV detection at 270 and 254 nm, linear gradient from 10% acetonitrile in water (0.1% TFA) to 100% acetonitrile (0.1% TFA) in 20 min, followed by 30 min of the last-named solvent. Compound 4 and 6 were resynthesized in-house following reported synthetic procedures.[17, 23] All biologically evaluated compounds are >95% pure.

Methyl 1-(2-chloropyrimidin-4-yl)indoline-4-carboxylate (8a). To a solution of 6 (354 mg, 2 mmol) and 2,4-dichloropyrimidine (7a) (300 mg, 2 mmol) in EtOH (5 mL) was added DIPEA (387 mg, 3 mmol) at rt, and the mixture solution was stirred at rt overnight. After the reaction completed (detected by TLC), the white solid was filtered and washed with water and cold EtOH. The cake was collected and dried to afford the product as a white solid 8a (387 mg, 67%). $^1$H NMR (300 MHz, DMSO-$d_6$) δ 8.53 (d, J=8.1 Hz, 1H), 8.34 (d, J=6.0 Hz, 1H), 7.57 (d, J=7.8 Hz, 1H), 7.40 (t, J=8.0 Hz, 1H), 6.87 (d, J=6.1 Hz, 1H), 4.08 (t, J=8.6 Hz, 2H), 3.85 (s, 3H), 3.50 (t, J=8.6 Hz, 2H).

Methyl 1-(5-chloropyridazin-3-yl)indoline-4-carboxylate (8b). Compound 8b (364 mg, 63%) was synthesized by a procedure similar to that used to prepare compound 8a as a light yellow solid. $^1$H NMR (300 MHz, DMSO-$d_6$) δ 8.89 (s, 1H), 8.68 (d, J=8.2 Hz, 1H), 7.55-7.47 (m, 2H), 7.37 (s, 1H), 4.11 (t, J=8.7 Hz, 2H), 3.86 (s, 3H), 3.53 (t, J=8.7 Hz, 2H).

Methyl 1-(6-chloropyrimidin-4-yl)indoline-4-carboxylate (8c). Compound 8c (370 mg, 64%) was synthesized by a procedure similar to that used to prepare compound 8a as a white solid. $^1$H NMR (300 MHz, DMSO-$d_6$) δ 8.69 (dd, J=8.2, 1.1 Hz, 1H), 8.61 (d, J=0.8 Hz, 1H), 7.56 (dd, J=7.9, 1.0 Hz, 1H), 7.37 (t, J=8.0 Hz, 1H), 6.97 (d, J=0.9 Hz, 1H), 4.07 (t, J=8.5 Hz, 2H), 3.85 (s, 3H), 3.50 (t, J=8.5 Hz, 2H).

Methyl 1-(2-(cyano(3-fluoro-5-(trifluoromethyl)phenyl)methyl)pyrimidin-4-yl)indoline-4-carboxylate (10a). 2-(3-Fluoro-5-(trifluoromethyl)phenyl)acetonitrile (9a) (336 mg, 1.6 mmol) was dissolved in 5 mL DMF and the mixture solution was cooled to 0° C. with ice bath. NaH (141 mg, 3.5 mmol) was added to the solution at 0° C., and the mixture solution was stirred at 0° C. for 30 min. Then 8a (480 mg, 1.6 mmol) was added to the solution at 0° C., and the mixture solution was stirred at rt for 2 h. After the reaction completed (detected by TLC), the reaction was quenched with NH$_4$Cl$_{(sat.\ aq.)}$. The solution was worked up by the addition of water and then extracted with EtOAc (20 mL×3). The combined EtOAc extracts were washed with brine, dried Na$_2$SO$_4$, filtered, and condensed by rotary evaporation to yield a yellow oil. The residue was purification by silica gel chromatography (Gradient: 1% to 5% MeOH in CH$_2$Cl$_2$) provided product 10a (300 mg, 66%) as a yellow solid. $^1$H NMR (300 MHz, Chloroform-d) δ 8.67 (d, J=8.3 Hz, 1H), 8.40 (d, J=6.1 Hz, 1H), 7.71 (dd, J=8.0, 1.0 Hz, 2H), 7.54 (dt, J=8.8, 2.0 Hz, 1H), 7.36 (t, J=8.0 Hz, 2H), 6.53 (d, J=6.1 Hz, 1H), 5.40 (s, 1H), 4.06 (dd, J=9.3, 7.8 Hz, 2H), 3.94 (s, 3H), 3.66 (t, J=8.5 Hz, 2H).

Methyl 1-(5-(cyano(3-fluoro-5-(trifluoromethyl)phenyl)methyl)pyridazin-3-yl)indoline-4-carboxylate (10b). Compound 10b (120 mg, 53%) was synthesized by a procedure similar to that used to prepare compound 10a as a yellow solid. $^1$H NMR (300 MHz, Chloroform-d) δ 8.74-8.62 (m, 2H), 7.66 (dd, J=7.9, 1.0 Hz, 1H), 7.48 (s, 1H), 7.43 (d, J=7.8 Hz, 1H), 7.33 (ddd, J=8.1, 4.9, 3.0 Hz, 2H), 7.01 (dd, J=1.9, 0.8 Hz, 1H), 5.25 (s, 1H), 4.14 (t, J=8.6 Hz, 2H), 3.94 (s, 3H), 3.69 (t, J=8.5 Hz, 2H).

Methyl 1-(6-(cyano(3-fluoro-5-(trifluoromethyl)phenyl)methyl)pyrimidin-4-yl)indoline-4-carboxylate (10c). Compound 10c (130 mg, 57%) was synthesized by a procedure similar to that used to prepare compound 10a as a yellow solid. $^1$H NMR (300 MHz, Chloroform-d) δ 8.83-8.70 (m, 2H), 7.71 (dd, J=7.9, 1.0 Hz, 1H), 7.60 (s, 1H), 7.48 (d, J=8.7 Hz, 1H), 7.36 (t, J=8.1 Hz, 2H), 6.80 (s, 1H), 5.22 (s, 1H), 4.19-4.07 (m, 2H), 3.95 (s, 3H), 3.69 (t, J=8.5 Hz, 2H).

1-(2-(3-Fluoro-5-(trifluoromethyl)benzyl)pyrimidin-4-yl)indoline-4-carboxylic acid (11a). To a solution of 10a (300 mg, 0.7 mmol) in con HCl (4 mL), H$_2$O (1 mL) and AcOH (1 mL), and the mixture solution was stirred at reflux overnight. The reaction was cooled to room temperature and yellow solid precipitated from the solution. The yellow solid was filtered and washed with water, and the cake was collected and dried to afford the product as a light yellow solid 11a (256 mg, 93%). $^1$H NMR (300 MHz, DMSO-$d_6$) δ 13.12 (s, 1H), 8.62-8.51 (m, 1H), 7.89 (d, J=8.3 Hz, 1H), 7.83-7.55 (m, 4H), 7.10-6.93 (m, 2H), 4.51 (s, 2H), 4.16 (t, J=8.4 Hz, 2H), 3.52 (t, J=8.3 Hz, 4H).

1-(5-(3-Fluoro-5-(trifluoromethyl)benzyl)pyridazin-3-yl)indoline-4-carboxylic acid (11b). Compound 11b (101 mg, 92%) was synthesized by a procedure similar to that used to prepare compound 11a as a white solid. $^1$H NMR (300 MHz, DMSO-$d_6$) δ 8.99 (d, J=1.4 Hz, 1H), 8.48 (d, J=8.1 Hz, 1H), 7.74-7.69 (m, 2H), 7.69-7.63 (m, 1H), 7.57 (dd, J=10.7, 7.6 Hz, 2H), 7.35 (d, J=8.0 Hz, 1H), 4.23 (s, 2H), 4.17 (t, J=8.5 Hz, 2H), 3.54 (s, 2H).

1-(6-(3-Fluoro-5-(trifluoromethyl)benzyl)pyrimidin-4-yl) indoline-4-carboxylic acid (11c). Compound 11c (100 mg, 91%) was synthesized by a procedure similar to that used to prepare compound 11a as a white solid. $^1$H NMR (300 MHz, DMSO-d$_6$) δ 8.92 (s, 1H), 8.71 (d, J=8.2 Hz, 1H), 7.73 (s, 1H), 7.71-7.65 (m, 2H), 7.62 (dd, J=8.8, 1.9 Hz, 1H), 7.43 (t, J=8.0 Hz, 1H), 7.21 (s, 1H), 4.28 (s, 2H), 4.21 (t, J=8.3 Hz, 2H), 3.59 (t, J=8.3 Hz, 2H).

1-(2-(3-Fuoro-5-(trifluoromethyl)benzyl)pyrimidin-4-yl)-N-(2-hydroxyethyl)indoline-4-carboxamide (12a). Compound 11a (42 mg, 0.1 mmol) and the 2-aminoethan-1-ol (13 mg, 0.2 mmol) were dissolved in 2 mL DMF and the mixture solution was cooled to 0° C. with ice bath. HOBt (14 mg, 0.1 mmol), EDCI (39 mg, 0.2 mmol) and DMAP (24 mg, 0.2 mmol) were added to the solution at 0° C. Then removed the ice bath, and the mixture solution was stirred at room temperature overnight. After the reaction completed (detected by TLC), the reaction was worked up by the addition of water and then extracted with EtOAc (20 mL×3). The combined EtOAc extracts were washed with brine, dried over Na$_2$SO$_4$, filtered, and condensed by rotary evaporation to yield a yellow oil. This material was further purified by preparative TLC plates using CH$_2$Cl$_2$/MeOH=50:1 as the eluent to yield 12a as a white solid (33 mg, 73%). $^1$H NMR (300 MHz, chloroform-d and MeOD) δ 8.26 (dd, J=6.3, 2.6 Hz, 1H), 8.14 (dd, J=7.9, 2.4 Hz, 1H), 7.45 (s, 1H), 7.29-7.04 (m, 5H), 6.39 (dd, J=6.5, 2.5 Hz, 1H), 4.20 (s, 2H), 3.93 (t, J=8.6 Hz, 2H), 3.71 (t, J=5.0 Hz, 2H), 3.48 (qd, J=8.7, 7.3, 2.6 Hz, 4H). $^{13}$C NMR (75 MHz, chloroform-d and MeOD) δ 168.9, 167.3, 159.0, 155.9, 144.1, 142.0, 132.4, 130.9, 127.5, 122.4-122.1 (m), 120.3, 120.0, 110.8 (d, J=24.5 Hz), 103.1, 61.2, 49.2, 45.0, 42.3, 27.5. HRMS (ESI) calcd for C$_{23}$H$_{21}$F$_4$N$_4$O$_2$ 461.1595 (M+H)+, found 461.1591.

1-(5-(3-Fluoro-5-(trifluoromethyl)benzyl)pyridazin-3-yl)-N-(2-hydroxyethyl)indoline-4-carboxamide (12b). Compound 12b (35 mg, 76%) was synthesized by a procedure similar to that used to prepare compound 12a as a white solid. $^1$H NMR (300 MHz, Methanol-d$_4$) δ 8.58 (s, 1H), 8.45 (dd, J=7.5, 1.7 Hz, 1H), 7.53 (s, 1H), 7.39 (tt, J=6.3, 2.0 Hz, 2H), 7.29-7.17 (m, 2H), 7.11 (d, J=1.6 Hz, 1H), 4.14 (s, 2H), 4.03 (t, J=8.6 Hz, 2H), 3.74 (t, J=5.8 Hz, 2H), 3.51 (t, J=5.8 Hz, 2H), 3.45 (t, J=8.6 Hz, 2H). $^{13}$C NMR (75 MHz, MeOD) δ 169.6, 164.4, 161.1, 144.6, 142.7 (d, J=7.7 Hz), 131.7, 131.6, 127.1, 121.6-121.4 (m), 119.7, 119.4, 116.7, 114.1, 111.1 (d, J=4.1 Hz), 111.0, 110.7 (d, J=4.0 Hz), 60.23, 48.81, 41.92, 37.30, 27.06. HRMS (ESI) calcd for C$_{23}$H$_{21}$F$_4$N$_4$O$_2$ 461.1595 (M+H)$^+$, found 461.1591.

1-(6-(3-Fluoro-5-(trifluoromethyl)benzyl)pyrimidin-4-yl)-N-(2-hydroxyethyl)indoline-4-carboxamide (12c). Compound 12c (38 mg, 83%) was synthesized by a procedure similar to that used to prepare compound 12a as a white solid. $^1$H NMR (300 MHz, chloroform-d) δ 8.70 (s, 1H), 8.57 (d, J=8.1 Hz, 1H), 7.37 (s, 1H), 7.30-7.16 (m, 3H), 7.10 (d, J=7.7 Hz, 1H), 6.71 (t, J=5.6 Hz, 1H), 6.33 (s, 1H), 4.04 (s, 2H), 3.91 (t, J=8.6 Hz, 2H), 3.83 (t, J=4.9 Hz, 2H), 3.60 (d, J=5.1 Hz, 2H), 3.49 (d, J=8.4 Hz, 3H). $^{13}$C NMR (75 MHz, CDCl$_3$) δ 168.6, 166.2, 164.2, 160.9, 159.4, 157.9, 144.5, 141.6, 132.5, 130.9, 127.8, 121.67, 120.0, 119.8, 119.5, 118.8, 111.6, 111.38 (d, J=24.8 Hz), 103.9, 62.1, 48.7, 43.7, 42.6, 27.6. HRMS (ESI) calcd for C$_{23}$H$_{21}$F$_4$N$_4$O$_2$ 461.1595 (M+H)$^+$, found 461.1591.

2-(2-Chloropyrimidin-4-yl)-2-(3-fluoro-5-(trifluoromethyl)phenyl)acetonitrile (13). 2-(3-Fluoro-5-(trifluoromethyl)phenyl)acetonitrile (9a) (406 mg, 2 mmol) was dissolved in 5 mL DMF and the mixture solution was cooled to 0° C. with ice bath. NaH (190 mg, 4.4 mmol) was added to the solution at 0° C., and the mixture solution was stirred at 0° C. for 30 min. Then 2,4-dichloropyrimidine (7a) (450 mg, 3 mmol) was added to the solution at 0° C., and the mixture solution was stirred at rt for 2 h. After the reaction completed (detected by TLC), the reaction mixture was worked up by the addition of water and then extracted with EtOAc (20 mL×3). The combined EtOAc extracts were washed with brine, dried over Na$_2$SO$_4$, filtered, and condensed by rotary evaporation to yield a yellow oil. The residue was purified by silica gel chromatography (Gradient: 10% to 20% EtOAc in hexane) to provide product 13 (460 mg, 73%) as a yellow oil. $^1$H NMR (300 MHz, Chloroform-d) δ 8.76 (d, J=5.0 Hz, 1H), 7.57 (s, 1H), 7.52 (d, J=5.0 Hz, 1H), 7.43 (ddd, J=14.3, 7.2, 1.8 Hz, 2H), 5.30 (s, 1H).

2-Chloro-4-(3-fluoro-5-(trifluoromethyl)benzyl)pyrimidine (14). To a solution of 13 (460 mg, 1.5 mmol) in con. HCl (4 mL), H$_2$O (1 mL) and AcOH (1 mL), and the mixture solution was stirred at reflux overnight. The reaction was cooled to room temperature and yellow solid precipitated from the solution. The yellow solid was filtered and washed with water, and the cake was collected and dried to afford the product as a light yellow solid. The yellow solid was dissolved in 2 mL of POCl$_3$ and the mixture solution was stirred at reflux overnight. The reaction was cooled to room temperature. After the reaction completed (detected by TLC), the reaction was poured into ice water, and the pH of the mixture solution was adjusted to pH=8 with Na$_2$CO$_3$ $_{(sat.\ aq.)}$ solution. The solution was extracted with EtOAc (20 mL×3). The organic phase was washed with brine, dried over Na$_2$SO$_4$, and then concentrated under reduced pressure. The residue was purified by silica gel chromatography (Gradient: 10% to 20% EtOAc in hexane) to provide product 14 as a brown colorless oil (222 mg, 51% for two steps). $^1$H NMR (300 MHz, chloroform-d) δ 8.57 (d, J=5.0 Hz, 1H), 7.36 (s, 1H), 7.30-7.26 (m, 1H), 7.22 (dd, J=8.8, 1.9 Hz, 1H), 7.09 (d, J=5.0 Hz, 1H), 4.17 (s, 2H).

Methyl 1-(4-(3-fluoro-5-(trifluoromethyl)benzyl)pyrimidin-2-yl)indoline-4-carboxylate (15). A mixture of 14 (145 mg, 0.5 mmol), Pd(OAc)$_2$ (6 mg, 0.025 mmol), XantPhos (29 mg, 0.05 mmol), Cs$_2$CO$_3$ (325 mg, 1 mmol) and 6 (89 mg, 0.5 mmol) in 1,4-dioxane (3 mL) was subjected to three rounds of vacuum evacuation followed by introduction of nitrogen. The reaction mixture was then stirred at 100° C. overnight. The reaction was cooled to room temperature and poured in water, and then extracted with EtOAc (10 mL×3). The organic phase was washed with brine, dried over Na$_2$SO$_4$, and then concentrated under reduced pressure. The residue was purified by silica gel chromatography (Gradient: 10% to 20% EtOAc in hexane) to provide product 15 (120 mg, 56%) as a yellow solid. $^1$H NMR (300 MHz, Chloroform-d) δ 8.52-8.42 (m, 2H), 7.60 (dd, J=7.8, 1.1 Hz, 1H), 7.45 (s, 1H), 7.26 (dd, J=8.4, 3.5 Hz, 3H), 6.62 (d, J=5.0 Hz, 1H), 4.28 (dd, J=9.3, 8.2 Hz, 2H), 4.10 (s, 2H), 3.93 (s, 3H), 3.60-3.53 (m, 2H).

1-(4-(3-Fluoro-5-(trifluoromethyl)benzyl)pyrimidin-2-yl) indoline-4-carboxylic acid (16). To a solution of 14 (120 mg, 0.28 mmol) in MeOH (4 mL) was added a 2 N solution of NaOH (1 mL), and the mixture solution was stirred at reflux for 1 h. The pH of the mixture solution was adjusted to pH=1 with 2 N HCl solution, and then yellow solid precipitated from the solution. The yellow solid was filtered and washed with water, and the cake was collected and dried to afford the product as a light yellow solid 16 (110 mg, 95%). $^1$H NMR (300 MHz, DMSO-d$_6$) δ 8.51 (d, J=5.0 Hz, 1H), 8.23 (d, J=8.1 Hz, 1H), 7.67 (s, 1H), 7.59 (dt, J=9.5, 2.0 Hz, 2H), 7.44 (dd, J=7.8, 1.1 Hz, 1H), 7.13 (t, J=8.0 Hz, 1H), 6.91 (d, J=5.0 Hz, 1H), 4.23 (s, 2H), 4.14 (t, J=8.7 Hz, 2H), 3.43 (t, J=8.6 Hz, 2H).

1-(4-(3-Fluoro-5-(trifluoromethyl)benzyl)pyrimidin-2-yl)-N-(2-hydroxyethyl)indoline-4-carboxamide (12d). Compound 12d (92 mg, 83%) was synthesized by a procedure similar to that used to prepare compound 12a as a white solid. $^1$H NMR (300 MHz, chloroform-d) δ 8.37 (d, J=5.0 Hz, 1H), 8.30 (dd, J=7.4, 1.5 Hz, 1H), 7.43 (s, 1H), 7.24 (dd, J=8.9, 1.4 Hz, 2H), 7.16-7.05 (m, 2H), 6.77 (t, J=5.6 Hz, 1H), 6.57 (d, J=5.0 Hz, 1H), 4.17 (t, J=8.7 Hz, 2H), 4.05 (s, 2H), 3.81 (t, J=4.9 Hz, 2H), 3.58 (d, J=5.1 Hz, 2H), 3.40 (q, J=9.6, 8.7 Hz, 3H). $^{13}$C NMR (75 MHz, CDCl$_3$) δ 169.2, 167.6, 164.1, 160.8, 159.0, 157.9, 144.6, 141.7 (d, J=7.7 Hz), 132.6, 130.8, 127.5, 122.1 (dd, J=7.1, 3.5 Hz), 120.1, 119.8, 119.2, 117.6, 111.3 (q, J=3.9 Hz), 111.0 (q, J=3.8 Hz), 110.6, 62.1, 49.0, 43.5, 42.6, 27.3. HRMS (ESI) calcd for C$_{23}$H$_{21}$F$_4$N$_4$O$_2$ 461.1595 (M+H)$^+$, found 461.1591.

2-(3-Fluoro-5-(trifluoromethyl)phenyl)-2-(5-methyl-6-oxo-1-(tetrahydro-2H-pyran-2-yl)-1,6-dihydropyridazin-4-yl)acetonitrile (17a). Compound 17a (150 mg, 36%) was synthesized by a procedure similar to that used to prepare compound 10a as a yellow oil. $^1$H NMR (300 MHz, chloroform-d) δ 7.75 (d, J=8.8 Hz, 1H), 7.46-7.37 (m, 2H), 7.27 (dt, J=8.5, 2.3 Hz, 1H), 6.06 (dt, J=10.6, 1.9 Hz, 1H), 5.30 (d, J=6.2 Hz, 1H), 4.17-4.09 (m, 1H), 3.75 (ddd, J=11.7, 9.0, 2.7 Hz, 1H), 2.18 (dd, J=10.7, 4.2 Hz, 1H), 1.85-1.58 (m, 4H).

2-(5-Chloro-6-oxo-1-(tetrahydro-2H-pyran-2-yl)-1,6-dihydropyridazin-4-yl)-2-(3-fluoro-5-(trifluoromethyl)phenyl)acetonitrile (17b). Compound 17b (520 mg, 63%) was synthesized by a procedure similar to that used to prepare compound 10a as a yellow oil. $^1$H NMR (300 MHz, chloroform-d) δ 7.90 (d, J=6.1 Hz, 1H), 7.51 (s, 1H), 7.43 (d, J=8.0 Hz, 1H), 7.39-7.33 (m, 1H), 6.07 (dt, J=10.6, 2.7 Hz, 1H), 5.59 (d, J=6.9 Hz, 1H), 4.13 (td, J=6.9, 3.2 Hz, 1H), 3.77 (ddd, J=11.5, 8.7, 3.0 Hz, 1H), 2.24-2.06 (m, 2H), 1.87-1.62 (m, 4H).

5-(3-Fluoro-5-(trifluoromethyl)benzyl)-4-methylpyridazin-3(2H)-one (18a). To a solution of 17a (830 mg, 2 mmol) in con HCl (8 mL), H$_2$O (2 mL) and AcOH (2 mL), and the mixture solution was stirred at reflux overnight. After the reaction completed (detected by TLC), the reaction was poured into ice water. The pH of the mixture solution was adjusted to pH=8 with Na$_2$CO$_{3(sat. aq.)}$ solution. Then the solution was extracted with EtOAc (20 mL×3). The organic phase was washed with brine, dried over Na$_2$SO$_4$, and then concentrated under reduced pressure. The residue purification by silica gel chromatography (Gradient: 30% to 50% EtOAc in hexane) provided product 18a (480 mg, 78%) as a white solid. $^1$H NMR (300 MHz, Chloroform-d) δ 11.67 (s, 1H), 7.58 (s, 1H), 7.25 (d, J=7.0 Hz, 2H), 7.07-6.99 (m, 1H), 3.97 (s, 2H), 2.23 (s, 3H).

4-Chloro-5-(3-fluoro-5-(trifluoromethyl)benzyl) pyridazin-3(2H)-one (18b). Compound 18b (410 mg, 83%) was synthesized by a procedure similar to that used to prepare compound 18a as a yellow oil. $^1$H NMR (300 MHz, Chloroform-d) δ 7.65 (s, 1H), 7.38-7.23 (m, 3H), 7.17-7.10 (m, 1H), 4.12 (s, 2H).

3-Chloro-5-(3-fluoro-5-(trifluoromethyl)benzyl)-4-methylpyridazine (19a). A solution of 18a (400 mg, 1.3 mmol) in POCl$_3$ (3 mL) was heated to reflux for 3 h. After the reaction completed (detected by TLC), the reaction was cooled to room temperature and poured in ice water. The pH of the mixture solution was adjusted to pH=8 with 2 N NaOH solution and then extracted with EtOAc (30 mL×3). The organic phase was washed with brine, dried over Na$_2$SO$_4$, and then concentrated under reduced pressure. The residue purification by silica gel chromatography (Gradient: 10% to 20% EtOAc in hexane) provided product 19a (350 mg, 83%) as a brown solid. $^1$H NMR (300 MHz, Chloroform-d) δ 8.83 (s, 1H), 7.29 (d, J=9.7 Hz, 2H), 7.22 (s, 1H), 6.99 (d, J=8.8 Hz, 1H), 4.12 (s, 2H), 2.39 (s, 3H).

3,4-Dichloro-5-(3-fluoro-5-(trifluoromethyl)benzyl) pyridazine (19b). Compound 19b (350 mg, 80%) was synthesized by a procedure similar to that used to prepare compound 19a as a brown solid. $^1$H NMR (300 MHz, Chloroform-d) δ 8.87 (s, 1H), 7.35-7.29 (m, 2H), 7.16-7.06 (m, 1H), 4.23 (s, 2H).

Methyl 1-(5-(3-fluoro-5-(trifluoromethyl)benzyl)-4-methylpyridazin-3-yl)indoline-4-carboxylate (20a). Compound 20a (142 mg, 64%) was synthesized by a procedure similar to that used to prepare compound 15 as a brown solid. $^1$H NMR (300 MHz, chloroform-d) δ 8.76 (s, 1H), 7.50 (dd, J=7.9, 0.9 Hz, 1H), 7.27 (d, J=7.9 Hz, 4H), 7.10 (q, J=9.6, 8.7 Hz, 2H), 6.46 (d, J=7.8 Hz, 1H), 4.27 (t, J=8.2 Hz, 2H), 4.13 (s, 2H), 3.94 (s, 3H), 3.57 (t, J=8.2 Hz, 2H), 2.18 (s, 3H).

Methyl 1-(4-chloro-5-(3-fluoro-5-(trifluoromethyl)benzyl)pyridazin-3-yl)indoline-4-carboxylate (20b). Compound 20b (280 mg, 60%) was synthesized by a procedure similar to that used to prepare compound 15 as a white solid. $^1$H NMR (300 MHz, chloroform-d) δ 8.71 (s, 1H), 7.59 (dd, J=7.9, 1.0 Hz, 1H), 7.37-7.29 (m, 2H), 7.25-7.12 (m, 2H), 7.00 (dd, J=8.0, 0.9 Hz, 1H), 4.34 (t, J=8.3 Hz, 2H), 4.23 (s, 2H), 3.94 (s, 3H), 3.60 (t, J=8.3 Hz, 2H).

1-(5-(3-Fluoro-5-(trifluoromethyl)benzyl)-4-methylpyridazin-3-yl)indoline-4-carboxylic acid (21a). Compound 21a (126 mg, 92%) was synthesized by a procedure similar to that used to prepare compound 16 as a yellow solid. $^1$H NMR (300 MHz, DMSO-d$_6$) δ 8.91 (d, J=1.8 Hz, 1H), 7.66-7.47 (m, 3H), 7.38 (d, J=7.9 Hz, 1H), 7.14 (t, J=7.9 Hz, 1H), 6.64 (d, J=7.9 Hz, 1H), 4.29 (s, 2H), 4.12 (t, J=8.3 Hz, 2H), 3.45 (t, J=8.0 Hz, 2H), 2.20 (d, J=1.9 Hz, 3H).

1-(4-Chloro-5-(3-fluoro-5-(trifluoromethyl)benzyl) pyridazin-3-yl)indoline-4-carboxylic acid (21b). Compound 21a (243 mg, 90%) was synthesized by a procedure similar to that used to prepare compound 16 as a yellow solid. $^1$H NMR (300 MHz, DMSO-d$_6$) δ 9.00 (s, 1H), 7.65-7.51 (m, 3H), 7.44 (dd, J=7.8, 1.0 Hz, 1H), 7.18 (t, J=7.9 Hz, 1H), 6.95 (dd, J=8.0, 1.0 Hz, 1H), 4.34 (s, 2H), 4.21 (t, J=8.3 Hz, 4H), 3.46 (t, J=8.2 Hz, 2H).

1-(5-(3-Fluoro-5-(trifluoromethyl)benzyl)-4-methylpyridazin-3-yl)-N-(2-hydroxyethyl)indoline-4-carboxamide (12e). Compound 12e (107 mg, 79%) was synthesized by a procedure similar to that used to prepare compound 12a as a white solid. $^1$H NMR (300 MHz, chloroform-d) δ 8.71 (s, 1H), 7.29 (d, J=9.7 Hz, 1H), 7.24 (s, 1H), 7.07 (d, J=9.0 Hz, 1H), 7.02-6.84 (m, 3H), 6.29 (dd, J=5.4, 3.4 Hz, 1H), 4.25-4.08 (m, 4H), 3.86 (t, J=4.8 Hz, 2H), 3.63 (q, J=5.1 Hz, 2H), 3.43 (t, J=8.1 Hz, 3H), 2.15 (s, 3H). $^{13}$C NMR (75 MHz, CDCl$_3$) δ 168.9, 158.9, 149.1, 147.8, 140.9 (d, J=7.3 Hz), 138.7, 132.0, 131.8, 131.2, 126.8, 121.0 (t, J=3.3 Hz), 119.3, 119.0, 118.4, 111.9, 62.1, 53.6, 42.8, 36.0, 28.8, 14.5. HRMS (ESI) calcd for C$_{24}$H$_{23}$F$_4$N$_4$O$_2$ 475.1752 (M+H)$^+$, found 475.1748.

1-(4-Chloro-5-(3-fluoro-5-(trifluoromethyl)benzyl) pyridazin-3-yl)-N-(2-hydroxyethyl)indoline-4-carboxamide (12f). Compound 12f (29 mg, 59%) was synthesized by a procedure similar to that used to prepare compound 12a as a white solid. $^1$H NMR (300 MHz, Chloroform-d) δ 8.66 (s, 1H), 7.36-7.24 (m, 2H), 7.14 (d, J=9.0 Hz, 1H), 7.11-7.02 (m, 2H), 6.89 (dd, J=6.4, 3.6 Hz, 2H), 4.34-4.15 (m, 4H), 3.81 (t, J=4.9 Hz, 2H), 3.60 (t, J=5.1 Hz, 2H), 3.47 (t, J=8.2 Hz, 2H). $^{13}$C NMR (75 MHz, CDCl$_3$) δ 168.8, 164.4, 161.0, 156.8, 148.2, 146.2, 139.9 (d, J=7.4 Hz), 138.7, 132.1, 131.6, 130.2, 126.8, 121.5-121.4 (m), 119.6, 119.4, 119.3, 115.3, 112.2 (d, J=3.6 Hz), 111.9 (d, J=3.9 Hz), 62.1, 53.6, 42.7, 36.1, 29.1. HRMS (ESI) calcd for C$_{23}$H$_{20}$ClF$_4$N$_4$O$_2$ 495.1205 (M+H)$^+$, found 495.1201.

1-(6-(3-(Trifluoromethyl)benzyl)pyrimidin-4-yl)indoline-4-carboxylic acid (22a). 2-(3-(Trifluoromethyl)phenyl)acetonitrile (9b) (370 mg, 2 mmol) was dissolved in 5 mL DMF and the mixture solution was cooled to 0° C. with ice bath. NaH (176 mg, 4.4 mmol) was added to the solution at 0° C., and the mixture solution was stirred at 0° C. for 30 min. Then 8c (580 mg, 2 mmol) was added to the solution at 0° C., and the mixture solution was stirred at rt for 2 h. After the reaction completed (detected by TLC), the reaction mixture was worked up by the addition of water and then extracted with EtOAc (20 mL×3). The combined EtOAc extracts were washed with brine, dried over Na$_2$SO$_4$, filtered, and condensed by rotary evaporation to yield a yellow solid. $^1$H NMR (300 MHz, DMSO-d$_6$) δ 8.75 (s, 1H), 8.67 (d, J=8.0 Hz, 1H), 7.93-7.85 (m, 2H), 7.77 (d, J=7.9 Hz, 1H), 7.71 (d, J=7.7 Hz, 1H), 7.54 (dd, J=7.9, 1.0 Hz, 1H), 7.35 (t, J=7.9 Hz, 1H), 7.07 (s, 1H), 6.00 (s, 1H), 4.08 (dd, J=8.8, 2.0 Hz, 2H), 3.85 (s, 3H), 3.51 (t, J=8.6 Hz, 2H).

To a solution of the yellow solid (100 mg, 0.23 mmol) in con. HCl (2 mL), H$_2$O (0.5 mL) and AcOH (0.5 mL), and the mixture solution was stirred at reflux overnight. The reaction was cooled to room temperature and yellow solid precipitated from the solution. The yellow solid was filtered and washed with water, and the cake was collected and dried to afford the product as a light yellow solid 22a (82 mg, 90% for two steps). $^1$H NMR (300 MHz, DMSO-d$_6$) δ 8.86 (s, 1H), 8.70 (d, J=8.1 Hz, 1H), 7.81 (s, 1H), 7.73 (d, J=7.5 Hz, 1H), 7.68-7.53 (m, 3H), 7.40 (t, J=8.0 Hz, 1H), 7.13 (s, 1H), 4.26-4.11 (m, 4H), 3.57 (t, J=8.4 Hz, 2H).

1-(6-(2-(Trifluoromethyl)benzyl)pyrimidin-4-yl)indoline-4-carboxylic acid (22b). Compound 22b (65 mg, 54% for two steps) was synthesized by a procedure similar to that used to prepare compound 22a as a white solid. $^1$H NMR (300 MHz, DMSO-d$_6$) δ 8.86 (s, 1H), 8.70 (d, J=8.1 Hz, 1H), 7.79 (d, J=7.7 Hz, 1H), 7.64 (dd, J=10.4, 7.6 Hz, 2H), 7.55 (d, J=7.4 Hz, 1H), 7.46 (d, J=7.8 Hz, 1H), 7.40 (d, J=8.1 Hz, 1H), 6.77 (s, 1H), 4.32 (s, 2H), 4.07 (t, J=8.4 Hz, 2H), 3.53 (t, J=8.4 Hz, 2H).

1-(6-(4-(Trifluoromethyl)benzyl)pyrimidin-4-yl)indoline-4-carboxylic acid (22c). Compound 22c (68 mg, 57% for two steps) was synthesized by a procedure similar to that used to prepare compound 22a as a white solid. $^1$H NMR (300 MHz, DMSO-d$_6$) δ 8.82 (s, 1H), 8.69-8.66 (m, 1H), 7.71 (d, J=8.1 Hz, 2H), 7.64-7.59 (m, 3H), 7.40 (d, J=8.2 Hz, 1H), 7.08 (s, 1H), 4.19-4.12 (m, 4H), 3.54 (d, J=8.7 Hz, 2H).

1-(6-(3-Methylbenzyl)pyrimidin-4-yl)indoline-4-carboxylic acid (22d). Compound 22d (86 mg, 83% for two steps) was synthesized by a procedure similar to that used to prepare compound 22a as a white solid. $^1$H NMR (300 MHz, DMSO-d$_6$) δ 8.86 (s, 1H), 8.70 (d, J=8.1 Hz, 1H), 7.81 (s, 1H), 7.73 (d, J=7.5 Hz, 1H), 7.68-7.53 (m, 3H), 7.40 (t, J=8.0 Hz, 1H), 7.13 (s, 1H), 4.26-4.11 (m, 4H), 3.57 (t, J=8.4 Hz, 2H), 2.49 (s, 3H).

1-(6-(3-Fluorobenzyl)pyrimidin-4-yl)indoline-4-carboxylic acid (22e). Compound 22e (71 mg, 68% for two steps) was synthesized by a procedure similar to that used to prepare compound 22a as a white solid. $^1$H NMR (300 MHz, DMSO-d$_6$) δ 8.91 (s, 1H), 8.71 (d, J=8.5 Hz, 1H), 7.67 (d, J=7.8 Hz, 1H), 7.47-7.38 (m, 2H), 7.31-7.23 (m, 2H), 7.16-7.06 (m, 2H), 4.24-4.13 (m, 4H), 3.58 (t, J=8.4 Hz, 2H).

1-(6-(3,5-Dimethylbenzyl)pyrimidin-4-yl)indoline-4-carboxylic acid (22f). Compound 22f (88 mg, 81% for two steps) was synthesized by a procedure similar to that used to prepare compound 22a as a white solid. $^1$H NMR (300 MHz, DMSO-d$_6$) δ 8.95 (s, 1H), 8.74 (d, J=5.7 Hz, 1H), 7.71 (d, J=7.7 Hz, 1H), 7.58 (s, 1H), 7.43 (d, J=8.3 Hz, 1H), 7.17 (s, 1H), 7.02 (s, 2H), 4.24 (d, J=8.1 Hz, 2H), 4.08 (s, 2H), 3.60 (d, J=8.4 Hz, 2H), 2.25 (s, 6H).

1-(6-(3,5-Difluorobenzyl)pyrimidin-4-yl)indoline-4-carboxylic acid (22g). Compound 22g (79 mg, 72% for two steps) was synthesized by a procedure similar to that used to prepare compound 22a as a white solid. $^1$H NMR (300 MHz, DMSO-d$_6$) δ 8.93 (s, 1H), 8.72 (d, J=8.2 Hz, 1H), 7.69 (d, J=7.6 Hz, 1H), 7.43 (t, J=8.0 Hz, 1H), 7.29-7.11 (m, 4H), 4.20 (d, J=8.3 Hz, 4H), 3.58 (t, J=8.3 Hz, 2H).

1-(6-(3-(Trifluoromethoxy)benzyl)pyrimidin-4-yl)indoline-4-carboxylic acid (22h). Compound 22h (87 mg, 70% for two steps) was synthesized by a procedure similar to that used to prepare compound 22a as a white solid. $^1$H NMR (300 MHz, DMSO-d$_6$) δ 8.95 (s, 1H), 8.71 (d, J=8.1 Hz, 1H), 7.69 (d, J=7.7 Hz, 1H), 7.50 (d, J=4.7 Hz, 3H), 7.43 (t, J=8.0 Hz, 1H), 7.33-7.27 (m, 1H), 7.20 (s, 1H), 4.25-4.16 (m, 4H), 3.58 (t, J=8.1 Hz, 2H).

1-(6-(3-Methoxybenzyl)pyrimidin-4-yl)indoline-4-carboxylic acid (22i). Compound 22i (90 mg, 83% for two steps) was synthesized by a procedure similar to that used to prepare compound 22a as a white solid. $^1$H NMR (300 MHz, DMSO-d$_6$) δ 8.89 (s, 1H), 8.70 (d, J=8.0 Hz, 1H), 7.66 (dt, J=7.8, 1.2 Hz, 2H), 7.45-7.38 (m, 2H), 7.13 (t, J=7.8 Hz, 1H), 7.08 (d, J=7.1 Hz, 1H), 6.79 (d, J=2.0 Hz, 1H), 4.13-4.04 (m, 4H), 3.75 (s, 3H), 3.58 (d, J=8.2 Hz, 2H).

1-(6-(3,5-Dimethoxybenzyl)pyrimidin-4-yl)indoline-4-carboxylic acid (22j). Compound 22j (94 mg, 80% for two steps) was synthesized by a procedure similar to that used to prepare compound 22a as a white solid. $^1$H NMR (300 MHz, DMSO-d$_6$) δ 13.12 (s, 1H), 8.94 (s, 1H), 8.71 (d, J=8.3 Hz, 1H), 7.69 (d, J=7.7 Hz, 1H), 7.43 (t, J=8.1 Hz, 1H), 7.15 (d, J=9.7 Hz, 1H), 6.44 (d, J=19.6 Hz, 2H), 6.24 (d, J=11.6 Hz, 1H), 4.20 (t, J=8.4 Hz, 2H), 4.02 (s, 2H), 3.71 (d, J=14.4 Hz, 6H), 3.58 (t, J=8.2 Hz, 2H).

1-(6-Benzylpyrimidin-4-yl)indoline-4-carboxylic acid (22k). Compound 22k (76 mg, 77% for two steps) was synthesized by a procedure similar to that used to prepare compound 22a as a white solid. $^1$H NMR (300 MHz, DMSO-d$_6$) δ 13.19 (s, 1H), 8.96 (s, 1H), 8.71 (d, J=8.2 Hz, 1H), 7.70 (dd, J=7.9, 1.0 Hz, 1H), 7.48-7.42 (m, 2H), 7.41-7.27 (m, 3H), 7.17 (s, 1H), 4.25-4.16 (m, 4H), 3.57 (t, J=8.2 Hz, 2H).

N-(2-Hydroxyethyl)-1-(6-(3-(trifluoromethyl)benzyl)pyrimidin-4-yl)indoline-4-carboxamide (23a). Compound 23a (52 mg, 59%) was synthesized by a procedure similar to that used to prepare compound 12a as a white solid. $^1$H NMR (300 MHz, Chloroform-d and MeOD) δ 8.62 (s, 1H), 8.48 (d, J=7.6 Hz, 1H), 7.52-7.37 (m, 4H), 7.21-7.09 (m, 2H), 6.32 (s, 1H), 4.01 (s, 2H), 3.87 (t, J=8.6 Hz, 2H), 3.70 (t, J=5.2 Hz, 2H), 3.53-3.37 (m, 4H). $^{13}$C NMR (75 MHz, CDCl$_3$ and MeOD) δ 168.8, 166.7, 159.4, 157.5, 144.2, 138.6, 132.5, 132.4, 131.1 (d, J=5.2 Hz), 131.0, 129.2, 127.7, 125.9-125.6 (m), 123.7 (d, J=3.9 Hz), 120.3, 118.6, 103.9, 61.1, 48.7, 43.5, 42.2, 27.4. HRMS (ESI) calcd for C$_{23}$H$_{22}$F$_3$N$_4$O$_2$ 443.1689 (M+H)$^+$, found 443.1685.

N-(2-Hydroxyethyl)-1-(6-(2-(trifluoromethyl)benzyl)pyrimidin-4-yl)indoline-4-carboxamide (23b). Compound 23b (36 mg, 61%) was synthesized by a procedure similar to that used to prepare compound 12a as a white solid. $^1$H NMR (300 MHz, chloroform-d and MeOD) δ 8.65 (s, 1H), 8.48 (d, J=7.8 Hz, 1H), 7.66 (d, J=7.8 Hz, 1H), 7.49 (t, J=7.6 Hz, 1H), 7.34 (d, J=8.1 Hz, 2H), 7.21 (ddd, J=28.3, 13.0, 6.8 Hz, 3H), 6.19 (s, 1H), 4.18 (s, 2H), 3.83 (t, J=8.5 Hz, 2H), 3.70 (t, J=5.3 Hz, 2H), 3.53-3.39 (m, 4H). $^{13}$C NMR (75 MHz, CDCl$_3$ and MeOD) δ 168.9, 166.9, 159.4, 157.3, 144.3, 135.7, 132.4, 132.1, 131.0, 127.7, 127.1, 126.2 (d, J=5.6 Hz), 120.2, 118.5, 104.0, 61.1, 48.6, 42.3, 40.1, 27.4. HRMS (ESI) calcd for C$_{23}$H$_{22}$F$_3$N$_4$O$_2$ 443.1689 (M+H)$^+$, found 443.1685.

N-(2-Hydroxyethyl)-1-(6-(4-(trifluoromethyl)benzyl)pyrimidin-4-yl)indoline-4-carboxamide (23c). Compound 23c (31 mg, 53%) was synthesized by a procedure similar to that used to prepare compound 12a as a white solid. $^1$H NMR (300 MHz, Chloroform-d and MeOD) δ 8.65 (s, 1H), 8.52 (d, J=7.8 Hz, 1H), 7.55 (d, J=7.9 Hz, 2H), 7.38 (d, J=7.9 Hz, 2H), 7.27-7.12 (m, 3H), 6.35 (s, 1H), 4.03 (s, 2H), 3.91 (t, J=8.6 Hz, 2H), 3.72 (t, J=5.2 Hz, 2H), 3.56-3.41 (m, 4H). $^{13}$C NMR (75 MHz, CDCl$_3$ and MeOD) δ 168.9, 166.8, 159.4, 157.5, 144.3, 141.8, 132.4, 131.0, 129.4, 127.7, 125.6 (q, J=3.7 Hz), 120.3, 118.6, 104.0, 61.2, 48.7, 43.6, 42.3, 27.5. HRMS (ESI) calcd for C$_{23}$H$_{22}$F$_3$N$_4$O$_2$ 443.1689 (M+H)$^+$, found 443.1685.

N-(2-Hydroxyethyl)-1-(6-(3-methylbenzyl)pyrimidin-4-yl)indoline-4-carboxamide (23d). Compound 23d (43 mg, 83%) was synthesized by a procedure similar to that used to prepare compound 12a as a white solid. $^1$H NMR (300 MHz, chloroform-d and MeOD) δ 8.63 (s, 1H), 8.49 (d, J=7.9 Hz, 1H), 7.34-7.09 (m, 4H), 7.03 (d, J=7.7 Hz, 3H), 6.33 (s, 1H), 3.99-3.82 (m, 4H), 3.71 (t, J=5.1 Hz, 2H), 3.56-3.34 (m, 5H), 2.30 (s, 3H). $^{13}$C NMR (75 MHz, CDCl$_3$ and MeOD) δ 168.9, 168.1, 159.4, 157.3, 144.4, 138.3, 137.5, 132.4, 131.0, 129.8, 128.6, 127.7, 127.5, 126.1, 120.2, 118.5, 103.9, 61.2, 49.1, 43.8, 42.2, 27.4, 21.2. HRMS (ESI) calcd for C$_{23}$H$_{25}$N$_4$O$_2$ 389.1972 (M+H)$^+$, found 389.1968.

1-(6-(3-Fluorobenzyl)pyrimidin-4-yl)-N-(2-hydroxyethyl)indoline-4-carboxamide (23e). Compound 23e (38 mg, 72%) was synthesized by a procedure similar to that used to prepare compound 12a as a white solid. $^1$H NMR (300 MHz, chloroform-d and MeOD) δ 8.68-8.57 (m, 1H), 8.51 (d, J=7.8 Hz, 1H), 7.32-7.11 (m, 4H), 7.02 (d, J=7.7 Hz, 1H), 6.98-6.86 (m, 2H), 6.34 (s, 1H), 4.02-3.86 (m, 4H), 3.71 (t, J=5.2 Hz, 2H), 3.55-3.40 (m, 4H). $^{13}$C NMR (75 MHz, CDCl$_3$ and MeOD) δ 168.9, 168.9, 167.1, 164.5, 161.2, 159.5, 157.4, 144.3, 140.0 (d, J=7.4 Hz), 132.4, 131.0 (2C), 130.2 (d, J=8.3 Hz), 127.7, 124.8 (d, J=2.9 Hz), 120.3, 118.6, 115.9 (d, J=21.4 Hz), 113.73 (d, J=21.0 Hz), 103.9, 61.1, 48.7, 43.5, 43.4, 42.2, 27.5. HRMS (ESI) calcd for C$_{22}$H$_{22}$FN$_4$O$_2$ 393.1721 (M+H)$^+$, found 393.1716.

1-(6-(3,5-Dimethylbenzyl)pyrimidin-4-yl)-N-(2-hydroxyethyl)indoline-4-carboxamide (23f). Compound 23f (42 mg, 78%) was synthesized by a procedure similar to that used to prepare compound 12a as a white solid. $^1$H NMR (300 MHz, chloroform-d and MeOD) δ 8.59 (s, 1H), 8.46 (d, J=7.9 Hz, 1H), 7.40-7.05 (m, 3H), 6.82 (s, 3H), 6.32 (s, 1H), 3.87 (d, J=5.0 Hz, 4H), 3.73-3.56 (m, 4H), 3.46 (d, J=6.6 Hz, 2H), 2.23 (s, 6H). $^{13}$C NMR (75 MHz, CDCl$_3$ and MeOD) δ 169.0, 168.1, 159.4, 157.2, 144.3, 138.2, 137.4, 132.3, 131.0, 128.4, 127.6, 126.8, 120.2, 118.4, 103.9, 61.0, 48.7, 43.7, 42.3, 27.4, 21.1 (2C). HRMS (ESI) calcd for C$_{24}$H$_{27}$N$_4$O$_2$ 403.2129 (M+H)$^+$, found 403.2125.

1-(6-(3,5-Difluorobenzyl)pyrimidin-4-yl)-N-(2-hydroxyethyl)indoline-4-carboxamide (23g). Compound 23g (37 mg, 67%) was synthesized by a procedure similar to that used to prepare compound 12a as a white solid. $^1$H NMR (300 MHz, chloroform-d) δ 8.81-8.40 (m, 2H), 7.63-7.05 (m, 3H), 6.96-6.55 (m, 3H), 6.43 (s, 1H), 3.97 (d, J=9.2 Hz, 4H), 3.89-3.66 (m, 4H), 3.54 (s, 2H). $^{13}$C NMR (75 MHz, CDCl$_3$) δ 173.0, 172.9, 170.1, 168.6 (d, J=13.3 Hz), 165.4, 163.4, 161.4, 148.1, 145.4, 136.3, 135.1, 131.7, 124.4, 122.6, 116.0, 115.7, 108.0, 106.6, 106.2, 105.9, 65.0, 52.7, 47.2, 46.2, 46.1, 31.4. HRMS (ESI) calcd for C$_{22}$H$_{21}$F$_2$N$_4$O$_2$ 411.1627 (M+H)$^+$, found 411.1623.

N-(2-Hydroxyethyl)-1-(6-(3-(trifluoromethoxy)benzyl)pyrimidin-4-yl)indoline-4-carboxamide (23h). Compound 23h (41 mg, 67%) was synthesized by a procedure similar to that used to prepare compound 12a as a white solid. $^1$H NMR (300 MHz, Methanol-d$_4$) δ 8.57 (d, J=3.4 Hz, 2H), 7.43 (t, J=7.9 Hz, 1H), 7.33 (d, J=7.8 Hz, 1H), 7.29-7.22 (m, 3H), 7.20-7.13 (m, 1H), 6.65 (s, 1H), 4.05 (s, 2H), 3.94 (t, J=8.6 Hz, 2H), 3.74 (t, J=5.8 Hz, 2H), 3.51 (t, J=5.8 Hz, 2H), 3.41 (t, J=8.5 Hz, 2H). $^{13}$C NMR (75 MHz, MeOD) δ 169.4, 166.6, 159.6, 156.9, 149.3, 144.0, 140.7, 132.1, 131.6, 129.9, 127.6, 127.1, 121.4, 120.6, 118.8, 118.4, 104.0, 60.2, 48.4, 42.5, 41.9, 26.9. HRMS (ESI) calcd for C$_{23}$H$_{22}$F$_3$N$_4$O$_3$ 459.1639 (M+H)$^+$, found 459.1636.

N-(2-Hydroxyethyl)-1-(6-(3-methoxybenzyl)pyrimidin-4-yl)indoline-4-carboxamide (23i). Compound 23i (26 mg, 48%) was synthesized by a procedure similar to that used to prepare compound 12a as a white solid. $^1$H NMR (300 MHz, Chloroform-d) δ 8.72 (s, 1H), 8.59 (d, J=8.2 Hz, 1H), 7.28-7.19 (m, 2H), 7.05 (d, J=7.7 Hz, 1H), 6.95-6.79 (m, 3H), 6.51 (t, J=5.4 Hz, 1H), 6.36 (s, 1H), 4.01 (s, 2H), 3.94 (t, J=8.6 Hz, 2H), 3.87 (t, J=4.9 Hz, 2H), 3.82 (s, 3H), 3.63 (q, J=5.3 Hz, 2H), 3.54 (t, J=8.5 Hz, 2H), 2.91 (s, 1H). $^{13}$C NMR (75 MHz, CDCl$_3$) δ 168.6, 168.0, 159.9, 159.4, 157.5, 144.7, 139.4, 132.6, 130.7, 129.7, 127.8, 121.6, 119.6, 118.6, 115.1, 112.1, 103.8, 62.4, 55.2, 48.7, 44.3, 42.7, 27.7. HRMS (ESI) calcd for C$_{23}$H$_{25}$N$_4$O$_3$ 405.1921 (M+H)$^+$, found 405.1917.

1-(6-(3,5-Dimethoxybenzyl)pyrimidin-4-yl)-N-(2-hydroxyethyl)indoline-4-carboxamide (23j). Compound 23j (17 mg, 29%) was synthesized by a procedure similar to that used to prepare compound 12a as a white solid. $^1$H NMR (300 MHz, chloroform-d) δ 8.67 (d, J=1.0 Hz, 1H), 8.55 (d, J=8.1 Hz, 1H), 7.18 (t, J=7.9 Hz, 1H), 6.98 (dd, J=7.8, 1.0 Hz, 1H), 6.56 (t, J=5.6 Hz, 1H), 6.48 (d, J=2.3 Hz, 2H), 6.39 (t, J=2.3 Hz, 1H), 6.32 (d, J=1.1 Hz, 1H), 3.94 (s, 2H), 3.91 (d, J=8.5 Hz, 2H), 3.87-3.83 (m, 2H), 3.80 (s, 6H), 3.62 (t, J=5.1 Hz, 2H), 3.50 (t, J=8.6 Hz, 2H). $^{13}$C NMR (75 MHz, CDCl$_3$) δ 168.5, 167.6, 161.0, 159.3, 157.4, 144.6, 140.0, 132.5, 130.7, 127.7, 119.7, 118.5, 107.4, 103.8, 98.6, 62.2, 55.4 (2C), 48.7, 44.5, 42.7, 27.6. HRMS (ESI) calcd for C$_{24}$H$_{27}$N$_4$O$_4$ 435.2027 (M+H)$^+$, found 435.2024.

1-(6-Benzylpyrimidin-4-yl)-N-(2-hydroxyethyl)indoline-4-carboxamide (23k). Compound 23k (39 mg, 78%) was synthesized by a procedure similar to that used to prepare compound 12a as a white solid. $^1$H NMR (300 MHz, chloroform-d and MeOD) δ 8.60 (s, 1H), 8.47 (d, J=7.9 Hz, 1H), 7.33-7.07 (m, 8H), 6.27 (s, 1H), 3.96 (s, 2H), 3.82 (t, J=8.5 Hz, 2H), 3.71 (t, J=5.1 Hz, 2H), 3.49 (q, J=5.3 Hz, 2H), 3.44-3.30 (m, 3H). $^{13}$C NMR (75 MHz, CDCl$_3$) δ 168.9, 167.9, 166.6, 159.3, 157.2, 144.3, 137.6, 132.3, 131.0, 129.1, 128.7, 127.6, 126.8, 120.2, 118.5, 103.9, 61.2, 48.6, 43.8, 42.3, 27.4. HRMS (ESI) calcd for C$_{22}$H$_{23}$N$_4$O$_2$ 375.1816 (M+H)$^+$, found 375.1812.

Methyl 1-(4-(3-fluoro-5-(trifluoromethyl)benzoyl)pyrimidin-2-yl)indoline-4-carboxylate (24a). Compound 9a (406 mg, 2 mmol) was dissolved in 5 mL DMF and the mixture solution was cooled to 0° C. with ice bath. NaH (190 mg, 4.4 mmol) was added to the solution at 0° C., and the mixture solution was stirred at 0° C. for 30 min. Then 2,4-dichloropyrimidine (450 mg, 3 mmol) was added to the solution at 0° C. After the mixture solution was stirred at rt for 2 h, the mixture was cooled to 0° C. with ice bath. Followed by adding mCPBA (516 mg, 3 mmol) and the mixture solution was stirred at 0° C. for 30 min. After the reaction completed (detected by TLC), the reaction was worked up by the addition of water and EtOAc extraction. The combined EtOAc extracts were washed with brine, dried over $Na_2SO_4$, filtered, and condensed by rotary evaporation to yield a yellow oil. The residue purification by silica gel chromatography (Gradient: 10% to 20% EtOAc in hexane) provided product (2-chloropyrimidin-4-yl)(3-fluoro-5-(trifluoromethyl)phenyl)methanone (280 mg, 47%) as a yellow solid. $^1$H NMR (300 MHz, chloroform-d) δ 8.98 (d, J=4.9 Hz, 1H), 8.30 (s, 1H), 8.14 (dt, J=8.9, 1.9 Hz, 1H), 7.96 (d, J=4.9 Hz, 1H), 7.63 (dt, J=8.1, 2.0 Hz, 1H).

A mixture of (2-chloropyrimidin-4-yl)(3-fluoro-5-(trifluoromethyl)phenyl)methanone (91 mg, 0.3 mmol), Pd(OAc)$_2$ (3 mg, 0.015 mmol), XantPhos (17 mg, 0.03 mmol), Cs$_2$CO$_3$ (196 mg, 0.6 mmol) and 6 (53 mg, 0.3 mmol) in 1,4-dioxane (3 mL) was subjected to three rounds of vacuum evacuation followed by introduction of nitrogen. The reaction mixture was then stirred at 100° C. overnight. The reaction mixture was cooled to room temperature and poured into water, and then extracted with EtOAc (10 mL×3). The organic phase was washed with brine, dried over Na$_2$SO$_4$, and then concentrated under reduced pressure. The residue purification by silica gel chromatography (Gradient: 10% to 20% EtOAc in hexane) provided product 24a (110 mg, 82%) as a yellow solid. $^1$H NMR (300 MHz, Chloroform-d) δ 8.84 (d, J=4.8 Hz, 1H), 8.43 (s, 2H), 8.15 (d, J=8.8 Hz, 1H), 7.64 (dd, J=7.9, 1.2 Hz, 2H), 7.39 (d, J=4.8 Hz, 1H), 7.23 (t, J=8.0 Hz, 1H), 4.32 (t, J=8.7 Hz, 2H), 3.94 (s, 3H), 3.62 (t, J=8.7 Hz, 2H).

Methyl 1-(6-(3-fluoro-5-(trifluoromethyl)benzoyl)pyrimidin-4-yl)indoline-4-carboxylate (24b). 2-(3-Fluoro-5-(trifluoromethyl)phenyl)acetonitrile (9a) (406 mg, 2 mmol) was dissolved in 5 mL DMF and the mixture solution was cooled to 0° C. with ice bath. NaH (190 mg, 4.4 mmol) was added to the solution at 0° C., and the mixture solution was stirred at 0° C. for 30 min. Then compound 8c (580 mg, 2 mmol) was added to the solution at 0° C. After the mixture solution was stirred at rt for 2 h, the mixture was cooled to 0° C. with ice bath. Followed by adding mCPBA (516 mg, 3 mmol) and the mixture solution was stirred at 0° C. for 10 min. After the reaction completed (detected by TLC), the reaction was worked up by the addition of water and then extracted with EtOAc (20 mL×3). The combined EtOAc extracts were washed with brine, dried over Na$_2$SO$_4$, filtered, and condensed by rotary evaporation to yield a yellow oil. The residue purification by silica gel chromatography (Gradient: 20% to 50% EtOAc in hexane) provided product 24b (440 mg, 49%) as a yellow solid. $^1$H NMR (300 MHz, Chloroform-d) δ 8.97 (d, J=1.1 Hz, 1H), 8.82 (d, J=8.1 Hz, 1H), 8.31 (s, 1H), 8.17 (d, J=9.0 Hz, 1H), 7.73 (dd, J=7.9, 1.0 Hz, 1H), 7.60 (d, J=8.0 Hz, 1H), 7.39 (t, J=8.0 Hz, 1H), 7.31 (s, 1H), 4.21 (t, J=8.6 Hz, 2H), 3.96 (s, 3H), 3.72 (t, J=8.6 Hz, 2H).

Methyl 1-(6-(3-(trifluoromethyl)benzoyl)pyrimidin-4-yl)indoline-4-carboxylate (24c). Compound 24c (162 mg, 79%) was synthesized by a procedure similar to that used to prepare compound 24b as a white solid. $^1$H NMR (300 MHz, DMSO-d$_6$) δ 8.75 (d, J=0.9 Hz, 1H), 8.67 (d, J=8.1 Hz, 1H), 7.94-7.84 (m, 2H), 7.77 (d, J=7.9 Hz, 1H), 7.71 (d, J=7.7 Hz, 1H), 7.54 (dd, J=7.9, 1.0 Hz, 1H), 7.35 (t, J=8.0 Hz, 1H), 7.08 (s, 1H), 6.01 (s, 1H), 4.10 (t, J=9.8 Hz, 2H), 3.85 (s, 3H), 3.51 (t, J=8.5 Hz, 2H).

1-(4-(3-Fluoro-5-(trifluoromethyl)benzoyl)pyrimidin-2-yl)-N-(2-hydroxyethyl)indoline-4-carboxamide (25a). To a solution of 24a (45 mg, 0.1 mmol) in con. HCl (4 mL), H$_2$O (1 mL) and AcOH (1 mL), and the mixture solution was stirred at reflux overnight. The reaction mixture was cooled to room temperature and a yellow solid precipitated from the solution. The yellow solid was filtered and washed with water, and the cake was collected and dried to afford the product as a light yellow solid. The yellow solid and the 2-aminoethan-1-ol (13 mg, 0.2 mmol) were dissolved in 2 mL of DMF and the mixture solution was cooled to 0° C. with ice bath. HOBt (14 mg, 0.1 mmol), EDCI (39 mg, 0.2 mmol) and DMAP (24 mg, 0.2 mmol) were added to the solution at 0° C. Then removed the ice bath, and the mixture solution was stirred at room temperature overnight. After the reaction completed (detected by TLC), the reaction was worked up by the addition of water and then extracted with EtOAc (20 mL×3). The combined EtOAc extracts were washed with brine, dried over Na$_2$SO$_4$, filtered, and condensed by rotary evaporation to yield a yellow oil. This material was further purified by preparative TLC plates using CH$_2$Cl$_2$/MeOH=50:1 as the eluent to yield 25a as a yellow solid (36 mg, 77% for two steps). $^1$H NMR (300 MHz, DMSO-d$_6$) δ 8.94 (d, J=4.9 Hz, 1H), 8.33 (s, 1H), 8.17 (dd, J=26.9, 8.6 Hz, 3H), 7.44 (d, J=4.9 Hz, 1H), 7.21 (d, J=7.6 Hz, 1H), 7.10 (s, 1H), 4.71 (t, J=5.6 Hz, 1H), 4.19 (t, J=8.6 Hz, 2H), 3.51 (q, J=6.1 Hz, 2H), 3.39 (t, J=8.7 Hz, 2H), 3.30 (s, 2H). $^{13}$C NMR (75 MHz, DMSO) δ 159.9, 143.8, 132.7, 127.4, 122.0, 120.9, 116.7, 110.5, 60.2, 49.4, 42.4, 42.3, 40.8, 27.3. HRMS (ESI) calcd for C$_{23}$H$_{19}$F$_4$N$_4$O$_3$ 475.1388 (M+H)$^+$, found 475.1385.

1-(6-(3-Fluoro-5-(trifluoromethyl)benzoyl)pyrimidin-4-yl)-N-(2-hydroxyethyl)indoline-4-carboxamide (25b). Compound 25b (35 mg, 75%) was synthesized by a procedure similar to that used to prepare compound 25a as a yellow solid. $^1$H NMR (300 MHz, chloroform-d and MeOD) δ 8.86 (d, J=1.1 Hz, 1H), 8.63 (d, J=7.7 Hz, 1H), 8.21 (s, 1H), 8.07 (dt, J=8.8, 2.0 Hz, 1H), 7.55 (dt, J=8.0, 2.0 Hz, 1H), 7.28-7.23 (m, 2H), 7.22-7.20 (m, 1H), 4.10 (t, J=8.5 Hz, 2H), 3.74 (t, J=5.1 Hz, 2H), 3.54 (dd, J=9.3, 7.1 Hz, 4H). $^{13}$C NMR (75 MHz, CDCl$_3$ and MeOD) δ 190.3, 168.8, 166.6, 163.7, 160.4, 159.5 (d, J=59.6 Hz), 157.3, 143.9, 138.0, 132.7, 131.2, 127.8, 123.9-123.3 (m), 121.3 (d, J=23.2 Hz), 120.9, 119.0, 117.34 (dd, J=24.4, 3.2 Hz), 105.1, 61.2, 49.0, 42.3, 27.5. HRMS (ESI) calcd for C$_{23}$H$_{19}$F$_4$N$_4$O$_3$ 475.1388 (M+H)$^+$, found 475.1386.

N-(2-Hydroxyethyl)-1-(6-(3-(trifluoromethyl)benzoyl)pyrimidin-4-yl)indoline-4-carboxamide (25c). Compound 25c (360 mg, 63%) was synthesized by a procedure similar to that used to prepare compound 25a as a yellow solid. $^1$H NMR (300 MHz, DMSO-d$_6$) δ 8.92 (d, J=1.1 Hz, 1H), 8.63 (dd, J=6.6, 2.6 Hz, 1H), 8.38-8.25 (m, 3H), 8.13-8.05 (m, 1H), 7.88-7.77 (m, 1H), 7.39-7.26 (m, 3H), 4.73 (t, J=5.6 Hz, 1H), 4.17 (t, J=8.5 Hz, 2H), 3.59-3.41 (m, 4H), 3.34 (m, 2H). $^{13}$C NMR (75 MHz, DMSO) δ 192.0, 167.4, 160.0, 159.9 (d, J=8.6 Hz), 157.5, 143.9, 136.4, 135.0, 132.9 (d, J=14.2 Hz), 132.7, 130.2, 129.4, 127.7, 127.3 (d, J=3.6 Hz), 127.2, 121.8, 118.3, 105.5, 60.2, 49.0, 42.4, 27.7. HRMS (ESI) calcd for C$_{23}$H$_{20}$F$_3$N$_4$O$_3$ 457.1482 (M+H)$^+$, found 457.1480.

1-(4-((3-Fluoro-5-(trifluoromethyl)phenyl)(hydroxy)methyl)pyrimidin-2-yl)-N-(2-hydroxyethyl)indoline-4-carboxamide (25d). To a solution of 25a (10 mg, 0.02 mmol) in MeOH (1 mL) was added NaBH$_4$ (1 mg, 0.02 mmol) at 0° C., and the mixture solution was stirred at rt for 1 h. After the reaction completed (detected by TLC), the reaction mixture was worked up by the addition of water and EtOAc extraction. The combined EtOAc extracts were washed with brine, dried over Na$_2$SO$_4$, filtered, and condensed by rotary evaporation to yield a colorless oil. This material was further purified by preparative TLC plates using CH$_2$Cl$_2$/MeOH=50:1 as the eluent to yield 25d as a white solid (9 mg, 93%). $^1$H NMR (300 MHz, chloroform-d) δ 8.50-8.35 (m, 2H), 7.57 (s, 1H), 7.37 (d, J=9.1 Hz, 1H), 7.24 (dd, J=15.9, 7.8 Hz, 2H), 7.12 (d, J=7.7 Hz, 1H), 6.66 (t, J=4.5 Hz, 2H), 5.67 (s, 1H), 4.94 (s, 1H), 4.24 (t, J=8.8 Hz, 2H), 3.85 (t, J=4.9 Hz, 2H), 3.63 (q, J=5.2 Hz, 2H), 3.44 (t, J=8.6 Hz, 2H). $^{13}$C NMR (75 MHz, CDCl$_3$) δ 169.1, 168.7, 164.2, 160.9, 158.4, 158.1, 145.8 (d, J=6.9 Hz), 144.4, 132.9 (d, J=8.1 Hz), 132.5 (d, J=8.0 Hz), 130.9, 127.7, 125.0 (d, J=3.0 Hz), 121.3 (d, J=3.0 Hz), 119.5-119.24 (m), 117.7, 117.3 (d, J=22.2 Hz), 112.5 (ddd, J=24.2, 7.1, 3.4 Hz), 108.0, 73.8, 62.3, 49.2, 42.6, 27.2. HRMS (ESI) calcd for C$_{23}$H$_{21}$F$_4$N$_4$O$_3$ 477.1544 (M+H)$^+$, found 477.1540.

1-(6-((3-Fluoro-5-(trifluoromethyl)phenyl)(hydroxy) methyl)pyrimidin-4-yl)-N-(2-hydroxyethyl)indoline-4-carboxamide (25e). Compound 25e (32 mg, 78%) was synthesized by a procedure similar to that used to prepare compound 25d as a white solid. $^1$H NMR (300 MHz, chloroform-d and MeOD) δ 8.66-8.27 (m, 2H), 7.51 (s, 1H), 7.34 (d, J=8.5 Hz, 2H), 7.26-7.01 (m, 3H), 6.68 (s, 1H), 5.60 (s, 1H), 3.90 (t, J=8.6 Hz, 2H), 3.70 (s, 2H), 3.46-3.27 (m, 4H). $^{13}$C NMR (75 MHz, CDCl$_3$ and MeOD) δ 168.7 (d, J=36.5 Hz), 164.0, 159.4, 156.8, 146.2, 144.1, 132.4, 131.0, 127.6, 120.5, 119.2, 118.7, 117.2 (d, J=22.5 Hz), 112.4-111.7 (m), 101.0, 73.9, 61.1, 42.3, 42.2, 27.3. HRMS (ESI) calcd for C$_{23}$H$_{21}$F$_4$N$_4$O$_3$ 477.1544 (M+H)$^+$, found 477.1540.

1-(6-(Hydroxy(3-(trifluoromethyl)phenyl)methyl)pyrimidin-4-yl)-N-(2-hydroxyethyl)indoline-4-carboxamide (25f). Compound 25f (41 mg, 90%) was synthesized by a procedure similar to that used to prepare compound 25d as a white solid. $^1$H NMR (300 MHz, DMSO-d$_6$) δ 8.64 (s, 1H), 8.54 (d, J=7.0 Hz, 1H), 8.25 (t, J=5.8 Hz, 1H), 7.89-7.72 (m, 2H), 7.69-7.52 (m, 2H), 7.28 (d, J=6.6 Hz, 2H), 7.09 (s, 1H), 6.45 (d, J=4.5 Hz, 1H), 5.72 (d, J=4.5 Hz, 1H), 4.71 (t, J=5.6 Hz, 1H), 4.11 (q, J=7.9 Hz, 2H), 3.60-3.33 (m, 6H). $^{13}$C NMR (75 MHz, DMSO) δ 170.9, 167.5, 159.7, 157.4, 145.2, 144.4, 132.6, 131.5, 129.6, 129.2 (d, J=31.4 Hz), 127.6, 126.5, 124.5 (t, J=3.9 Hz), 123.7 (t, J=3.9 Hz), 121.1, 117.9, 101.3, 74.5, 60.3, 49.0, 42.4, 27.7. HRMS (ESI) calcd for C$_{23}$H$_{22}$F$_3$N$_4$O$_3$ 459.1639 (M+H)$^+$, found 459.1635.

1-(4-((3-Fluoro-5-(trifluoromethyl)phenyl)(hydroxy) methyl)pyrimidin-2-yl)indoline-4-carboxylic acid (26a). To a solution of 24a (427 mg, 1 mmol) in DMF (5 mL) and MeOH (5 mL) was added NaBH$_4$ (38 mg, 1 mmol) at 0° C., and the mixture solution was stirred at rt for 30 min. After the reaction completed (detected by TLC), the reaction mixture was worked up by the addition of water and then extracted with EtOAc (20 mL×3). The combined EtOAc extracts were washed with brine, dried over Na$_2$SO$_4$, filtered, and condensed by rotary evaporation to yield a colorless oil. The colorless oil was dissolved in con. HCl (4 mL), H$_2$O (1 mL) and AcOH (1 mL), and the mixture solution was stirred at reflux overnight. The reaction was cooled to room temperature and a yellow solid precipitated from the solution. The yellow solid was filtered and washed with water, and the cake was collected and dried to afford the product as a light yellow solid (210 mg, 78%). $^1$H NMR (300 MHz, Chloroform-d) δ 8.63 (s, 1H), 8.51 (d, J=4.8 Hz, 1H), 7.74 (dd, J=7.9, 1.0 Hz, 1H), 7.57 (s, 1H), 7.36 (t, J=10.4 Hz, 3H), 6.67 (d, J=5.1 Hz, 1H), 5.73 (s, 1H), 4.39 (t, J=8.3 Hz, 2H), 3.66 (t, J=8.6 Hz, 2H).

1-(6-((3-Fluoro-5-(trifluoromethyl)phenyl)(hydroxy) methyl)pyrimidin-4-yl)indoline-4-carboxylic acid (26b). Compound 26b (390 mg, 90%) was synthesized by a procedure similar to that used to prepare compound 26a as a yellow solid. $^1$H NMR (300 MHz, DMSO-d$_6$) δ 8.86 (s, 1H), 8.71 (d, J=7.8 Hz, 1H), 7.84 (s, 1H), 7.77 (d, J=9.5 Hz, 1H), 7.64 (d, J=7.8 Hz, 2H), 7.45-7.40 (m, 1H), 7.32 (d, J=2.9 Hz, 1H), 6.00 (s, 1H), 4.24 (dt, J=9.0, 3.9 Hz, 2H), 3.61-3.50 (m, 3H).

1-(6-(Hydroxy(3-(trifluoromethyl)phenyl)methyl)pyrimidin-4-yl)indoline-4-carboxylic acid (26c). Compound 26c (117 mg, 68%) was synthesized by a procedure similar to that used to prepare compound 26a as a yellow solid. $^1$H NMR (300 MHz, DMSO-d$_6$) δ 8.86 (d, J=3.4 Hz, 1H), 8.71 (d, J=7.8 Hz, 1H), 7.96 (s, 1H), 7.87 (d, J=7.6 Hz, 1H), 7.73-7.58 (m, 3H), 7.42 (t, J=8.0 Hz, 1H), 7.31 (d, J=2.3 Hz, 1H), 5.99 (s, 1H), 4.32-4.14 (m, 2H), 3.58 (t, J=8.2 Hz, 2H).

1-(4-(Fluoro(3-fluoro-5-(trifluoromethyl)phenyl)methyl) pyrimidin-2-yl)indoline-4-carboxylic acid (27a). To a solution of 26a (210 mg, 0.6 mmol) in DCM (5 mL) was added DAST (322 mg, 1.8 mmol) at 0° C., and the mixture solution was stirred at 0° C. for 10 min. After the reaction completed (detected by TLC), the reaction mixture was worked up by the addition of water and then extracted with EtOAc (20 mL×3). The combined EtOAc extracts were washed with brine, dried over Na$_2$SO$_4$, filtered, and condensed by rotary evaporation to yield a yellow oil. The residue was dissolved in THF (2 mL) and H$_2$O (2 mL), and the mixture solution was stirred at reflux overnight. The reaction was cooled to room temperature and a yellow solid precipitated from the solution. The yellow solid was filtered and washed with water, and the cake was collected and dried to afford the product as a light yellow solid 27a (140 mg, 54% for two steps). $^1$H NMR (300 MHz, chloroform-d) δ 8.63 (d, J=5.0 Hz, 1H), 8.49 (d, J=8.2 Hz, 1H), 7.73-7.64 (m, 2H), 7.46 (d, J=8.9 Hz, 1H), 7.40-7.29 (m, 2H), 7.04 (dd, J=5.1, 1.7 Hz, 1H), 6.41 (d, J=46.4 Hz, 1H), 4.28 (dd, J=8.3, 3.1 Hz, 2H), 3.61 (t, J=8.8 Hz, 2H).

1-(6-(Fluoro(3-fluoro-5-(trifluoromethyl)phenyl)methyl) pyrimidin-4-yl)indoline-4-carboxylic acid (27b). Compound 27b (260 mg, 60%) was synthesized by a procedure similar to that used to prepare compound 27a as a yellow solid. $^1$H NMR (300 MHz, DMSO-d$_6$) δ 13.01 (s, 1H), 8.71 (d, J=7.6 Hz, 2H), 7.80-7.71 (m, 3H), 7.56 (ddd, J=7.8, 3.3, 1.2 Hz, 1H), 7.35 (dd, J=9.1, 6.9 Hz, 1H), 7.11 (s, 1H), 6.75 (d, J=45.7 Hz, 1H), 4.26-4.13 (m, 2H), 3.55 (t, J=8.4 Hz, 2H).

1-(6-(Fluoro(3-(trifluoromethyl)phenyl)methyl)pyrimidin-4-yl)indoline-4-carboxylic acid (27c). Compound 27c (110 mg, 76%) was synthesized by a procedure similar to that used to prepare compound 27a as a yellow solid. $^1$H NMR (300 MHz, DMSO-d$_6$) δ 8.71 (s, 1H), 7.90 (s, 1H), 7.83-7.74 (m, 1H), 7.69 (d, J=7.7 Hz, 1H), 7.56 (dd, J=7.3, 3.1 Hz, 1H), 7.38 (t, J=8.0 Hz, 1H), 7.10 (s, 1H), 6.72 (d, J=45.7 Hz, 1H), 4.20 (dd, J=9.4, 4.7 Hz, 2H), 3.55 (t, J=8.6 Hz, 2H).

1-(4-(Fluoro(3-fluoro-5-(trifluoromethyl)phenyl)methyl) pyrimidin-2-yl)-N-(2-hydroxyethyl)indoline-4-carboxamide (25g). Compound 25g (140 mg, 86%) was synthesized by a procedure similar to that used to prepare compound 12a as a light yellow solid. $^1$H NMR (300 MHz, chloroform-d and MeOD) δ 8.54 (d, J=5.0 Hz, 1H), 8.27 (d, J=7.7 Hz, 1H), 7.63 (s, 1H), 7.41 (d, J=8.9 Hz, 1H), 7.31 (d, J=8.4 Hz, 1H), 7.21-7.09 (m, 2H), 7.07-6.90 (m, 2H), 6.35 (d, J=46.3 Hz, 1H), 4.17 (tt, J=9.1, 3.5 Hz, 2H), 3.75 (t, J=5.1 Hz, 2H), 3.54 (q, J=5.3 Hz, 2H), 3.41 (t, J=8.7 Hz, 2H). $^{13}$C NMR (75 MHz, CDCl$_3$ and MeOD) δ 169.2, 169.1, 166.6 (d, J=28.5 Hz), 164.0, 160.7, 159.0, 158.4 (d, J=3.6 Hz), 144.3, 141.5 (dd, J=21.8, 7.5 Hz), 132.7, 132.5, 131.0, 131.0, 127.5, 119.13-118.56 (m), 116.8 (dd, J=22.9, 7.7 Hz), 113.2 (d, J=23.1 Hz), 106.5 (d, J=6.7 Hz), 91.95 (d, J=179.2 Hz), 61.5, 49.1, 42.4, 27.2. HRMS (ESI) calcd for $C_{23}H_{20}F_5N_4O_2$ 479.1501 (M+H)$^+$, found 479.1498.

1-(6-(Fluoro(3-fluoro-5-(trifluoromethyl)phenyl)methyl) pyrimidin-4-yl)-N-(2-hydroxyethyl)indoline-4-carboxamide (25h). Compound 25h (162 mg, 68%) was synthesized by a procedure similar to that used to prepare compound 12a as a white solid. $^1$H NMR (300 MHz, chloroform-d) δ 8.74 (s, 1H), 8.66 (d, J=8.1 Hz, 1H), 7.60 (s, 1H), 7.44 (d, J=8.9 Hz, 1H), 7.37-7.31 (m, 1H), 7.28 (t, J=4.0 Hz, 1H), 7.19 (d, J=7.6 Hz, 1H), 6.86 (s, 1H), 6.61 (t, J=5.8 Hz, 1H), 6.39 (d, J=46.4 Hz, 1H), 4.11 (t, J=8.6 Hz, 2H), 3.87 (q, J=4.8 Hz, 2H), 3.72-3.53 (m, 4H), 2.73 (t, J=5.0 Hz, 1H). $^{13}$C NMR (75 MHz, CDCl$_3$) δ 168.6, 164.9 (d, J=26.3 Hz), 164.1, 160.7, 159.6, 157.7 (d, J=3.4 Hz), 144.4, 141.4, 132.8, 130.9, 127.9, 124.8, 121.2, 120.2, 119.1, 117.3 (d, J=15.5 Hz), 113.4 (d, J=23.9 Hz), 100.1 (d, J=8.2 Hz), 92.07 (d, J=179.4 Hz), 77.4, 62.3, 49.0, 42.6, 27.7. $^{19}$F NMR (282 MHz, Chloroform-d) δ −62.8, −109.5 (t, J=8.7 Hz), −183.9 (d, J=46.4 Hz). HRMS (ESI) calcd for $C_{23}H_{20}F_5N_4O_2$ 479.1501 (M+H)$^+$, found 479.1498.

1-(6-(Fluoro(3-(trifluoromethyl)phenyl)methyl)pyrimidin-4-yl)-N-(2-hydroxyethyl)indoline-4-carboxamide (25i). Compound 25i (240 mg, 72%) was synthesized by a procedure similar to that used to prepare compound 12a as a white solid. $^1$H NMR (300 MHz, chloroform-d and MeOD) δ 8.59 (dd, J=15.6, 5.0 Hz, 2H), 7.76-7.42 (m, 4H), 7.18 (dt, J=12.7, 7.0 Hz, 3H), 6.80 (d, J=4.2 Hz, 1H), 6.35 (dd, J=46.3, 4.4 Hz, 1H), 4.00 (q, J=7.3 Hz, 2H), 3.74 (d, J=5.6 Hz, 2H), 3.49 (dt, J=20.7, 6.7 Hz, 4H). $^{13}$C NMR (75 MHz, CDCl$_3$) δ 168.8, 165.3 (d, J=26.5 Hz), 159.5, 157.4, 144.1, 138.4 (d, J=20.5 Hz), 132.5, 131.2, 131.1, 130.8, 130.3 (d, J=6.5 Hz), 129.2, 127.7, 125.9, 123.5 (dt, J=6.1, 2.8 Hz) 123.5, 120.5, 118.9, 100.2 (d, J=8.1 Hz), 92.7 (d, J=177.7 Hz), 61.3, 48.9, 42.4, 27.5. $^{19}$F NMR (282 MHz, CDCl$_3$) δ −62.8, −181.1. HRMS (ESI) calcd for $C_{23}H_{21}F_4N_4O_2$ 461.1595 (M+H)$^+$, found 461.1590.

Methyl 1-(6-((3-(trifluoromethyl)phenyl)amino)pyrimidin-4-yl)indoline-4-carboxylate (29a). A mixture of 28a (48 mg, 0.3 mmol), Pd(OAc)$_2$ (3 mg, 0.015 mmol), XantPhos (17 mg, 0.03 mmol), Cs$_2$CO$_3$ (196 mg, 0.6 mmol) and 8c (87 mg, 0.3 mmol) in 1,4-dioxane (3 mL) was subjected to three rounds of vacuum evacuation followed by introduction of nitrogen. The reaction mixture was then stirred at 100° C. overnight. The reaction mixture was cooled to room temperature and poured into water, and then extracted with EtOAc (10 mL×3). The organic phase was washed with brine, dried over Na$_2$SO$_4$, and then concentrated under reduced pressure. The residue was purified by silica gel chromatography (Gradient: 10% to 20% EtOAc in hexane) to provide product 29a (86 mg, 69%) as a yellow solid. $^1$H NMR (300 MHz, DMSO-d$_6$) δ 9.72 (s, 1H), 8.65 (dd, J=8.2, 1.1 Hz, 1H), 8.49 (s, 1H), 8.24 (s, 1H), 7.86 (d, J=8.0 Hz, 1H), 7.55-7.46 (m, 2H), 7.36-7.27 (m, 2H), 6.11 (s, 1H), 4.03 (t, J=8.7 Hz, 2H), 3.86 (s, 3H), 3.52 (t, J=8.7 Hz, 2H).

Methyl 1-(6-(3-(trifluoromethyl)phenoxy)pyrimidin-4-yl)indoline-4-carboxylate (29b). To a solution of 28b (49 mg, 0.3 mmol) in DMF (2 mL), was added cesium carbonate (195 mg, 0.6 mmol) and 8c (87 mg, 0.3 mmol), and the reaction was heated to 120° C. overnight. At this point, the reaction mixture was cooled to rt, poured into water (15 mL), and extracted with ethyl acetate (3×10 mL). The combined organic extracts were washed with water (10 mL), brine (10 mL), dried over anhydrous sodium sulfate, filtered and concentrated in vacuo. The residue was purified by chromatography on silica gel (Eluent: 1% MeOH in CH$_2$Cl$_2$) and yielded the product 29b (79 mg, 63%) as a white solid. $^1$H NMR (300 MHz, DMSO-d$_6$) δ 8.69 (t, J=8.2 Hz, 1H), 8.47 (s, 1H), 7.73-7.50 (m, 5H), 7.36 (t, J=8.2 Hz, 1H), 6.47 (d, J=5.4 Hz, 1H), 4.10 (t, J=8.5 Hz, 2H), 3.86 (s, 3H), 3.54 (t, J=8.6 Hz, 2H).

Methyl 1-(6-((3-(trifluoromethyl)phenyl)thio)pyrimidin-4-yl)indoline-4-carboxylate (29c). Compound 29c (92 mg, 71%) was synthesized by a procedure similar to that used to prepare compound 29b as a white solid. $^1$H NMR (300 MHz, DMSO-d$_6$) δ 8.63-8.50 (m, 2H), 8.01-7.85 (m, 3H), 7.75 (t, J=7.8 Hz, 1H), 7.52 (dd, J=7.9, 1.1 Hz, 1H), 7.32 (t, J=8.1 Hz, 1H), 6.52 (d, J=1.1 Hz, 1H), 3.91 (t, J=8.6 Hz, 2H), 3.84 (s, 3H), 3.45 (t, J=8.6 Hz, 2H).

N-(2-Hydroxyethyl)-1-(6-((3-(trifluoromethyl)phenyl) amino)pyrimidin-4-yl)indoline-4-carboxamide (25j). To a solution of 29a (41 mg, 0.1 mmol) in con. HCl (4 mL), H$_2$O (1 mL) and AcOH (1 mL), and the mixture solution was stirred at reflux overnight. The reaction was cooled to room temperature and a yellow solid precipitated from the solution. The yellow solid was filtered and washed with water, and the cake was collected and dried to afford the product as a light yellow solid. The yellow solid and the 2-aminoethan-1-ol (13 mg, 0.2 mmol) were dissolved in 2 mL DMF and the mixture solution was cooled to 0° C. with ice bath. HOBt (14 mg, 0.1 mmol), EDCI (39 mg, 0.2 mmol) and DMAP (24 mg, 0.2 mmol) were added to the solution at 0° C. Then removed the ice bath, and the mixture solution was stirred at rt overnight. After the reaction completed (detected by TLC), the reaction mixture was worked up by the addition of water and then extracted with EtOAc (20 mL×3). The combined EtOAc extracts were washed with brine, dried over Na$_2$SO$_4$, filtered, and condensed by rotary evaporation to yield a yellow oil. This material was further purified by preparative TLC plates using CH$_2$Cl$_2$/MeOH=50:1 as the eluent to yield 25j as a white solid (43 mg, 73% for two steps). $^1$H NMR (300 MHz, chloroform-d and MeOD) δ 8.43-8.25 (m, 2H), 7.66 (s, 1H), 7.55 (d, J=8.2 Hz, 1H), 7.40 (t, J=7.9 Hz, 1H), 7.32-7.23 (m, 2H), 7.19-7.03 (m, 2H), 5.89 (s, 1H), 3.80 (t, J=8.5 Hz, 2H), 3.70 (t, J=5.2 Hz, 2H), 3.49 (t, J=5.3 Hz, 2H), 3.34 (t, J=8.5 Hz, 2H). $^{13}$C NMR (75 MHz, CDCl$_3$ and MeOD) δ 169.2, 166.6, 160.5, 159.7, 157.4, 153.0, 144.8, 139.9, 132.0, 131.6, 131.2, 131.0, 129.7, 127.6, 124.1, 119.6, 117.8, 117.5, 85.9, 61.1, 42.3, 27.4. HRMS (ESI) calcd for $C_{22}H_{21}F_3N_5O_2$ 444.1642 (M+H)$^+$, found 444.1639.

N-(2-Hydroxyethyl)-1-(6-(3-(trifluoromethyl)phenoxy) pyrimidin-4-yl)indoline-4-carboxamide (25k). Compound 25k (48 mg, 43%) was synthesized by a procedure similar to that used to prepare compound 25j as a white solid. $^1$H NMR (300 MHz, chloroform-d and MeOD) δ 8.50 (d, J=7.8 Hz, 1H), 8.39 (d, J=3.5 Hz, 1H), 7.59-7.08 (m, 7H), 6.05 (d, J=3.5 Hz, 1H), 3.93 (t, J=8.8 Hz, 2H), 3.69 (q, J=4.5 Hz, 2H), 3.48 (s, 4H). $^{13}$C NMR (75 MHz, CDCl$_3$ and MeOD) δ 169.3, 169.0, 161.2, 157.4, 152.9, 144.4, 132.3, 131.1, 130.3, 127.7, 124.9, 122.1, 120.3, 118.4, 89.3, 61.1, 42.3, 27.5. HRMS (ESI) calcd for $C_{22}H_{20}F_3N_4O_3$ 445.1482 (M+H)$^+$, found 445.1480.

N-(2-Hydroxyethyl)-1-(6-((3-(trifluoromethyl)phenyl) thio)pyrimidin-4-yl)indoline-4-carboxamide (25l). Compound 25l (64 mg, 56%) was synthesized by a procedure similar to that used to prepare compound 25j as a white solid. $^1$H NMR (300 MHz, chloroform-d and MeOD) δ 8.47 (d, J=3.9 Hz, 1H), 8.42-8.28 (m, 1H), 7.92-7.52 (m, 4H), 7.31-7.07 (m, 3H), 6.03 (d, J=3.8 Hz, 1H), 3.71 (t, J=5.7 Hz, 4H), 3.49 (t, J=5.0 Hz, 2H), 3.40 (t, J=9.4 Hz, 2H). $^{13}$C NMR (75 MHz, CDCl$_3$ and MeOD) δ 169.0, 168.8, 158.5, 157.1, 144.1, 138.6, 132.4, 132.3, 131.9, 131.1, 130.2, 130.2, 127.6, 126.5, 120.4, 118.4, 100.4, 61.2, 48.6, 42.3, 42.2, 27.4. HRMS (ESI) calcd for $C_{22}H_{20}F_3N_4O_2S$ 461.1254 (M+H)$^+$, found 461.1250.

N-(1,3-Dihydroxypropan-2-yl)-1-(6-(3-fluoro-5-(trifluoromethyl)benzyl)pyrimidin-4-yl)indoline-4-carboxamide (30a). Compound 30a (28 mg, 57%) was synthesized by a procedure similar to that used to prepare compound 12a as a white solid. $^1$H NMR (300 MHz, chloroform-d and MeOD) δ 8.68 (s, 1H), 8.55 (d, J=7.5 Hz, 1H), 7.33 (s, 1H), 7.28-7.11 (m, 4H), 6.40 (s, 1H), 4.10-3.90 (m, 5H), 3.82 (dd, J=11.3, 4.3 Hz, 2H), 3.70 (dd, J=11.3, 5.1 Hz, 2H), 3.49 (t, J=8.5 Hz, 2H). $^{13}$C NMR (75 MHz, CDCl$_3$ and MeOD) δ 168.5, 166.6, 166.0, 159.5, 157.7, 144.3, 141.6, 132.3, 130.9, 127.8, 121.8-121.5 (m), 120.5, 119.7, 119.4, 118.8, 111.5 (d, J=3.9 Hz), 111.13 (d, J=3.8 Hz), 104.0, 61.6, 52.6, 48.8, 43.4, 27.5. HRMS (ESI) calcd for $C_{24}H_{23}F_4N_4O_3$ 491.1701 (M+H)$^+$, found 491.1697.

1-(6-(3-Fluoro-5-(trifluoromethyl)benzyl)pyrimidin-4-yl)-N-(2-methoxyethyl)indoline-4-carboxamide (30b). Compound 30b (30 mg, 65%) was synthesized by a procedure similar to that used to prepare compound 12a as a white solid. $^1$H NMR (300 MHz, chloroform-d) δ 8.78 (s, 1H), 8.63 (d, J=8.1 Hz, 1H), 7.38 (s, 1H), 7.31-7.21 (m, 3H), 7.17 (d, J=7.7 Hz, 1H), 6.47 (d, J=6.2 Hz, 1H), 6.43 (s, 1H), 4.08 (s, 2H), 4.02 (t, J=8.6 Hz, 2H), 3.61 (ddd, J=16.4, 10.7, 6.9 Hz, 6H), 3.42 (s, 3H). $^{13}$C NMR (75 MHz, CDCl$_3$) δ 167.6, 166.2, 164.2, 160.9, 159.5, 158.0, 144.5, 141.8 (d, J=7.6 Hz), 132.9, 132.5, 132.5, 131.2, 127.8, 125.0, 121.7 (t, J=3.6 Hz), 120.0, 119.6 (d, J=21.4 Hz), 118.6, 111.3 (dd, J=24.6, 3.9 Hz), 103.9, 77.4, 77.0, 76.6, 71.2, 48.8, 43.8, 39.5, 27.7. HRMS (ESI) calcd for $C_{24}H_{23}F_4N_4O_2$ 475.1752 (M+H)$^+$, found 475.1749.

1-(6-(3-Fluoro-5-(trifluoromethyl)benzyl)pyrimidin-4-yl)-N-(3-hydroxypropyl)indoline-4-carboxamide (30c). Compound 30c (26 mg, 56%) was synthesized by a procedure similar to that used to prepare compound 12a as a white solid. $^1$H NMR (300 MHz, chloroform-d) δ 8.77 (s, 1H), 8.63 (d, J=8.1 Hz, 1H), 7.38 (s, 1H), 7.29-7.20 (m, 3H), 7.14 (d, J=7.7 Hz, 1H), 6.64 (t, J=6.1 Hz, 1H), 6.43 (s, 1H), 4.07 (s, 2H), 4.00 (t, J=8.6 Hz, 2H), 3.76 (t, J=5.5 Hz, 2H), 3.69-3.50 (m, 4H), 3.23 (s, 1H), 1.82 (p, J=5.7 Hz, 2H). $^{13}$C NMR (75 MHz, CDCl$_3$) δ 168.7, 166.2, 164.2, 160.9, 159.5, 158.0, 144.6, 141.8 (d, J=7.5 Hz), 132.6, 131.0, 127.9, 121.8-121.6 (m), 119.8, 119.5, 118.8, 111.7-111.0 (m), 103.9, 59.9, 48.8, 43.8, 37.0, 32.1, 27.7. HRMS (ESI) calcd for $C_{24}H_{23}F_4N_4O_2$ 475.1752 (M+H)$^+$, found 475.1749.

1-(6-(3-Fluoro-5-(trifluoromethyl)benzyl)pyrimidin-4-yl)-N-(4-hydroxybutyl)indoline-4-carboxamide (30d). Compound 30d (30 mg, 61%) was synthesized by a procedure similar to that used to prepare compound 12a as a white solid. $^1$H NMR (300 MHz, chloroform-d and MeOD) δ 8.66 (s, 1H), 8.52 (d, J=8.1 Hz, 1H), 7.33 (s, 1H), 7.27-7.06 (m, 5H), 6.39 (s, 1H), 4.02 (s, 2H), 3.94 (t, J=8.5 Hz, 2H), 3.61 (t, J=5.8 Hz, 2H), 3.47 (t, J=8.5 Hz, 2H), 3.38 (t, J=6.2 Hz, 2H), 1.63 (dq, J=12.9, 6.7 Hz, 4H). $^{13}$C NMR (75 MHz, CDCl$_3$ and MeOD) δ 168.5, 165.9, 164.1, 160.8, 159.5, 157.7, 144.2, 141.6 (d, J=7.7 Hz), 132.3, 131.5, 127.7, 121.6, 120.3, 119.7, 119.4, 118.5, 111.4 (d, J=3.8 Hz), 111.1 (d, J=3.7 Hz), 104.0, 61.7, 48.8, 43.3, 39.6, 29.6, 27.4, 25.9. HRMS (ESI) calcd for $C_{25}H_{25}F_4N_4O_2$ 489.1908 (M+H)$^+$, found 489.1904.

(1-(6-(3-Fluoro-5-(trifluoromethyl)benzyl)pyrimidin-4-yl)indolin-4-yl)(3-hydroxyazetidin-1-yl)methanone (30e). Compound 30e (17 mg, 37%) was synthesized by a procedure similar to that used to prepare compound 12a as a white solid. $^1$H NMR (300 MHz, chloroform-d) δ 8.76 (d, J=1.0 Hz, 1H), 8.56 (d, J=8.2 Hz, 1H), 7.38 (s, 1H), 7.24 (d, J=8.4 Hz, 3H), 7.00 (dd, J=7.7, 1.0 Hz, 1H), 6.45-6.39 (m, 1H), 4.79-4.66 (m, 1H), 4.41 (s, 2H), 4.11-3.94 (m, 6H), 3.52-3.39 (m, 2H), 3.06 (s, 1H). $^{13}$C NMR (75 MHz, CDCl$_3$) δ 169.6, 166.2, 164.2, 160.9, 159.5, 158.0, 144.5, 141.7 (d, J=7.6 Hz), 132.0, 129.5, 127.5, 121.8-121.6 (m), 120.9, 119.6 (d, J=21.7 Hz), 118.3, 111.3 (d, J=28.0 Hz), 103.9, 62.2, 61.7, 58.2, 48.7, 43.7, 27.2. HRMS (ESI) calcd for $C_{24}H_{21}F_4N_4O_2$ 473.1595 (M+H)$^+$, found 473.1593.

1-(6-(3-Fluoro-5-(trifluoromethyl)benzyl)pyrimidin-4-yl)-N-(2-fluoroethyl)indoline-4-carboxamide (30f). Compound 30f (36 mg, 78%) was synthesized by a procedure similar to that used to prepare compound 12a as a white solid. $^1$H NMR (300 MHz, chloroform-d) δ 8.83-8.73 (m, 1H), 8.66 (d, J=8.1 Hz, 1H), 7.39 (s, 1H), 7.33-7.15 (m, 4H), 6.45 (d, J=9.4 Hz, 2H), 4.71 (t, J=4.7 Hz, 1H), 4.55 (t, J=4.7 Hz, 1H), 4.14-3.95 (m, 4H), 3.83 (q, J=5.1 Hz, 1H), 3.74 (q, J=5.1 Hz, 1H), 3.58 (t, J=8.5 Hz, 2H). $^{13}$C NMR (75 MHz, CDCl$_3$) δ 167.8, 166.3, 164.2, 160.9, 159.5, 158.0, 144.7, 141.8 (d, J=7.6 Hz), 132.6, 130.8, 128.0, 121.7 (t, J=3.5 Hz), 119.9, 119.8, 119.5, 118.9, 111.5 (d, J=3.7 Hz), 111.2 (d, J=3.8 Hz), 103.9, 82.8 (d, J=166.7 Hz), 48.8, 43.8, 40.2 (d, J=19.5 Hz), 27.7. $^{19}$F NMR (282 MHz, chloroform-d) δ −62.7, −110.6 (t, J=8.8 Hz), −224.2 (tt, J=47.4, 28.3 Hz). HRMS (ESI) calcd for $C_{23}H_{20}F_5N_4O$ 473.1595 (M+H)$^+$, found 473.1593.

1-(6-(3-Fluoro-5-(trifluoromethyl)benzyl)pyrimidin-4-yl)-N,N-bis(2-hydroxyethyl)indoline-4-carboxamide (30g). Compound 30g (27 mg, 53%) was synthesized by a procedure similar to that used to prepare compound 12a as a white solid. $^1$H NMR (300 MHz, chloroform-d) δ 8.71 (s, 1H), 8.45 (d, J=8.2 Hz, 1H), 7.37 (s, 1H), 7.29-7.17 (m, 3H), 6.97 (d, J=7.6 Hz, 1H), 6.40 (s, 1H), 4.10-3.57 (m, 12H), 3.44 (t, J=5.0 Hz, 2H), 3.26 (t, J=8.5 Hz, 2H). $^{13}$C NMR (75 MHz, CDCl$_3$) δ 172.3, 166.2, 164.2, 160.9, 159.5, 158.0, 144.0, 141.7 (d, J=7.5 Hz), 133.0, 129.7, 127.8, 122.0-121.5 (m), 120.2, 119.8, 119.5, 117.0, 111.3 (d, J=24.4 Hz), 103.8, 61.1, 60.1, 52.9, 49.1, 48.5, 43.6, 26.1. HRMS (ESI) calcd for $C_{25}H_{25}F_4N_4O_3$ 505.1857 (M+H)$^+$, found 505.1853.

Molecular Docking Protocol. The molecular docking study was performed using Schrödinger Small-Molecule Drug Discovery Suite (Schrödinger, LLC, New York, NY, 2020). The co-crystal structures of GPR52 and compound 2 (PDB code: 6LI0) was downloaded from RCS PDB bank. The co-crystal structure was preprocessed and minimized with Schrödinger Protein Preparation Wizard using default settings. The grid center was chosen on the centroid of existing ligand and the size of grid box was set to 30 Å on each side. The 3D structure of ligand 12c was created using Schrödinger Maestro and a low energy conformation was calculated using LigPrep. Docking was employed with Glide using the SP precision. Docked poses were incorporated into Schrödinger Maestro for visualization and analysis of binding site interactions.

In Vitro Pharmacology

Cell Culture and Plasmids. Wildtype (WT) human embryonic kidney 293 (HEK293) cells were a generous gift from Dr. Asuka Inoue, Tohoku University.[32] The wild type HEK293 cells were cultured in DMEM (Gibco, Carlsbad, CA) with 10% FBS (Omega Scientific, Tarzana, CA), 10,000 U/mL penicillin-streptomycin (Gibco, Carlsbad, CA) in a humidified incubator at 37° C. in 5% $CO_2$. GPR52 TANGO construct was purchased from Addgene (Watertown, MA). A stop codon was placed in frame immediately after the receptor coding sequence to generate a human GPR52 WT coding construct. Point mutation of GPR52 WT from GPR52 TANGO was made by polymerase chain reaction (PCR) using the QuikChange II Site-Directed Mutagenesis Kit (Agilent Technologies, Santa Clara, CA) according to the manufacturer's protocol. Mutagenesis and sequencing primers were obtained from ThermoFisher (Pittsburgh, PA). The primers used to make the GPR52 WT point mutant were 5 gctaacagctgttccatctaagataccggtggacgcacc-3' (sense) (SEQ ID NO 1 and 5'-cgattstcgacaaggtagattctatggccacctgcgtgg-3' (antisense) (SEQ ID NO:2). Parental DNA in the reaction mixture was digested using restriction endonuclease DpnI (from diplococcus pneumoniae) at 37° C. for one hour. Digestion mixture (2 μL) was transformed into XL1-Blue supercompetent cells by heat shock at 42° C. for 45 seconds. The reaction was incubated in Super Optimal broth with Catabolite repression medium (Sigma-Aldrich) and then plated onto Luria-Bertani (LB) agar plates containing 100 μg/mL ampicillin. A single colony was selected for sequencing, and the point mutation verified prior to use (Molecular Genomics Core, University of Texas Medical Branch, Galveston, TX).

Transfections. For the cAMP Glosensor assays, 6.5×10$^5$ wildtype HEK293 cells were plated in 6-well plates (Corning, Oneonta, NY) 24 h before transfection to achieve 70-80% confluency the following day. Each well of wildtype HEK293 cells were transiently transfected with 0.10 μg of wild type human GPR52 cDNA and 1 μg of 22F Glosensor plasmid (Promega, Madison, WI) using 10 μL Lipofectamine 2000 (Invitrogen, Waltham, MA) in 1 mL of OptiMEM (Gibco, Carlsbad, CA) and 1 mL growth media.

cAMP Glosensor Assay. 18 h after transfection, wildtype HEK293 cells with GPR52 and Glosensor constructs (see transfections above), cells were seeded at 60,000 cells/well in growth media into poly-L-lysine (Trevigen, Gaithersburg, MD) coated 96-well white clear-bottomed cell culture plates (Greiner Bio-One, Monroe, NC). 4 h later complete media was aspirated and replaced with 90 μL of 1% Glosensor reagent (Promega, Madison, WI) in 1×Hanks balanced salt solution (HBSS) and 20 mM HEPES. Cells were serum starved for 2 h at room temperature in the dark. Test compounds were weighed and diluted to 2 mM in DMSO. Serial dilutions of each test compound were prepared at 10× final concentration and transferred to a 96 well source plate. Cells were incubated with 10 μL of 10× drug solutions for 15 min. LCPS were recorded on a Microbeta2 Microplate counter (Perkin Elmer, Waltham, MA). Data from at least three independent experiments (n=3 to 21) conducted in technical triplicate are presented as percentage of compound 4 response. All in vitro pharmacological data were analyzed using GraphPad Prism 7.05 software (La Jolla, CA). Data from cAMP ligand dose response assays are presented as the half maximum (EC$_{50}$, nM) and maximum effect (E$_{max}$) (means±SEM) as computed by GraphPad using a four-parameter nonlinear regression curve-fitting algorithm. All E$_{max}$ ligand responses were scaled relative to 3 μM of compound 4 in cells treated for each assay (3 μM compound 4 response set to 100%).

TANGO β-arrestin recruitment assay. 18 h after transfection, HTLA cells expressing GPR52 TANGO plasmid (see transfections above) were seeded at 80,000 cells/well in 100 μL growth media into poly-L-lysine coated 96-well white clear-bottomed cell culture plates. Test compounds were weighed and diluted to 2 mM in DMSO. Serial dilutions of each compound were prepared at 10× final concentration in growth media in a 96-well source plate. At 24 h post-transfection, cells were treated with 11 μL of 10× drug solutions and returned to the incubator. After 20 h incubation, growth media was aspirated and the cells were lysed with 50 μL of 40-fold diluted Bright-Glo luciferase substrate (Promega, Madison, WI) in 1×HBSS for 20 min at room temperature. Luminescence in light counts per second (lcps) was recorded on a MicroBeta2 Microplate counter. Data from at least three independent experiments (n=3 to 6) conducted in technical triplicate are presented as percentage of compound 4a response (compound 4a response set to 100%). All data were analyzed using GraphPad Prism 8.4.3 software (La Jolla, CA). Data from β-arrestin recruitment dose response assays are presented as the half maximum (EC$_{50}$, nM) and maximum effect (E$_{max}$) (means±SEM) as computed by GraphPad using a four-parameter nonlinear regression curve-fitting algorithm. Notably, some compounds when tested for β-arrestin recruitment did not show saturating concentration responses; in these cases, the curve-fitting algorithm in GraphPad Prism was constrained by defining the maximum efficacy as the maximal observed luminescence.

Bias factor calculations. Mean efficacy (E$_{max}$) and potency (EC$_{50}$) were taken from at least three independent experiments for all compounds tested in both the cAMP and β-arrestin recruitment assays. Formulas for bias factor calculations were adapted from Kenakin[37]. The bias factor calculation method requires an agonist to have an E$_{max}$>35% compared to the reference agonist, which all tested compounds displayed. E$_{max}$ and EC$_{50}$ values for each compound were entered into the equation log(E$_{max}$/EC$_{50}$) for both cAMP and β-arrestin recruitment assays, then subtracted from the respective log(E$_{max}$/EC$_{50}$) for the reference compound 4a to obtain a Δ log(E$_{max}$/EC$_{50}$) for each compound. A ΔΔ log(E$_{max}$/EC$_{50}$) value for each compound was calculated by subtraction of Δ log(E$_{max}$/EC$_{50}$)$_{β-arrestin}$ from Δ log(E$_{max}$/EC$_{50}$)$_{cAMP}$. The inverse log of this ΔΔ log(E$_{max}$/EC$_{50}$) value is the G protein bias factor. Conversely, the β-arrestin bias factor is calculated from the inverse log of ΔΔ log(E$_{max}$/EC$_{50}$) when Δ log(E$_{max}$/EC$_{50}$)$_{cAMP}$ is subtracted from Δ log(E$_{max}$/EC$_{50}$)$_{β-arrestin}$. The calculated bias factors represent relative propensity to activate one pathway over another in reference to compound 4a.

In Vivo PK and Brain Permeability Studies. Male Sprague-Dawley rats (n=3 per treatment group; Beijing Vital River Laboratory, Animal Technology Co., Ltd, Beijing, China) weighing 200-250 g at the beginning of the experiment were housed three per cage in a pathogen-free, temperature-controlled (20-26° C.), and humidity-controlled (40-70%) environment with a 12 h light-dark cycle and ad libitum access to food and filtered water. Rats were randomly assigned to treatment groups. Vehicle [10% dimethyl sulfoxide (DMSO) and 90% 2-hydroxypropyl-β-cyclodextrin (HP-β-CD); Cyclodextrin Technologies Development, Inc., High Springs, FL, USA] or compound 12c dissolved in vehicle was administered to rats IV at 10 mg/kg or PO at 20 mg/kg. The rat was restrained manually at the designated time points (0.08, 0.25, 0.5, 1.0, 2.0, 4.0, 8.0, and 24 h post-dosing for IV; 0.25, 0.5, 1.0, 2.0, 4.0, 8.0, and 24 h post-dosing for PO). 100 μL of blood (yielding ~50 μL of plasma) samples are taken from the animal's jugular vein and placed into micro K$_2$EDTA tubes. Blood samples were placed on ice and centrifuged at 8000 rpm for 5 min at 4° C. to generate plasma sample within 0.5 h of collection. Brain samples were collected at 0.25 and 1 h post-dosing. All samples were stored at −20° C. The concentration of 12c in each sample was analyzed by Sundia MediTech Co., Ltd. The study and the related standard operating procedures were reviewed and approved by the Sundia Institutional Animal Care and Use Committee. The Sundia animal facility is approved with yearly inspection by the Shanghai Laboratory Animal Management Committee. All treatment assignments were blinded to investigators who performed PK assays and end point statistical analyses.

The PK parameters of compound 12c were calculated according to a non-compartmental model using WinNonlin (Pharsight Corporation, ver 5.3, Mountain View, CA, USA). The peak concentration ($C_{max}$) was directly obtained by visual inspection of the plasma concentration-time profile. The elimination rate constant ($\lambda$) was obtained by the least-squares fitted terminal log-linear portion of the slope of the plasma concentration-time profile. The elimination half-life ($t_{1/2}$) was evaluated according to $0.693/\lambda$. The area under the plasma concentration-time curve from 0 to time t ($AUC_{0-t}$) was evaluated using the linear trapezoidal rule and further extrapolated to infinity ($AUC_{0-\infty}$) according to the following equation: $AUC_{0-\infty} = AUC_{0-t} + C_{last}/\lambda$. The pharmacokinetic parameters were presented as mean±SEM.

In Vivo Pharmacology of Compound 12c

Animals. Naïve male C57/BL6 mice (n=60; Jackson Laboratory, Bar Harbor, ME) weighing between 24-31 g (~60 days of age) at the beginning of the experiment were housed four/cage in a temperature- (21-23° C.) and humidity-controlled (40-50%) environment on a 12 h light/dark cycle (lights on at 0600). Mice were provided ad libitum access to chow and water for 14-20 days prior to experiments which were carried out in accordance with the National Institutes of Health Guide for the Care and Use of Laboratory Animals (2011) and with the approval of the Institutional Animal Care and Use Committee at University of Texas Medical Branch.

Drugs. Compound 12c was dissolved in 0.9% saline containing in 20% of HP-β-CD with a final pH of the solution adjusted to 7.4. Amphetamine was prepared in 0.9% saline. Compounds were then administered IP at 2 mL/1 kg body weight.

Locomotor activity assessment. A modified open field activity system (San Diego Instruments, San Diego, California, U.S.A.) was employed to quantify activity under low-light conditions.[33-35] Clear Plexiglas chambers (40×40×40 cm) were surrounded by a 4×4 photobeam matrix positioned ~1 cm above the chamber floor. Horizontal activity was quantified as the sum of photobeam breaks that occurred within the inner central 16×16 cm area and in the surrounding outer 12×12 cm perimeter of the activity monitor.

A between-subjects design was employed to study the efficacy of compound 12c to impact horizontal activity. Mice were handled three times/week for two weeks prior to the study and were habituated to the motor activity monitors 1 h/day for three days. Mice were transported in their home cages and allowed to acclimate to the testing room for 1 h prior to evaluation. On the day of the test, mice were weighed and randomized into five treatment groups for compound administration (n=12/group). Due to missed injections, 2 mice were excluded from analysis with the final n=11-12/group). Following IP administration of vehicle or compound 12c (0.3, 1, 3, 10 mg/kg), automated activity monitoring began immediately and continued for 30 min. Mice were then injected with AMPH (3 mg/kg, IP) and activity monitored for the next 90 min. All testing occurred between 0800 and 1700 hrs.

Statistical analyses. Locomotor activity are presented as mean horizontal activity (mean±SEM). A one-way ANOVA for a between-subjects design was employed to analyze horizontal activity. A priori comparisons were defined prior to the start of experimentation and conducted by Dunnett's procedure,[36] with an experiment-wise error rate set at α=0.05. Investigators who performed compound administration were blinded to treatment assignments and endpoint statistical analyses.

| COMPOUND | Structure | $EC_{50}$ (nM) | $E_{max}$ (%) |
|---|---|---|---|
| PW0671 | 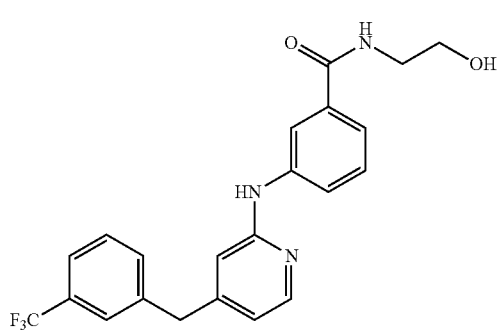 [SMILES: O=C(NCCO)c1cccc(Nc2cc(Cc3cccc(C(F)(F)F)c3)ccn2)c1] | 282 ± 46 | 197 ± 26 |
| PW0673 | 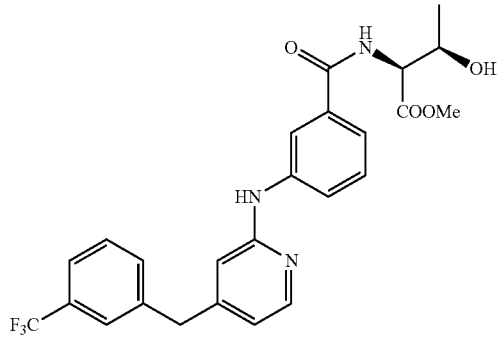 [SMILES: COC(=O)[C@@H](NC(=O)c1cccc(Nc2cc(Cc3cccc(C(F)(F)F)c3)ccn2)c1)[C@@H](C)O] | 448 ± 59 | 164 ± 12 |

-continued

| COMPOUND | Structure | EC$_{50}$ (nM) | E$_{max}$ (%) |
|---|---|---|---|
| PW0674 | 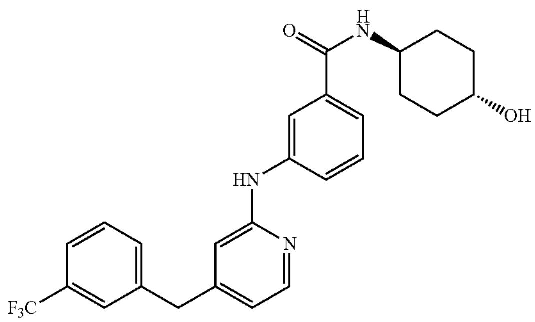 [SMILES: O=C(N[C@H]1CC[C@H](O)CC1)c1cccc(Nc2cc(Cc3cccc(C(F)(F)F)c3)ccn2)c1] | 467 ± 60 | 131 ± 13 |
| PW0675 | 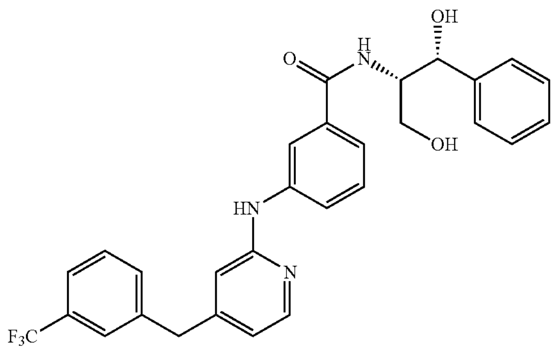 [SMILES: O=C(N[C@@H](CO)[C@H](O)c1ccccc1)c1cccc(Nc2cc(Cc3cccc(C(F)(F)F)c3)ccn2)c1] | 862 ± 157 | 188 ± 11 |
| PW0676 | 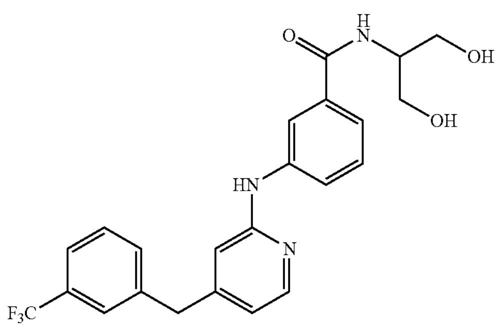 [SMILES: O=C(NC(CO)CO)c1cccc(Nc2cc(Cc3cccc(C(F)(F)F)c3)ccn2)c1] | 220 ± 39 | 214 ± 19 |
| PW0677 | 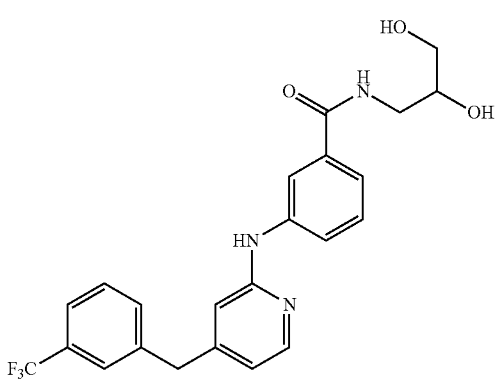 [SMILES: O=C(NCC(O)CO)c1cccc(Nc2cc(Cc3cccc(C(F)(F)F)c3)ccn2)c1] | 286 ± 3 | 268 ± 12 |

-continued

| COMPOUND | Structure | EC$_{50}$ (nM) | E$_{max}$ (%) |
|---|---|---|---|
| PW0689 | 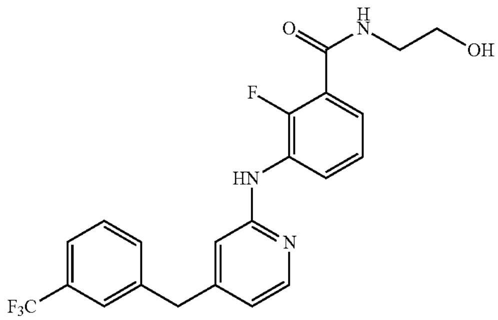 [SMILES: O=C(NCCO)c1cccc(Nc2cc(Cc3cccc(C(F)(F)F)c3)ccn2)c1F] | 342 ± 78 | 134 ± 2 |
| PW0693 | 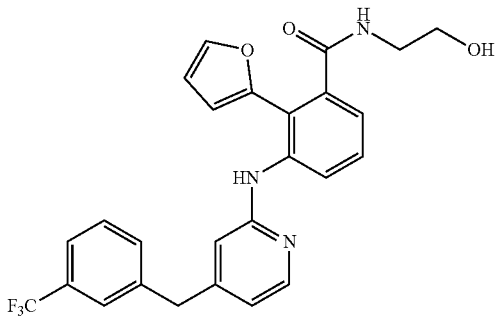 [SMILES: O=C(NCCO)c1cccc(Nc2cc(Cc3cccc(C(F)(F)F)c3)ccn2)c1-c1ccco1] | 84 ± 12 | 147 ± 6 |
| PW0698 | 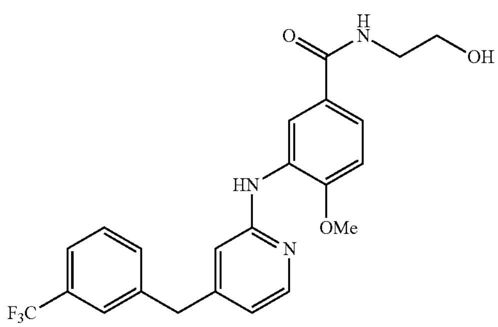 [SMILES: COc1ccc(C(=O)NCCO)cc1Nc1cc(Cc2cccc(C(F)(F)F)c2)ccn1] | 1432 ± 207 | 111 ± 7 |
| PW0729 | 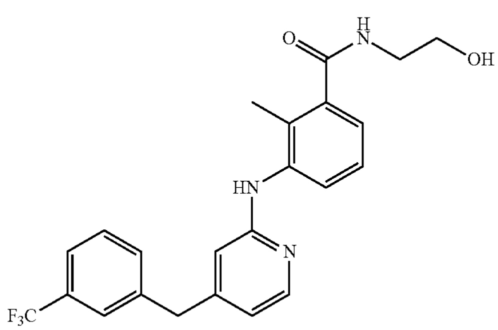 [SMILES: Cc1c(Nc2cc(Cc3cccc(C(F)(F)F)c3)ccn2)cccc1C(=O)NCCO] | 47 ± 8 | 143 ± 5 |

-continued

| COMPOUND | Structure | EC$_{50}$ (nM) | E$_{max}$ (%) |
| --- | --- | --- | --- |
| PW0730 | 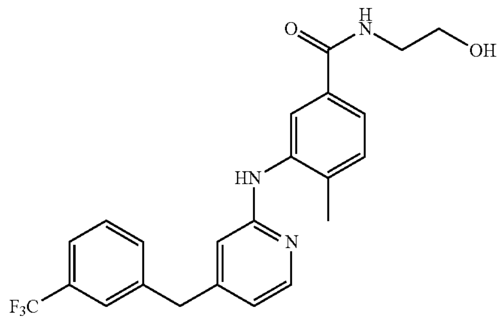 [SMILES: Cc1ccc(C(=O)NCCO)cc1Nc1cc(Cc2cccc(C(F)(F)F)c2)ccn1] | 984 ± 18 | 94 ± 6 |
| PW0823 | 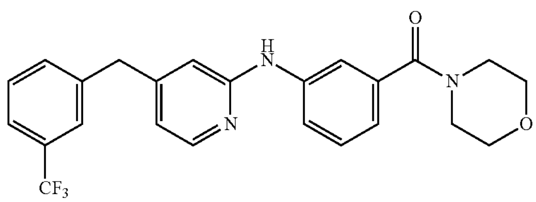 [SMILES: O=C(c1cccc(Nc2cc(Cc3cccc(C(F)(F)F)c3)ccn2)c1)N1CCOCC1] | 774 ± 124 | 93 ± 7 |
| PW0824 | 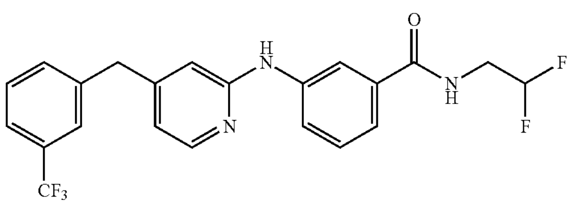 [SMILES: O=C(NCC(F)F)c1cccc(Nc2cc(Cc3cccc(C(F)(F)F)c3)ccn2)c1] | 638 ± 137 | 152 ± 7 |
| PW0825 | 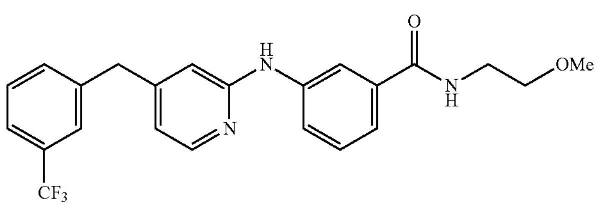 [SMILES: COCCNC(=O)c1cccc(Nc2cc(Cc3cccc(C(F)(F)F)c3)ccn2)c1] | 252 ± 54 | 131 ± 15 |
| PW0826 | 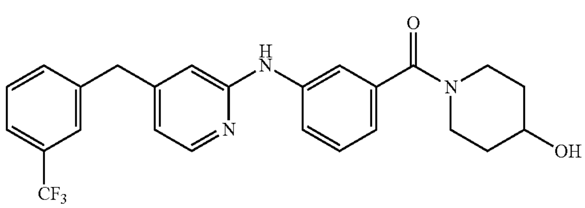 [SMILES: O=C(c1cccc(Nc2cc(Cc3cccc(C(F)(F)F)c3)ccn2)c1)N1CCC(O)CC1] | 672 ± 134 | 99 ± 12 |
| PW0831 | 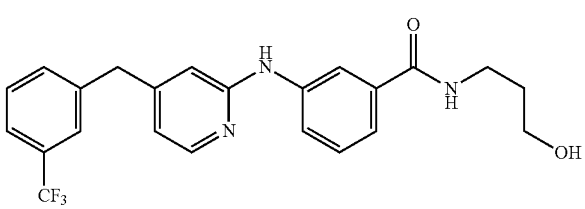 [SMILES: O=C(NCCCO)c1cccc(Nc2cc(Cc3cccc(C(F)(F)F)c3)ccn2)c1] | 220 ± 43 | 129 ± 7 |
| PW0832 | 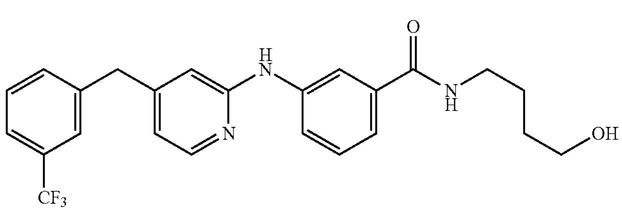 [SMILES: O=C(NCCCCO)c1cccc(Nc2cc(Cc3cccc(C(F)(F)F)c3)ccn2)c1] | 198 ± 37 | 129 ± 8 |

-continued

| COMPOUND | Structure | EC$_{50}$ (nM) | E$_{max}$ (%) |
|---|---|---|---|
| PW0839 | 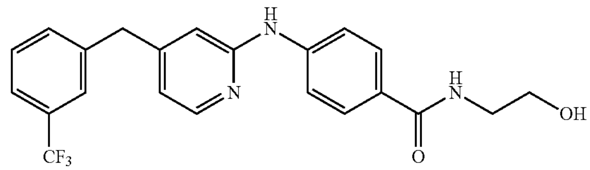 [SMILES: O=C(NCCO)c1ccc(Nc2cc(Cc3cccc(C(F)(F)F)c3)ccn2)cc1] | 1086 ± 85 | 115 ± 10 |
| PW0840 | 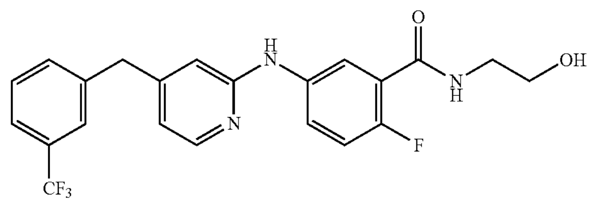 [SMILES: O=C(NCCO)c1cc(Nc2cc(Cc3cccc(C(F)(F)F)c3)ccn2)ccc1F] | 229 ± 38 | 126 ± 9 |
| PW0841 | 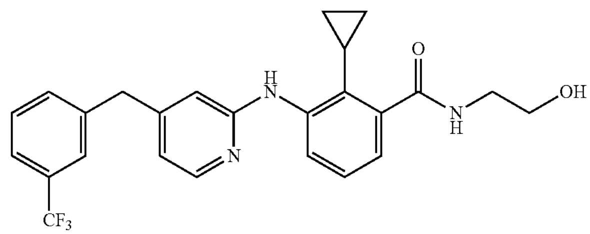 [SMILES: O=C(NCCO)c1cccc(Nc2cc(Cc3cccc(C(F)(F)F)c3)ccn2)c1C1CC1] | 30 ± 9 | 146 ± 9 |
| PW0842 | 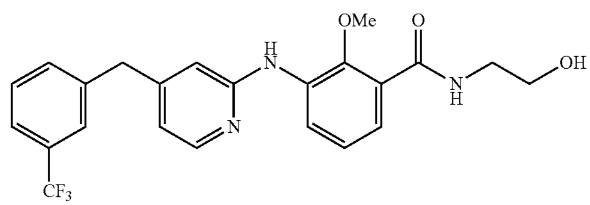 [SMILES: COc1c(Nc2cc(Cc3cccc(C(F)(F)F)c3)ccn2)cccc1C(=O)NCCO] | 64 ± 19 | 149 ± 8 |
| PW0861 | 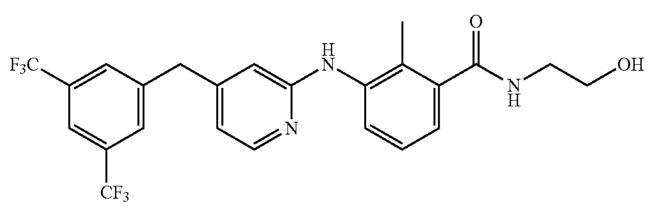 [SMILES: Cc1c(Nc2cc(Cc3cc(C(F)(F)F)cc(C(F)(F)F)c3)ccn2)cccc1C(=O)NCCO] | 211 ± 51 | 127 ± 11 |
| PW0862 | 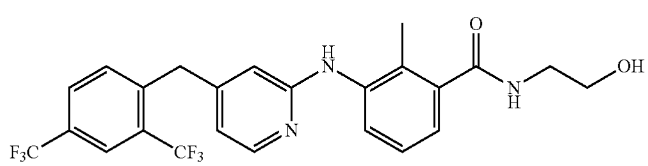 [SMILES: Cc1c(Nc2cc(Cc3ccc(C(F)(F)F)cc3C(F)(F)F)ccn2)cccc1C(=O)NCCO] | 52 ± 11 | 150 ± 12 |
| PW0863 | 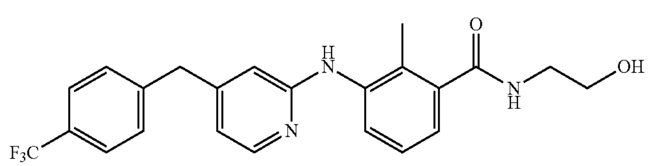 [SMILES: Cc1c(Nc2cc(Cc3ccc(C(F)(F)F)cc3)ccn2)cccc1C(=O)NCCO] | 220 ± 58 | 120 ± 9 |
| PW0864 | 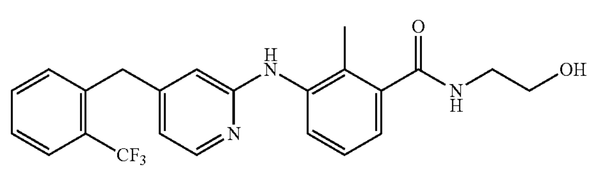 [SMILES: Cc1c(Nc2cc(Cc3ccccc3C(F)(F)F)ccn2)cccc1C(=O)NCCO] | 143 ± 33 | 122 ± 13 |

-continued

| COMPOUND | Structure | EC$_{50}$ (nM) | E$_{max}$ (%) |
|---|---|---|---|
| PW0865 | 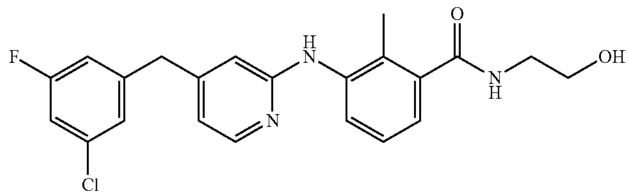 [SMILES: Cc1c(Nc2cc(Cc3cc(F)cc(Cl)c3)ccn2)cccc1C(=O)NCCO] | 46 ± 8 | 135 ± 9 |
| PW0866 | 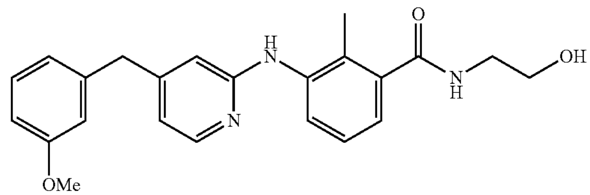 [SMILES: COc1cccc(Cc2ccnc(Nc3cccc(C(=O)NCCO)c3C)c2)c1] | 53 ± 10 | 133 ± 10 |
| PW0867 | 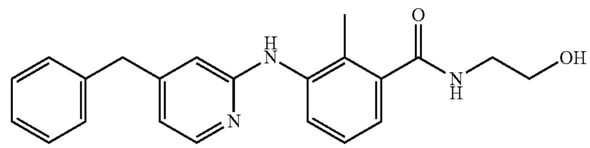 [SMILES: Cc1c(Nc2cc(Cc3ccccc3)ccn2)cccc1C(=O)NCCO] | 278 ± 48 | 139 ± 9 |
| PW0868 | 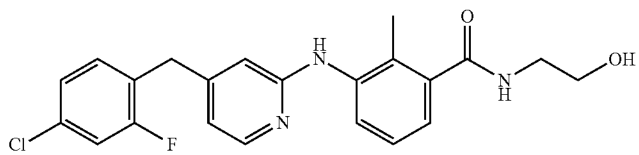 [SMILES: Cc1c(Nc2cc(Cc3ccc(Cl)cc3F)ccn2)cccc1C(=O)NCCO] | 235 ± 47 | 131 ± 8 |
| PW0869 | 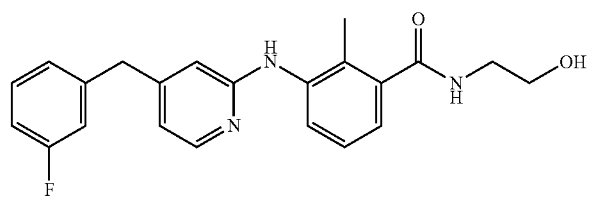 [SMILES: Cc1c(Nc2cc(Cc3cccc(F)c3)ccn2)cccc1C(=O)NCCO] | 136 ± 33 | 137 ± 7 |
| PW0870 | 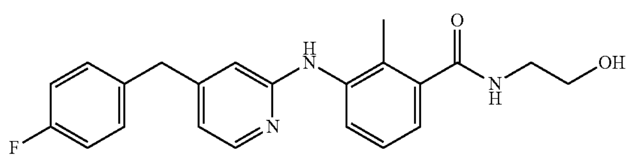 [SMILES: Cc1c(Nc2cc(Cc3ccc(F)cc3)ccn2)cccc1C(=O)NCCO] | 90 ± 17 | 146 ± 9 |
| PW0753 (25a) | 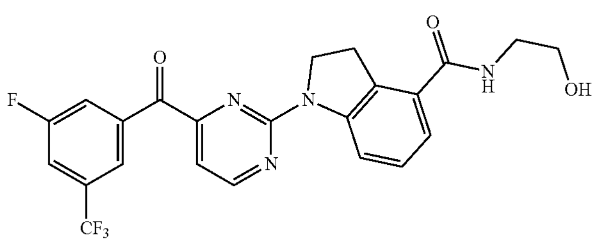 [SMILES: O=C(c1cc(F)cc(C(F)(F)F)c1)c1ccnc(N2CCc3c(C(=O)NCCO)cccc32)n1] | 1589 ± 166 | 96 ± 7 |
| PW0758 (12e) | 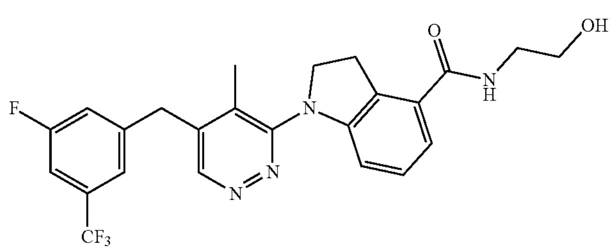 [SMILES: Cc1c(Cc2cc(F)cc(C(F)(F)F)c2)cnnc1N1CCc2c(C(=O)NCCO)cccc21] | 754 ± 62 | 119 ± 6 |

| COMPOUND | Structure | EC$_{50}$ (nM) | E$_{max}$ (%) |
|---|---|---|---|
| PW0760 (25d) | 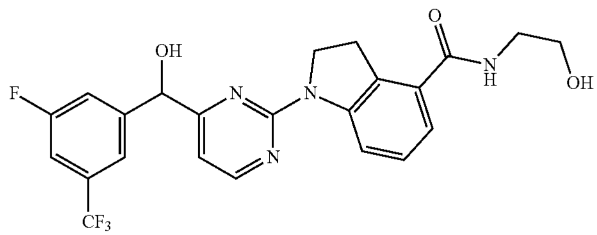 [SMILES: O=C(NCCO)c1cccc2c1CCN2c1nccc(C(O)c2cc(F)cc(C(F)(F)F)c2)n1] | 399 ± 68 | 130 ± 9 |
| PW0774 (25b) | 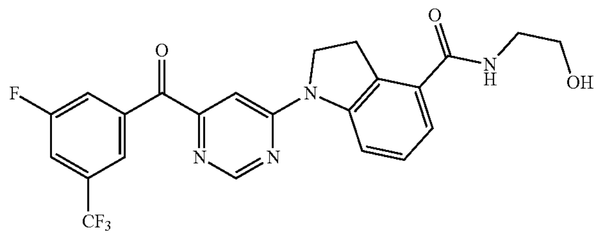 [SMILES: O=C(c1cc(F)cc(C(F)(F)F)c1)c1cc(N2CCc3c(C(=O)NCCO)cccc32)ncn1] | 1693 ± 437 | 22 ± 3 |
| PW0776 (12a) | 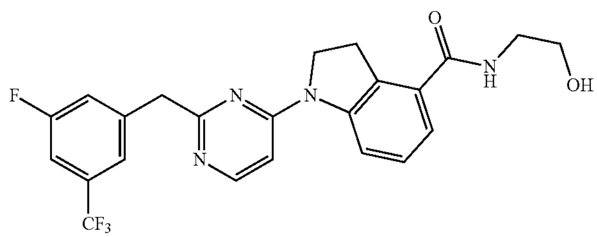 [SMILES: O=C(NCCO)c1cccc2c1CCN2c1ccnc(Cc2cc(F)cc(C(F)(F)F)c2)n1] | 373 ± 35 | 144 ± 7 |
| PW0781 (25h) | 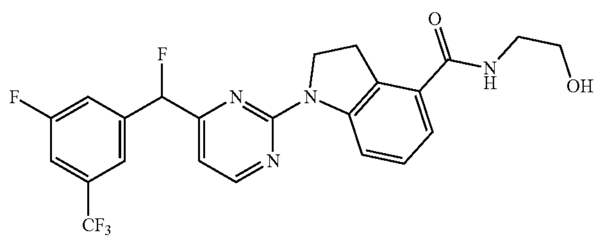 | 329 ± 113 | 144 ± 9 |
| PW0787 (12c) | 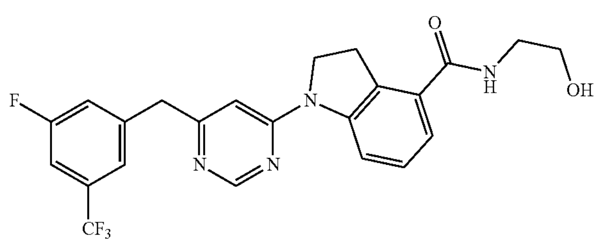 | 135 ± 16 | 136 ± 6 |
| PW0788 (25e) | 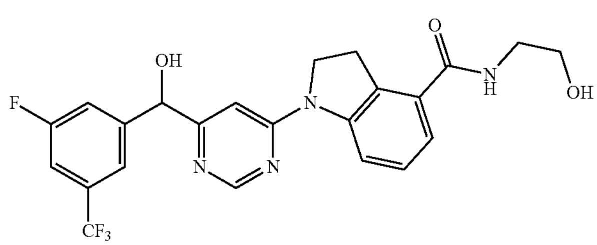 [SMILES: O=C(NCCO)c1cccc2c1CCN2c1cc(C(O)c2cc(F)cc(C(F)(F)F)c2)ncn1] | 338 ± 26 | 134 ± 28 |

-continued
| COMPOUND | Structure | EC$_{50}$ (nM) | E$_{max}$ (%) |
|---|---|---|---|
| PW0796 (12f) | 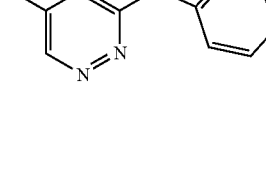 | 562 ± 80 | 97 ± 7 |
| PW0799 (12b) | 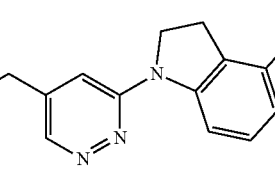 | 158 ± 48 | 158 ± 12 |
| PW0807 (12d) | 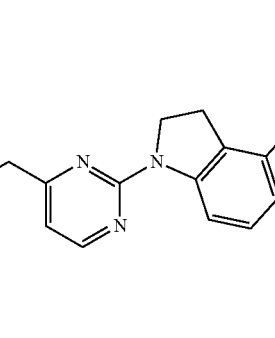 | 186 ± 44 | 138 ± 8 |
| PW0860 (23a) | 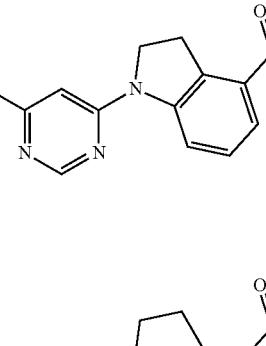 | 101.0 ± 31 | 127 ± 10 |
| PW0873 (25c) | 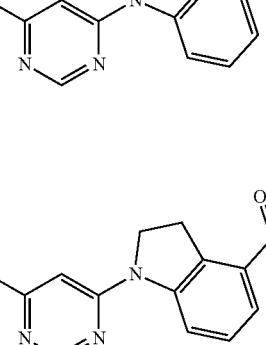 | 1008 ± 237 | 22 ± 4 |
| PW0875 (25i) | 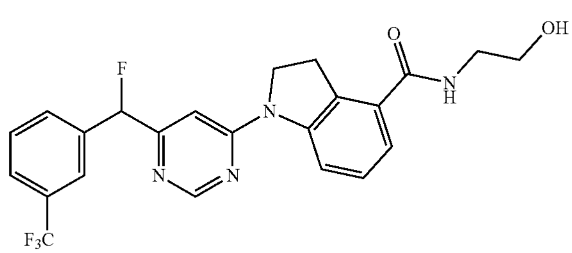 [SMILES: O=C(NCCO)c1cccc2c1CCN2c1cc(C(F)c2cccc(C(F)(F)F)c2)ncn1] | 557 ± 273 | 83 ± 5 |

-continued
| COMPOUND | Structure | EC$_{50}$ (nM) | E$_{max}$ (%) |
|---|---|---|---|
| PW0878 (23d) | 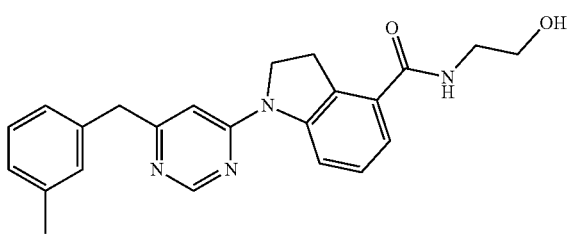 [SMILES: Cc1cccc(Cc2cc(N3CCc4c(C(=O)NCCO)cccc43)ncn2)c1] | 90 ± 19 | 144 ± 9 |
| PW0882 (23b) | 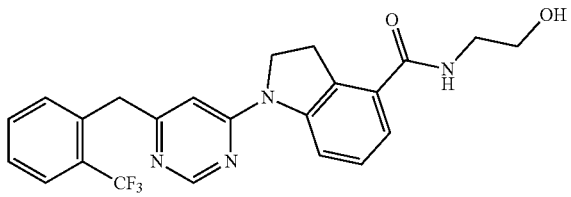 [SMILES: O=C(NCCO)c1cccc2c1CCN2c1cc(Cc2ccccc2C(F)(F)F)ncn1] | 711 ± 60 | 115 ± 6 |
| PW0884 (23c) | 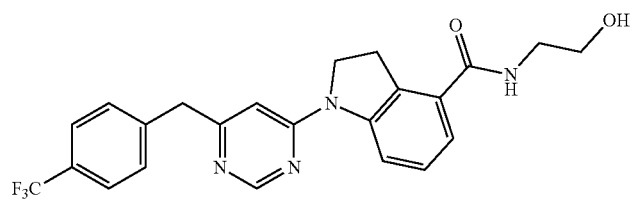 [SMILES: O=C(NCCO)c1cccc2c1CCN2c1cc(Cc2ccc(C(F)(F)F)cc2)ncn1] | 109 ± 19 | 136 ± 7 |
| PW0885 (23e) | 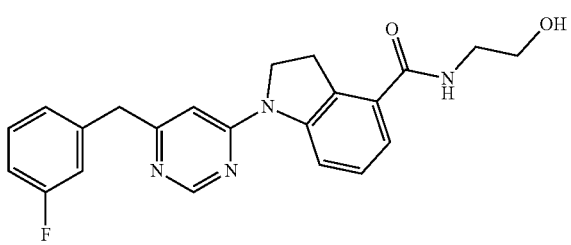 [SMILES: O=C(NCCO)c1cccc2c1CCN2c1cc(Cc2cccc(F)c2)ncn1] | 106 ± 35 | 148 ± 14 |
| PW0888 (23f) | 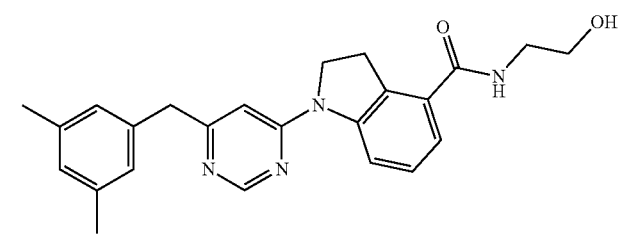 [SMILES: Cc1cc(C)cc(Cc2cc(N3CCc4c(C(=O)NCCO)cccc43)ncn2)c1] | 97 ± 20 | 140 ± 11 |
| PW0889 (23g) | 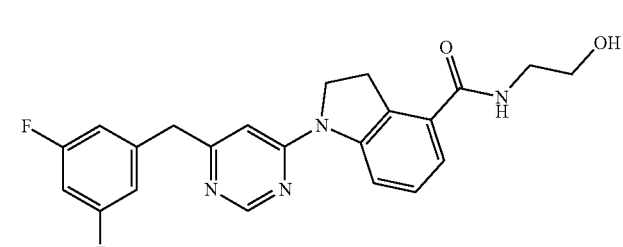 | 115 ± 19 | 142 ± 10 |

-continued

| COMPOUND | Structure | EC$_{50}$ (nM) | E$_{max}$ (%) |
|---|---|---|---|
| PW0890 (23h) | 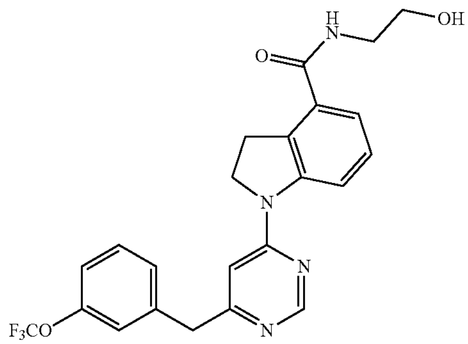 [SMILES: O=C(NCCO)c1cccc2c1CCN2c1cc(Cc2cccc(OC(F)(F)F)c2)ncn1] | 131 ± 24 | 113 ± 11 |
| PW0894 (23i) | 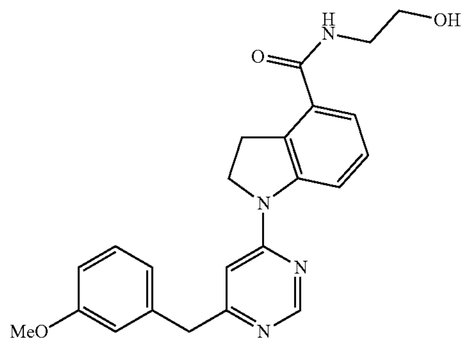 [SMILES: COc1cccc(Cc2cc(N3CCc4c(C(=O)NCCO)cccc43)ncn2)c1] | 351 ± 6 | 122 ± 8 |
| PW0896 (23j) | 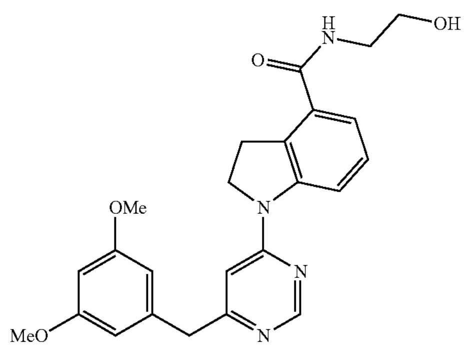 [SMILES: COc1cc(Cc2cc(N3CCc4c(C(=O)NCCO)cccc43)ncn2)cc(OC)c1] | 850 ± 35 | 113 ± 2 |
| PW0898 (25j) | 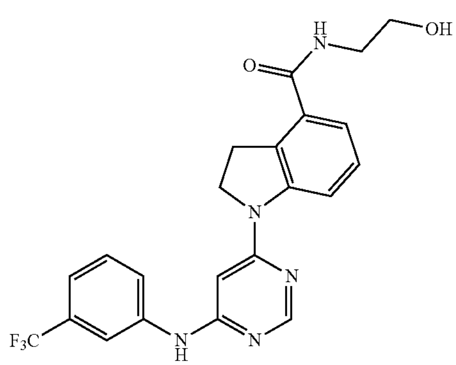 [SMILES: O=C(NCCO)c1cccc2c1CCN2c1cc(Nc2cccc(C(F)(F)F)c2)ncn1] | 1105 ± 24 | 81 ± 2 |

-continued

| COMPOUND | Structure | EC$_{50}$ (nM) | E$_{max}$ (%) |
|---|---|---|---|
| PW0899 (23g) | 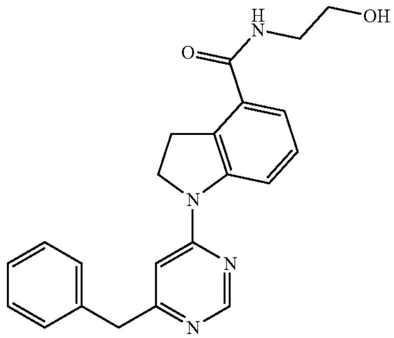 [SMILES: O=C(NCCO)c1cccc2c1CCN2c1cc(Cc2ccccc2)ncn1] | 292 ± 17 | 134 ± 4 |
| PW0903 (25k) | 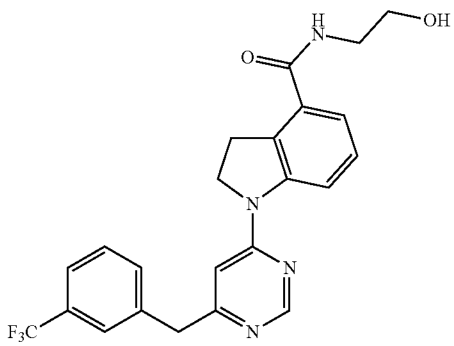 [SMILES: O=C(NCCO)c1cccc2c1CCN2c1cc(Cc2cccc(C(F)(F)F)c2)ncn1] | 2404 ± 292 | 99 ± 4 |
| PW0904 (25l) | 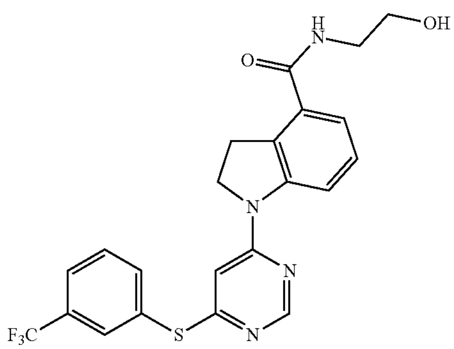 [SMILES: O=C(NCCO)c1cccc2c1CCN2c1cc(Sc2cccc(C(F)(F)F)c2)ncn1] | 371 ± 47 | 123 ± 6 |
| PW0936 (30a) | 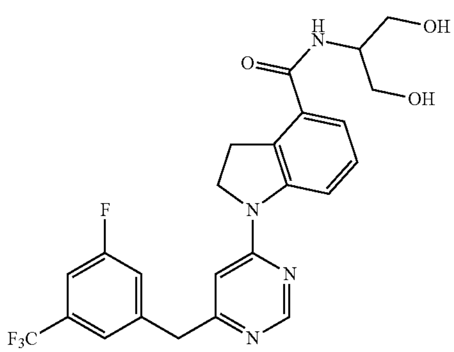 [SMILES: O=C(NC(CO)CO)c1cccc2c1CCN2c1cc(Cc2cc(F)cc(C(F)(F)F)c2)ncn1] | 346 ± 19 | 115 ± 15 |

-continued
| COMPOUND | Structure | EC$_{50}$ (nM) | E$_{max}$ (%) |
|---|---|---|---|
| PW0937 (30b) | 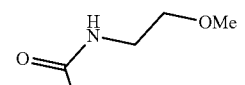 | 489 ± 86 | 119 ± 7 |
| PW0938 (30c) | 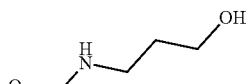 | 275 ± 13 | 120 ± 15 |
| PW0939 (30d) | 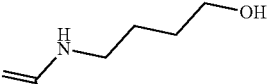 | 399 ± 51 | 120 ± 18 |
| PW0940 (30e) | 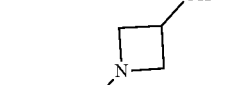 | 760 ± 176 | 111 ± 10 |

-continued
| COMPOUND | Structure | EC$_{50}$ (nM) | E$_{max}$ (%) |
|---|---|---|---|
| PW0948 (30f) | 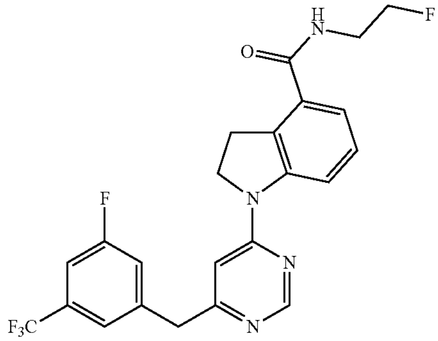 [SMILES: O=C(NCCF)c1cccc2c1CCN2c1cc(Cc2cc(F)cc(C(F)(F)F)c2)ncn1] | 431 ± 7 | 129 ± 17 |
| PW0955 (30g) | 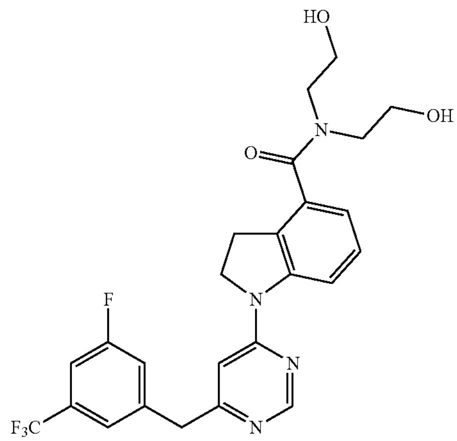 [SMILES: O=C(c1cccc2c1CCN2c1cc(Cc2cc(F)cc(C(F)(F)F)c2)ncn1)N(CCO)CCO] | 673 ± 135 | 119 ± 15 |
A. Experiment Procedures
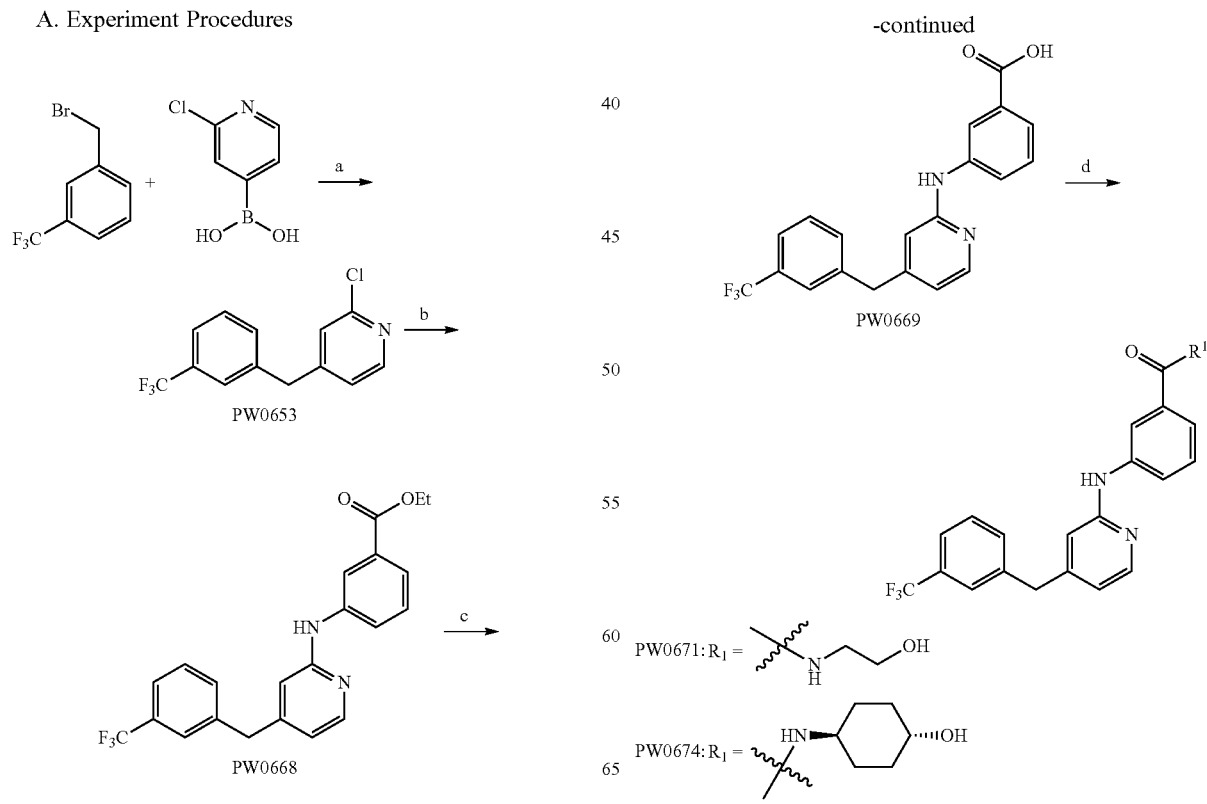

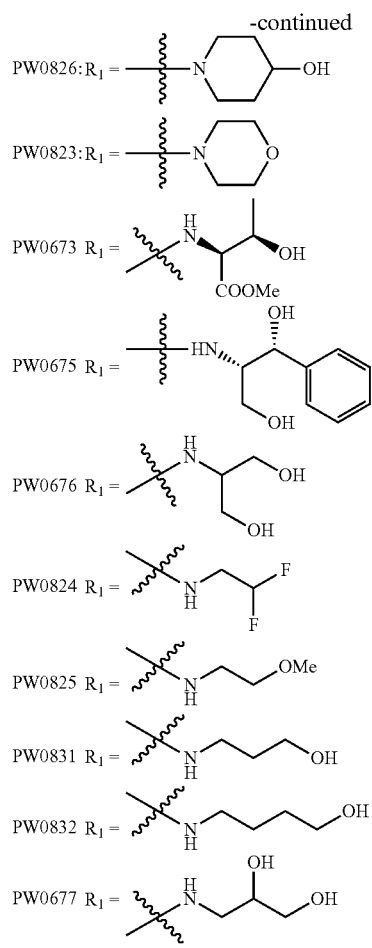

Reagents and conditions: (a) Pd(PPh$_3$)$_4$, Na$_2$CO$_3$, toluene, EtOH, 85° C., 1.5 h, 48%; (b) ethyl 3-aminobenzoate, Pd(OAc)$_2$, XantPhos, Cs$_2$CO$_3$, 1,4-dioxnae, 100° C., 12 h, 76%; (c) i) 4 N NaOH, EtOH, reflux, 2 h; ii) 2 N HCl, 80%; (d) R$^1$H, EDCI, DMAP, HOBt, DMF, rt, 12 h, 41-87%.

Reagents and conditions: (a) Pd(PPh$_3$)$_4$, Na$_2$CO$_3$, toluene, EtOH, 85° C., 1.5 h, 48%; (b) ethyl 3-aminobenzoate, Pd(OAc)$_2$, XantPhos, Cs$_2$CO$_3$, 1,4-dioxnae, 100° C., 12 h, 76%; (c) i) 4 N NaOH, EtOH, reflux, 2 h; ii) 2 N HCl, 80%; (d) R$^1$H, EDCI, DMAP, HOBt, DMF, rt, 12 h, 41-87%.

2-Chloro-4-(3-(trifluoromethyl)benzyl)pyridine (PW0653). Under an atmosphere of nitrogen, a mixture of 1-(bromomethyl)-3-(trifluoromethyl)benzene (287 mg, 1.2 mmol), Na$_2$CO$_3$ (424 mg, 4 mmol), Pd(PPh$_3$)$_4$(115 mg, 0.05 mmol) and (2-chloropyridin-4-yl)boronic acid (157 mg, 1 mmol) in a mixture of toluene (5 mL) and ethanol (2.5 mL) was heated to 85° C. for 1.5 hours. The reaction was cooled to room temperature and poured in water, and then extracted with EtOAc (20 mL×3). The organic phase was washed with brine, dried over Na$_2$SO$_4$, and then concentrated under reduced pressure. The residue was purification by silica gel chromatography (Gradient: 10% to 20% EtOAc in hexane) provided product compound PW0653 as a light yellow oil (131 mg, 48%). $^1$H NMR (300 MHz, Chloroform-d) δ 8.32 (d, J=5.1 Hz, 1H), 7.56 (d, J=7.8 Hz, 1H), 7.52-7.42 (m, 2H), 7.36 (d, J=7.7 Hz, 1H), 7.16 (s, 1H), 7.04 (d, J=5.0 Hz, 1H), 4.04 (s, 2H).

Ethyl 3-((4-(3-(trifluoromethyl)benzyl)pyridin-2-yl) amino)benzoate (PW0668). A mixture of PW0653 (542 mg, 2 mmol), Pd(OAc)$_2$ (44 mg, 0.2 mmol), XantPhos (231 mg, 0.4 mmol), Cs$_2$CO$_3$ (1.3 g, 4 mmol) and ethyl 3-aminobenzoate (330 mg, 2 mmol) in 1,4-dioxane (10 mL) was subjected to three rounds of vacuum evacuation followed by introduction of nitrogen. The reaction mixture was then stirred at 100° C. overnight. The reaction was cooled to room temperature and poured in water, and then extracted with EtOAc (20 mL×3). The organic phase was washed with brine, dried over Na$_2$SO$_4$, and then concentrated under reduced pressure. The residue was purification by silica gel chromatography (Gradient: 10% to 20% EtOAc in hexane) provided product PW0668 as a colorless oil (610 mg, 76%). $^1$H NMR (300 MHz, Chloroform-d) δ 8.16 (d, J=5.1 Hz, 1H), 7.97 (t, J=1.9 Hz, 1H), 7.75-7.61 (m, 2H), 7.56-7.35 (m, 6H), 6.72 (s, 1H), 6.66-6.58 (m, 2H), 4.39 (q, J=7.0 Hz, 3H), 3.96 (s, 2H), 1.43-1.38 (m, 3H).

3-((4-(3-(Trifluoromethyl)benzyl)pyridin-2-yl)amino) benzoic acid (PW0669). To a solution of PW0668 (600 mg, 1.5 mmol) in MeOH (4 mL) was added a 4 N solution of NaOH (2 mL), and the mixture solution was stirred at reflux for 2 hours. The pH of the mixture solution was adjusted to pH 1 with 2 N HCl solution, then white solid precipitated from the solution. The white solid was filtered and washed with water, the cake was collected and dried to afford the product as a white solid PW0669 (445 mg, 80%). $^1$H NMR (300 MHz, DMSO-d$_6$) δ 12.77 (s, 1H), 9.20 (s, 1H), 8.26 (t, J=1.9 Hz, 1H), 8.09 (d, J=5.2 Hz, 1H), 7.93 (dd, J=7.8, 2.3 Hz, 1H), 7.70-7.51 (m, 4H), 7.45 (d, J=7.6 Hz, 1H), 7.34 (t, J=7.9 Hz, 1H), 6.70 (d, J=5.2 Hz, 1H), 6.63 (s, 1H), 4.03 (s, 2H).

N-(2-Hydroxyethyl)-3-((4-(3-(trifluoromethyl)benzyl) pyridin-2-yl)amino)benzamide (PW0671). Compound PW0669 (74 mg, 0.2 mmol) and the 2-aminoethan-1-ol (25 mg, 0.4 mmol) were dissolved in 5 mL DMF and the mixture solution was cooled to 0° C. with ice bath. HOBt (28 mg, 0.2 mmol), EDCI (39 mg, 0.2 mmol) and DMAP (48 mg, 0.4 mmol) were added to the solution at 0° C. Then removed the ice bath, the mixture solution was stirred at room temperature overnight. After the reaction completed (detected by TLC), the reaction was worked up by the addition of water and then extracted with EtOAc (20 mL×3). The combined EtOAc extracts were washed with brine, dried Na$_2$SO$_4$, filtered, and condensed by rotary evaporation to yield a yellow oil. This material was further purified by preparative TLC plates using CH$_2$Cl$_2$/MeOH=50:1 as the eluent to yield PW0671 as a colorless oil (71 mg, 87%). $^1$H NMR (300 MHz, Chloroform-d) δ 8.03 (d, J=5.2 Hz, 1H), 7.68 (d, J=2.0 Hz, 1H), 7.60-7.45 (m, 2H), 7.44-7.29 (m, 4H), 7.28-7.13 (m, 3H), 6.60-6.47 (m, 2H), 3.86 (s, 3H), 3.69 (t, J=5.0 Hz, 2H), 3.50 (t, J=5.2 Hz, 2H). $^{13}$C NMR (75 MHz, CDCl$_3$) δ 168.7, 155.9, 150.8, 147.9, 141.0, 139.9, 135.2, 132.4, 130.9 (d, J=32.1 Hz), 129.2, 129.1, 125.8, 125.6 (q, J=3.8 Hz), 123.5 (q, J=3.7 Hz), 122.2, 120.4, 118.3, 116.1, 109.9, 61.6, 42.8, 40.9. HRMS (ESI) calcd for C$_{22}$H$_{21}$F$_3$N$_3$O$_2$ 416.1580 (M+H)$^+$, found 416.1578.

N-((1r,4r)-4-Hydroxycyclohexyl)-3-((4-(3-(trifluoromethyl)benzyl)pyridin-2-yl)amino)benzamide (PW0674). Compound PW0674 (41 mg, 65%) was synthesized by a procedure similar to that used to prepare compound PW0671 as a white solid. $^1$H NMR (300 MHz, DMSO-d$_6$) δ 9.09 (s, 1H), 8.05 (dd, J=9.1, 6.4 Hz, 2H), 7.92 (d, J=6.2 Hz, 2H), 7.68-7.53 (m, 4H), 7.28 (d, J=4.6 Hz, 2H), 6.73-6.59 (m, 2H), 4.53 (d, J=4.4 Hz, 1H), 4.01 (s, 2H), 3.77-3.60 (m, 1H), 3.45-3.35 (m, 1H), 1.92-1.74 (m, 4H), 1.30 (dt, J=24.8, 12.5 Hz, 4H). $^{13}$C NMR (75 MHz, DMSO) δ 166.5, 156.5, 150.8, 147.8, 142.2, 141.6, 136.0, 133.6, 130.1, 128.7, 126.0-125.6 (m), 123.8-123.4 (m), 120.7, 119.2, 117.8, 115.8, 110.8, 68.8, 48.3, 34.7, 30.7. HRMS (ESI) calcd for C$_{26}$H$_{27}$F$_3$N$_3$O$_2$ 470.2049 (M+H)$^+$, found 470.2048.

(4-Hydroxypiperidin-1-yl)(3-((4-(3-(trifluoromethyl)benzyl)pyridin-2-yl)amino)phenyl)methanone (PW0826). Compound PW0826 (40 mg, 67%) was synthesized by a procedure similar to that used to prepare compound PW0671 as a colorless oil. $^1$H NMR (300 MHz, Chloroform-d) δ 8.09 (d, J=5.2 Hz, 1H), 7.53-7.38 (m, 5H), 7.37-7.25 (m, 2H), 7.21 (s, 1H), 6.96 (d, J=7.5 Hz, 1H), 6.61 (s, 1H), 6.55 (d, J=5.2 Hz, 1H), 4.17 (s, 1H), 3.91 (s, 3H), 3.69 (s, 1H), 3.24 (d, J=37.9 Hz, 2H), 2.75 (s, 1H), 1.85 (d, J=32.6 Hz, 2H), 1.55 (d, J=22.3 Hz, 2H). $^{13}$C NMR (75 MHz, CDCl$_3$) δ 170.3, 155.9, 150.6, 148.2, 141.0, 140.0, 136.8, 132.4, 131.1, 130.9 (d, J=32.2 Hz), 130.7, 129.2, 129.1, 125.6 (d, J=3.8 Hz), 123.5 (d, J=3.8 Hz), 120.3, 120.1, 117.7, 116.1, 109.6, 66.9, 45.0, 41.0, 39.5, 34.6, 33.9. HRMS (ESI) calcd for C$_{25}$H$_{25}$F$_3$N$_3$O$_2$ 456.1893 (M+H)$^+$, found 456.1890.

Morpholino(3-((4-(3-(trifluoromethyl)benzyl)pyridin-2-yl)amino)phenyl)methanone (PW0823). Compound PW0823 (46 mg, 78%) was synthesized by a procedure similar to that used to prepare compound PW0671 as a white solid. $^1$H NMR (300 MHz, Chloroform-d) δ 8.10 (d, J=5.2 Hz, 1H), 7.51 (d, J=7.3 Hz, 2H), 7.47-7.39 (m, 3H), 7.38-7.26 (m, 2H), 7.23 (s, 1H), 6.99 (d, J=7.5 Hz, 1H), 6.63-6.54 (m, 2H), 3.92 (s, 2H), 3.80-3.41 (m, 8H). $^{13}$C NMR (75 MHz, CDCl$_3$) δ 170.3, 155.8, 150.6, 148.2, 141.1, 140.0, 136.0, 132.4, 130.9 (q, J=31.9 Hz), 129.3, 129.1, 125.6 (q, J=3.8 Hz), 123.5 (q, J=3.8 Hz), 120.5, 120.4, 118.0, 116.2, 109.6, 77.5, 77.1, 76.7, 66.9, 41.0. HRMS (ESI) calcd for C$_{24}$H$_{23}$F$_3$N$_3$O$_2$ 442.1737 (M+H)$^+$, found 442.1734.

Methyl (3-((4-(3-(trifluoromethyl)benzyl)pyridin-2-yl)amino)benzoyl)-D-allothreoninate (PW0673). Compound PW0673 (47 mg, 72%) was synthesized by a procedure similar to that used to prepare compound PW0671 as a colorless oil. $^1$H NMR (300 MHz, Chloroform-d) δ 8.04 (d, J=5.2 Hz, 1H), 7.73 (s, 1H), 7.59 (d, J=8.1 Hz, 1H), 7.53-7.29 (m, 7H), 7.22 (t, J=7.9 Hz, 1H), 6.61 (s, 1H), 6.53 (d, J=5.2 Hz, 1H), 4.77 (dd, J=8.7, 2.8 Hz, 1H), 4.41 (dd, J=6.6, 2.9 Hz, 1H), 3.88 (s, 2H), 3.69 (s, 4H), 1.23 (d, J=6.4 Hz, 3H). $^{13}$C NMR (75 MHz, CDCl$_3$) δ 171.8, 168.3, 155.8, 150.9, 147.9, 141.0, 139.9, 134.7, 132.4, 131.1, 129.3, 129.1, 125.7-125.4 (m), 123.5 (q, J=3.8 Hz), 122.5, 120.6, 118.4, 116.1, 109.6, 68.0, 58.3, 52.5, 41.0, 20.1. HRMS (ESI) calcd for C$_{25}$H$_{25}$F$_3$N$_3$O$_4$ 488.1791 (M+H)$^+$, found 488.1792.

N-((1S)-1,3-Dihydroxy-1-phenylpropan-2-yl)-3-((4-(3-(trifluoromethyl)benzyl)pyridin-2-yl)amino)benzamide (PW0675). Compound PW0675 (38 mg, 55%) was synthesized by a procedure similar to that used to prepare compound PW0671 as a white solid. $^1$H NMR (300 MHz, DMSO-d$_6$) δ 9.12 (s, 1H), 8.09 (d, J=5.3 Hz, 1H), 7.98 (s, 1H), 7.86 (d, J=8.0 Hz, 1H), 7.67-7.55 (m, 4H), 7.49 (d, J=8.7 Hz, 1H), 7.37 (d, J=7.5 Hz, 2H), 7.24 (dt, J=21.9, 7.2 Hz, 5H), 6.69 (d, J=5.3 Hz, 1H), 6.63 (s, 1H), 5.55 (d, J=5.3 Hz, 1H), 4.96 (t, J=4.5 Hz, 1H), 4.79 (t, J=5.6 Hz, 1H), 4.13 (s, 1H), 4.02 (s, 2H), 3.60 (dt, J=12.5, 6.7 Hz, 1H), 3.45-3.36 (m, 1H). $^{13}$C NMR (75 MHz, DMSO) δ 166.9, 156.5, 150.8, 147.8, 144.1, 142.3, 141.6, 135.7, 133.6, 130.1, 128.8, 128.2, 127.1, 126.6, 125.8 (d, J=4.2 Hz), 123.6 (d, J=4.1 Hz), 120.8, 119.2, 117.3, 115.9, 110.9, 70.6, 61.0, 57.5. HRMS (ESI) calcd for C$_{29}$H$_{27}$F$_3$N$_3$O$_3$ 522.1999 (M+H)$^+$, found 522.2001.

N-(1,3-Dihydroxypropan-2-yl)-3-((4-(3-(trifluoromethyl)benzyl)pyridin-2-yl)amino)benzamide (PW0676). Compound PW0676 (36 mg, 60%) was synthesized by a procedure similar to that used to prepare compound PW0671 as a white solid. $^1$H NMR (300 MHz, Chloroform-d) δ 8.03 (d, J=5.4 Hz, 1H), 7.66 (d, J=16.9 Hz, 1H), 7.57-7.21 (m, 9H), 6.64-6.44 (m, 2H), 3.81 (d, J=50.4 Hz, 9H). $^{13}$C NMR (75 MHz, CDCl$_3$) δ 168.7, 155.8, 151.1, 147.6, 140.8, 139.8, 135.0, 132.4, 129.2, 129.1, 125.6 (d, J=3.8 Hz), 123.5 (d, J=3.7 Hz), 122.3, 120.6, 118.2, 116.0, 109.9, 61.9, 53.1, 40.9. HRMS (ESI) calcd for C$_{23}$H$_{23}$F$_3$N$_3$O$_3$ 446.1682 (M+H)$^+$, found 446.1683.

N-(2,2-Difluoroethyl)-3-((4-(3-(trifluoromethyl)benzyl)pyridin-2-yl)amino)benzamide (PW0824). Compound PW0824 (34 mg, 62%) was synthesized by a procedure similar to that used to prepare compound PW0671 as a white solid. $^1$H NMR (300 MHz, Chloroform-d) δ 8.12 (d, J=5.1 Hz, 1H), 7.86 (t, J=1.8 Hz, 1H), 7.60-7.48 (m, 2H), 7.48-7.40 (m, 2H), 7.39-7.29 (m, 3H), 7.00 (s, 1H), 6.78 (t, J=6.2 Hz, 1H), 6.65-6.53 (m, 2H), 5.96 (tt, J=56.1, 4.1 Hz, 1H), 3.94 (s, 2H), 3.81 (tdd, J=14.8, 6.2, 4.1 Hz, 2H). $^{13}$C NMR (75 MHz, CDCl$_3$) δ 168.1, 166.6, 155.7, 150.8, 148.2, 141.2, 139.9, 134.5, 132.4, 131.2, 130.8, 129.4, 129.2, 125.8, 125.6 (d, J=3.8 Hz), 123.6 (d, J=3.8 Hz), 122.6, 120.3, 118.2, 116.9, 116.4, 113.7 (t, J=241.4 Hz), 110.5, 109.6, 42.23 (t, J=26.7 Hz), 41.0. HRMS (ESI) calcd for C$_{22}$H$_{19}$F$_5$N$_3$O 436.1443 (M+H)$^+$, found 436.1439.

N-(2-Methoxyethyl)-3-((4-(3-(trifluoromethyl)benzyl)pyridin-2-yl)amino)benzamide (PW0825). Compound PW0825 (38 mg, 66%) was synthesized by a procedure similar to that used to prepare compound PW0671 as a white solid. $^1$H NMR (300 MHz, Chloroform-d) δ 8.13 (d, J=5.2 Hz, 1H), 7.82 (t, J=1.9 Hz, 1H), 7.59 (dt, J=7.0, 2.2 Hz, 1H), 7.53-7.39 (m, 3H), 7.34 (q, J=7.4 Hz, 3H), 7.07 (s, 1H), 6.72 (t, J=5.5 Hz, 1H), 6.65-6.53 (m, 2H), 3.93 (s, 2H), 3.65 (q, J=5.1 Hz, 2H), 3.56 (t, J=4.9 Hz, 2H), 3.39 (s, 3H). $^{13}$C NMR (75 MHz, CDCl$_3$) δ 167.5, 155.9, 150.7, 148.3, 141.1, 140.0, 135.6, 132.4, 129.3, 129.1, 125.6 (d, J=3.7 Hz), 123.5 (d, J=3.9 Hz), 122.3, 120.3, 118.4, 116.2, 109.3, 71.2, 58.8, 41.0, 39.7. HRMS (ESI) calcd for C$_{23}$H$_{23}$F$_3$N$_3$O$_2$ 430.1737 (M+H)$^+$, found 430.1735.

N-(3-Hydroxypropyl)-3-((4-(3-(trifluoromethyl)benzyl)pyridin-2-yl)amino)benzamide (PW0831). Compound PW0831 (37 mg, 64%) was synthesized by a procedure similar to that used to prepare compound PW0671 as a white solid. $^1$H NMR (300 MHz, Chloroform-d) δ 8.04 (d, J=5.4 Hz, 1H), 7.74 (s, 1H), 7.56 (d, J=6.7 Hz, 1H), 7.38 (dt, J=33.9, 12.4 Hz, 7H), 7.25-7.17 (m, 1H), 6.55 (d, J=13.4 Hz, 2H), 3.87 (s, 2H), 3.63 (d, J=5.8 Hz, 2H), 3.50 (t, J=6.1 Hz, 3H), 1.71 (q, J=5.8 Hz, 2H). $^{13}$C NMR (75 MHz, CDCl$_3$) δ 168.7, 166.6, 155.8, 150.9, 147.7, 141.0, 139.9, 135.2, 132.4, 131.1, 129.2, 129.1, 125.6 (d, J=4.1 Hz), 123.5 (d, J=3.8 Hz), 122.2, 120.4, 118.2, 116.1, 109.9, 59.8, 41.0, 37.4, 31.8. HRMS (ESI) calcd for C$_{23}$H$_{23}$F$_3$N$_3$O$_2$ 430.1737 (M+H)$^+$, found 430.1736.

N-(4-Hydroxybutyl)-3-((4-(3-(trifluoromethyl)benzyl)pyridin-2-yl)amino)benzamide (PW0832). Compound PW0832 (41 mg, 69%) was synthesized by a procedure similar to that used to prepare compound PW0671 as a white solid. $^1$H NMR (300 MHz, Chloroform-d) δ 8.02 (d, J=5.1 Hz, 1H), 7.75 (s, 1H), 7.40 (ddt, J=45.2, 31.4, 12.5 Hz, 9H), 6.62-6.42 (m, 2H), 3.86 (d, J=4.0 Hz, 2H), 3.58 (q, J=5.4 Hz, 2H), 3.35 (t, J=5.8 Hz, 2H), 3.21 (s, 1H), 1.58 (dt, J=12.7, 6.1 Hz, 4H). $^{13}$C NMR (75 MHz, CDCl$_3$) δ 168.1, 155.9, 150.8, 147.8, 141.0, 139.9, 135.7, 132.4, 130.87 (d, J=32.5 Hz), 129.1, 125.6 (d, J=3.7 Hz), 123.5 (d, J=3.4 Hz), 122.0, 120.4, 118.1, 116.0, 110.0, 62.0, 40.9, 39.9, 29.8, 26.1. HRMS (ESI) calcd for C$_{24}$H$_{25}$F$_3$N$_3$O$_2$ 444.1893 (M+H)$^+$, found 444.1889.

N-(2,3-Dihydroxypropyl)-3-((4-(3-(trifluoromethyl)benzyl)pyridin-2-yl)amino)benzamide (PW0677). Compound PW0677 (40 mg, 67%) was synthesized by a procedure similar to that used to prepare compound PW0671 as a colorless oil. $^1$H NMR (300 MHz, Chloroform-d) δ 7.92-

7.72 (m, 2H), 7.60-7.49 (m, 2H), 7.29 (ddd, J=37.2, 22.4, 7.8 Hz, 5H), 7.02 (t, J=7.4 Hz, 1H), 6.48 (s, 1H), 6.36 (d, J=4.9 Hz, 1H), 4.43 (s, 2H), 4.10 (s, 1H), 3.75 (d, J=26.6 Hz, 4H), 3.57-3.19 (m, 3H). $^{13}$C NMR (75 MHz, CDCl$_3$) δ 169.2, 168.8, 155.7, 150.9, 147.5, 141.0, 139.9, 134.9, 134.7, 132.3, 131.0, 130.6, 129.0, 125.8, 125.5 (d, J=3.6 Hz), 123.4 (d, J=3.7 Hz), 122.2, 122.0, 120.4, 118.4, 115.9, 110.0, 70.9, 63.9, 61.5, 42.8, 40.8. HRMS (ESI) calcd for C$_{23}$H$_{23}$F$_3$N$_3$O$_3$ 446.1686 (M+H)$^+$, found 446.1683.

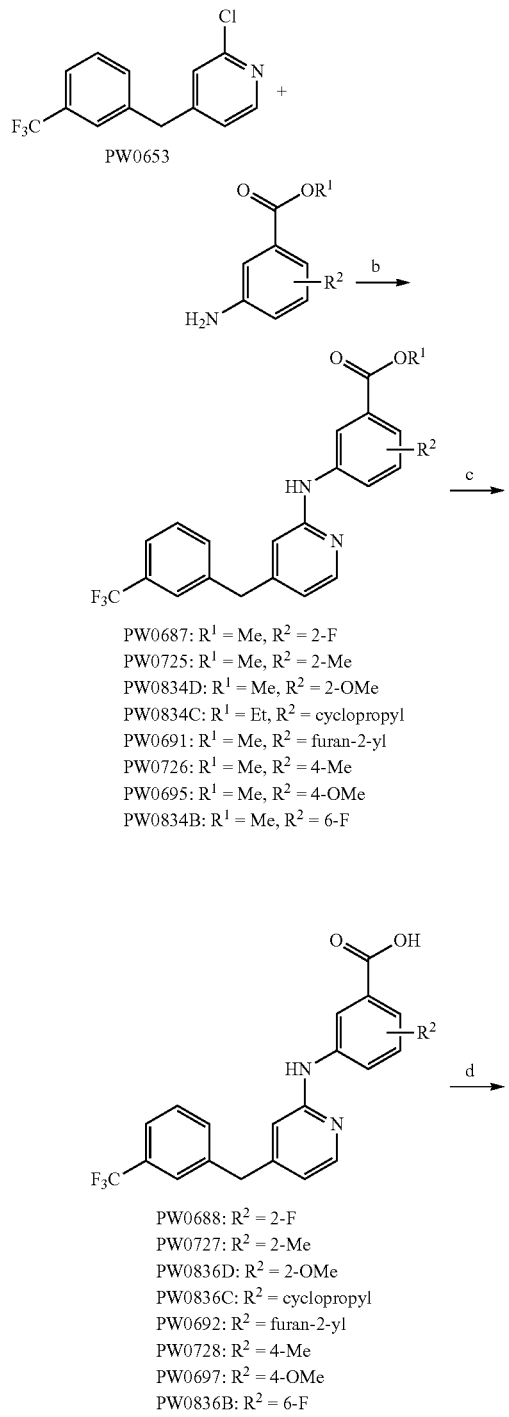

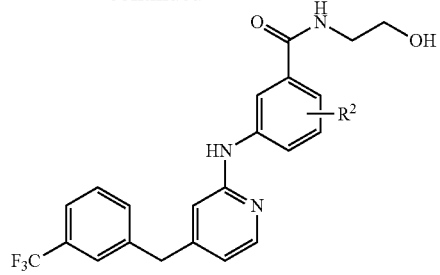

PW0689: R$^2$ = 2-F
PW0729: R$^2$ = 2-Me
PW0842: R$^2$ = 2-OMe
PW0841: R$^2$ = cyclopropyl
PW0693: R$^2$ = furan-2-yl
PW0730: R$^2$ = 4-Me
PW0698: R$^2$ = 4-OMe
PW0840: R$^2$ = 6-F Reagents and conditions: (a) cyclopropylboronic acid or furan-2-ylboronic acid, Pd(dppf)$_2$Cl$_2$, K$_3$PO$_4$, 1,4-dioxnae, H$_2$O, 85° C., 12 h; (b) Pd(OAc)$_2$, XantPhos, Cs$_2$CO$_3$, 1,4-dioxnae, 100° C., 12 h, 37-81%; (c) i) 4 N NaOH, EtOH, reflux, 2 h; ii) 2 N HCl, 79-94%; (d) NH$_2$CH$_2$CH$_2$OH, EDCI, DMAP, HOBt, DMF, rt, 12 h, 38-86%.

Reagents and conditions: (a) cyclopropylboronic acid or furan-2-ylboronic acid, Pd(dppf)$_2$Cl$_2$, K$_3$PO$_4$, 1,4-dioxnae, H$_2$O, 85° C., 12 h; (b) Pd(OAc)$_2$, XantPhos, Cs$_2$CO$_3$, 1,4-dioxnae, 100° C., 12 h, 37-81%; (c) i) 4 N NaOH, EtOH, reflux, 2 h; ii) 2 N HCl, 79-94%; (d) NH$_2$CH$_2$CH$_2$OH, EDCI, DMAP, HOBt, DMF, rt, 12 h, 38-86%.

Methyl 2-fluoro-3-((4-(3-(trifluoromethyl)benzyl)pyridin-2-yl)amino)benzoate (PW0687). Compound PW0687 (154 mg, 38%) was synthesized by a procedure similar to that used to prepare compound PW0668 as a colorless oil. $^1$H NMR (300 MHz, Chloroform-d) δ 8.42 (t, J=8.0 Hz, 1H), 8.19 (d, J=5.2 Hz, 1H), 7.58-7.36 (m, 5H), 7.17 (t, J=8.0 Hz, 1H), 6.73-6.52 (m, 3H), 3.99 (s, 2H), 3.95 (s, 3H).

Methyl 2-methyl-3-((4-(3-(trifluoromethyl)benzyl)pyridin-2-yl)amino)benzoate (PW0725). Compound PW0725 (242 mg, 61%) was synthesized by a procedure similar to that used to prepare compound PW0668 as a light yellow oil. $^1$H NMR (300 MHz, Chloroform-d) δ 8.10 (d, J=5.2 Hz, 1H), 7.64 (d, J=7.8 Hz, 1H), 7.53 (dd, J=14.0, 7.7 Hz, 2H), 7.44 (d, J=7.0 Hz, 2H), 7.34 (d, J=7.7 Hz, 1H), 7.24 (t, J=7.9 Hz, 1H), 6.55 (d, J=5.2 Hz, 1H), 6.37 (s, 2H), 3.90 (s, 2H), 2.46 (s, 3H).

Methyl 2-methoxy-3-((4-(3-(trifluoromethyl)benzyl)pyridin-2-yl)amino)benzoate (PW0834D). Compound PW0834D (157 mg, 75%) was synthesized by a procedure similar to that used to prepare compound PW0668 as a light yellow oil. $^1$H NMR (300 MHz, Chloroform-d) δ 8.36 (dd, J=8.2, 1.6 Hz, 1H), 8.22-8.16 (m, 1H), 7.57-7.40 (m, 5H), 7.14 (t, J=8.0 Hz, 1H), 7.06 (s, 1H), 6.64 (d, J=4.3 Hz, 2H), 3.99 (s, 2H), 3.95 (s, 3H), 3.90 (s, 3H).

Ethyl 2-cyclopropyl-3-((4-(3-(trifluoromethyl)benzyl)pyridin-2-yl)amino)benzoate (PW0834C). Compound PW06834C (154 mg, 70%) was synthesized by a procedure similar to that used to prepare compound PW0668 as a light yellow oil. $^1$H NMR (300 MHz, Chloroform-d) δ 8.17 (d, J=5.2 Hz, 1H), 7.84 (dd, J=5.5, 4.1 Hz, 1H), 7.53 (d, J=8.0 Hz, 1H), 7.47 (d, J=6.9 Hz, 2H), 7.38 (d, J=7.5 Hz, 1H), 7.27-7.19 (m, 2H), 7.07 (s, 1H), 6.68 (s, 1H), 6.61 (dd, J=5.2, 1.4 Hz, 1H), 4.39 (s, 2H), 3.97 (s, 2H), 1.97-1.86 (m, 1H), 1.42 (s, 3H), 1.11-1.01 (m, 2H), 0.55-0.45 (m, 2H).

Methyl 2-(furan-2-yl)-3-((4-(3-(trifluoromethyl)benzyl)pyridin-2-yl)amino)benzoate (PW0691). Compound PW0691 (83 mg, 37%) was synthesized by a procedure similar to that used to prepare compound PW0668 as a light yellow oil. $^1$H NMR (300 MHz, Chloroform-d) δ 8.21-8.07 (m, 2H), 7.63-7.50 (m, 2H), 7.40 (dt, J=21.8, 7.4 Hz, 5H), 6.88 (s, 1H), 6.65-6.46 (m, 4H), 3.94 (s, 2H), 3.74 (s, 3H).

Methyl 4-methyl-3-((4-(3-(trifluoromethyl)benzyl)pyridin-2-yl)amino)benzoate (PW0725). Compound PW0725 (270 mg, 68%) was synthesized by a procedure similar to that used to prepare compound PW0668 as a light yellow oil. $^1$H NMR (300 MHz, Chloroform-d) δ 8.23-8.02 (m, 2H), 7.73 (dd, J=7.8, 1.7 Hz, 1H), 7.55-7.29 (m, 5H), 6.58 (d, J=5.3 Hz, 1H), 6.49 (s, 1H), 6.28 (s, 1H), 3.93 (s, 2H), 2.19 (s, 2H).

Methyl 4-methoxy-3-((4-(3-(trifluoromethyl)benzyl)pyridin-2-yl)amino)benzoate (PW0695). Compound PW0695 (313 mg, 75%) was synthesized by a procedure similar to that used to prepare compound PW0668 as a light yellow oil. $^1$H NMR (300 MHz, Chloroform-d) δ 8.79 (d, J=2.1 Hz, 1H), 8.22 (d, J=5.2 Hz, 1H), 7.71 (dd, J=8.5, 2.1 Hz, 1H), 7.46 (dq, J=21.3, 7.8 Hz, 4H), 6.92 (d, J=8.6 Hz, 2H), 6.71-6.57 (m, 2H), 3.97 (d, J=5.9 Hz, 5H), 3.91 (s, 3H).

Methyl 2-fluoro-5-((4-(3-(trifluoromethyl)benzyl)pyridin-2-yl)amino)benzoate (PW0834B). Compound PW0834B (163 mg, 81%) was synthesized by a procedure similar to that used to prepare compound PW0668 as a light yellow oil. $^1$H NMR (300 MHz, Chloroform-d) δ 8.14 (d, J=5.2 Hz, 1H), 7.87 (dd, J=6.1, 2.9 Hz, 1H), 7.64 (ddd, J=8.9, 4.1, 3.0 Hz, 1H), 7.53 (d, J=7.6 Hz, 1H), 7.48-7.44 (m, 2H), 7.38 (d, J=7.7 Hz, 1H), 7.11 (dd, J=10.1, 8.9 Hz, 1H), 6.62 (dd, J=5.2, 1.4 Hz, 1H), 6.50 (d, J=1.3 Hz, 1H), 6.45 (s, 1H), 3.95 (d, J=3.4 Hz, 5H).

2-Fluoro-3-((4-(3-(trifluoromethyl)benzyl)pyridin-2-yl)amino)benzoic acid (PW0688). Compound PW0688 (140 mg, 90%) was synthesized by a procedure similar to that used to prepare compound PW0669 as a light yellow solid. $^1$H NMR (300 MHz, DMSO-d$_6$) δ 13.11 (s, 1H), 8.74 (s, 1H), 8.36 (t, J=8.0 Hz, 1H), 8.04 (d, J=5.2 Hz, 1H), 7.69-7.53 (m, 4H), 7.39 (t, J=6.7 Hz, 1H), 7.19 (q, J=8.7, 8.0 Hz, 1H), 6.84 (s, 1H), 6.72 (d, J=5.1 Hz, 1H), 4.01 (s, 2H).

2-Methyl-3-((4-(3-(trifluoromethyl)benzyl)pyridin-2-yl)amino)benzoic acid (PW0727). Compound PW0727 (230 mg, 91%) was synthesized by a procedure similar to that used to prepare compound PW0669 as a light yellow solid. $^1$H NMR (300 MHz, DMSO-d$_6$) δ 10.45 (s, 1H), 7.90 (d, J=6.4 Hz, 1H), 7.81-7.68 (m, 2H), 7.59 (dq, J=17.1, 7.7 Hz, 4H), 7.38 (t, J=7.8 Hz, 1H), 7.01-6.76 (m, 2H), 4.16 (s, 2H), 2.37 (s, 3H).

2-Methoxy-3-((4-(3-(trifluoromethyl)benzyl)pyridin-2-yl)amino)benzoic acid (PW0836D). Compound PW0836D (179 mg, 89%) was synthesized by a procedure similar to that used to prepare compound PW0669 as a light yellow solid. $^1$H NMR (300 MHz, DMSO-d$_6$) δ 13.04 (s, 1H), 10.49 (s, 1H), 7.95 (d, J=6.4 Hz, 1H), 7.78-7.54 (m, 6H), 7.28 (t, J=7.8 Hz, 1H), 7.10 (d, J=1.4 Hz, 1H), 6.94 (dd, J=6.5, 1.5 Hz, 1H), 4.19 (s, 2H), 3.70 (s, 3H).

2-Cyclopropyl-3-((4-(3-(trifluoromethyl)benzyl)pyridin-2-yl)amino)benzoic acid (PW0836C). Compound PW0836C (194 mg, 94%) was synthesized by a procedure similar to that used to prepare compound PW0669 as a light yellow solid. $^1$H NMR (300 MHz, DMSO-d$_6$) δ 10.50 (s, 1H), 7.92 (dd, J=6.5, 4.6 Hz, 1H), 7.72 (s, 1H), 7.63 (q, J=5.3, 4.4 Hz, 3H), 7.56-7.41 (m, 3H), 7.01 (s, 1H), 6.93 (dt, J=6.5, 1.7 Hz, 1H), 4.19 (s, 2H), 1.89-1.74 (m, 1H), 0.78 (d, J=8.2 Hz, 2H), 0.40-0.22 (m, 2H).

2-(Furan-2-yl)-3-((4-(3-(trifluoromethyl)benzyl)pyridin-2-yl)amino)benzoic acid (PW0692). Compound 1PW0692 (63 mg, 79%) was synthesized by a procedure similar to that used to prepare compound PW0669 as a light yellow solid. $^1$H NMR (300 MHz, Chloroform-d) δ 10.34 (s, 1H), 7.81-7.61 (m, 2H), 7.56-7.38 (m, 4H), 7.24 (t, J=10.9 Hz, 3H), 6.68-6.15 (m, 4H), 3.84 (s, 2H).

4-Methyl-3-((4-(3-(trifluoromethyl)benzyl)pyridin-2-yl)amino)benzoic acid (PW0728). Compound PW0728 (240 mg, 92%) was synthesized by a procedure similar to that used to prepare compound PW0669 as a light yellow solid. $^1$H NMR (300 MHz, DMSO-d$_6$) δ 10.49 (s, 1H), 7.97-7.87 (m, 2H), 7.83 (d, J=8.0 Hz, 1H), 7.72 (s, 1H), 7.61 (q, J=7.4, 5.3 Hz, 3H), 7.49 (d, J=8.0 Hz, 1H), 7.05-6.74 (m, 2H), 4.16 (s, 2H), 2.26 (s, 3H).

4-Methoxy-3-((4-(3-(trifluoromethyl)benzyl)pyridin-2-yl)amino)benzoic acid (PW0697). Compound PW0697 (254 mg, 81%) was synthesized by a procedure similar to that used to prepare compound PW0669 as a light yellow solid. $^1$H NMR (300 MHz, DMSO-d$_6$) δ 10.00 (s, 1H), 8.06 (s, 1H), 7.90 (t, J=7.7 Hz, 2H), 7.77-7.53 (m, 4H), 7.26 (d, J=8.7 Hz, 1H), 7.00-6.82 (m, 2H), 4.15 (s, 2H), 3.85 (s, 3H).

2-Fluoro-5-((4-(3-(trifluoromethyl)benzyl)pyridin-2-yl)amino)benzoic acid (PW0836B). Compound PW0836B (181 mg, 93%) was synthesized by a procedure similar to that used to prepare compound PW0669 as a light yellow solid. $^1$H NMR (300 MHz, DMSO-d$_6$) δ 10.27 (s, 1H), 8.03-7.91 (m, 2H), 7.77-7.69 (m, 2H), 7.62 (d, J=5.7 Hz, 3H), 7.36 (dd, J=10.5, 8.7 Hz, 1H), 6.95-6.82 (m, 2H), 4.13 (s, 2H).

2-Fluoro-N-(2-hydroxyethyl)-3-((4-(3-(trifluoromethyl)benzyl)pyridin-2-yl)amino)benzamide (PW0689). Compound PW0689 (33 mg, 38%) was synthesized by a procedure similar to that used to prepare compound PW0671 as a colorless oil (33 mg, 38%). $^1$H NMR (300 MHz, Chloroform-d) δ 8.09 (q, J=7.1, 5.8 Hz, 2H), 7.62-7.30 (m, 5H), 7.20 (dt, J=10.4, 5.6 Hz, 1H), 7.07 (t, J=8.0 Hz, 1H), 6.97 (s, 1H), 6.69-6.47 (m, 2H), 3.92 (s, 2H), 3.75 (t, J=5.0 Hz, 2H), 3.57 (q, J=5.2 Hz, 3H). $^{13}$C NMR (75 MHz, CDCl$_3$) δ 164.6, 164.6, 155.4, 152.8, 150.9, 148.0, 139.8, 132.4, 129.4, 129.2, 125.6 (d, J=3.6 Hz), 124.3 (d, J=4.2 Hz), 123.9, 123.6 (d, J=3.9 Hz), 123.4, 121.7 (d, J=11.1 Hz), 116.7, 110.1, 61.5, 42.7, 40.9. HRMS (ESI) calcd for $C_{22}H_{20}F_4N_3O_2$ 434.1486 (M+H)$^+$, found 434.1481.

N-(2-Hydroxyethyl)-2-methyl-3-((4-(3-(trifluoromethyl)benzyl)pyridin-2-yl)amino)benzamide (PW0729). Compound PW0729 (33 mg, 77%) was synthesized by a procedure similar to that used to prepare compound PW0671 as a white solid. $^1$H NMR (300 MHz, Chloroform-d) δ 8.03 (d, J=5.4 Hz, 1H), 7.43 (td, J=24.9, 22.2, 7.7 Hz, 5H), 7.24-7.09 (m, 2H), 6.86 (s, 1H), 6.62-6.38 (m, 3H), 4.16 (s, 1H), 3.91 (s, 2H), 3.79 (t, J=5.0 Hz, 2H), 3.57 (q, J=5.3 Hz, 2H), 2.30 (s, 3H). $^{13}$C NMR (75 MHz, CDCl$_3$) δ 171.0, 166.6, 156.8, 151.2, 147.9, 139.9, 139.1, 138.5, 132.3, 129.3, 129.1, 126.5, 124.6, 122.9, 115.6, 108.2, 62.1, 42.6, 41.1, 14.7. HRMS (ESI) calcd for $C_{23}H_{23}F_3N_3O_2$ 430.1737 (M+H)$^+$, found 430.1734.

N-(2-Hydroxyethyl)-2-methoxy-3-((4-(3-(trifluoromethyl)benzyl)pyridin-2-yl)amino)benzamide (PW0842). Compound PW0842 (36 mg, 60%) was synthesized by a procedure similar to that used to prepare compound PW0671 as a white solid. $^1$H NMR (300 MHz, Chloroform-d) δ 8.16 (d, J=5.2 Hz, 1H), 8.05 (dt, J=8.1, 3.1 Hz, 2H), 7.61 (dd, J=7.9, 1.6 Hz, 1H), 7.54-7.37 (m, 4H), 7.16 (t, J=8.0 Hz, 1H), 6.96 (s, 1H), 6.63 (dd, J=6.7, 1.4 Hz, 2H), 3.97 (s, 2H), 3.82 (d, J=8.3 Hz, 5H), 3.65 (t, J=5.0 Hz, 2H). $^{13}$C NMR (75 MHz, CDCl$_3$) δ 166.4, 155.6, 150.9, 148.4, 147.9, 139.9, 134.2, 132.4, 129.2, 126.6, 125.6 (d, J=3.7 Hz), 124.9, 123.9, 123.6 (d, J=3.8 Hz), 122.7, 116.5, 109.6, 62.2, 61.7, 42.7, 41.0. HRMS (ESI) calcd for $C_{23}H_{23}F_3N_3O_3$ 446.1686 (M+H)$^+$, found 446.1682.

2-Cyclopropyl-N-(2-hydroxyethyl)-3-((4-(3-(trifluoromethyl)benzyl)pyridin-2-yl)amino)benzamide (PW0841). Compound PW0841 (42 mg, 69%) was synthesized by a procedure similar to that used to prepare compound PW0671 as a white solid. $^1$H NMR (300 MHz, Chloroform-d) δ 8.13 (d, J=5.2 Hz, 1H), 7.74 (dd, J=8.2, 1.3 Hz, 1H), 7.53 (d, J=7.7 Hz, 1H), 7.48-7.42 (m, 2H), 7.38 (d, J=7.6 Hz, 1H), 7.19 (t, J=7.9 Hz, 1H), 7.09-6.99 (m, 2H), 6.66 (d, J=5.1 Hz, 1H), 6.61 (dd, J=5.2, 1.4 Hz, 1H), 6.52 (t, J=5.6 Hz, 1H), 3.97 (d, J=5.5 Hz, 2H), 3.80 (t, J=4.9 Hz, 2H), 3.61-3.54 (m, 2H), 1.87-1.73 (m, 1H), 1.03 (dd, J=8.3, 1.8 Hz, 2H), 0.62-0.47 (m, 2H). $^{13}$C NMR (75 MHz, CDCl$_3$) δ 171.2, 155.8, 150.8, 148.4, 141.3, 139.9, 139.5, 132.4, 129.2, 128.6, 127.3, 125.6, 123.5, 121.2, 120.6, 116.3, 109.3, 62.1, 42.9, 41.1, 10.4, 7.2. HRMS (ESI) calcd for $C_{25}H_{25}F_3N_3O_2$ 456.1893 (M+H)$^+$, found 456.1890.

2-(Furan-2-yl)-N-(2-hydroxyethyl)-3-((4-(3-(trifluoromethyl)benzyl)pyridin-2-yl)amino)benzamide (PW0693). Compound PW0693 (26 mg, 54%) was synthesized by a procedure similar to that used to prepare compound PW0671 as a white solid. $^1$H NMR (300 MHz, Chloroform-d) δ 8.06 (d, J=5.1 Hz, 1H), 7.86 (d, J=8.2 Hz, 1H), 7.56-7.39 (m, 4H), 7.31 (dd, J=19.7, 7.8 Hz, 2H), 7.14 (d, J=7.6 Hz, 1H), 6.93 (s, 1H), 6.63-6.41 (m, 4H), 6.33 (t, J=5.8 Hz, 1H), 3.91 (s, 2H), 3.52 (d, J=5.0 Hz, 2H), 3.31 (d, J=5.2 Hz, 2H), 3.16 (s, 1H). $^{13}$C NMR (75 MHz, CDCl$_3$) δ 170.3, 155.6, 150.8, 148.4, 148.2, 143.2, 139.9, 139.3, 138.4, 131.0 (d, J=31.9 Hz), 129.2, 125.7-125.5 (m), 123.5 (d, J=4.0 Hz), 121.6, 121.3, 118.8, 116.6, 111.5, 111.0, 109.7, 61.6, 42.7, 41.0. HRMS (ESI) calcd for $C_{26}H_{23}F_3N_3O_3$ 482.1686 (M+H)$^+$, found 482.1686.

N-(2-Hydroxyethyl)-4-methyl-3-((4-(3-(trifluoromethyl)benzyl)pyridin-2-yl)amino)benzamide (PW0730). Compound PW0730 (37 mg, 86%) was synthesized by a procedure similar to that used to prepare compound PW0671 as a white solid. $^1$H NMR (300 MHz, Chloroform-d) δ 8.04 (d, J=5.3 Hz, 1H), 7.88 (d, J=1.9 Hz, 1H), 7.57-7.30 (m, 5H), 7.20 (d, J=7.9 Hz, 1H), 6.98 (t, J=5.6 Hz, 1H), 6.72 (s, 1H), 6.53 (d, J=5.3 Hz, 1H), 6.41 (s, 1H), 4.31 (s, 1H), 3.89 (s, 2H), 3.75 (t, J=5.0 Hz, 2H), 3.55 (q, J=5.2 Hz, 2H), 2.23 (s, 3H). $^{13}$C NMR (75 MHz, CDCl$_3$) δ 168.3, 156.6, 151.1, 148.0, 139.9, 138.5, 134.9, 133.1, 132.3, 131.1, 129.1, 125.6 (d, J=3.9 Hz), 123.5 (d, J=3.7 Hz), 122.7, 121.4, 115.8, 108.6, 62.0, 42.9, 41.1, 18.0. HRMS (ESI) calcd for $C_{23}H_{23}F_3N_3O_2$ 430.1737 (M+H)$^+$, found 430.1734.

N-(2-Hydroxyethyl)-4-methoxy-3-((4-(3-(trifluoromethyl)benzyl)pyridin-2-yl)amino)benzamide (PW0698). Compound PW0698 (36 mg, 41%) was synthesized by a procedure similar to that used to prepare compound PW0671 as a white solid. $^1$H NMR (300 MHz, Chloroform-d) δ 8.56 (d, J=2.2 Hz, 1H), 8.10 (d, J=5.2 Hz, 1H), 7.56-7.32 (m, 5H), 7.22 (t, J=5.6 Hz, 1H), 7.02 (s, 1H), 6.81 (d, J=8.5 Hz, 1H), 6.56 (d, J=5.3 Hz, 2H), 3.92 (s, 3H), 3.85 (s, 3H), 3.75 (t, J=4.9 Hz, 2H), 3.54 (d, J=5.1 Hz, 2H). $^{13}$C NMR (75 MHz, CDCl$_3$) δ 168.7, 155.5, 150.7, 147.8, 139.9, 132.4, 130.9 (d, J=32.4 Hz) 129.8, 129.1, 126.9, 125.6 (d, J=3.8 Hz), 123.5 (d, J=3.8 Hz), 121.2, 116.5, 116.2, 110.6, 109.6, 62.1, 55.8, 43.0, 41.0. HRMS (ESI) calcd for $C_{23}H_{23}F_3N_3O_3$ 446.1686 (M+H)$^+$, found 446.1683.

2-Fluoro-N-(2-hydroxyethyl)-5-((4-(3-(trifluoromethyl)benzyl)pyridin-2-yl)amino)benzamide (PW0840). Compound PW0840 (37 mg, 64%) was synthesized by a procedure similar to that used to prepare compound PW0671 as a white solid. $^1$H NMR (300 MHz, Chloroform-d and MeOD) δ 8.07 (d, J=5.6 Hz, 1H), 7.88 (dd, J=6.6, 2.9 Hz, 1H), 7.69 (ddd, J=8.8, 4.3, 2.9 Hz, 1H), 7.50 (d, J=7.7 Hz, 1H), 7.46-7.39 (m, 2H), 7.35 (d, J=7.8 Hz, 1H), 7.31-7.20 (m, 2H), 7.00 (dd, J=11.3, 8.9 Hz, 1H), 6.56 (dd, J=3.9, 1.6 Hz, 2H), 3.91 (s, 2H), 3.80 (t, J=5.1 Hz, 2H), 3.63 (d, J=5.3 Hz, 2H). $^{13}$C NMR (75 MHz, CDCl$_3$) δ 164.4, 157.4, 156.0, 154.2, 150.8, 148.1, 139.9, 137.5, 132.4, 131.1, 129.1, 125.6 (d, J=3.9 Hz), 124.5 (d, J=8.6 Hz), 123.5 (d, J=3.8 Hz), 122.6, 121.1 (d, J=12.5 Hz), 116.7, 116.3, 116.1, 109.2, 61.8, 42.9, 41.0. HRMS (ESI) calcd for $C_{22}H_{20}F_4N_3O_2$ 434.1486 (M+H)$^+$, found 434.1483.

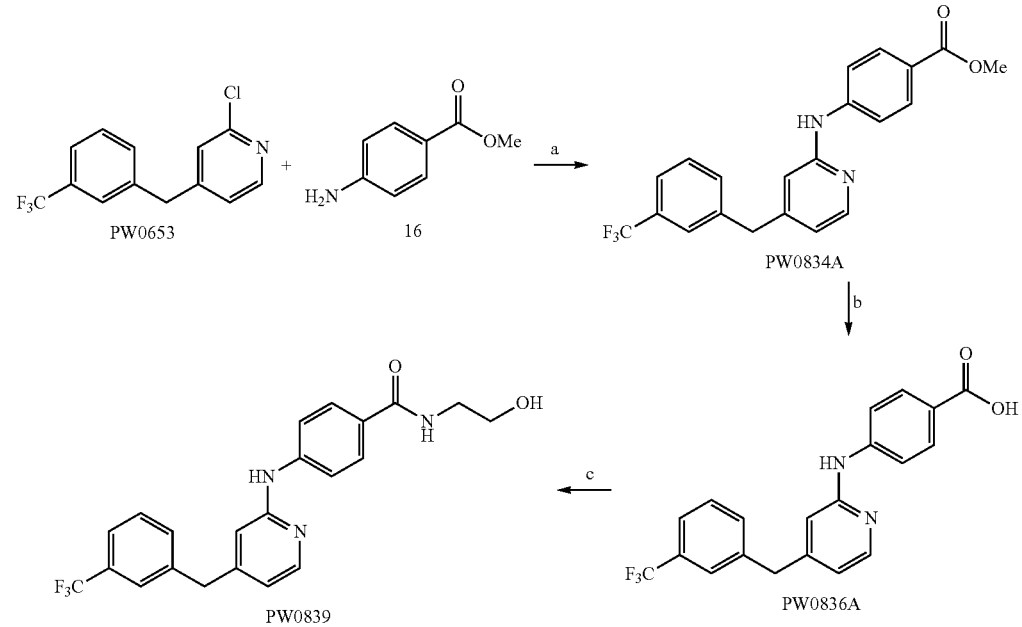

Reagents and conditions: (a) Pd(OAc)$_2$, XantPhos, Cs$_2$CO$_3$, 1,4-dioxnae, 100° C., 12 h, 87%; (c) i) 4 N NaOH, EtOH, reflux, 2 h; ii) 2 N HCl, 91%; (d) NH$_2$CH$_2$CH$_2$OH, EDCI, DMAP, HOBt, DMF, rt, 12 h, 77%.

Methyl 4-((4-(3-(trifluoromethyl)benzyl)pyridin-2-yl)amino)benzoate (PW0834A). Compound PW0834A (168 mg, 87%) was synthesized by a procedure similar to that used to prepare compound PW0668 as a white solid. $^1$H NMR (300 MHz, Chloroform-d) δ 8.26-8.17 (m, 1H), 8.04-7.94 (m, 2H), 7.61-7.33 (m, 6H), 6.80-6.64 (m, 3H), 4.00 (s, 2H), 3.91 (s, 3H).

4-((4-(3-(Trifluoromethyl)benzyl)pyridin-2-yl)amino)benzoic acid (PW0836A). Compound PW0836A (169 mg, 91%) was synthesized by a procedure similar to that used to prepare compound PW0669 as a white solid. $^1$H NMR (300 MHz, DMSO-$d_6$) δ 10.03 (s, 1H), 8.10 (d, J=5.7 Hz, 1H), 7.96-7.84 (m, 2H), 7.76-7.50 (m, 6H), 6.89 (dd, J=7.5, 2.0 Hz, 2H), 4.11 (s, 2H).

N-(2-Hydroxyethyl)-4-((4-(3-(trifluoromethyl)benzyl)pyridin-2-yl)amino)benzamide (PW0839). Compound PW0839 (43 mg, 77%) was synthesized by a procedure similar to that used to prepare compound PW0671 as a white solid. $^1$H NMR (300 MHz, Chloroform-d and MeoD) δ 8.03 (dd, J=5.1, 2.3 Hz, 1H), 7.67 (dd, J=8.8, 2.5 Hz, 2H), 7.50-7.25 (m, 7H), 6.71-6.50 (m, 2H), 3.90 (d, J=2.3 Hz, 2H), 3.68 (d, J=2.4 Hz, 2H), 3.50-3.44 (m, 2H). $^{13}$C NMR (75 MHz, CDCl$_3$ and MeoD) δ 168.6, 155.3, 151.1, 147.8, 144.0, 139.8, 132.4, 129.1, 128.3, 126.5, 125.5 (d, J=3.8 Hz), 123.5 (d, J=3.5 Hz), 117.7, 116.5, 110.4, 61.3, 42.5, 40.9. HRMS (ESI) calcd for $C_{22}H_{21}F_3N_3O_2$ 416.1580 (M+H)$^+$, found 416.1576.

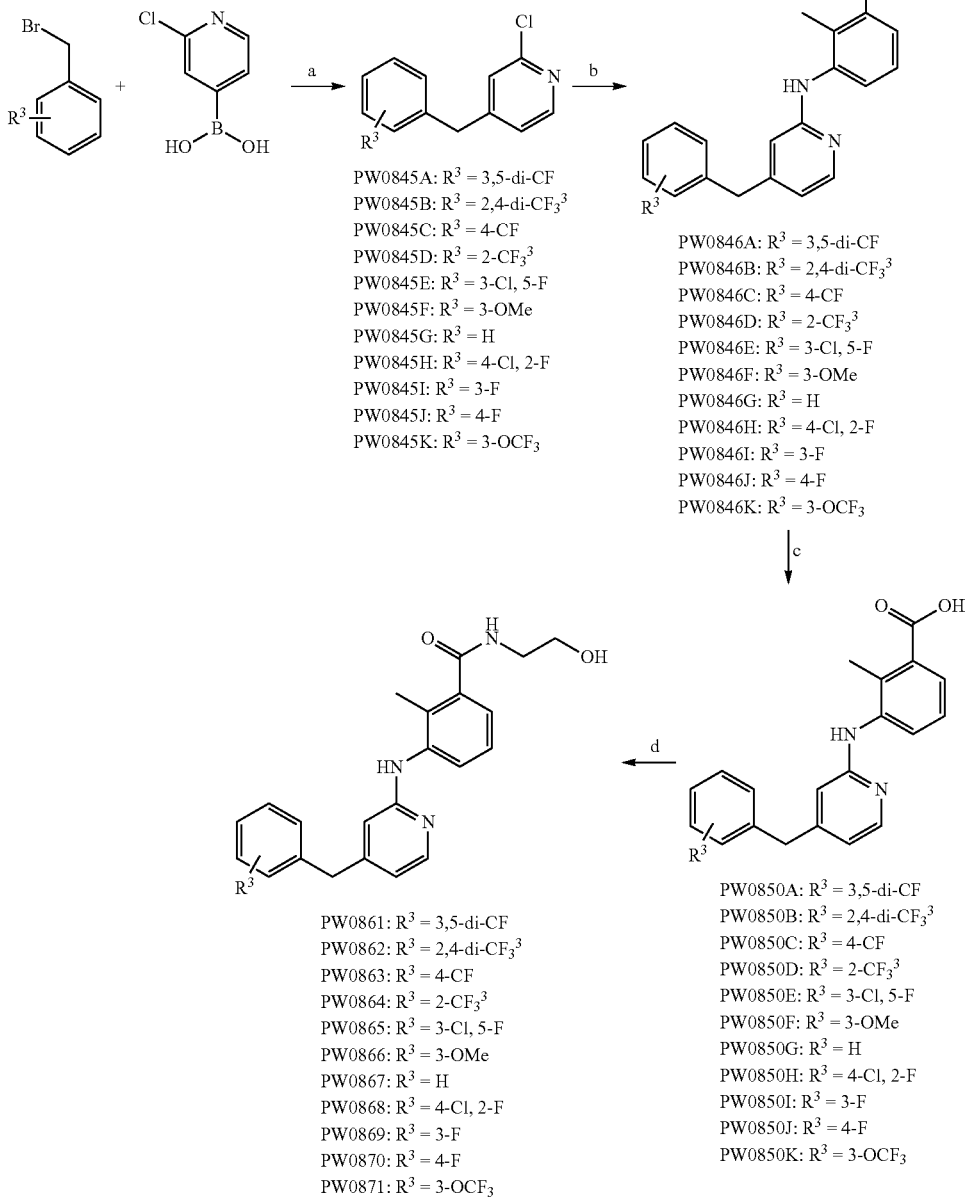

Reagents and conditions: (a) Pd(PPh$_3$)$_4$, Na$_2$CO$_3$, toluene, EtOH, 85° C., 1.5 h, 53-93%; (b methyl 3-amino-2-methylbenzoate, Pd(OAc)$_2$, XantPhos, Cs$_2$CO$_3$, 1,4-dioxnae, 100° C., 12 h 65-83%; (c) i) 4 N NaOH, EtOH, reflux, 2 h; ii) 2 N HCl, 73-93%; (d) R$^1$H, EDCI, DMAP, HOBt, DMF, rt, 12 h, 38-93%.

Reagents and conditions. (a) Pd(PPh$_3$)$_4$, Na$_2$CO$_3$, toluene, EtOH, 85° C., 1.5 h, 53-93%; (b methyl 3-amino-2-methylbenzoate, Pd(OAc)$_2$, XantPhos, Cs$_2$CO$_3$, 1,4-dioxnae, 100° C., 12 h, 65-83%; (c) i) 4 N NaOH, EtOH, reflux, 2 h; ii) 2 N HCR, 73-93%; (d) R$^1$H, EDCI, DMAP, HOBt, DMF, rt, 12 h, 38-93%.

4-(3,5-Bis(trifluoromethyl)benzyl)-2-chloropyridine (PW0845A). Compound PW0845A (540 mg, 80%) was synthesized by a procedure similar to that used to prepare compound PW0653 as a colorless oil. RH NMR (300 MHz, Chloroform-d) δ 8.37 (d, J=5.1 Hz, 1H), 7.83 (s, 1H), 7.64 (s, 2H), 7.17 (s, 1H), 7.08-6.96 (m, 1H), 4.11 (s, 2H).

4-(2,4-Bis(trifluoromethyl)benzyl)-2-chloropyridine (PW0845B). Compound PW0845B (260 mg, 77%) was synthesized by a procedure similar to that used to prepare compound PW0653 as a colorless oil. $^1$H NMR (300 MHz, Chloroform-d) δ 8.34 (d, J=5.1 Hz, 1H), 8.00 (s, 1H), 7.80 (d, J=8.1 Hz, 1H), 7.37 (d, J=8.1 Hz, 1H), 7.10 (s, 1H), 6.99 (d, J=5.1 Hz, 1H), 4.24 (s, 2H).

2-Chloro-4-(4-(trifluoromethyl)benzyl)pyridine (PW0845C). Compound PW0845C (81 mg, 75%) was synthesized by a procedure similar to that used to prepare compound PW0653 as a colorless oil. $^1$H NMR (300 MHz, Chloroform-d) δ 8.34-8.27 (m, 1H), 7.61 (d, J=8.0 Hz, 2H), 7.31 (d, J=8.0 Hz, 2H), 7.15 (dd, J=1.6, 0.7 Hz, 1H), 7.08-7.00 (m, 1H), 4.04 (s, 2H).

2-Chloro-4-(2-(trifluoromethyl)benzyl)pyridine (PW0845D). Compound PW0845D (64 mg, 79%) was synthesized by a procedure similar to that used to prepare compound PW0653 as a colorless oil. $^1$H NMR (300 MHz, Chloroform-d) δ 8.29 (d, J=5.1 Hz, 1H), 7.73 (dd, J=7.9, 1.4 Hz, 1H), 7.54 (td, J=7.6, 1.4 Hz, 1H), 7.42 (t, J=7.6 Hz, 1H), 7.22 (d, J=7.7 Hz, 1H), 7.12-7.05 (m, 1H), 6.99 (dd, J=5.1, 1.5 Hz, 1H), 4.18 (s, 2H).

2-Chloro-4-(3-chloro-5-fluorobenzyl)pyridine (PW0845E). Compound PW0845E (70 mg, 91%) was synthesized by a procedure similar to that used to prepare compound PW0653 as a colorless oil. $^1$H NMR (300 MHz, Chloroform-d) δ 8.33 (d, J=5.1 Hz, 1H), 7.14 (dd, J=1.6, 0.7 Hz, 1H), 7.08-6.94 (m, 3H), 6.79 (dt, J=8.9, 1.9 Hz, 1H), 3.93 (s, 2H).

2-Chloro-4-(3-methoxybenzyl)pyridine (PW0845F). Compound PW0845F (60 mg, 86%) was synthesized by a procedure similar to that used to prepare compound PW0653 as a colorless oil. $^1$H NMR (300 MHz, Chloroform-d) δ 8.28 (d, J=5.1 Hz, 1H), 7.32-7.25 (m, 1H), 7.20-7.14 (m, 1H), 7.05 (dd, J=5.1, 1.4 Hz, 1H), 6.90-6.68 (m, 3H), 3.94 (s, 2H), 3.81 (s, 3H).

4-Benzyl-2-chloropyridine (PW0845G). Compound PW0845G (53 mg, 87%) was synthesized by a procedure similar to that used to prepare compound PW0653 as a colorless oil. $^1$H NMR (300 MHz, Chloroform-d) δ 8.28 (d, J=5.1 Hz, 1H), 7.40-7.26 (m, 3H), 7.23-7.12 (m, 3H), 7.05 (dd, J=5.1, 1.4 Hz, 1H), 3.97 (s, 2H).

2-Chloro-4-(4-chloro-2-fluorobenzyl)pyridine (PW0845H). Compound PW0845H (59 mg, 77%) was synthesized by a procedure similar to that used to prepare compound PW0653 as a colorless oil. $^1$H NMR (300 MHz, Chloroform-d) δ 8.29 (d, J=5.1 Hz, 1H), 7.18-7.09 (m, 4H), 7.04 (dd, J=5.1, 1.4 Hz, 1H), 3.95 (d, J=1.3 Hz, 2H).

2-Chloro-4-(3-fluorobenzyl)pyridine (PW08451). Compound PW08451 (54 mg, 80%) was synthesized by a procedure similar to that used to prepare compound PW0653 as a colorless oil. $^1$H NMR (300 MHz, Chloroform-d) δ 8.30 (d, J=5.1 Hz, 1H), 7.37-7.27 (m, 1H), 7.17-7.12 (m, 1H), 7.08-6.93 (m, 3H), 6.88 (dt, J=9.6, 2.1 Hz, 1H), 3.96 (s, 2H).

2-Chloro-4-(4-fluorobenzyl)pyridine (PW0845J). Compound PW0845J (35 mg, 53%) was synthesized by a procedure similar to that used to prepare compound PW0653 as a colorless oil. $^1$H NMR (300 MHz, Chloroform-d) δ 8.29 (d, J=5.1 Hz, 1H), 7.20-7.10 (m, 3H), 7.09-6.98 (m, 3H), 3.95 (s, 2H).

2-Chloro-4-(3-(trifluoromethoxy)benzyl)pyridine (PW0845K). Compound PW0845K (80 mg, 93%) was synthesized by a procedure similar to that used to prepare compound PW0653 as a colorless oil. $^1$H NMR (300 MHz, Chloroform-d) δ 8.31 (d, J=5.1 Hz, 1H), 7.38 (t, J=7.9 Hz, 1H), 7.19-7.08 (m, 3H), 7.04 (dd, J=5.1, 1.5 Hz, 2H), 3.99 (s, 2H).

Methyl 3-((4-(3,5-bis(trifluoromethyl)benzyl)pyridin-2-yl)amino)-2-methylbenzoate (PW0846A). Compound PW0846A (110 mg, 79%) was synthesized by a procedure similar to that used to prepare compound PW0668 as a colorless oil. $^1$H NMR (300 MHz, Chloroform-d) δ 8.15 (d, J=5.2 Hz, 1H), 7.77 (s, 1H), 7.69 (s, 1H), 7.62 (s, 2H), 7.55 (d, J=8.0 Hz, 1H), 7.24 (d, J=8.1 Hz, 1H), 6.54 (d, J=5.3 Hz, 1H), 6.34 (s, 2H), 3.97 (s, 2H), 3.93 (s, 3H), 2.47 (s, 3H).

Methyl 3-((4-(2,4-bis(trifluoromethyl)benzyl)pyridin-2-yl)amino)-2-methylbenzoate (PW0846B). Compound PW0846B (91 mg, 65%) was synthesized by a procedure similar to that used to prepare compound PW0668 as a colorless oil. $^1$H NMR (300 MHz, Chloroform-d) δ 8.13 (d, J=5.2 Hz, 1H), 7.66 (dd, J=7.8, 1.3 Hz, 1H), 7.56 (dd, J=8.2, 1.3 Hz, 1H), 7.26-7.20 (m, 3H), 7.05 (d, J=11.4 Hz, 1H), 6.55 (dd, J=5.2, 1.4 Hz, 1H), 6.34 (d, J=5.0 Hz, 2H), 3.93 (s, 3H), 3.90 (s, 2H), 2.47 (s, 3H).

Methyl 2-methyl-3-((4-(4-(trifluoromethyl)benzyl)pyridin-2-yl)amino)benzoate (PW0846C). Compound PW0846C (88 mg, 73%) was synthesized by a procedure similar to that used to prepare compound PW0668 as a colorless oil. $^1$H NMR (300 MHz, Chloroform-d) δ 8.11 (d, J=5.2 Hz, 1H), 7.65 (dd, J=7.8, 1.3 Hz, 1H), 7.61-7.52 (m, 3H), 7.34-7.20 (m, 4H), 6.55 (dd, J=5.2, 1.4 Hz, 1H), 6.36 (s, 1H), 6.32 (s, 1H), 3.93 (s, 3H), 3.91 (s, 2H), 2.47 (s, 3H).

Methyl 2-methyl-3-((4-(2-(trifluoromethyl)benzyl)pyridin-2-yl)amino)benzoate (PW0846D). Compound PW0846D (86 mg, 72%) was synthesized by a procedure similar to that used to prepare compound PW0668 as a colorless oil. $^1$H NMR (300 MHz, Chloroform-d) δ 8.10 (d, J=5.2 Hz, 1H), 7.73-7.55 (m, 3H), 7.47 (d, J=7.5 Hz, 1H), 7.37 (d, J=7.6 Hz, 1H), 7.26-7.17 (m, 2H), 6.52 (d, J=5.2 Hz, 1H), 6.37 (s, 1H), 6.27 (s, 1H), 4.07 (s, 2H), 3.93 (s, 3H), 2.47 (s, 3H).

Methyl 3-((4-(3-chloro-5-fluorobenzyl)pyridin-2-yl)amino)-2-methylbenzoate (PW0846E). Compound PW0846E (85 mg, 74%) was synthesized by a procedure similar to that used to prepare compound PW0668 as a colorless oil. $^1$H NMR (300 MHz, Chloroform-d) δ 8.12 (d, J=5.2 Hz, 1H), 7.66 (dd, J=7.8, 1.3 Hz, 1H), 7.58 (dd, J=8.0, 1.3 Hz, 1H), 7.28 (d, J=4.1 Hz, 1H), 6.98 (dd, J=7.6, 2.0 Hz, 2H), 6.77 (dt, J=9.4, 2.0 Hz, 1H), 6.55 (dd, J=5.2, 1.4 Hz, 1H), 6.40-6.28 (m, 2H), 3.93 (s, 3H), 3.81 (s, 2H), 2.48 (s, 3H).

Methyl 3-((4-(3-methoxybenzyl)pyridin-2-yl)amino)-2-methylbenzoate (PW0846F). Compound PW0846F (48 mg, 67%) was synthesized by a procedure similar to that used to prepare compound PW0668 as a colorless oil. $^1$H NMR (300 MHz, Chloroform-d) δ 8.09 (d, J=5.2 Hz, 1H), 7.61 (td, J=8.2, 1.3 Hz, 2H), 7.24 (td, J=7.8, 3.9 Hz, 2H), 6.78 (ddd, J=7.4, 5.6, 2.0 Hz, 2H), 6.71 (t, J=2.1 Hz, 1H), 6.59 (dd, J=5.2, 1.4 Hz, 1H), 6.43 (s, 1H), 6.28 (s, 1H), 3.93 (s, 3H), 3.83 (s, 2H), 3.80 (s, 3H), 2.47 (s, 3H).

Methyl 3-((4-benzylpyridin-2-yl)amino)-2-methylbenzoate (PW0846G). Compound PW0846G (72 mg, 72%) was synthesized by a procedure similar to that used to prepare compound PW0668 as a colorless oil. $^1$H NMR (300 MHz, Chloroform-d) δ 8.09 (d, J=5.2 Hz, 1H), 7.61 (ddd, J=10.4, 8.1, 1.3 Hz, 2H), 7.37-7.21 (m, 4H), 7.20-7.13 (m, 2H), 6.58 (dd, J=5.2, 1.3 Hz, 1H), 6.46-6.39 (m, 1H), 6.28 (s, 1H), 3.93 (s, 3H), 3.86 (s, 2H), 2.47 (s, 3H).

Methyl 3-((4-(4-chloro-2-fluorobenzyl)pyridin-2-yl)amino)-2-methylbenzoate (PW0846H). Compound PW0846H (61 mg, 80%) was synthesized by a procedure similar to that used to prepare compound PW0668 as a colorless oil. $^1$H NMR (300 MHz, Chloroform-d) δ 8.10 (d, J=5.2 Hz, 1H), 7.65 (dd, J=7.7, 1.4 Hz, 1H), 7.58 (dd, J=8.0, 1.3 Hz, 1H), 7.24 (d, J=7.9 Hz, 1H), 7.11-7.03 (m, 3H), 6.56 (dd, J=5.2, 1.4 Hz, 1H), 6.40 (s, 1H), 6.30 (s, 1H), 3.93 (s, 3H), 3.83 (s, 2H), 2.47 (s, 3H).

Methyl 3-((4-(3-fluorobenzyl)pyridin-2-yl)amino)-2-methylbenzoate (PW0846I). Compound PW0846I (54 mg, 77%) was synthesized by a procedure similar to that used to prepare compound PW0668 as a colorless oil. $^1$H NMR (300 MHz, Chloroform-d) δ 8.11 (d, J=5.2 Hz, 1H), 7.64 (dd, J=7.9, 1.3 Hz, 1H), 7.61-7.56 (m, 1H), 7.28-7.21 (m, 3H), 6.95 (dd, J=8.0, 2.0 Hz, 2H), 6.87 (d, J=9.6 Hz, 1H), 6.57 (dd, J=5.2, 1.4 Hz, 1H), 6.40 (s, 1H), 6.29 (s, 1H), 3.93 (s, 3H), 3.84 (s, 2H), 2.47 (s, 3H).

Methyl 3-((4-(4-fluorobenzyl)pyridin-2-yl)amino)-2-methylbenzoate (PW0846J). Compound PW0846J (58 mg, 83%) was synthesized by a procedure similar to that used to prepare compound PW0668 as a colorless oil. $^1$H NMR (300 MHz, Chloroform-d) δ 8.09 (d, J=5.2 Hz, 1H), 7.64 (dd, J=7.8, 1.3 Hz, 1H), 7.57 (dd, J=8.0, 1.3 Hz, 1H), 7.24 (d, J=7.8 Hz, 1H), 7.12 (dd, J=8.5, 5.5 Hz, 2H), 7.00 (t, J=8.7 Hz, 2H), 6.55 (dd, J=5.2, 1.4 Hz, 1H), 6.36 (d, J=8.6 Hz, 2H), 3.93 (s, 3H), 3.82 (s, 2H), 2.46 (s, 3H).

Methyl 2-methyl-3-((4-(3-(trifluoromethoxy)benzyl)pyridin-2-yl)amino)benzoate (PW0846K). Compound PW0846K (68 mg, 82%) was synthesized by a procedure similar to that used to prepare compound PW0668 as a colorless oil. $^1$H NMR (300 MHz, Chloroform-d) δ 8.09 (d, J=5.2 Hz, 1H), 7.64 (dd, J=7.8, 1.3 Hz, 1H), 7.56 (dd, J=7.9, 1.4 Hz, 1H), 7.32 (dd, J=7.8, 3.6 Hz, 1H), 7.23 (d, J=7.7 Hz, 1H), 7.11-7.07 (m, 2H), 7.02 (s, 1H), 6.55 (dd, J=5.3, 1.4 Hz, 2H), 6.37 (s, 1H), 3.92 (s, 3H), 3.86 (s, 2H), 2.46 (s, 3H).

3-((4-(3,5-Bis(trifluoromethyl)benzyl)pyridin-2-yl)amino)-2-methylbenzoic acid (PW0850A). Compound PW0850A (76 mg, 84%) was synthesized by a procedure similar to that used to prepare compound 9PW0669 as a white solid. $^1$H NMR (300 MHz, DMSO-$d_6$) δ 10.55 (s, 1H), 8.01 (d, J=11.6 Hz, 2H), 7.92-7.88 (m, 1H), 7.82-7.78 (m, 1H), 7.57-7.52 (m, 2H), 7.42 (d, J=7.7 Hz, 1H), 6.98-6.93 (m, 2H), 4.29 (s, 2H), 2.36 (s, 3H).

3-((4-(2,4-Bis(trifluoromethyl)benzyl)pyridin-2-yl)amino)-2-methylbenzoic acid (PW0850B). Compound PW0850B (78 mg, 86%) was synthesized by a procedure similar to that used to prepare compound PW0669 as a white solid. $^1$H NMR (300 MHz, DMSO-$d_6$) δ 10.69 (d, J=4.5 Hz, 1H), 7.91 (dd, J=6.5, 4.5 Hz, 1H), 7.80 (ddd, J=7.8, 4.1, 1.4 Hz, 1H), 7.66-7.54 (m, 4H), 7.47-7.40 (m, 1H), 7.00-6.88 (m, 2H), 4.19 (s, 2H), 2.38 (s, 3H).

2-Methyl-3-((4-(4-(trifluoromethyl)benzyl)pyridin-2-yl)amino)benzoic acid (PW0850C). Compound PW0850C (70 mg, 91%) was synthesized by a procedure similar to that used to prepare compound PW0669 as a white solid. $^1$H NMR (300 MHz, DMSO-$d_6$) δ 13.14 (s, 1H), 10.63 (s, 1H), 7.89 (dd, J=6.5, 4.3 Hz, 1H), 7.83-7.69 (m, 3H), 7.56 (ddd, J=13.2, 8.0, 1.4 Hz, 3H), 7.42 (q, J=7.5 Hz, 1H), 7.00-6.83 (m, 2H), 4.17 (s, 2H), 2.37 (s, 3H).

2-Methyl-3-((4-(2-(trifluoromethyl)benzyl)pyridin-2-yl)amino)benzoic acid (PW0850D). Compound PW0850D (59 mg, 76%) was synthesized by a procedure similar to that used to prepare compound PW0669 as a white solid. $^1$H NMR (300 MHz, DMSO-$d_6$) δ 13.04 (s, 1H), 10.27 (s, 1H), 7.87 (d, J=6.4 Hz, 1H), 7.83-7.66 (m, 3H), 7.61-7.47 (m, 3H), 7.39 (t, J=7.8 Hz, 1H), 6.79 (dd, J=6.5, 1.6 Hz, 1H), 6.68 (s, 1H), 4.26 (s, 2H), 2.34 (s, 3H).

3-((4-(3-Chloro-5-fluorobenzyl)pyridin-2-yl)amino)-2-methylbenzoic acid (PW0850E). Compound PW0850E (58 mg, 78%) was synthesized by a procedure similar to that used to prepare compound PW0669 as a white solid. $^1$H NMR (300 MHz, DMSO-$d_6$) δ 13.11 (s, 1H), 10.51 (s, 1H), 7.88 (dd, J=6.5, 4.5 Hz, 1H), 7.80 (dd, J=7.8, 1.4 Hz, 1H), 7.56 (dd, J=7.9, 1.4 Hz, 1H), 7.47-7.29 (m, 3H), 7.24 (dt, J=9.6, 1.8 Hz, 1H), 6.98-6.85 (m, 2H), 4.08 (s, 2H), 2.38 (s, 3H).

3-((4-(3-Methoxybenzyl)pyridin-2-yl)amino)-2-methylbenzoic acid (PW0850F). Compound PW0850F (58 mg, 83%) was synthesized by a procedure similar to that used to prepare compound PW0669 as a white solid. $^1$H NMR (300 MHz, DMSO-$d_6$) δ 10.58 (s, 1H), 7.83 (td, J=7.6, 7.1, 2.1 Hz, 2H), 7.54 (dd, J=7.9, 1.5 Hz, 1H), 7.42 (t, J=7.8 Hz, 1H), 7.27 (t, J=7.8 Hz, 1H), 6.95-6.78 (m, 4H), 6.68 (dd, J=4.5, 1.9 Hz, 1H), 4.02 (s, 2H), 3.75 (s, 3H), 2.37 (s, 3H).

3-((4-Benzylpyridin-2-yl)amino)-2-methylbenzoic acid (PW0850G). Compound PW0850G (59 mg, 93%) was synthesized by a procedure similar to that used to prepare compound PW0669 as a white solid. $^1$H NMR (300 MHz, DMSO-$d_6$) δ 13.02 (s, 1H), 10.65 (s, 1H), 7.87 (dd, J=6.5, 4.0 Hz, 1H), 7.79 (ddd, J=6.1, 4.8, 1.4 Hz, 1H), 7.61-7.52 (m, 1H), 7.44-7.25 (m, 6H), 6.95 (d, J=1.6 Hz, 1H), 6.87 (dt, J=6.5, 1.7 Hz, 1H), 4.05 (s, 2H), 2.37 (s, 3H).

3-((4-(4-Chloro-2-fluorobenzyl)pyridin-2-yl)amino)-2-methylbenzoic acid (PW0850H). Compound PW0850H (54 mg, 73%) was synthesized by a procedure similar to that used to prepare compound PW0669 as a white solid. $^1$H NMR (300 MHz, DMSO-$d_6$) δ 13.14 (s, 1H), 10.29 (s, 1H), 7.82 (dd, J=18.5, 7.1 Hz, 2H), 7.57-7.32 (m, 5H), 6.91-6.77 (m, 2H), 4.09 (s, 2H), 2.36 (s, 3H).

3-((4-(3-Fluorobenzyl)pyridin-2-yl)amino)-2-methylbenzoic acid (PW0850I). Compound PW0850I (59 mg, 88%) was synthesized by a procedure similar to that used to prepare compound PW0669 as a white solid. $^1$H NMR (300 MHz, DMSO-$d_6$) δ 13.06 (s, 1H), 10.52 (s, 1H), 7.92-7.76 (m, 2H), 7.55 (dd, J=7.9, 1.4 Hz, 1H), 7.47-7.35 (m, 2H), 7.24-7.06 (m, 3H), 6.97-6.83 (m, 2H), 4.08 (s, 2H), 2.37 (s, 3H).

3-((4-(4-Fluorobenzyl)pyridin-2-yl)amino)-2-methylbenzoic acid (PW0850J). Compound PW0850J (53 mg, 79%) was synthesized by a procedure similar to that used to prepare compound PW0669 as a white solid. $^1$H NMR (300 MHz, DMSO-$d_6$) δ 13.00 (s, 1H), 10.44 (s, 1H), 7.92-7.73 (m, 2H), 7.54 (dd, J=7.9, 1.4 Hz, 1H), 7.46-7.32 (m, 3H), 7.24-7.13 (m, 2H), 6.87 (d, J=7.3 Hz, 2H), 4.05 (s, 2H), 2.36 (s, 3H).

2-Methyl-3-((4-(3-(trifluoromethoxy)benzyl)pyridin-2-yl)amino)benzoic acid (PW0850K). Compound PW0850K (68 mg, 85%) was synthesized by a procedure similar to that used to prepare compound PW0669 as a white solid. $^1$H NMR (300 MHz, DMSO-$d_6$) δ 13.04 (s, 1H), 10.42 (s, 1H), 7.90-7.77 (m, 2H), 7.58-7.47 (m, 2H), 7.43-7.34 (m, 3H), 7.28 (d, J=8.2 Hz, 1H), 6.90 (d, J=6.5 Hz, 2H), 4.13 (s, 2H), 2.37 (s, 3H).

3-((4-(3,5-Bis(trifluoromethyl)benzyl)pyridin-2-yl)amino)-N-(2-hydroxyethyl)-2-methylbenzamide (PW0861). Compound PW0861 (68 mg, 68%) was synthesized by a procedure similar to that used to prepare compound PW0671 as a white solid. $^1$H NMR (300 MHz, Chloroform-d and MeOD) δ 7.98 (d, J=5.3 Hz, 1H), 7.75 (s, 1H), 7.61 (s, 2H), 7.34 (t, J=4.7 Hz, 1H), 7.15 (d, J=4.6 Hz, 2H), 6.49 (dd, J=5.3, 1.4 Hz, 1H), 6.44 (s, 1H), 3.95 (s, 2H), 3.71 (t, J=5.1 Hz, 2H), 3.50 (t, J=5.3 Hz, 2H), 2.23 (s, 3H). $^{13}$C NMR (75 MHz, CDCl$_3$ and MeOD) δ 171.4, 171.3, 166.6, 157.1, 149.9, 148.3, 141.5, 138.8, 138.5, 132.1, 131.6, 130.0, 129.3, 129.0, 126.4, 125.2, 125.0, 123.3, 121.4, 120.7, 115.2, 108.4, 61.3, 42.4, 40.8, 14.7. HRMS (ESI) calcd for C$_{24}$H$_{22}$F$_6$N$_3$O$_2$ 498.1611 (M+H)$^+$, found 498.1609.

3-((4-(2,4-Bis(trifluoromethyl)benzyl)pyridin-2-yl)amino)-N-(2-hydroxyethyl)-2-methylbenzamide (PW0862). Compound PW0862 (50 mg, 75%) was synthesized by a procedure similar to that used to prepare compound PW0671 as a white solid. $^1$H NMR (300 MHz, Chloroform-d) δ 7.99 (d, J=5.2 Hz, 1H), 7.37 (dd, J=6.7, 2.6 Hz, 1H), 7.26-7.16 (m, 2H), 7.14-7.00 (m, 3H), 6.90 (t, J=5.6 Hz, 1H), 6.71 (s, 1H), 6.50 (dd, J=5.3, 1.4 Hz, 1H), 6.44 (s, 1H), 3.87 (s, 2H), 3.69 (t, J=5.0 Hz, 2H), 3.48 (d, J=5.2 Hz, 2H), 3.23 (s, 1H), 2.21 (s, 3H). $^{13}$C NMR (75 MHz, CDCl$_3$) δ 171.1, 164.2, 160.9, 157.0, 150.1, 148.3, 142.8 (d, J=7.4 Hz), 139.0, 138.5, 129.4, 126.4, 124.7, 123.0, 121.5-121.4 (m), 119.4 (d, J=20.9 Hz), 115.5, 111.10 (d, J=24.7 Hz), 108.4, 61.5, 42.5, 40.8, 14.7. HRMS (ESI) calcd for C$_{24}$H$_{22}$F$_6$N$_3$O$_2$ 498.1611 (M+H)$^+$, found 498.1609.

N-(2-Hydroxyethyl)-2-methyl-3-((4-(4-(trifluoromethyl)benzyl)pyridin-2-yl)amino)benzamide (PW0863). Compound PW0863 (54 mg, 93%) was synthesized by a procedure similar to that used to prepare compound PW0671 as a white solid. $^1$H NMR (300 MHz, Chloroform-d and MeOD) δ 7.92 (d, J=5.3 Hz, 1H), 7.53 (d, J=8.0 Hz, 2H), 7.34-7.23 (m, 3H), 7.17-7.07 (m, 2H), 6.49 (dd, J=5.3, 1.4 Hz, 1H), 6.43 (s, 1H), 3.87 (s, 2H), 3.69 (t, J=5.2 Hz, 2H), 3.48 (t, J=5.1 Hz, 2H), 2.21 (s, 3H). $^{13}$C NMR (75 MHz, CDCl$_3$ and MeOD) δ 171.4, 156.9, 151.2, 147.8, 143.1, 138.9, 138.4, 129.8, 129.3, 129.1, 128.7, 126.3, 125.9, 125.5 (q, J=3.8 Hz), 125.1, 123.2, 115.5, 108.6, 61.2, 42.5, 42.3, 41.0, 14.7. HRMS (ESI) calcd for C$_{23}$H$_{23}$F$_3$N$_3$O$_2$ 430.1737 (M+H)$^+$, found 430.1735.

N-(2-Hydroxyethyl)-2-methyl-3-((4-(2-(trifluoromethyl)benzyl)pyridin-2-yl)amino)benzamide (PW0864). Compound PW0864 (67 mg, 78%) was synthesized by a procedure similar to that used to prepare compound PW0671 as a white solid. $^1$H NMR (300 MHz, Chloroform-d) δ 7.93 (d, J=5.3 Hz, 1H), 7.66 (dd, J=7.9, 1.4 Hz, 1H), 7.50-7.42 (m, 1H), 7.34 (dd, J=8.5, 6.2 Hz, 2H), 7.19 (d, J=7.7 Hz, 1H), 7.11-6.96 (m, 3H), 6.72 (s, 1H), 6.50-6.37 (m, 2H), 4.03 (s, 2H), 3.64 (t, J=5.1 Hz, 3H), 3.44 (t, J=5.2 Hz, 2H), 2.17 (s, 3H). $^{13}$C NMR (75 MHz, CDCl$_3$) δ 171.2, 156.7, 151.1, 147.7, 139.1, 138.4, 137.1, 132.0, 131.8, 129.0, 128.6, 126.8, 126.3, 126.2, 126.1 (q, J=5.8, 5.3 Hz), 124.3, 122.7, 115.7, 108.9, 61.4, 42.5, 37.5, 37.4, 14.7. HRMS (ESI) calcd for C$_{23}$H$_{23}$F$_3$N$_3$O$_2$ 430.1737 (M+H)$^+$, found 430.1735.

3-((4-(3-Chloro-5-fluorobenzyl)pyridin-2-yl)amino)-N-(2-hydroxyethyl)-2-methylbenzamide (PW0865). Compound PW0865 (55 mg, 66%) was synthesized by a procedure similar to that used to prepare compound PW0671 as a white solid. $^1$H NMR (300 MHz, Chloroform-d) δ 7.94 (d, J=5.3 Hz, 1H), 7.34 (dd, J=7.0, 2.3 Hz, 1H), 7.14-7.02 (m, 3H), 6.94 (dp, J=4.4, 2.0 Hz, 2H), 6.87-6.70 (m, 3H), 6.52-6.39 (m, 2H), 3.76 (s, 2H), 3.64 (t, J=5.1 Hz, 3H), 3.43 (q, J=5.0 Hz, 2H), 2.18 (s, 3H). $^{13}$C NMR (75 MHz, CDCl$_3$) δ 171.2, 166.6, 164.3, 161.0, 156.9, 150.4, 148.1, 142.7 (d, J=8.2 Hz), 139.1, 138.4, 135.0 (d, J=10.8 Hz), 129.4, 126.4, 125.0 (d, J=3.1 Hz), 124.7, 122.9, 115.5, 114.6 (d, J=6.4 Hz), 114.3 (d, J=3.2 Hz), 108.6, 61.3, 42.5, 40.7, 14.8. HRMS (ESI) calcd for C$_{22}$H$_{22}$ClFN$_3$O$_2$ 414.1379 (M+H)$^+$, found 414.1377.

N-(2-Hydroxyethyl)-3-((4-(3-methoxybenzyl)pyridin-2-yl)amino)-2-methylbenzamide (PW0866). Compound PW0866 (20 mg, 38%) was synthesized by a procedure similar to that used to prepare compound PW0671 as a white solid. $^1$H NMR (300 MHz, Chloroform-d) δ 8.00 (s, 1H), 7.41 (t, J=5.4 Hz, 1H), 7.31-6.92 (m, 4H), 6.80-6.41 (m, 6H), 3.97-3.62 (m, 7H), 3.52 (t, J=5.2 Hz, 2H), 3.05 (s, 1H), 2.24 (d, J=3.9 Hz, 3H). $^{13}$C NMR (75 MHz, CDCl$_3$) δ 171.1, 159.8, 156.5, 152.1, 147.8, 140.5, 139.2, 138.4, 129.6, 128.9, 126.4, 124.2, 122.6, 121.4, 116.0, 114.9, 111.7, 108.6, 61.9, 55.2, 42.6, 41.4, 14.7. HRMS (ESI) calcd for C$_{23}$H$_{26}$N$_3$O$_3$ 392.1969 (M+H)$^+$, found 392.1964.

3-((4-Benzylpyridin-2-yl)amino)-N-(2-hydroxyethyl)-2-methylbenzamide (PW0867). Compound PW0867 (37 mg, 77%) was synthesized by a procedure similar to that used to prepare compound PW0671 as a white solid. $^1$H NMR (300 MHz, Chloroform-d) δ 7.94 (d, J=5.3 Hz, 1H), 7.35 (dd, J=7.1, 2.2 Hz, 1H), 7.33-7.27 (m, 2H), 7.26-7.20 (m, 1H), 7.19-7.13 (m, 2H), 7.12-7.04 (m, 2H), 6.96 (t, J=5.6 Hz, 1H), 6.54 (dd, J=5.3, 1.3 Hz, 2H), 6.47 (s, 1H), 3.83 (s, 2H), 3.66 (t, J=5.0 Hz, 2H), 3.45 (d, J=5.2 Hz, 3H). $^{13}$C NMR (75 MHz, CDCl$_3$) δ 171.2, 156.6, 152.2, 147.7, 139.2, 139.0, 138.4, 129.0, 129.0, 128.6, 126.6, 126.3, 124.4, 122.7, 115.9, 108.8, 61.5, 42.5, 41.4, 14.8. HRMS (ESI) calcd for C$_{22}$H$_{24}$N$_3$O$_2$ 362.1863 (M+H)$^+$, found 362.1862.

3-((4-(4-Chloro-2-fluorobenzyl)pyridin-2-yl)amino)-N-(2-hydroxyethyl)-2-methylbenzamide (PW0868). Compound PW0868 (36 mg, 65%) was synthesized by a procedure similar to that used to prepare compound PW0671 as a white solid. $^1$H NMR (300 MHz, Chloroform-d) δ 7.96 (d, J=5.3 Hz, 1H), 7.37 (dd, J=7.2, 2.1 Hz, 1H), 7.18-7.03 (m, 5H), 6.87 (t, J=5.7 Hz, 1H), 6.72-6.50 (m, 2H), 6.46 (s, 1H), 3.81 (s, 2H), 3.69 (t, J=5.0 Hz, 2H), 3.48 (q, J=5.2 Hz, 2H), 3.20 (s, 1H), 2.20 (s, 3H). $^{13}$C NMR (75 MHz, CDCl$_3$) δ 171.1, 159.0, 156.7, 150.3, 148.0, 138.8 (d, J=53.6 Hz), 133.4 (d, J=10.0 Hz), 131.7 (d, J=5.3 Hz), 129.1, 126.4, 124.9, 124.7 (d, J=3.5 Hz), 124.4, 122.7, 116.3 (d, J=25.6 Hz), 115.4, 108.4, 61.6, 42.6, 34.0, 34.0, 14.7. HRMS (ESI) calcd for C$_{22}$H$_{22}$ClFN$_3$O$_2$ 414.1379 (M+H)$^+$, found 414.1377.

3-((4-(3-Fluorobenzyl)pyridin-2-yl)amino)-N-(2-hydroxyethyl)-2-methylbenzamide (PW0869). Compound PW0869 (33 mg, 65%) was synthesized by a procedure similar to that used to prepare compound PW0671 as a white solid. $^1$H NMR (300 MHz, Chloroform-d) δ 7.93 (s, 1H), 7.33 (dd, J=6.7, 2.7 Hz, 1H), 7.24 (td, J=8.2, 6.2 Hz, 1H), 7.11-7.03 (m, 3H), 6.96-6.89 (m, 2H), 6.88-6.74 (m, 2H), 6.55-6.38 (m, 2H), 3.80 (s, 2H), 3.64 (t, J=5.1 Hz, 3H), 3.43 (q, J=5.2 Hz, 2H), 2.18 (s, 3H). $^{13}$C NMR (75 MHz, CDCl$_3$) δ 171.2, 164.5, 161.3, 156.8, 151.4, 147.8, 141.4 (d, J=7.2 Hz), 139.1, 138.4, 130.1 (d, J=8.4 Hz), 129.3, 126.3, 124.7, 124.6, 122.8, 115.8 (d, J=21.3 Hz), 113.5 (d, J=21.0 Hz), 108.7, 61.3, 42.5, 41.0, 14.8. HRMS (ESI) calcd for C$_{22}$H$_{23}$FN$_3$O$_2$ 380.1769 (M+H)$^+$, found 380.1765.

3-((4-(4-Fluorobenzyl)pyridin-2-yl)amino)-N-(2-hydroxyethyl)-2-methylbenzamide (PW0870). Compound PW0870 (27 mg, 71%) was synthesized by a procedure similar to that used to prepare compound PW0671 as a white solid. $^1$H NMR (300 MHz, Chloroform-d) δ 7.97 (d, J=5.2 Hz, 1H), 7.38 (dd, J=7.2, 2.2 Hz, 1H), 7.16-7.04 (m, 4H), 7.03-6.92 (m, 2H), 6.83 (t, J=5.6 Hz, 1H), 6.64-6.47 (m, 2H), 6.44 (s, 1H), 3.81 (s, 2H), 3.70 (t, J=5.0 Hz, 2H), 3.49

(q, J=5.3 Hz, 2H), 3.00 (s, 1H), 2.21 (s, 3H). $^{13}$C NMR (75 MHz, CDCl$_3$) δ 171.2, 166.6, 163.2, 160.0, 156.7, 152.0, 147.9, 139.2, 138.4, 134.7 (d, J=3.2 Hz), 130.4 (d, J=8.0 Hz), 129.1, 126.4, 124.4, 122.7, 115.7, 115.6, 115.3, 108.5, 61.6, 42.6, 40.5, 14.7. HRMS (ESI) calcd for C$_{22}$H$_{23}$FN$_3$O$_2$ 380.1769 (M+H)$^+$, found 380.1765.

N-(2-Hydroxyethyl)-2-methyl-3-((4-(3-(trifluoromethoxy)benzyl)pyridin-2-yl)amino)benzamide (PW0871). Compound PW0871 (47 mg, 78%) was synthesized by a procedure similar to that used to prepare compound PW0671 as a white solid. $^1$H NMR (300 MHz, Chloroform-d) δ 8.01 (d, J=4.5 Hz, 1H), 7.44-7.25 (m, 2H), 7.20-6.97 (m, 5H), 6.78 (d, J=5.1 Hz, 1H), 6.65-6.37 (m, 3H), 3.85 (d, J=3.6 Hz, 2H), 3.71 (d, J=5.1 Hz, 2H), 3.50 (t, J=5.1 Hz, 2H), 3.26 (s, 1H), 2.23 (t, J=2.8 Hz, 3H). $^{13}$C NMR (75 MHz, CDCl$_3$) δ 171.1, 166.6, 156.8, 151.1, 149.4, 148.1, 141.3, 139.1, 138.4, 129.9, 129.1, 127.4, 126.4, 124.4, 122.8, 121.4, 119.0, 115.7, 108.5, 61.7, 42.6, 41.0, 14.7. HRMS (ESI) calcd for C$_{23}$H$_{23}$F$_3$N$_3$O$_3$ 446.1686 (M+H)$^+$, found 446.1682.

ABBREVIATIONS USED: GPCRs, G-protein-coupled receptors; FDA, U.S food and drug administration; CNS, central nervous system; NAc, nucleus accumbens; MSNs, medium spiny neurons; cAMP, cyclic adenosine monophosphate; NMDA, N-methyl-$_D$-aspartate; SUD, substance-use disorder; ECL2, extracellular loop 2; EC$_{50}$, half maximal effective concentration; HTS, high-throughput screening; TM, transmembrane helix; SAR, structure-activity relationship; PK, pharmacokinetic; DMF, N,N-dimethylformamide; EDCI, N-(3-dimethylaminopropyl)-N'-ethylcarbodiimide hydrochloride; DMAP, 4-dimethylaminopyridine; XantPhos, 4,5-bis(diphenylphosphino)-9,9-dimethylxanthene; mCPBA, meta-chloroperoxybenzoic acid; DAST, diethylaminosulfur trifluoride; DMSO, dimethyl sulfoxide; NIMH, national institute of mental health; PDSP, psychoactive drug screening program; hERG, human ether-a-go-go-related gene; PO, oral; IV, intravenous; amphetamine, AMPH; WT, Wildtype; HEK293, human embryonic kidney 293; PCR, polymerase chain reaction; HBSS, Hanks balanced salt solution; IP, intraperitoneal.

REFERENCES

1. Allen and Roth, Annu. Rev. Pharmacol. Toxicol. 2011, 51, 117-144.
2. Wold et al., J. Med. Chem. 2019, 62, 88-127.
3. Zhou and Wild, Curr. Top. Med. Chem. 2019, 19, 1363-1364.
4. Overington et al., Nat. Rev. Drug Discov. 2006, 5, 993-996.
5. Lagerstrom and Schioth, Nat. Rev. Drug Discov. 2008, 7, 339-357.
6. Hauser et al., Nat. Rev. Drug Discov. 2017, 16, 829-842.
7. Roth et al., Nat. Chem. Biol. 2017, 13, 1143-1151.
8. Ye et al., ACS Chem. Neurosci. 2019, 10, 190-200.
9. Ye et al., ACS Chem Neurosci 2019, 10, 190-200.
10. Sawzdargo et al., Mol. Brain Res. 1999, 64, 193-198.
11. Komatsu et al., PLoS One 2014, 9, e90134.
12. Yang et al., bioRxiv 2018, 311563.
13. Lin et al., Nature 2020, 579, 152-157.
14. Martin et al., PLoS One 2015, 10, e0138463.
15. Setoh et al., J. Med. Chem. 2014, 57, 5226-5237.
16. Nishiyama et al., J. Pharmacol. Exp. Ther. 2017, 363, 253-264.
17. Xiong et al., WO2016176571 A1, Nov. 3, 2016.
18. Tokumaru et al., Bioorg. Med. Chem. 2017, 25, 3098-3115.
19. Nakahata et al., Bioorg. Med. Chem. 2018, 26, 1598-1608.
20. Meanwell, J. Med. Chem. 2011, 54, 2529-2591.
21. Meanwell, Top. Med. Chem. 2015, 9, 283-382.
22. Pennington and Moustakas, J. Med. Chem. 2017, 60, 3552-3579.
23. Cesta et al., Asian J. Org. Chem. 2019, 8, 1053-1057.
24. Sengmany et al., Tetrahedron 2015, 71, 4859-4867.
25. Loksha, J. Het. Chem. 2009, 46, 1296-1301.
26. Gray et al., Nat. Commun. 2018, 9, 674.
27. Besnard et al., Nature 2012, 492, 215-220.
28. Kalyaanamoorthy and Barakat, Med. Res. Rev. 2018, 38, 525-555.
29. Jones et al., Br. J. Pharmacol. 2011, 164, 1162-1194.
30. Dichter et al., J. Neurodev. Disord. 2012, 4, 19.
31. Komatsu, Int. J. Mol. Sci. 2015, 16, 14109-14121.
32. Grundmann et al., Nat. Commun. 2018, 9, 341.
33. Simmler et al., Br. J. Pharmacol. 2017, 174, 2716-2738.
34. Cortez et al., Behav. Brain Res. 2017, 322, 212-222.
35. Cunningham et al., ACS Chem. Neurosci. 2013, 4, 110-121.
36. Keppel and Wickens, T. D. Design and analysis: a researcher's handbook. Pearson Prentice Hall: 2004.
37. Kenakin. Mol Pharmacol. 2017 October; 92(4):414-424. doi: 10.1124/mol.117.108787.

The invention claimed is:

1. A compound according to Formula I or pharmaceutically acceptable salt thereof, wherein:

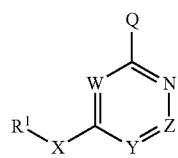

Formula I wherein:

R$^1$ is aryl optionally substituted with one or more groups selected independently from: H, alkyl, cycloalkyl, alkenyl, aryl, heteroaryl, benzyl, alkoxy, halogen, cyan, nitro, amino, hydroxyl, CF$_3$ or —OCF$_3$, wherein alkyl is optionally substituted with one or more chosen substituents chosen from: hydroxyl, cyan, amino, or halogen;

X is CH$_2$;

W is CH;

Y is CH;

Z is CH;

Q is

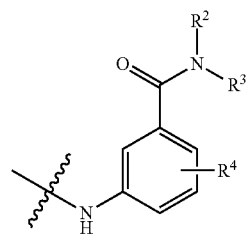

R$^2$ is H; and

R$^3$ is selected from: H, alkyl, heteroaryl, heterocyclyl, heterocyclyl-alkyl, and hydroxyl-alkyl; and each group is optionally substituted with one or more groups selected independently from: alkyl, cycloalkyl, alkenyl, aryl, heteroaryl, benzyl, alkoxy, halogen, cyan, nitro, amino, hydroxyl, CF$_3$ or —OCF$_3$;

or R$^2$ and R$^3$ together form a 4-12 membered cycloalkyl ring, and the -12 membered cycloalkyl is optionally substituted with one or more groups selected independently from: alkyl, cycloalkyl, alkenyl, aryl, heteroaryl, benzyl, alkoxy, halogen, cyan, nitro, amino, hydroxyl, CF$_3$ or —OCF$_3$;

R$^4$ is independently chosen from H, alkyl, alkoxy, halogen, cyan, amino, A hydroxyl, nitro, CF$_3$ or —OCF$_3$.

2. A compound of claim 1, wherein the compound is:

PW0671

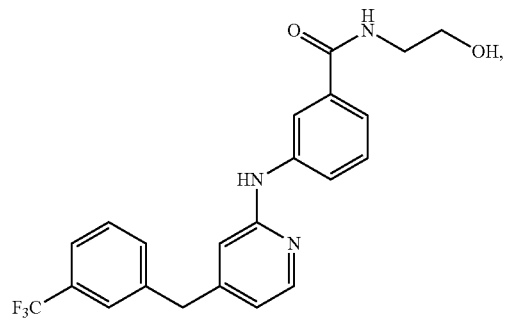

PW0715

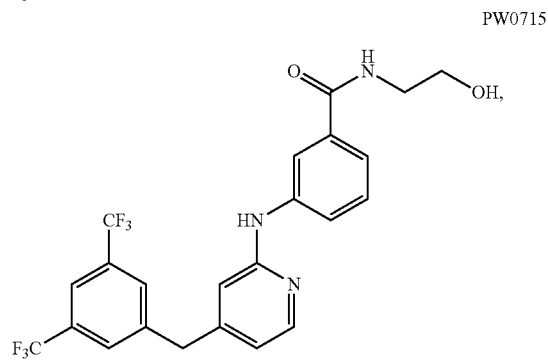

PW0724

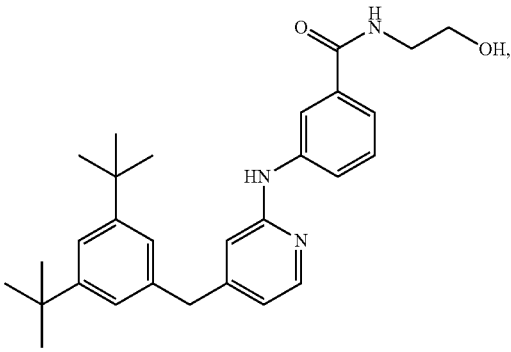

PW0723

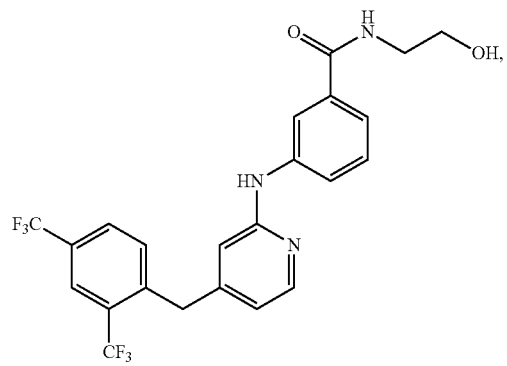

-continued
PW0673
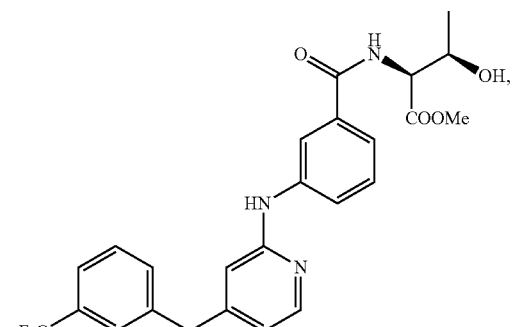
PW0674
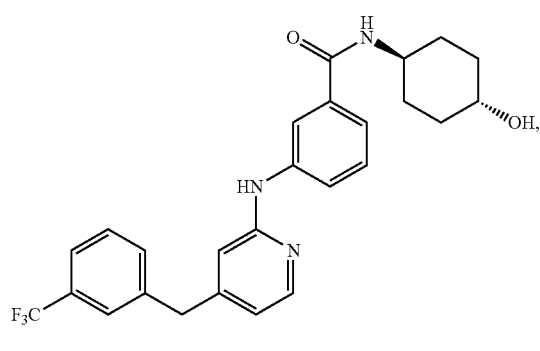
PW0675
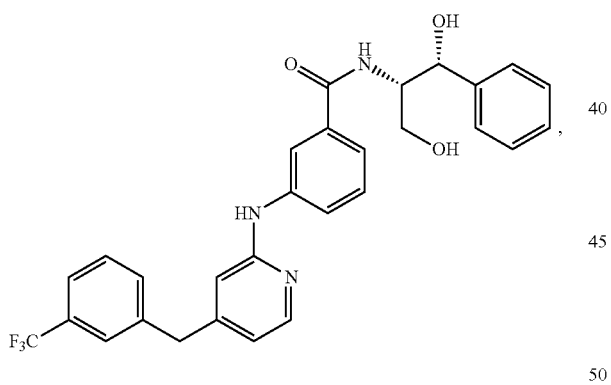
PW0676
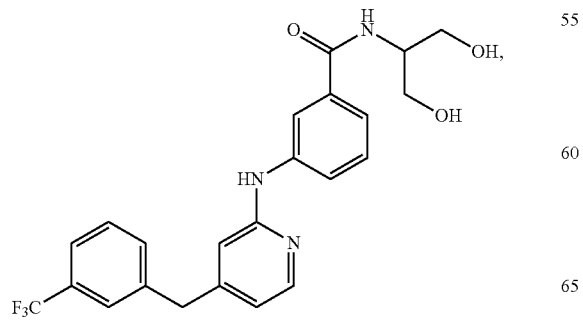
-continued
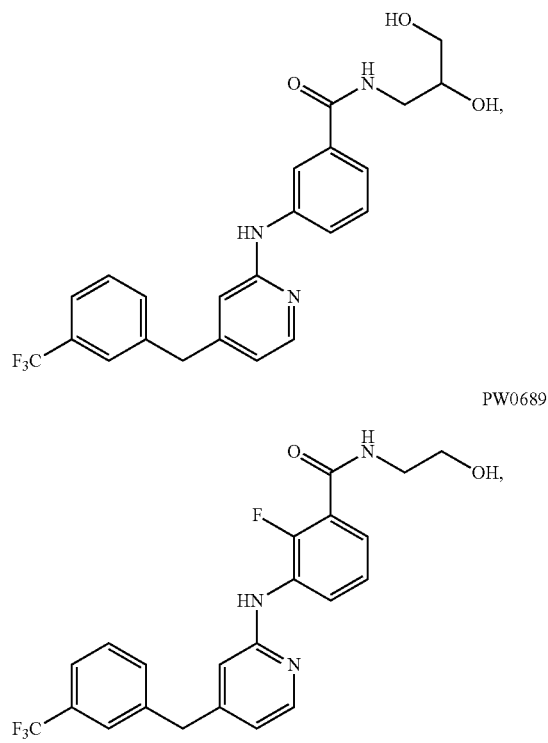
PW0677
PW0689
PW0693
PW0698
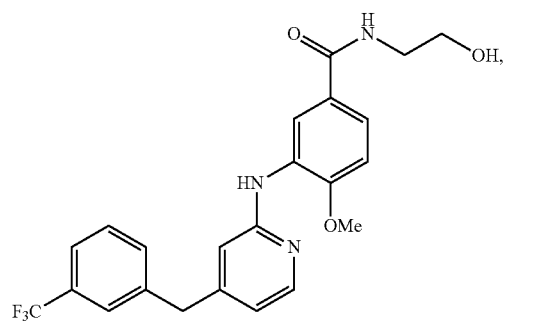

-continued
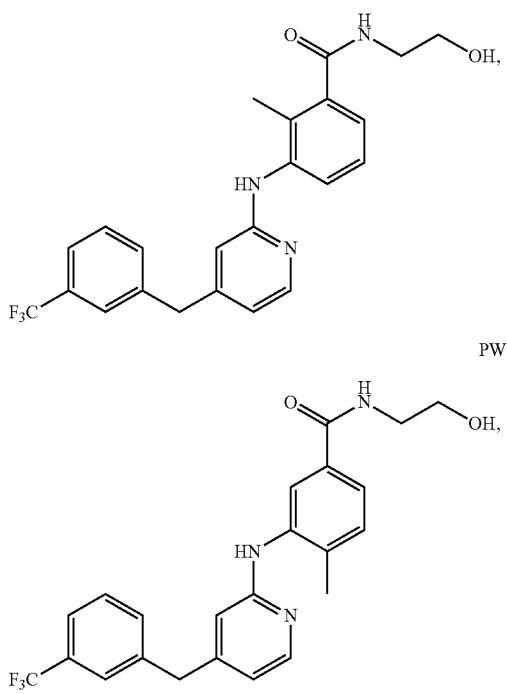
PW0729
PW0730
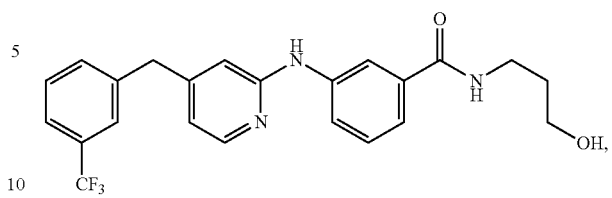
PW0831
PW0832
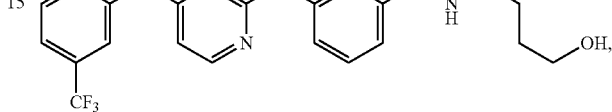
PW0839
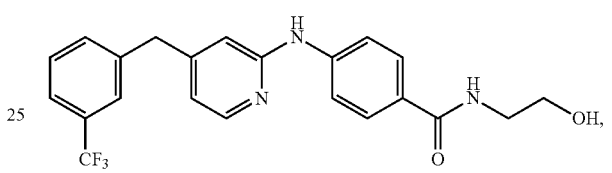
PW0840
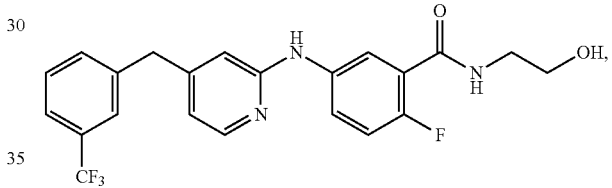
PW0841
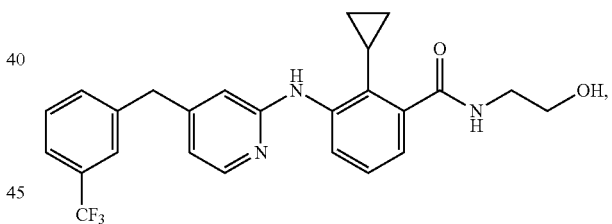
PW0842
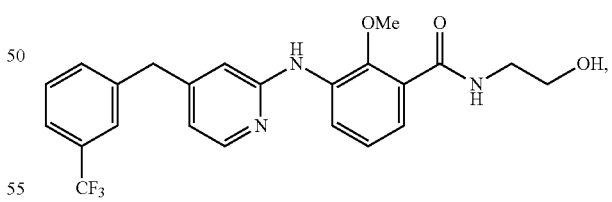
PW0861
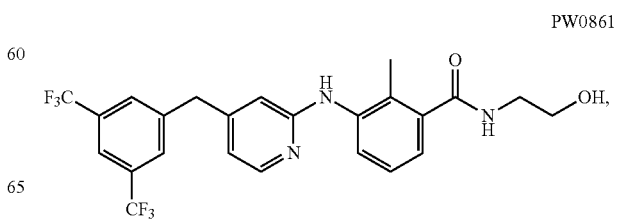

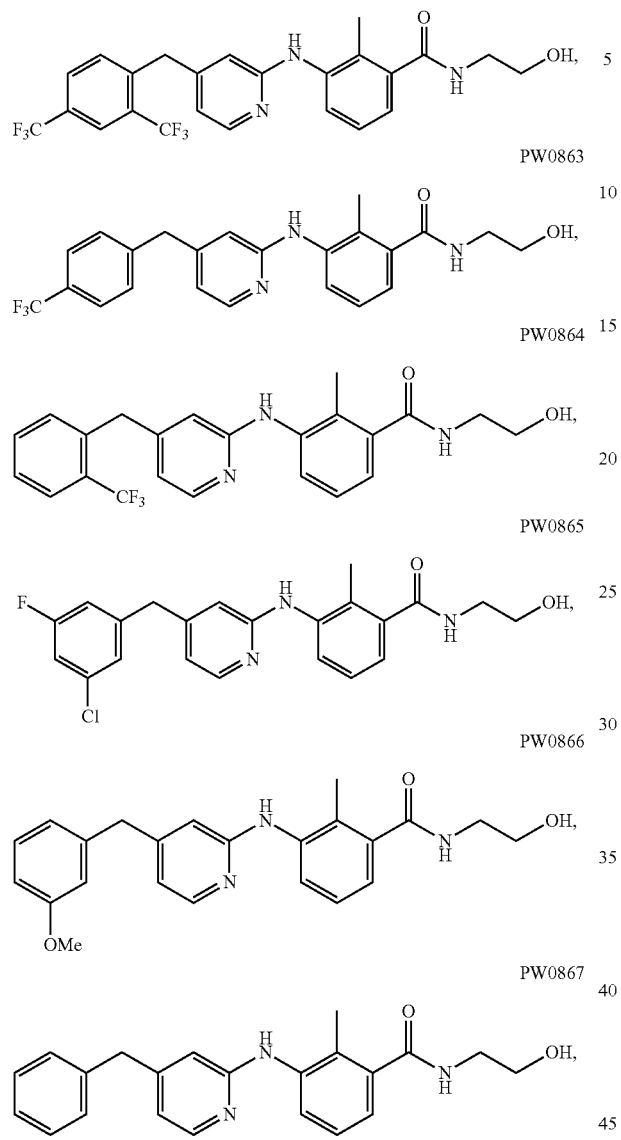
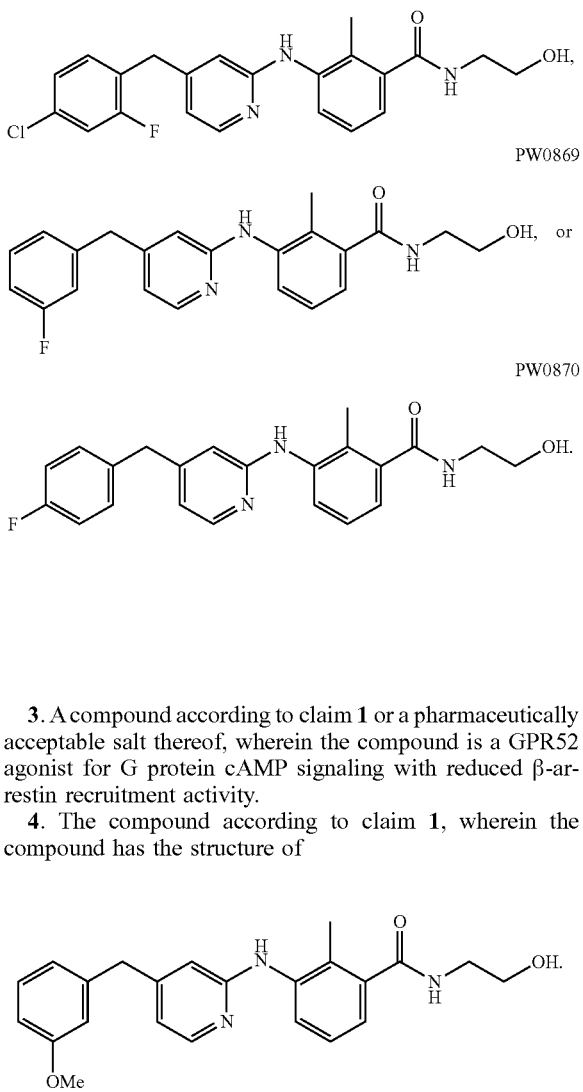
3. A compound according to claim 1 or a pharmaceutically acceptable salt thereof, wherein the compound is a GPR52 agonist for G protein cAMP signaling with reduced β-arrestin recruitment activity.
4. The compound according to claim 1, wherein the compound has the structure of
* * * * *